United States Patent
Mosrin et al.

(10) Patent No.: US 9,084,425 B2
(45) Date of Patent: Jul. 21, 2015

(54) 2,3-DIPHENYL-VALERONITRILE DERIVATIVES, METHOD FOR THE PRODUCTION THEREOF AND USE THEREOF AS HERBICIDES AND PLANT GROWTH REGULATORS

(75) Inventors: Marc Mosrin, Frankfurt am Main (DE); Harald Jakobi, Frankfurt (DE); Alfred Angermann, Kriftel (DE); Elmar Gatzweiler, Bad Nauheim (DE); Isolde Häuser-Hahn, Leverkusen (DE); Ines Heinemann, Hofheim (DE); Christopher Hugh Rosinger, Hofheim (DE); Stefan Lehr, Lyons (FR); Stefan Schnatterer, Hattersheim (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/131,891

(22) PCT Filed: Jul. 11, 2012

(86) PCT No.: PCT/EP2012/063613
§ 371 (c)(1),
(2), (4) Date: Apr. 23, 2014

(87) PCT Pub. No.: WO2013/010882
PCT Pub. Date: Jan. 24, 2013

(65) Prior Publication Data
US 2014/0235446 A1    Aug. 21, 2014

Related U.S. Application Data

(60) Provisional application No. 61/508,306, filed on Jul. 15, 2011.

(30) Foreign Application Priority Data

Jul. 15, 2011   (DE) .................. 10 2011 079 241

(51) Int. Cl.
| | | |
|---|---|---|
| A01N 43/80 | (2006.01) | |
| A01N 43/56 | (2006.01) | |
| A01N 43/16 | (2006.01) | |
| A01N 43/32 | (2006.01) | |
| A01N 37/42 | (2006.01) | |
| A01N 37/34 | (2006.01) | |
| C07C 255/62 | (2006.01) | |
| C07C 255/66 | (2006.01) | |
| C07D 319/06 | (2006.01) | |
| C07D 231/12 | (2006.01) | |
| C07D 231/16 | (2006.01) | |
| C07D 231/20 | (2006.01) | |
| C07D 261/08 | (2006.01) | |
| C07C 255/40 | (2006.01) | |
| C07C 255/56 | (2006.01) | |
| C07C 255/41 | (2006.01) | |

(52) U.S. Cl.
CPC ................ *A01N 43/80* (2013.01); *A01N 37/34* (2013.01); *A01N 37/42* (2013.01); *A01N 43/16* (2013.01); *A01N 43/32* (2013.01); *A01N 43/56* (2013.01); *C07C 255/40* (2013.01); *C07C 255/41* (2013.01); *C07C 255/56* (2013.01); *C07C 255/62* (2013.01); *C07C 255/66* (2013.01); *C07D 231/12* (2013.01); *C07D 231/16* (2013.01); *C07D 231/20* (2013.01); *C07D 261/08* (2013.01); *C07D 319/06* (2013.01); *C07C 2101/10* (2013.01); *C07C 2101/16* (2013.01); *C07C 2102/44* (2013.01)

(58) Field of Classification Search
CPC ....... A01N 37/34; A01N 37/42; A01N 43/16; A01N 43/32; A01N 43/56; A01N 43/80; C07C 2101/10; C07C 2101/16; C07C 2102/44; C07C 255/40; C07C 255/41; C07C 255/56; C07C 255/62; C07C 255/66; C07D 231/12; C07D 231/16; C07D 231/20; C07D 261/08; C07D 319/06
See application file for complete search history.

(56) References Cited

U.S. PATENT DOCUMENTS 4,224,052 A    9/1980   Szucs

FOREIGN PATENT DOCUMENTS

| EP | 0005341 | | 11/1979 |
|---|---|---|---|
| EP | 0005341 | A2 | 11/1979 |
| EP | 0005341 | A3 | 11/1979 |

(Continued)

OTHER PUBLICATIONS

Liepa, A. J. et al. "An Improved Phenanthrene Synthesis : a Simple Route to (+/−)-Tylophorine" J.C.S. Chem. Comm. 1977, 22, 826-827.*

(Continued)

*Primary Examiner* — Joseph Kosack
*Assistant Examiner* — Amanda L Aguirre
(74) *Attorney, Agent, or Firm* — Miles and Stockbridge

(57) ABSTRACT

The invention describes compounds of formula (I),

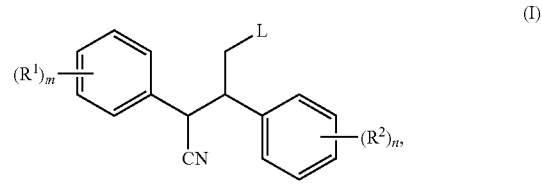

processes for preparing the compounds and methods of using the compounds as herbicides for the control of harmful plants or as plant growth regulators.

18 Claims, No Drawings

(56) References Cited

FOREIGN PATENT DOCUMENTS

| | | |
|---|---|---|
| EP | 0266725 | 5/1988 |
| EP | 0266725 A1 | 5/1988 |
| EP | 0270830 | 6/1988 |
| EP | 0270830 A1 | 6/1988 |
| JP | 4-297454 | 10/1992 |
| JP | 4-297455 | 10/1992 |
| JP | 04297454 | 10/1992 |
| JP | 04297455 | 10/1992 |
| JP | 5-58979 | 3/1993 |
| JP | 05058979 | 3/1993 |
| WO | 2011003775 | 1/2011 |
| WO | 2011003776 | 1/2011 |
| WO | 2011003776 A2 | 1/2011 |
| WO | 2011042378 | 4/2011 |
| WO | 2011073143 | 6/2011 |

OTHER PUBLICATIONS

International Search Report corresponding to PCT/EP2012/063613 mailed on Feb. 7, 2013.
International Search Report for PCT/EP2012/063613 Mailed Feb. 2, 2013.

* cited by examiner

2,3-DIPHENYL-VALERONITRILE DERIVATIVES, METHOD FOR THE PRODUCTION THEREOF AND USE THEREOF AS HERBICIDES AND PLANT GROWTH REGULATORS

CROSS REFERENCE TO RELATED APPLICATIONS

This application is a §371 National Stage Application of PCT/EP2012/063613, filed Jul. 11, 2012, which claims priority to European Application No. 10 2011 079 241.4, filed Jul. 15, 2011, and claims benefit of U.S. Provisional Application No. 61/508,306, filed Jul. 15, 2011.

BACKGROUND OF THE INVENTION

Field of the Invention

Description of Related Art

The invention relates to the technical field of the herbicides and plant growth regulators, for example the herbicides for controlling broad-leaved weeds and weed grasses, optionally in crops of useful plants, or the plant growth regulators which can be used for influencing the growth of crop plants.

In their application, crop protection agents known to date for the selective control of harmful plants in crops of useful plants or active compounds for controlling unwanted vegetation sometimes have disadvantages, be it (a) that they have no or else insufficient herbicidal activity against particular harmful plants, (b) that the spectrum of harmful plants which can be controlled with an active compound is not wide enough, (c) that their selectivity in crops of useful plants is too low and/or (d) that they have a toxicologically unfavourable profile. Furthermore, some active compounds which can be used as plant growth regulators for a number of useful plants cause unwanted reduced harvest yields in other useful plants or are not compatible with the crop plant, or only within a narrow application rate range. Some of the known active compounds cannot be produced economically on an industrial scale owing to precursors and reagents which are difficult to obtain, or they have only insufficient chemical stabilities. In the case of other active compounds, the activity is too highly dependent on environmental conditions, such as weather and soil conditions.

Herbicidal cyanobutyrates are disclosed in the published patent applications EP-A-5341, EP-A-266725 (U.S. Pat. No. 4,224,052), EP-A-270830, JP-04/297454, JP-04/297455, JP-05/058979, WO 2011/003775, WO 2011/003776, WO 2011/042378 and WO 2011/073143.

EP-A-5341 describes herbicidal esters and amides of 4-cyano-3,4-diphenylbutanoic acids which are optionally substituted at the phenyl radicals. According to EP-A-5341, the threo isomers are generally suitable for the non-selective control of harmful plants, whereas the erythro/threo isomer mixtures are suitable for the selective control of harmful plants in some crops of useful plants. Moreover, EP-A-5341 mentions that the 2 enantiomers belonging to the threo form have different activities, which was investigated in an exemplary manner on the different activities of the enantiomers of the enantiomer pair of 4-cyano-3,4-diphenylbutanoic acid unsubstituted in the phenyl radicals.

EP-A-266725 discloses some erythro/threo isomer mixtures which can be used selectively for controlling weeds in rice crops.

EP-A-270830 describes that threo isomers and erythro/threo isomer mixtures can be used as plant regulators, preventing the development of an infructescence in various harmful grasses.

WO 2011/003775 discloses specific esters of 4-cyano-3,4-diphenylbutanoic acids which can be used as effective herbicides, preferably also in crops of useful plants. WO 2011/003776, WO 2011/042378 and WO 2011/073143 disclose 4-cyano-3,4-diphenylbutanoic acids and esters which have specific substitutions at the phenyl radicals and can be used as effective herbicides, preferably also in crops of useful plants.

The herbicidal activity of the known compounds of the class of substances mentioned, in particular at low application rates, and/or their compatibility with crop plants, remain deserving of improvement.

For the reasons mentioned, there is still a need for alternative, highly active herbicides for the selective application in plant crops or use on non-crop land. It is also desirable to provide alternative chemical active compounds which may be used in an advantageous manner as herbicides or plant growth regulators.

It is therefore an object of the present invention to provide compounds having herbicidal activity which are highly effective against economically important harmful plants even at relatively low application rates and can be used selectively in crop plants, preferably with good activity for harmful plants.

SUMMARY

Surprisingly, it has now been found that compounds with further structural modification at the acid or ester group compared to the active compounds of the cyanobutyrates mentioned and belonging to the group of the 2,3-diphenylvaleronitrile derivatives have special herbicidal actions and, in some crops, can preferably be used for the selective control of harmful plants.

The present invention provides compounds of the formula (I) or salts thereof

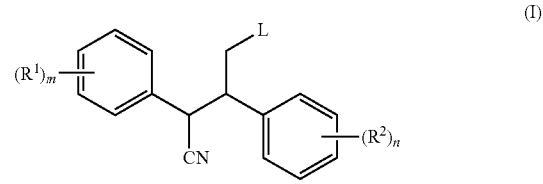

in which
L represents a radical of the formula

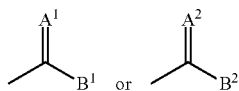

$A^1$ represents oxygen, sulphur or $=N-R^4$,
$B^1$ represents a radical of the formulae (B1) to (B14),

-continued
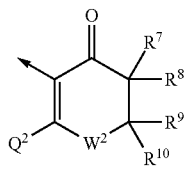
(B2)
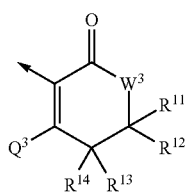
(B3)
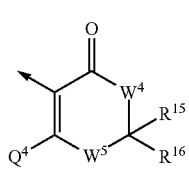
(B4)
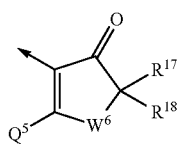
(B5)
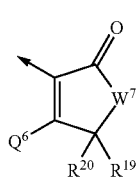
(B6)
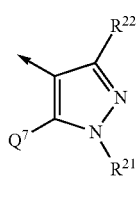
(B7)
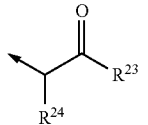
(B8)
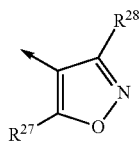
(B10)
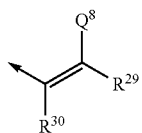
(B11)
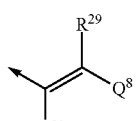
(B12)
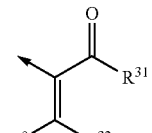
(B13)
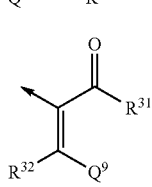
(B14)
$A^2$ represents a radical of the formulae (A1) to (A12),
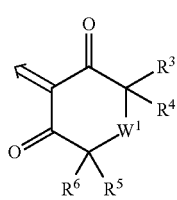
(A1)
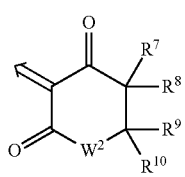
(A2)
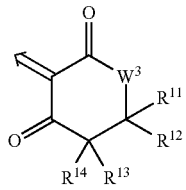
(A3)
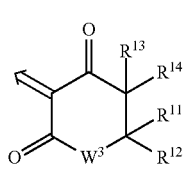
(A4)
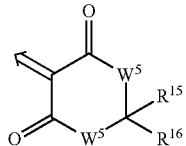
(A5)

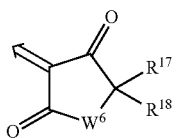 (A6)

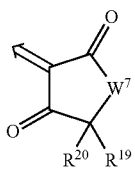 (A7)

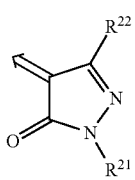 (A8)

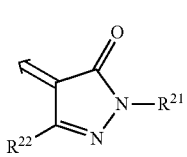 (A9)

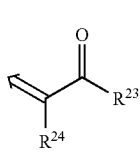 (A10)

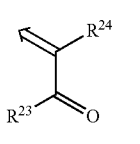 (A11)

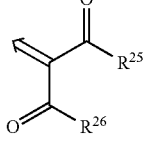 (A12)

$B^2$ represents hydroxy, thio, halogen or a group of the formula $OR^{33}$, OM, $SR^{34}$, SM or $-NR^B-R^C$, $W^1$ and $W^6$ independently of one another each represent the divalent group oxygen, sulphur or a group of the formula NH, N—[$(C_1-C_4)$-alkyl], C=O (carbonyl), S=O (sulphinyl), $SO_2$ (sulphonyl) or $CR^{35}R^{36}$, $W^2$, $W^3$, $W^4$, $W^5$ and $W^7$ independently of one another each represent the divalent group oxygen, sulphur or a group of the formula NH, N—[$(C_1-C_4)$-alkyl], C=O (carbonyl), S=O (sulphinyl) or $SO_2$ (sulphonyl), $Q^1$, $Q^2$, $Q^3$, $Q^4$, $Q^5$, $Q^6$, $Q^7$, $Q^8$ and $Q^9$ independently of one another each represent hydroxy, thio, halogen or a group of the formula $OR^{37}$, $SR^{38}$, SM or OM, M represents an equivalent of a cation,
preferably a metal ion equivalent, an ammonium ion which is optionally substituted by 1 to 4 identical or different radicals from the group consisting of $(C_1-C_6)$-alkyl, $(C_2-C_6)$-alkenyl, $(C_2-C_6)$-alkynyl, $(C_3-C_6)$-cycloalkyl, $(C_5-C_6)$-cycloalkenyl, $(C_5-C_6)$-cycloalkynyl, phenyl, $(C_3-C_6)$-cycloalkyl-$(C_1-C_4)$-alkyl, $(C_5-C_6)$-cycloalkenyl-$(C_1-C_4)$-alkyl, phenyl-$(C_1-C_4)$-alkyl, or a tertiary sulphonium ion which is preferably substituted by 3 identical or different radicals from the group consisting of $(C_1-C_6)$-alkyl, $(C_2-C_6)$-alkenyl, $(C_2-C_6)$-alkynyl, $(C_3-C_6)$-cycloalkyl, $(C_5-C_6)$-cycloalkenyl, $(C_5-C_6)$-cycloalkynyl, phenyl, $(C_3-C_6)$-cycloalkyl-$(C_1-C_4)$-alkyl, $(C_5-C_6)$-cycloalkenyl-$(C_1-C_4)$-alkyl, phenyl-$(C_1-C_4)$-alkyl, in particular $(C_1-C_4)$-alkyl, $R^A$, $R^B$ and $R^C$ independently of one another each represent hydrogen, hydroxy, $(C_1-C_4)$-alkoxy, $(C_1-C_4)$-alkyl, $(C_1-C_4)$-haloalkyl, phenyl or benzyl, where each of the two last-mentioned radicals is optionally mono- or polysubstituted by identical or different substituents and preferably independently of one another unsubstituted or substituted by one or more radicals from the group consisting of halogen, $(C_1-C_4)$-alkyl, $(C_1-C_4)$-haloalkyl, $(C_1-C_4)$-alkoxy and $(C_1-C_4)$-haloalkoxy, or —NR*R**, where R*, R** independently of one another each represent H, $(C_1-C_8)$-alkyl, $(C_2-C_8)$-alkenyl, $(C_2-C_8)$-alkynyl, $(C_1-C_4)$-alkoxy-$(C_1-C_4)$-alkyl, $(C_1-C_6)$-alkanoyl, [$(C_1-C_4)$-haloalkyl]carbonyl, [$(C_1-C_4)$-alkoxy]carbonyl, [$(C_1-C_4)$-haloalkoxy]carbonyl, $(C_3-C_6)$-cycloalkyl, $(C_3-C_6)$-cycloalkyl-$(C_1-C_4)$-alkyl, phenyl, phenyl-$(C_1-C_4)$-alkyl, where each of the 4 last-mentioned radicals is unsubstituted in the cycle or substituted by one or more radicals from the group consisting of halogen, $(C_1-C_4)$-alkyl, $(C_1-C_4)$-haloalkyl, $(C_1-C_4)$-alkoxy and $(C_1-C_4)$-haloalkoxy or, in the case of cycloalkyl, also oxo, or R* and R** together with the nitrogen atom represent a 3- to 8-membered heterocycle which, in addition to the nitrogen atom, may contain one or two further ring heteroatoms from the group consisting of N, O and S and which may be unsubstituted or substituted by one or more radicals from the group consisting of $(C_1-C_4)$-alkyl, $(C_1-C_4)$-haloalkyl and oxo, $(R^1)_m$ represents m substituents $R^1$,
where $R^1$, if m=1, or each of the substituents $R^1$, if m is greater than 1, independently of the others represents halogen, cyano, nitro, hydroxy, $(C_1-C_8)$-alkyl, $(C_2-C_6)$-alkenyl, $(C_2-C_6)$-alkynyl, $(C_1-C_8)$-alkoxy, $(C_1-C_8)$-alkylthio, $(C_1-C_8)$-alkylsulphinyl, $(C_1-C_8)$-alkylsulphonyl, $(C_1-C_8)$-haloalkyl, $(C_1-C_6)$-haloalkoxy, $(C_1-C_6)$-haloalkylthio, $(C_1-C_6)$-haloalkylsulphinyl, $(C_1-C_6)$-haloalkylsulphonyl, $(C_2-C_6)$-haloalkenyl, $(C_2-C_6)$-haloalkynyl, $(C_1-C_6)$-alkoxy-$(C_1-C_4)$-alkyl, $(C_1-C_8)$-haloalkoxy-$(C_1-C_4)$-alkyl, $(C_3-C_6)$-cycloalkyl which is optionally substituted by one or more radicals from the group consisting of halogen and $(C_1-C_4)$-alkyl, $(C_3-C_6)$-cycloalkoxy which is optionally substituted by one or more radicals from the group consisting of halogen and $(C_1-C_4)$-alkyl, or a radical of the formula $C(O)OR^{39}$, $C(O)NR^{40}R^{41}$, C(O)—$Het^1$, $NR^{42}R^{43}$ or $Het^2$ or where in each case two groups $R^1$ located ortho at the ring together are a group of the formula $-Z^1-A^*-Z^2$ in which A* represents an alkylene group having 1 to 4 carbon atoms which is optionally substituted by one or more radicals from the group consisting of halogen, $(C_1-C_4)$-alkyl, $(C_1-C_4)$-haloalkyl, $(C_1-C_4)$-alkoxy and $(C_1-C_4)$-haloalkoxy, $Z^1$ represents a direct bond, O or S and $Z^2$ represents a direct bond, O or S, where the group $-Z^1-A^*-Z^2$ together with the carbon atoms, attached to the group, of the phenyl ring form a fused-on 5- or 6-membered ring, and $(R^2)_n$ represents n substituents $R^2$,
  where $R^2$, if n=1, or each of the substituents $R^2$, if n is greater than 1, independently of the others represents halogen, cyano, nitro, hydroxy, $(C_1-C_8)$-alkyl, $(C_2-C_6)$-alkenyl, $(C_2-C_6)$-alkynyl, $(C_1-C_8)$-alkoxy, $(C_1-C_8)$-alkylthio, $(C_1-C_8)$-alkylsulphinyl, $(C_1-C_8)$-alkylsulphonyl, $(C_1-C_8)$-haloalkyl, $(C_1-C_6)$-haloalkoxy, $(C_1-C_6)$-haloalkylthio, $(C_1-C_6)$-haloalkylsulphinyl, $(C_1-C_6)$-haloalkylsulphonyl, $(C_2-C_6)$-haloalkenyl, $(C_2-C_6)$-haloalkynyl, $(C_1-C_6)$-alkoxy-$(C_1-C_4)$-alkyl, $(C_1-C_8)$-haloalkoxy-$(C_1-C_4)$-alkyl, $(C_3-C_6)$-cycloalkyl which is optionally substituted by one or more radicals from the group consisting of halogen and $(C_1-C_4)$-alkyl, $(C_3-C_6)$-cycloalkoxy which is optionally substituted by one or more radicals from the group consisting of halogen and $(C_1-C_4)$-alkyl, or a radical of the formula $C(O)OR^{44}$, $C(O)NR^{45}R^{46}$, $C(O)$—$Het^3$, $NR^{47}R^{48}$ or $Het^4$
  or
  where in each case two groups $R^2$ located ortho at the ring together are a group of the formula —$Z^3$-$A^{**}$-$Z^4$ in which
    $A^{**}$ represents an alkylene group having 1 to 4 carbon atoms which is optionally substituted by one or more radicals from the group consisting of halogen, $(C_1-C_4)$-alkyl, $(C_1-C_4)$-haloalkyl, $(C_1-C_4)$-alkoxy and $(C_1-C_4)$-haloalkoxy,
    $Z^3$ represents a direct bond, O or S and
    $Z^4$ represents a direct bond, O or S,
    where the group —$Z^3$-$A^{**}$-$Z^4$ together with the carbon atoms, attached to the group, of the phenyl ring form a fused-on 5- or 6-membered ring,
$R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ independently of one another each represent hydrogen, halogen, cyano, nitro, hydroxy, $(C_1-C_4)$-alkyl, $(C_1-C_4)$-haloalkyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_3-C_6)$-cycloalkyl, $(C_3-C_6)$-halocycloalkyl, $(C_3-C_6)$-cycloalkoxy, $(C_2-C_6)$-alkenyl, $(C_2-C_6)$-haloalkenyl, $(C_2-C_6)$-alkynyl, $(C_2-C_6)$-haloalkynyl, $(C_1-C_4)$-alkylthio, $(C_1-C_4)$-alkylsulphonyl, $(C_1-C_4)$-alkylsulphinyl, phenyl which is optionally substituted, preferably unsubstituted or substituted by one or more radicals from the group consisting of halogen, $(C_1-C_4)$-alkyl, $(C_1-C_4)$-haloalkyl, $(C_1-C_4)$-alkoxy and $(C_1-C_4)$-haloalkoxy, or a group $C(O)OR^{49}$, $C(O)NR^{50}R^{51}$, $C(O)Het^5$, $NR^{52}R^{53}$ or $Het^6$ or
  $R^3$ and $R^5$ in the group of the formula (B1) or (A1) together represent a divalent bridge of a straight-chain alkylene or alkenylene group having 2 or 3 carbon atoms where a $CH_2$ group in the chain may also be replaced by an oxygen atom and where a $CH_2$ group or CH group in the chain is optionally substituted by one or more radicals from the group consisting of $(C_1-C_4)$-alkyl, $(C_1-C_4)$-haloalkyl, $(C_1-C_4)$-alkoxy and $(C_1-C_4)$-haloalkoxy, preferably a divalent aliphatic bridge of the formula —$CH_2CH_2$—, —$CH_2CH_2CH_2$—, —$CH(CH_3)CH_2$—, —$C(CH_3)_2CH_2$—, —$CH_2CH(CH_3)$—, —$CH_2C(CH_3)_2$—, —$C(CH_3)CH(CH_3)$—, —$CH_2CH_2CH_2$—, —CH=CH—, —CH=CHCH$_2$—, —$CH_2$CH=CH—, —$OCH_2$—, —$CH_2$O—, —$OCH_2CH_2$—, —$CH_2OCH_2$—, —$CH_2CH_2$O— or —$OCH_2$O—, in particular of the formula —$CH_2CH_2$— or —CH=CH—,
$R^{21}$ represents hydrogen, $(C_1-C_4)$-alkyl, $(C_1-C_4)$-haloalkyl, $(C_3-C_6)$-cycloalkyl, $(C_3-C_6)$-halocycloalkyl or a group $C(O)OR^{54}$, $C(O)NR^{55}R^{56}$, $C(O)Het^7$, $NR^{57}R^{58}$ or $Het^8$, $R^{22}$ represents hydrogen, $(C_1-C_4)$-alkyl, $(C_1-C_4)$-haloalkyl, $(C_3-C_6)$-cycloalkyl, $(C_3-C_6)$-halocycloalkyl, $(C_1-C_4)$-alkylthio, $(C_1-C_4)$-alkylsulphonyl, $(C_1-C_4)$-alkylsulphinyl or a group of the formula $C(O)OR^{59}$, $C(O)NR^{60}R^{61}$, $C(O)Het^9$, $NR^{62}R^{63}$ or $Het^{10}$,
$R^{23}$ and $R^{29}$ independently of one another each represent hydrogen, $(C_1-C_4)$-alkyl, $(C_1-C_4)$-haloalkyl, $(C_3-C_6)$-cycloalkyl, $(C_3-C_6)$-halocycloalkyl, $(C_1-C_4)$-alkoxy or $(C_1-C_4)$-haloalkoxy,
$R^{24}$ and $R^{30}$ independently of one another each represent hydrogen, halogen, cyano, $(C_1-C_4)$-alkyl, $(C_1-C_4)$-haloalkyl, $(C_3-C_6)$-cycloalkyl, $(C_3-C_6)$-halocycloalkyl, $(C_1-C_4)$-alkoxy or $(C_1-C_4)$-haloalkoxy,
$R^{25}$, $R^{26}$, $R^{31}$ and $R^{32}$ independently of one another each represent hydrogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_3-C_6)$-cycloalkyl, $(C_3-C_6)$-halocycloalkyl, $(C_3-C_6)$-cycloalkoxy, $(C_2-C_6)$-alkenyl, $(C_2-C_6)$-haloalkenyl, $(C_2-C_6)$-alkynyl, $(C_2-C_6)$-haloalkynyl, $(C_1-C_4)$-alkylthio, $(C_1-C_4)$-alkylsulphonyl, $(C_1-C_4)$-alkylsulphinyl, $NR^{64}R^{65}$ or $Het^{11}$,
$R^{27}$ represents hydrogen, $(C_1-C_6)$-alkyl, $(C_1-C_6)$-haloalkyl, $(C_3-C_6)$-cycloalkyl or $(C_3-C_6)$-halocycloalkyl,
$R^{28}$ represents hydrogen, $(C_1-C_6)$-alkyl, $(C_1-C_4)$-haloalkyl or a radical of the formula $C(O)OR^{66}$,
$R^{33}$, $R^{34}$, $R^{37}$ and $R^{38}$ independently of one another each represent $(C_1-C_8)$-alkyl, $(C_3-C_6)$-cycloalkyl, phenyl, where each of the three last-mentioned radicals in each case independently of the others is unsubstituted or substituted by one or more radicals from the group consisting of halogen, cyano, nitro, hydroxy, $(C_1-C_4)$-alkoxy, $(C_1-C_4)$-alkylthio and, in the case of a cycloalkyl or phenyl radical as parent radical, also $(C_1-C_4)$-alkyl and $(C_1-C_4)$-haloalkyl, or a group of the formula —$C(O)R^{67}$, —$C(O)OR^{68}$, —$C(O)NR^{69}R^{70}$, —$C(O)Het^{12}$ or —$SO_2R^{71}$,
$R^{35}$ and $R^{36}$ independently of one another are each as defined for $R^3$ or preferably hydrogen, $(C_1-C_4)$-alkyl or $(C_1-C_4)$-haloalkyl,
$R^{39}$, $R^{44}$, $R^{49}$, $R^{54}$, $R^{59}$ and $R^{66}$ independently of one another each represent hydrogen, $(C_1-C_4)$-alkyl, $(C_1-C_4)$-haloalkyl, $(C_3-C_6)$-cycloalkyl, $(C_3-C_6)$-halocycloalkyl, $(C_2-C_4)$-alkenyl, $(C_2-C_4)$-haloalkenyl, $(C_2-C_4)$-alkynyl or the group M mentioned, preferably $(C_1-C_4)$-alkyl,
$R^{40}$, $R^{41}$, $R^{42}$, $R^{43}$, $R^{45}$, $R^{46}$, $R^{47}$, $R^{48}$, $R^{50}$, $R^{51}$, $R^{52}$, $R^{53}$, $R^{55}$, $R^{56}$, $R^{57}$, $R^{58}$, $R^{60}$, $R^{61}$, $R^{62}$, $R^{63}$, $R^{64}$, $R^{65}$, $R^{69}$ and $R^{70}$ independently of one another each represent hydrogen, $(C_1-C_6)$-alkyl, $(C_2-C_6)$-alkenyl or $(C_2-C_6)$-alkynyl, where each of the 3 last-mentioned radicals in each case independently of the others is unsubstituted or substituted by one or more radicals from the group consisting of halogen, nitro, cyano and phenyl, which is optionally substituted, preferably unsubstituted or substituted by one or more radicals from the group consisting of halogen, nitro, cyano, $(C_1-C_4)$-alkyl and $(C_1-C_4)$-haloalkyl, or $(C_3-C_6)$-cycloalkyl or phenyl, where each of the 2 last-mentioned radicals in each case independently of the other is unsubstituted or substituted by one or more radicals from the group consisting of halogen, nitro, cyano, $(C_1-C_4)$-alkyl, $(C_1-C_4)$-haloalkyl, phenyl and benzyl, where each of the 2 last-mentioned radicals is optionally substituted, preferably unsubstituted or substituted by one or more radicals from the group consisting of halogen, nitro, cyano, $(C_1-C_4)$-alkyl and $(C_1-C_4)$-haloalkyl,
$R^{67}$ represents hydrogen, $(C_1-C_8)$-alkyl or $(C_1-C_8)$-haloalkyl, where each of the 2 last-mentioned radicals independently of the other is optionally interrupted in the alkyl moiety by oxygen or sulphur, or phenyl or benzyl, where each of the 2 last-mentioned radicals independently of the other is unsubstituted or substituted by one or more radicals from the group consisting of halogen, cyano, ($C_1$-$C_4$)-alkyl, ($C_2$-$C_4$)-alkenyl, ($C_2$-$C_4$)-alkynyl, ($C_3$-$C_6$)-cycloalkyl, ($C_1$-$C_4$)-haloalkyl and ($C_3$-$C_6$)-halocycloalkyl, $R^{68}$ represents ($C_1$-$C_8$)-alkyl, ($C_1$-$C_8$)-haloalkyl, ($C_3$-$C_6$)-cycloalkyl, ($C_3$-$C_6$)-halocycloalkyl, ($C_2$-$C_8$)-alkenyl, ($C_2$-$C_8$)-haloalkenyl or ($C_2$-$C_4$)-alkynyl, $R^{71}$ represents ($C_1$-$C_6$)-alkyl, ($C_1$-$C_6$)-haloalkyl or phenyl or benzyl, where each of the 2 last-mentioned radicals independently of the other is unsubstituted or substituted by one or more radicals from the group consisting of halogen, cyano, ($C_1$-$C_4$)-alkyl, ($C_2$-$C_4$)-alkenyl, ($C_2$-$C_4$)-alkynyl, ($C_3$-$C_6$)-cycloalkyl, ($C_1$-$C_4$)-haloalkyl and ($C_3$-$C_6$)-halocycloalkyl, $Het^1$, $Het^2$, $Het^3$, $Het^4$, $Het^5$, $Het^6$, $Het^7$, $Het^8$, $Het^9$, $Het^{10}$, $Het^{11}$ and $Het^{12}$ independently of one another are each a saturated or partially unsaturated radical of a heterocycle having 3 to 9 ring atoms and at least one nitrogen atom as ring heteroatom at position 1 of the ring and optionally 1, 2 or 3 further ring heteroatoms from the group consisting of N, O and S, where the radical of the heterocycle is attached at the nitrogen atom in position 1 of the ring to the remainder of the molecule of the compound of the formula (I) and where the heterocycle is unsubstituted or substituted by one or more radicals from the group consisting of halogen, ($C_1$-$C_4$)-alkyl, ($C_1$-$C_4$)-haloalkyl, ($C_1$-$C_4$)-alkoxy, ($C_1$-$C_4$)-haloalkoxy, ($C_1$-$C_4$)-alkylthio and oxo, preferably the radical of a saturated heterocycle of the type mentioned, in particular a morpholino, piperidino or pyrrolidino group and m, n independently of one another each represent 0, 1, 2, 3, 4 or 5, preferably 0, 1, 2 or 3.

DETAILED DESCRIPTION OF A PREFERRED EMBODIMENT

In the formula (I), the formula "(R1)m" means m radicals R1 which are attached as substituents at the phenyl ring in question, where the radicals in the case of m greater than 1 may be identical or different and have the meaning mentioned in each case in more detail. In the case m=0, the phenyl ring in question is not substituted by substituents $R^1$, i.e. all ring carbon atoms of the phenyl ring in positions 2 to 6 are attached to a hydrogen atom. This applies correspondingly to the substitution of the other phenyl ring according to formula $(R^2)_n$.

In the formulae (B1) to (B14) for radicals of group B1, the free bond through which group B1 in the group of the formula —C(=$A^1$)-B1 is attached to the carbon atom shown in the formula is marked by an arrow (←——) to avoid mistaking it for the short notation for the "methyl" radical.

In the formulae (A1) to (A12) for radicals of group $A^2$, the free double bond through which group $A^2$ in the group of the formula —C(=$A^2$)-$B^2$ is attached to the carbon atom shown in the formula is marked by an arrow (⇐) to avoid mistaking it for the short notation in the formulae for the "methylene" radical ("$H_2C=$").

The compounds of the formula (I) according to the invention include all stereoisomers which can occur on the basis of the centres of asymmetry or double bonds in the molecule whose configuration is not designated specifically in the formula or which are not specified explicitly, and mixtures thereof, including the racemic compounds and the mixtures enriched partly with particular stereoisomers. The invention also includes all tautomers, such as keto and enol tautomers, and their mixtures and salts, if appropriate functional groups are present.

In positions 2 and 3 of the substituted valeronitrile skeleton, the compounds of the formula (I) contain two centres of chirality, and they therefore occur in at least four stereoisomers and mixtures thereof, i.e. 2 enantiomeric erythro isomers and 2 enantiomeric threo isomers. Depending on the substituents $(R^1)_m$ and $(R^2)_n$, one or more further centres of chirality may be present.

Accordingly, the invention also provides erythro/threo mixtures (diastereomer mixtures) of the compounds of the formula (I).

The invention also provides the racemic erythro isomers or the racemic threo isomers of the compounds of the formula (I).

The invention also provides the optically active (2R,3S) and (2S,3R) erythro isomers and mixtures thereof having an excess of one enantiomer (see formula (I) below where the positions at the valeronitrile skeleton are numbered 1 to 5).

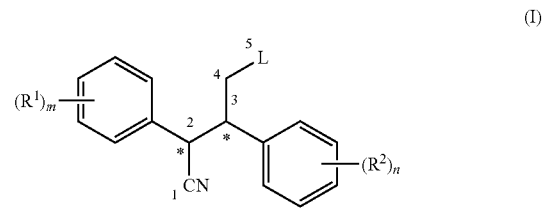

(I)

The invention also provides the optically active (2R,3R) and (2S,3S) threo isomers and mixtures thereof having an excess of one enantiomer.

Owing to the two centres of chirality in positions 2 and 3, compounds of the same chemical constitution exist as 4 stereoisomeric configurations, namely two erythro enantiomers having the configurations (2R,3S) [=erythro-1] and (2S,3R) [=erythro-2], respectively, and two threo enantiomers having the configurations (2S,3S) [=threo-1] and (2R,3R) [=threo-2], respectively; see the scheme below:

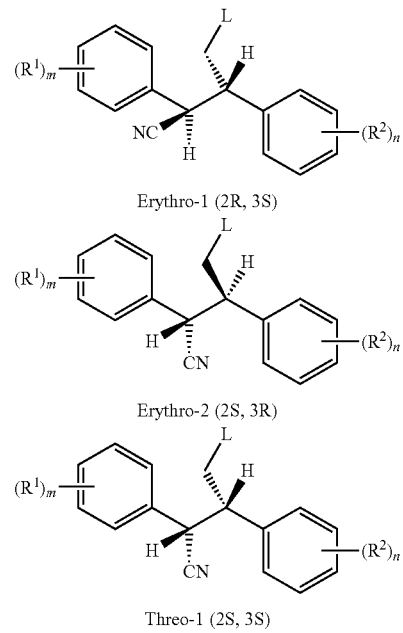

Erythro-1 (2R, 3S)

Erythro-2 (2S, 3R)

Threo-1 (2S, 3S)

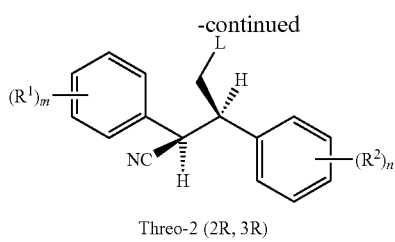

Threo-2 (2R, 3R)

The compounds (I) according to the invention represent diastereomer mixtures of the 4 stereoisomers, but also embrace the separated diastereomeric erythro or threo forms, in each case as a racemic mixture of the erythro enantiomers or threo enantiomers or as pure or stereochemically enriched enantiomers erythro-1, erythro-2, threo-1 or threo-2.

Preference is given to the diastereomer mixtures of the formula (I) (erythro/threo mixtures).

Preference is furthermore given to the racemic threo mixtures of the formula (I) of the aforementioned enantiomers threo-1 and threo-2 in a ratio of 50:50.

More preference is given to the (2R,3R) enantiomers threo-2 of the formula (Ia) or salts thereof

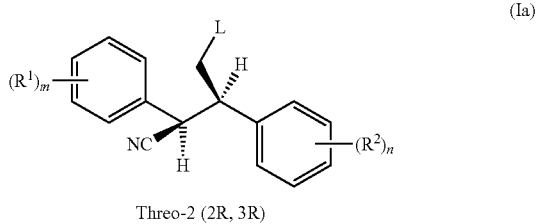

Threo-2 (2R, 3R)

in which $(R^1)_m$ and $(R^2)_n$ are as defined in formula (I),
where the stereochemical configuration at the carbon atom in position 2 of the valeronitrile derivative has a stereochemical purity of 60 to 100% (R), preferably 70 to 100% (R), more preferably 80 to 100% (R), in particular 90 to 100% (R), based on the mixture of threo enantiomers present, and
the stereochemical configuration at the carbon atom in position 3 of the valeronitrile derivative has a stereochemical purity of 60 to 100% (R), preferably 70 to 100% (R), more preferably 80 to 100% (R), in particular 90 to 100% (R), based on the mixture of threo enantiomers present.

In the case of suitable acidic substituents, the compounds of the formula (I) are able to form salts by reaction with bases where the acidic hydrogen is replaced by an agriculturally suitable cation.

By addition of a suitable inorganic or organic acid onto a basic group, such as, for example, amino or alkylamino, the compounds of the formula (I) are able to form salts. Suitable acidic groups present, such as, for example, carboxylic acid groups, are able to form inner salts with groups which for their part can be protonated, such as amino groups.

The compounds of the formula (I) may preferably be present in the form of agriculturally usable salts, where the type of salt is otherwise immaterial. In general, suitable salts are the salts of those cations or the acid additions salts of those acids whose cations and anions, respectively, have no adverse effect on the herbicidal activity of the compounds (I).

Suitable cations are in particular the ions of the alkali metals, preferably lithium, sodium or potassium, of the alkaline earth metals, preferably calcium or magnesium, and of the transition metals, preferably manganese, copper, zinc or iron. The cation used may also be ammonium or substituted ammonium, where one to four hydrogen atoms may be replaced by $(C_1-C_4)$-alkyl, hydroxy-$(C_1-C_4)$-alkyl, $(C_1-C_4)$-alkoxy-$(C_1-C_4)$-alkyl, hydroxy-$(C_1-C_4)$-alkoxy-$(C_1-C_4)$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium. Also suitable are phosphonium ions, sulphonium ions, preferably tri$(C_1-C_4)$methylsulphonium, or sulphoxonium ions, preferably tri$(C_1-C_4)$methylsulphoxonium.

Anions of useful acid addition salts are primarily chloride, bromide, fluoride, hydrogensulphate, sulphate, dihydrogenphosphate, hydrogenphosphate, nitrate, bicarbonate, carbonate, hexafluorosilicate, hexafluorophosphate, benzoate and also the anions of $(C_1-C_4)$-alkanoic acids, preferably formate, acetate, propionate, butyrate or trifluoroacetate.

In formula (I) and in all subsequent formulae, chemical radicals are referred to by names which are collective terms for the enumeration of individual group members or specifically refer to individual chemical radicals. In general, terms are used which are familiar to the person skilled in the art and/or in particular have the meanings illustrated below.

A hydrocarbon radical is an aliphatic, cycloaliphatic or aromatic monocyclic or, in the case of an optionally substituted hydrocarbon radical, also a bicyclic or polycyclic organic radical based on the elements carbon and hydrogen, including, for example, the radicals alkyl, alkenyl, alkynyl, cycloalkyl, cycloalkenyl, aryl, phenyl, naphthyl, indanyl, indenyl, etc.; this applies correspondingly to hydrocarbon radicals in composite meanings, such as hydrocarbonoxy radicals or other hydrocarbon radicals attached via heteroatom groups.

Unless defined in more detail, the hydrocarbon radicals preferably have 1 to 20 carbon atoms, more preferably 1 to 16 carbon atoms, in particular 1 to 12 carbon atoms. The hydrocarbon radicals, also in the special radicals alkyl, alkoxy, haloalkyl, haloalkoxy, alkylamino and alkylthio, and also the corresponding unsaturated and/or substituted radicals may in each case be straight-chain or branched in the carbon skeleton.

The expression "$(C_1-C_4)$-alkyl" is a brief notation for alkyl having from 1 to 4 carbon atoms, i.e. encompasses the methyl, ethyl, 1-propyl, 2-propyl, 1-butyl, 2-butyl, 2-methylpropyl or tert-butyl radicals. General alkyl radicals with a larger specified range of carbon atoms, e.g. "$(C_1-C_6)$-alkyl", correspondingly also encompass straight-chain or branched alkyl radicals with a greater number of carbon atoms, i.e. according to the example also the alkyl radicals having 5 and 6 carbon atoms.

Unless stated specifically, preference is given to the lower carbon skeletons, for example having from 1 to 6 carbon atoms, or having from 2 to 6 carbon atoms in the case of unsaturated groups, in the case of the hydrocarbyl radicals such as alkyl, alkenyl and alkynyl radicals, including in composite radicals. Alkyl radicals, including in the combined definitions such as alkoxy, haloalkyl, etc., are, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals; alkenyl is, for example, vinyl, allyl, 1-methyl-2-propenyl, 2-methyl-2-propenyl, 2-butenyl, pentenyl, 2-methylpentenyl or hexenyl group, preferably allyl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl.

Alkenyl also includes in particular straight-chain or branched hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl.

Alkynyl is, for example, propargyl, but-2-yn-1-yl, but-3-yn-1-yl, 1-methylbut-3-yn-1-yl. Alkynyl also includes, in particular, straight-chain or branched hydrocarbon radicals having more than one triple bond or else having one or more triple bonds and one or more double bonds, for example 1,3-butatrienyl or 3-penten-1-yn-1-yl.

A 3- to 9-membered carbocyclic ring is $(C_3$-$C_9)$-cycloalkyl or $(C_5$-$C_9)$-cycloalkenyl. $(C_3$-$C_9)$-Cycloalkyl is a carbocyclic saturated ring system having preferably 3-9 carbon atoms, for example cyclopropyl, cyclobutyl, cyclopentyl, cyclohexyl, cycloheptyl, cyclooctyl or cyclononyl. In the case of substituted cycloalkyl, cyclic systems with substituents are included, where the substituents may also be bonded by a double bond on the cycloalkyl radical, for example an alkylidene group such as methylidene.

$(C_5$-$C_9)$-Cycloalkenyl is a carbocyclic, nonaromatic, partially unsaturated ring system having 5-9 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. In the case of substituted cycloalkenyl, the explanations for substituted cycloalkyl apply correspondingly.

Alkylidene, for example also in the form of $(C_1$-$C_{10})$-alkylidene, is the radical of a straight-chain or branched alkane which is bonded via a double bond, the position of the binding site not being fixed. In the case of a branched alkane, the only positions possible are, of course, those in which two hydrogen atoms can be replaced by the double bond; radicals are, for example, $=CH_2$, $=CH-CH_3$, $=C(CH_3)-CH_3$, $=C(CH_3)-C_2H_5$ or $=C(C_2H_5)-C_2H_5$.

Halogen is, for example, fluorine, chlorine, bromine or iodine. Haloalkyl, -alkenyl and -alkynyl are alkyl, alkenyl and alkynyl, respectively, which are partially or fully substituted by identical or different halogen atoms, preferably from the group consisting of fluorine, chlorine, bromine and iodine, in particular from the group consisting of fluorine, chlorine and bromine, very particularly from the group consisting of fluorine and chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals such as, for example, halocycloalkyl.

Aryl is a mono-, bi- or polycyclic aromatic system, for example phenyl, naphthyl, tetrahydronaphthyl, indenyl, indanyl, pentalenyl, fluorenyl and the like, preferably phenyl.

Optionally substituted aryl also includes polycyclic systems, such as tetrahydronaphthyl, indenyl, indanyl, fluorenyl, biphenylyl, where the point of attachment is at the aromatic system.

A heterocyclic radical (heterocyclyl) comprises at least one heterocyclic ring (=carbocyclic ring in which at least one carbon atom is replaced by a heteroatom, preferably by a heteroatom from the group consisting of N, O, S, P, B, Si, Se), which is saturated, unsaturated or heteroaromatic and may be unsubstituted or substituted, where the point of attachment is located at a ring atom.

Unless defined otherwise it preferably contains one or more, in particular 1, 2 or 3, heteroatoms in the heterocyclic ring, preferably from the group consisting of N, O, and S; it is preferably an aliphatic heterocyclyl radical having 3 to 7 ring atoms or a heteroaromatic radical having 5 or 6 ring atoms. The heterocyclic radical may, for example, be a heteroaromatic radical or ring (heteroaryl), such as, for example, a monocyclic, bicyclic or polycyclic aromatic system in which at least 1 ring contains one or more heteroatoms.

If the heterocyclyl radical or the heterocyclic ring is optionally substituted, it can be fused to other carbocyclic or heterocyclic rings. Preference is given to benzo-fused heterocyclic or heteroaromatic rings.

Optionally substituted heterocyclyl also includes polycyclic systems, such as, for example, 8-aza-bicyclo[3.2.1]octanyl or 1-aza-bicyclo[2.2.1]heptyl.

Optionally substituted heterocyclyl also includes spirocyclic systems, such as, for example, 1-oxa-5-aza-spiro[2.3]hexyl.

It is preferably a radical of a heteroaromatic ring having a heteroatom from the group consisting of N, O and S, for example the radical of a five- or six-membered ring, such as pyridyl, pyrrolyl, thienyl or furyl;
it is furthermore preferably a radical of a corresponding heteroaromatic ring having 2, 3 or 4 heteroatoms, for example pyrimidinyl, pyridazinyl, pyrazinyl, triazinyl, tetrazinyl, thiazolyl, thiadiazolyl, oxazolyl, isoxazolyl, pyrazolyl, imidazolyl or triazolyl or tetrazolyl.

Here, preference is given to a radical of a heteroaromatic five- or six-membered ring having 1 to 4 heteroatoms, such as, for example, 1,2,3-triazolyl, 1,2,4-triazolyl, tetrazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, tetrazolyl, 1,2,3-triazinyl, 1,2,4-triazinyl, 1,3,5-triazinyl, 1,2,3,4-tetrazinyl, 1,2,3,5-tetrazinyl, 1,2,4,5-tetrazinyl, thiazolyl, isothiazolyl, oxazolyl, isoxazolyl, pyrazolyl, imidazolyl.

More preference is given here to heteroaromatic radicals of five-membered heterocycles having 3 nitrogen atoms, such as 1,2,3-triazol-1-yl, 1,2,3-triazol-4-yl, 1,2,3-triazol-5-yl, 1,2,5-triazol-1-yl, 1,2,5-triazol-3-yl, 1,3,4-triazol-1-yl, 1,3,4-triazol-2-yl, 1,2,4-triazol-3-yl, 1,2,4-triazol-5-yl;
more preference is also given here to heteroaromatic radicals of six-membered heterocycles having 3 nitrogen atoms, such as 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl;
more preference is also given here to heteroaromatic radicals of five-membered heterocycles having two nitrogen atoms and one oxygen atom, such as 1,2,4-oxadiazol-3-yl; 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl,
more preference is also given here to heteroaromatic radicals of five-membered heterocycles having two nitrogen atoms and one sulphur atom, such as 1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl;
more preference is also given here to heteroaromatic radicals of five-membered heterocycles having four nitrogen atoms, such as 1,2,3,4-tetrazol-1-yl, 1,2,3,4-tetrazol-5-yl, 1,2,3,5-tetrazol-1-yl, 1,2,3,5-tetrazol-4-yl, 2H-1,2,3,4-tetrazol-5-yl, 1H-1,2,3,4-tetrazol-5-yl,
more preference is also given here to heteroaromatic radicals of six-membered heterocycles such as 1,2,4,5-tetrazin-3-yl;
more preference is also given here to heteroaromatic radicals of five-membered heterocycles having three nitrogen atoms and one oxygen or sulphur atom, such as 1,2,3,4-oxatriazol-5-yl; 1,2,3,5-oxatriazol-4-yl; 1,2,3,4-thiatriazol-5-yl; 1,2,3,5-thiatriazol-4-yl;

more preference is also given here to heteroaromatic radicals of six-membered heterocycles such as, for example, 1,2,4,6-thiatriazin-1-yl; 1,2,4,6-thiatriazin-3-yl; 1,2,4,6-thiatriazin-5-yl.

Furthermore preferably, the heterocyclic radical or ring is a partially or fully hydrogenated heterocyclic radical having one heteroatom from the group of N, O and S, for example oxiranyl, oxetanyl, oxolanyl (=tetrahydrofuryl), oxanyl, pyrrolinyl, pyrrolidyl or piperidyl.

It is also preferably a partially or fully hydrogenated heterocyclic radical having 2 heteroatoms from the group of N, O and S, for example piperazinyl, dioxolanyl, oxazolinyl, isoxazolinyl, oxazolidinyl, isoxazolidinyl and morpholinyl. Suitable substituents for a substituted heterocyclic radical are the substituents specified later on below, and additionally also oxo. The oxo group may also occur on the hetero-ring atoms which are able to exist in different oxidation states, as in the case of N and S, for example.

Preferred examples of heterocyclyl are a heterocyclic radical having from 3 to 6 ring atoms from the group of pyridyl, thienyl, furyl, pyrrolyl, oxiranyl, 2-oxetanyl, 3-oxetanyl, oxolanyl (=tetrahydrofuryl), pyrrolidyl, piperidyl, especially oxiranyl, 2-oxetanyl, 3-oxetanyl or oxolanyl, or is a heterocyclic radical having two or three heteroatoms, for example pyrimidinyl, pyridazinyl, pyrazinyl, triazinyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl or morpholinyl.

Preferred heterocyclic radicals are also benzo-fused heteroaromatic rings, for example benzofuryl, benzisofuryl, benzothiophenyl, benzisothiophenyl, isobenzothiophenyl, indolyl, isoindolyl, indazolyl, benzimidazolyl, benzotriazolyl, benzoxazolyl, 1,2-benzisoxazolyl, 2,1-benzisoxazolyl, benzothiazolyl, 1,2-benzisothiazolyl, 2,1-benzisothiazolyl, 1,2,3-benzoxadiazolyl, 2,1,3-benzoxadiazolyl, 1,2,3-benzothiadiazolyl, 2,1,3-benzothiadiazolyl, quinolyl (quinolinyl), isoquinolyl (isoquinolinyl), quinnolinyl, phthalazinyl, quinazolinyl, quinoxalinyl, naphthyridinyl, benzotriazinyl, purinyl, pteridinyl, indolizinyl, benzo-1,3-dioxylyl, 4H-benzo-1,3-dioxinyl and 4H-benzo-1,4-dioxinyl, and, where possible, N-oxides and salts thereof. When a base structure is substituted "by one or more radicals" from a list of radicals (=group) or a generically defined group of radicals, this in each case includes simultaneous substitution by a plurality of identical and/or structurally different radicals.

Substituted radicals, such as a substituted alkyl, alkenyl, alkynyl, cycloalkyl, aryl, phenyl, benzyl, heterocyclyl and heteroaryl radical, are, for example, a substituted radical derived from the unsubstituted base structure, where the substituents are, for example, one or more, preferably 1, 2 or 3, radicals from the group of halogen, alkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulphinyl, alkylsulphonyl and, in the case of cyclic radicals, also alkyl, haloalkyl, alkylthioalkyl, alkoxyalkyl, optionally substituted mono- and dialkylaminoalkyl and hydroxyalkyl; in the term "substituted radicals", such as substituted alkyl, etc., substituents include, in addition to the saturated hydrocarbon radicals mentioned, corresponding unsaturated aliphatic and aromatic radicals, such as optionally substituted alkenyl, alkynyl, alkenyloxy, alkynyloxy, phenyl and phenoxy. In the case of substituted cyclic radicals having aliphatic moieties in the ring, cyclic systems with those substituents which are bonded on the ring by a double bond are also included, for example substituted by an alkylidene group such as methylidene or ethylidene.

The term "radicals from the group consisting of (followed by the group=list of the substituents)" is, wherever used, meant to be synonymous with "radicals selected from the group consisting of ( . . . )". The term "one or more radicals from the group consisting of (followed by the group=list of the substituents)" is, wherever used, meant to be synonymous with "one or more identical or different radicals selected from the group consisting of ( . . . )".

The substituents given by way of example ("first substituent level") can, if they include hydrocarbon-containing fractions, be further substituted therein if desired ("second substituent level"), by for example one of the substituents as defined for the first substituent level. Corresponding further substituent levels are possible. The term "substituted radical" preferably embraces just one or two substituent levels. "Parent radical" refers to the respective base structure of a radical to which substituents of a substituent level are attached.

Preferred substituents for the substituent levels are, for example, amino, hydroxyl, halogen, nitro, cyano, mercapto, carboxyl, carbonamide, $SF_5$, aminosulphonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulphinyl, alkylsulphonyl, monoalkylaminosulphonyl, dialkylaminosulphonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino and benzylamino. Two substituents together may also form a saturated or unsaturated hydrocarbon bridge or a corresponding bridge in which carbon atoms, CH groups or $CH_2$ groups are replaced by heteroatoms, thus forming a fused-on or fused cycle. Here, with preference benzo-fused systems based on the base structure are formed.

Optionally substituted phenyl is preferably phenyl or phenyl which is unsubstituted or substituted by one or more radicals from the group consisting of halogen, cyano, $(C_1-C_4)$-alkyl, $(C_1-C_4)$-haloalkyl, $(C_1-C_4)$-alkoxy-$(C_1-C_4)$alkyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio and nitro, in particular phenyl which is optionally substituted by one or more radicals from the group consisting of halogen, $(C_1-C_4)$-alkyl, $(C_1-C_4)$-haloalkyl and $(C_1-C_4)$-alkoxy.

In the case of radicals having carbon atoms, preference is given to those having 1 to 6 carbon atoms, preferably 1 to 4 carbon atoms, especially 1 or 2 carbon atoms. Preference is generally given to substituents from the group of halogen, e.g. fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given here to the substituents methyl, methoxy, fluorine and chlorine.

Substituted amino, such as mono- or disubstituted amino, is a radical from the group of the substituted amino radicals which are N-substituted, for example, by one or two identical or different radicals from the group of alkyl, alkoxy, acyl and aryl; preferably mono- and dialkylamino, mono- and diarylamino, acylamino, N-alkyl-N-arylamino, N-alkyl-N-acylamino and N-heterocycles; preference is given to alkyl radicals having from 1 to 4 carbon atoms; aryl is preferably phenyl or substituted phenyl; acyl is as defined below, preferably ($C_1$-$C_4$)-alkanoyl. The same applies to substituted hydroxylamino or hydrazino.

Acyl is a radical of an organic acid which arises in a formal sense by removal of a hydroxyl group on the acid function, and the organic radical in the acid may also be bonded to the acid function via a heteroatom. Examples of acyl are the —CO—R radical of a carboxylic acid HO—CO—R and radicals of acids derived therefrom, such as those of thiocarboxylic acid, optionally N-substituted iminocarboxylic acids or the radical of carbonic monoesters, N-substituted carbamic acid, sulphonic acids, sulphinic acids, N-substituted sulphonamide acids, phosphonic acids or phosphinic acids.

Acyl is, for example, formyl, alkylcarbonyl such as [($C_1$-$C_4$)-alkyl]carbonyl, phenylcarbonyl, alkyloxycarbonyl, phenyloxycarbonyl, benzyloxycarbonyl, alkylsulphonyl, alkylsulphinyl, N-alkyl-1-iminoalkyl and other radicals of organic acids. The radicals may each be substituted further in the alkyl or phenyl moiety, for example in the alkyl moiety by one or more radicals from the group of halogen, alkoxy, phenyl and phenoxy; examples of substituents in the phenyl moiety are the substituents already mentioned above in general for substituted phenyl.

Acyl is preferably an acyl radical in the narrower sense, i.e. a radical of an organic acid in which the acid group is bonded directly to the carbon atom of an organic radical, for example formyl, alkylcarbonyl such as acetyl or [($C_1$-$C_4$)-alkyl]carbonyl, phenylcarbonyl, alkylsulphonyl, alkylsulphinyl and other radicals of organic acids. More preferably, acyl is an alkanoyl radical having 1 to 6 carbon atoms, in particular 1 to 4 carbon atoms. Here, ($C_1$-$C_4$)-alkanoyl is the radical of an alkanoic acid having 1 to 4 carbon atoms formed after removal of the OH group of the acid group, i.e. formyl, acetyl, n-propionyl, isopropionyl or n-, i-, sec- or tert-butanoyl.

The "yl position" of a radical denotes the carbon atom having the free bond. Compounds of the formula (I) according to the invention and compounds of the formula (I) used according to the invention and/or salts thereof are in short also referred to as "compounds (I)".

The invention also provides all stereoisomers which are encompassed by formula (I) and mixtures thereof. Such compounds of the formula (I) contain one or more asymmetric carbon atoms or else double bonds which are not stated separately in the general formulae (I). The possible stereoisomers defined by their specific three-dimensional shape, such as enantiomers, diastereomers, Z- and E-isomers, are all encompassed by the formula (I) and can be obtained from mixtures of the stereoisomers by customary methods or else prepared by stereoselective reactions in combination with the use of stereochemically pure starting materials.

The invention also provides all tautomers of the compounds of the formula (I) which may result from a hydrogen atom shift (for example keto-enol tautomers). The compound of the formula (I) also includes the tautomers, even if formally the formula (I) correctly describes only one of the respective tautomers which are in equilibrium with one another or which can be converted into one another.

For example, compounds of the formula (I) in which L represents a radical of the formula (L'), corresponding to L a radical of the formula —C(=$A^1$)-$B^1$, $A^1$ represents an oxygen atom and $B^1$ represents a radical of the formula (B1) in which $Q^1$ represents OH, are tautomers of compounds of the formula (I) in which L represents a radical of the formula (L"), corresponding to L a radical of the formula —C(=$A^2$)-$B^2$, $A^2$ represents a radical of the formula (A1) and $B^2$ represents a group OH (see scheme):

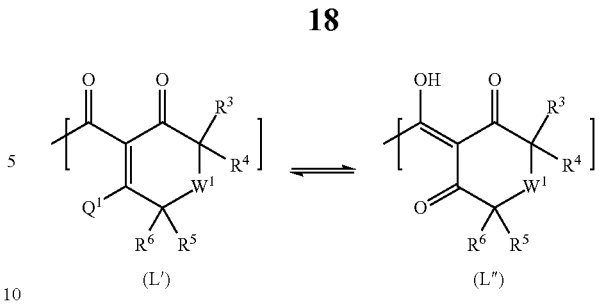

Thus, the tautomers of the compounds (I) with (L') and (L") are embraced both by the scope of the formula (I) in which L represents a radical of the formula —C(=$A^1$)-$B^1$ and by the scope of the formula (I) in which L represents a radical of the formula —C(=$A^2$)-$B^2$.

The compounds of the formula (I) also include all physical forms in which they may be present as a pure substance or, if appropriate, as a mixture with other compounds, in particular also polymorphic crystal forms of the compounds of the formula (I) and salts thereof and solvent adducts (for example hydrates).

Primarily for reasons of higher herbicidal activity, better selectivity, better producibility, better formulatability and/or other relevant properties, compounds of the abovementioned formula (I) according to the invention or their salts or their use according to the invention are of particular interest in which individual radicals have one of the preferred meanings already specified or specified below, or in particular those in which one or more of the preferred meanings already specified or specified below occur in combination.

Compounds of the formula (I) according to the invention and their uses according to the invention with the preferred meanings listed below of the symbols or chemical radicals or chemical groups in question are of particular interest, irrespective of the respective other radicals according to the symbols ($R^1$)$_m$ and ($R^2$)$_n$, L and the definitions of m and n in formula (I) and the definitions of the radicals (or chemical groups) according to the symbols $A^1$, $A^2$, $B^1$, $B^2$, $R^A$, $R^B$, $W^1$ to $W^7$, $Q^1$ to $Q^9$, M, $R^3$ to $R^{71}$, R* and R** in the corresponding sub-meanings of radicals in the formula (I).

Preference is given to compounds (I) in which
($R^1$)$_m$ represents m substituents $R^1$,
where $R^1$, if m=1, or each of the substituents $R^1$, if m is greater than 1, independently of the others represents halogen, cyano, nitro, hydroxy, ($C_1$-$C_6$)-alkyl, ($C_2$-$C_4$)-alkenyl, ($C_2$-$C_4$)-alkynyl, ($C_1$-$C_6$)-alkoxy, ($C_1$-$C_6$)-alkylthio, ($C_1$-$C_6$)-alkylsulphinyl, ($C_1$-$C_6$)-alkylsulphonyl, ($C_1$-$C_4$)-haloalkyl, ($C_1$-$C_4$)-haloalkoxy, ($C_1$-$C_4$)-haloalkylthio, ($C_1$-$C_4$)-haloalkylsulphinyl, ($C_1$-$C_4$)-haloalkylsulphonyl, ($C_2$-$C_4$)-haloalkenyl, ($C_2$-$C_4$)-haloalkynyl, ($C_1$-$C_4$)-alkoxy-($C_1$-$C_4$)-alkyl, ($C_1$-$C_4$)-haloalkoxy-($C_1$-$C_4$)-alkyl, ($C_3$-$C_6$)-cycloalkyl which is optionally substituted by one or more radicals from the group consisting of halogen and ($C_1$-$C_4$)-alkyl, ($C_3$-$C_6$)-cycloalkoxy which is optionally substituted by one or more radicals from the group consisting of halogen and ($C_1$-$C_4$)-alkyl, or a radical of the formula C(O)O$R^{39}$, C(O)N$R^{40}R^{41}$, C(O)—Het$^1$, N$R^{42}R^{43}$ or Het$^2$
or where in each case two groups $R^1$ located ortho at the ring together are a group of the formula —$Z^1$-A*-$Z^2$ in which
A* represents an alkylene group having 1 to 4 carbon atoms which is optionally substituted by one or more radicals from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^1$ represents a direct bond, O or S and $Z^2$ represents a direct bond, O or S, where the group —$Z^1$-A*-$Z^2$ together with the carbon atoms, attached to the group, of the phenyl ring form a fused-on 5- or 6-membered ring, $R^{39}$ represents hydrogen, ($C_1$-$C_4$)-alkyl, ($C_1$-$C_4$)-haloalkyl, ($C_3$-$C_6$)-cycloalkyl, ($C_3$-$C_6$)-halocycloalkyl, ($C_2$-$C_4$)-alkenyl, ($C_2$-$C_4$)-haloalkenyl, ($C_2$-$C_4$)-alkynyl or the group M mentioned, preferably hydrogen, ($C_1$-$C_4$)-alkyl or the group M mentioned, $R^{40}$, $R^{41}$, $R^{42}$, $R^{43}$, $Het^1$ and $Het^2$ have the meanings mentioned, preferably $R^{40}$, $R^{41}$, $R^{42}$ and $R^{43}$ independently of one another each represent hydrogen or ($C_1$-$C_4$)-alkyl which is unsubstituted or substituted by one or more radicals from the group consisting of halogen, nitro, cyano and phenyl, or ($C_3$-$C_6$)-cycloalkyl or phenyl, where each of the 2 last-mentioned radicals in each case independently of the other is unsubstituted or substituted by one or more radicals from the group consisting of halogen, ($C_1$-$C_4$)-alkyl, ($C_1$-$C_4$)-haloalkyl, phenyl and benzyl, in particular hydrogen, ($C_1$-$C_4$)-alkyl or ($C_1$-$C_4$)-haloalkyl, $Het^1$ and $Het^2$ independently of one another each represent a saturated or partially unsaturated radical of a heterocycle having 3 to 6 ring atoms and at least one nitrogen atom as ring heteroatoms at position 1 of the ring and optionally 1, 2 or 3 further ring heteroatoms from the group consisting of N, O and S, where the radical of the heterocycle is attached at the nitrogen atom in position 1 of the ring to the remainder of the molecule of the compound of the formula (I) and where the heterocycle is unsubstituted or substituted by one or more radicals from the group consisting of halogen, ($C_1$-$C_4$)-alkyl, ($C_1$-$C_4$)-haloalkyl and oxo, preferably the radical of a saturated heterocycle of the type mentioned, in particular a morpholino, piperidino or pyrrolidino group, and m represents 0, 1, 2, 3, 4 or 5, preferably 0, 1, 2 or 3.

More preference is given to compounds (I) in which $(R^1)_m$ represents m substituents $R^1$, where $R^1$, if m=1, or each of the substituents $R^1$, if m is greater than 1, independently of the others represents halogen, cyano, nitro, hydroxy, ($C_1$-$C_4$)-alkyl, ($C_1$-$C_4$)-alkoxy, ($C_1$-$C_4$)-alkylthio, ($C_1$-$C_4$)-alkylsulphinyl, ($C_1$-$C_4$)-alkylsulphonyl, ($C_1$-$C_4$)-haloalkyl, ($C_1$-$C_4$)-haloalkoxy, ($C_1$-$C_4$)-haloalkylthio, ($C_1$-$C_4$)-haloalkylsulphinyl, ($C_1$-$C_4$)-haloalkylsulphonyl, ($C_1$-$C_4$)-alkoxy-($C_1$-$C_4$)-alkyl, ($C_3$-$C_6$)-cycloalkyl, or a radical of the formula C(O)$OR^{39}$, C(O)$NR^{40}R^{41}$, C(O)—$Het^1$, $NR^{42}R^{43}$ or $Het^2$, or where in each case two groups $R^1$ located ortho at the ring together are a group of the formula —$Z^1$-A*-$Z^2$ in which A* represents an alkylene group having 1 to 4 carbon atoms which is optionally substituted by one or more radicals from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^1$ represents a direct bond, O or S and $Z^2$ represents a direct bond, O or S, where the group —$Z^1$-A*-$Z^2$ together with the carbon atoms, attached to the group, of the phenyl ring form a fused-on 5- or 6-membered ring, $R^{39}$ represents hydrogen, ($C_1$-$C_4$)-alkyl or the group M mentioned, $R^{40}$, $R^{41}$, $R^{42}$ and $R^{43}$ independently of one another each represent hydrogen, ($C_1$-$C_4$)-alkyl, ($C_1$-$C_4$)-haloalkyl, benzyl, ($C_3$-$C_6$)-cycloalkyl or phenyl, in particular hydrogen, methyl or ethyl, $Het^1$ and $Het^2$ independently of one another each represent a morpholino, piperidino or pyrrolidino group and m represents 0, 1, 2, 3, 4 or 5, preferably 0, 1, 2 or 3.

Here, more preference is given to compounds (I) in which $(R^1)_m$ represents m substituents $R^1$, where $R^1$, if m=1, or each of the substituents $R^1$, if m is greater than 1, independently of the others represents halogen, cyano, nitro, methyl, ethyl, methoxy, ethoxy, methylthio, ethylthio, ($C_1$-$C_2$)-alkylsulphinyl, ($C_1$-$C_2$)-alkylsulphonyl, ($C_1$-$C_2$)-haloalkyl, ($C_1$-$C_2$)-haloalkoxy, ($C_1$-$C_2$)-haloalkylthio, ($C_1$-$C_2$)-haloalkylsulphinyl, ($C_1$-$C_2$)-haloalkylsulphonyl or ($C_1$-$C_2$)-alkoxy-($C_1$-$C_2$)-alkyl, in particular each of the substituents $R^1$ independently of the others represents halogen, such as fluorine, chlorine, bromine or iodine, or cyano, nitro, methyl, methoxy, methylthio, methylsulphinyl, methylsulphonyl, trifluoromethyl, trifluoromethoxy, trifluoroalkylthio, trifluoromethylsulphinyl or trifluoromethylsulphonyl, in particular halogen such as fluorine, chlorine or bromine, and m represents 0, 1, 2, 3, 4 or 5, preferably 0, 1, 2, 3 or 4, in particular 0, 1, 2 or 3.

More preference is given to compounds of the formula (I) or salts thereof in which m is 0 (=the number zero, i.e. no substituents $R^1$ are present, i.e. all free bonds at the ring are occupied by hydrogen) or preferably $(R^1)_m$ is 2-bromo, 3-bromo, 4-bromo, 2-chloro, 3-chloro, 4-chloro, 2-fluoro, 3-fluoro, 4-fluoro, 2-cyano, 3-cyano, 4-cyano, 2-methyl, 3-methyl, 4-methyl, 2-ethyl, 3-ethyl, 4-ethyl, 2-$CF_3$, 3-$CF_3$, 4-$CF_3$, 2-methoxy, 3-methoxy, 4-methoxy, 2-ethoxy, 3-ethoxy, 4-ethoxy, 2-methylthio, 3-methylthio, 4-methylthio, 2-methylsulphinyl, 3-methylsulphinyl, 4-methylsulphinyl, 2-methylsulphonyl, 3-methylsulphonyl, 4-methylsulphonyl, 2-nitro, 3-nitro, 4-nitro, 2,3-dimethyl, 2,4-dimethyl, 2,5-dimethyl, 2,6-dimethyl, 3,4-dimethyl, 3,5-dimethyl, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro, 3,4,5-trichloro or else (4-Br-3-F), (3-Br-4-F), (3-Br-5-F), (4-Br-3-Cl), (3-Br-4-Cl), (4-CN-3-F), (3-CN-4-F), (3-CN-5-F), (4-CN-3-Cl) or (3-CN-4-Cl), where the numbering of the radicals refers to the position of the radical at the phenyl-1-yl radical in which the carbon atom attached to the 2-position at the valeronitrile skeleton has the 1-position in the ring.

More preference is given to compounds of the formula (I) or salts thereof in which $(R^1)_m$ represents 3-bromo, 4-bromo, 3-chloro, 4-chloro, 3-fluoro, 4-fluoro, 2-cyano, 3-cyano, 4-cyano, 2,5-difluoro, 3,4-difluoro, 3,5-difluoro, 3,4-dichloro, 3,5-dichloro, (3-Cl-4-F), (3-Cl-5-F), (4-Cl-3-F), (3-Br-4-F), (4-Br-3-F), 3,4,5-trifluoro, 3,4,5-trichloro or else (4-Br-3-F), (3-Br-4-F), (3-Br-5-F), (4-Br-3-Cl), (3-Br-4-Cl), (4-CN-3-F), (3-CN-4-F), (3-CN-5-F), (4-CN-3-Cl) or (3-CN-4-Cl).

Here, particular preference is given to:

Compounds of the formula (I) or salts thereof in which $(R^1)_m$ is 3-chloro.

Compounds of the formula (I) or salts thereof in which $(R^1)_m$ is 4-chloro.

Compounds of the formula (I) or salts thereof in which $(R^1)_m$ is 3-fluoro.

Compounds of the formula (I) or salts thereof in which $(R^1)_m$ is 4-fluoro.

Compounds of the formula (I) or salts thereof in which $(R^1)_m$ is 3-cyano.

Compounds of the formula (I) or salts thereof in which $(R^1)_m$ is (3-CN-4-F).

Compounds of the formula (I) or salts thereof in which $(R^1)_m$ is (3-Br-4-F).

Compounds of the formula (I) or salts thereof in which $(R^1)_m$ is 3,4-difluoro.

Compounds of the formula (I) or salts thereof in which $(R^1)_m$ is 3,4-dichloro.

Compounds of the formula (I) or salts thereof in which $(R^1)_m$ is 3,5-difluoro.

Compounds of the formula (I) or salts thereof in which $(R^1)_m$ is 3,5-dichloro.

Compounds of the formula (I) or salts thereof in which $(R^1)_m$ is (3-Cl-4-F).

Compounds of the formula (I) or salts thereof in which $(R^1)_m$ is (3-Cl-5-F).

Compounds of the formula (I) or salts thereof in which $(R^1)_m$ is (4-Cl-3-F).

Preference is also given to compounds (I) in which $(R^2)_n$ represents n substituents $R^2$, where $R^2$, if n=1, or each of the substituents $R^2$, if n is greater than 1, independently of the others represents halogen, cyano, nitro, hydroxy, $(C_1-C_6)$-alkyl, $(C_2-C_4)$-alkenyl, $(C_2-C_4)$-alkynyl, $(C_1-C_6)$-alkoxy, $(C_1-C_6)$-alkylthio, $(C_1-C_6)$-alkylsulphinyl, $(C_1-C_6)$-alkylsulphonyl, $(C_1-C_4)$-haloalkyl, $(C_1-C_4)$-haloalkoxy, $(C_1-C_4)$-haloalkylthio, $(C_1-C_4)$-haloalkylsulphinyl, $(C_1-C_4)$-haloalkylsulphonyl, $(C_2-C_4)$-haloalkenyl, $(C_2-C_4)$-haloalkynyl, $(C_1-C_4)$-alkoxy-$(C_1-C_4)$-alkyl, $(C_1-C_4)$-haloalkoxy-$(C_1-C_4)$-alkyl, $(C_3-C_6)$-cycloalkyl which is optionally substituted by one or more radicals from the group consisting of halogen and $(C_1-C_4)$-alkyl, $(C_3-C_6)$-cycloalkoxy which is optionally substituted by one or more radicals from the group consisting of halogen and $(C_1-C_4)$-alkyl, or a radical of the formula $C(O)OR^{44}$, $C(O)NR^{45}R^{46}$, $C(O)$—$Het^3$, $NR^{47}R^{48}$ or $Het^4$ or where in each case two groups $R^2$ located ortho at the ring together are a group of the formula —$Z^3$-$A^{}$-$Z^4$ in which $A^{}$ represents an alkylene group having 1 to 4 carbon atoms which is optionally substituted by one or more radicals from the group consisting of halogen, $(C_1-C_4)$-alkyl, $(C_1-C_4)$-haloalkyl, $(C_1-C_4)$-alkoxy and $(C_1-C_4)$-haloalkoxy, $Z^3$ represents a direct bond, O or S and $Z^4$ represents a direct bond, O or S, where the group —$Z^3$-$A^{**}$-$Z^4$ together with the carbon atoms, attached to the group, of the phenyl ring form a fused-on 5- or 6-membered ring, $R^{44}$ represents hydrogen, $(C_1-C_4)$-alkyl, $(C_1-C_4)$-haloalkyl, $(C_3-C_6)$-cycloalkyl, $(C_3-C_6)$-halocycloalkyl, $(C_2-C_4)$-alkenyl, $(C_2-C_4)$-haloalkenyl, $(C_2-C_4)$-alkynyl or the group M mentioned, $R^{45}$, $R^{46}$, $R^{47}$, $R^{48}$, $Het^3$ and $Het^4$ have the meanings mentioned, preferably $R^{45}$, $R^{46}$, $R^{47}$ and $R^{48}$ independently of one another each represent hydrogen or $(C_1-C_4)$-alkyl which is unsubstituted or substituted by one or more radicals from the group consisting of halogen, nitro, cyano and phenyl, or $(C_3-C_6)$-cycloalkyl or phenyl, where each of the 2 last-mentioned radicals in each case independently of the other is unsubstituted or substituted by one or more radicals from the group consisting of halogen, $(C_1-C_4)$-alkyl, $(C_1-C_4)$-haloalkyl, phenyl and benzyl, $Het^3$ and $Het^4$ independently of one another each represent a saturated or partially unsaturated radical of a heterocycle having 3 to 6 ring atoms and at least one nitrogen atom as ring heteroatom at position 1 of the ring and optionally 1, 2 or 3 further ring heteroatoms from the group consisting of N, O and S, where the radical of the heterocycle is attached at the nitrogen atom in position 1 of the ring to the remainder of the molecule of the compound of the formula (I) and where the heterocycle is unsubstituted or substituted by one or more radicals from the group consisting of halogen, $(C_1-C_4)$-alkyl, $(C_1-C_4)$-haloalkyl and oxo, preferably the radical of a saturated heterocycle of the type mentioned, in particular a morpholino, piperidino or pyrrolidino group, and n represents 0, 1, 2, 3, 4 or 5, preferably 0, 1, 2 or 3.

Here, more preference is given to compounds (I) in which $(R^2)_n$ represents n substituents $R^2$, where $R^2$, if n=1, or each of the substituents $R^2$, if n is greater than 1, independently of one another represent halogen, cyano, nitro, hydroxy, $(C_1-C_4)$-alkyl, $(C_1-C_4)$-alkoxy, $(C_1-C_4)$-alkylthio, $(C_1-C_4)$-alkylsulphinyl, $(C_1-C_4)$-alkylsulphonyl, $(C_1-C_4)$-haloalkyl, $(C_1-C_4)$-haloalkoxy, $(C_1-C_4)$-haloalkylthio, $(C_1-C_4)$-haloalkylsulphinyl, $(C_1-C_4)$-haloalkylsulphonyl, $(C_1-C_4)$-alkoxy-$(C_1-C_4)$-alkyl, $(C_3-C_6)$-cycloalkyl, or a radical of the formula $C(O)OR^{44}$, $C(O)NR^{45}R^{46}$, $C(O)$—$Het^3$, $NR^{47}R^{48}$ or $Het^4$, or where in each case two groups $R^2$ located ortho at the ring together are a group of the formula —$Z^3$-$A^{}$-$Z^4$ in which $A^{}$ represents an alkylene group having 1 to 4 carbon atoms which is optionally substituted by one or more radicals from the group consisting of halogen, $(C_1-C_4)$-alkyl, $(C_1-C_4)$-haloalkyl, $(C_1-C_4)$-alkoxy and $(C_1-C_4)$-haloalkoxy, $Z^3$ represents a direct bond, O or S and $Z^4$ represents a direct bond, O or S, where the group —$Z^3$-$A^{**}$-$Z^4$ together with the carbon atoms, attached to the group, of the phenyl ring form a fused-on 5- or 6-membered ring, $R^{44}$ represents hydrogen, $(C_1-C_4)$-alkyl or the group M mentioned, $R^{45}$, $R^{46}$, $R^{47}$, $R^{48}$, $Het^3$ and $Het^4$ have the meanings mentioned, preferably $R^{45}$, $R^{46}$, $R^{47}$ and $R^{48}$ independently of one another each represent hydrogen, $(C_1-C_4)$-alkyl, $(C_1-C_4)$-haloalkyl, benzyl, $(C_3-C_6)$-cycloalkyl or phenyl, $Het^3$ and $Het^4$ independently of one another each represent a morpholino, piperidino or pyrrolidino group and n represents 0, 1, 2, 3, 4 or 5, preferably 0, 1, 2, 3 or 4, in particular 0, 1, 2 or 3.

Here, more preference is given to compounds (I) in which $(R^2)_n$ represents n substituents $R^2$, where $R^2$, if n=1, or each of the substituents $R^2$, if n is greater than 1, independently of the others represents halogen, cyano, nitro, methyl, ethyl, methoxy, ethoxy, methylthio, ethylthio, $(C_1-C_2)$-alkylsulphinyl, $(C_1-C_2)$-alkylsulphonyl, $(C_1-C_2)$-haloalkyl, $(C_1-C_2)$-haloalkoxy, $(C_1-C_2)$-haloalkylthio, $(C_1-C_2)$-haloalkylsulphinyl, $(C_1-C_2)$-haloalkylsulphonyl or $(C_1-C_2)$-alkoxy-$(C_1-C_2)$-alkyl,
  in particular each of the substituents $R^2$ independently of the others represents
    halogen, such as fluorine, chlorine, bromine or iodine, or cyano, nitro, methyl, methoxy, methylthio, methylsulphinyl, methylsulphonyl, trifluoromethyl, trifluoromethoxy, trifluoroalkylthio, trifluoromethylsulphinyl or trifluoromethylsulphonyl, in particular halogen such as fluorine, chlorine or bromine, and
n represents 0, 1, 2, 3, 4 or 5, preferably 0, 1, 2, 3 or 4, in particular 0, 1, 2 or 3.

More preference is given to compounds of the formula (I) or salts thereof in which
n is 0 (=the number zero, i.e. no substituents $R^2$ are present, i.e. all free bonds at the ring are occupied by hydrogen) or preferably
$(R^2)_n$ is 2-bromo, 3-bromo, 4-bromo, 2-chloro, 3-chloro, 4-chloro, 2-fluoro, 3-fluoro, 4-fluoro, 2-cyano, 3-cyano, 4-cyano, 2-methyl, 3-methyl, 4-methyl, 2-ethyl, 3-ethyl, 4-ethyl, 2-$CF_3$, 3-$CF_3$, 4-$CF_3$, 2-methoxy, 3-methoxy, 4-methoxy, 2-ethoxy, 3-ethoxy, 4-ethoxy, 2-methylthio, 3-methylthio, 4-methylthio, 2-methylsulphinyl, 3-methylsulphinyl, 4-methylsulphinyl, 2-methylsulphonyl, 3-methylsulphonyl, 4-methylsulphonyl, 2-nitro, 3-nitro, 4-nitro, 2,3-dimethyl, 2,4-dimethyl, 2,5-dimethyl, 2,6-dimethyl, 3,4-dimethyl, 3,5-dimethyl, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro, 3,4,5-trichloro or else 2-nitro, 3-nitro, 4-nitro, 2,5-dicyano, 2,6-dicyano, (4-Br-2-F), (4-Br-3-F), (4-CN-3-F), (4-nitro-3-F), (4-methoxy-3-F), (3-cyano-4-F), (3-nitro-4-F), (3-cyano-4-Cl), (3-nitro-4-Cl) or (5-cyano-2-F), where the numbering of the radicals refers to the position of the radical at the phenyl-1-yl radical in which the carbon atom attached to the 3-position at the valeronitrile skeleton has the 1-position in the ring.

More preference is given to compounds of the formula (I) or salts thereof in which
$(R^2)_n$ is 2-bromo, 3-bromo, 4-bromo, 2-chloro, 3-chloro, 4-chloro, 2-fluoro, 3-fluoro, 4-fluoro, 2-nitro, 3-nitro, 4-nitro, 2-methoxy, 3-methoxy, 4-methoxy, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro, 3,4,5-trichloro or else 2-nitro, 3-nitro, 4-nitro, 2,5-dicyano, 2,6-dicyano, (4-Br-2-F), (4-Br-3-F), (4-CN-3-F), (4-$NO_2$-3-F), (4-OMe-3-F), (3-CN-4-F), (3-$NO_2$-4-F), (3-CN-4-Cl), (3-$NO_2$-4-Cl) or (5-CN-2-F).

More preference is also given to compounds of the formula (I) or salts thereof in which
$(R^2)_n$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, 3,4-dichloro, 3,5-dichloro, (3-Cl-2-F), (3-Cl-4-F), (3-Cl-5-F), (3-Cl-6-F), (4-Cl-2-F), (4-Cl-3-F).

Here, particular preference is given to:
Compounds of the formula (I) or salts thereof in which $(R^2)_n$ is 3-chloro.
Compounds of the formula (I) or salts thereof in which $(R^2)_n$ is 4-chloro.
Compounds of the formula (I) or salts thereof in which $(R^2)_n$ is 2-fluoro.
Compounds of the formula (I) or salts thereof in which $(R^2)_n$ is 3-fluoro.
Compounds of the formula (I) or salts thereof in which $(R^2)_n$ is 4-fluoro.
Compounds of the formula (I) or salts thereof in which $(R^2)_n$ is 2,3-difluoro.
Compounds of the formula (I) or salts thereof in which $(R^2)_n$ is 2,4-difluoro.
Compounds of the formula (I) or salts thereof in which $(R^2)_n$ is 2,5-difluoro.
Compounds of the formula (I) or salts thereof in which $(R^2)_n$ is 2,6-difluoro.
Compounds of the formula (I) or salts thereof in which $(R^2)_n$ is 3,4-difluoro.
Compounds of the formula (I) or salts thereof in which $(R^2)_n$ is 3,5-difluoro.
Compounds of the formula (I) or salts thereof in which $(R^2)_n$ is (3-Cl-2-F).
Compounds of the formula (I) or salts thereof in which $(R^2)_n$ is (3-Cl-4-F).
Compounds of the formula (I) or salts thereof in which $(R^2)_n$ is (3-Cl-5-F).
Compounds of the formula (I) or salts thereof in which $(R^2)_n$ is (3-Cl-6-F).
Compounds of the formula (I) or salts thereof in which $(R^2)_n$ is (4-Cl-2-F).
Compounds of the formula (I) or salts thereof in which $(R^2)_n$ is (4-Cl-3-F).

More preference is given to:
Compounds of the formula (I) or salts thereof in which m=0 and $(R^2)_n$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F).

Compounds of the formula (I) or salts thereof in which $(R^1)_m$ is 3-chloro and $(R^2)_n$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F).

Compounds of the formula (I) or salts thereof in which $(R^1)_m$ is 4-chloro and $(R^2)_n$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F).

Compounds of the formula (I) or salts thereof in which $(R^1)_m$ is 3-fluoro and $(R^2)_n$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F).

Compounds of the formula (I) or salts thereof in which $(R^1)_m$ is (3-CN-4-F) and $(R^2)_n$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F).

Compounds of the formula (I) or salts thereof in which $(R^1)_m$ is (3-Br-4-F) and $(R^2)_n$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F).

Compounds of the formula (I) or salts thereof in which $(R^1)_m$ is 4-fluoro and $(R^2)_n$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F).

Compounds of the formula (I) or salts thereof in which $(R^1)_m$ is 3-cyano and $(R^2)_n$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F).

Compounds of the formula (I) or salts thereof in which $(R^1)_m$ is 3,4-difluoro and $(R^2)_n$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F).

Compounds of the formula (I) or salts thereof in which $(R^1)_m$ is 3,4-dichloro and $(R^2)_n$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F).

Compounds of the formula (I) or salts thereof in which $(R^1)_m$ is 3,5-difluoro and $(R^2)_n$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F).

Compounds of the formula (I) or salts thereof in which $(R^1)_m$ is 3,5-dichloro and $(R^2)_n$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F).

Compounds of the formula (I) or salts thereof in which $(R^1)_m$ is (3-Cl-4-F) and $(R^2)_n$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F).

Compounds of the formula (I) or salts thereof in which $(R^1)_m$ is (4-Cl-3-F) and $(R^2)_n$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F).

More preference is also given to:

Compounds of the formula (I) or salts thereof in which n=0 and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

Compounds of the formula (I) or salts thereof in which $(R^2)_n$ is 3-chloro and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

Compounds of the formula (I) or salts thereof in which $(R^2)_n$ is 4-chloro and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

Compounds of the formula (I) or salts thereof in which $(R^2)_n$ is 3-fluoro and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

Compounds of the formula (I) or salts thereof in which $(R^2)_n$ is 4-fluoro and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

Compounds of the formula (I) or salts thereof in which $(R^2)_n$ is 2,3-difluoro and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

Compounds of the formula (I) or salts thereof in which $(R^2)_n$ is 2,4-difluoro and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

Compounds of the formula (I) or salts thereof in which $(R^2)_n$ is 2,5-difluoro and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

Compounds of the formula (I) or salts thereof in which $(R^2)_n$ is 2,6-difluoro and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

Compounds of the formula (I) or salts thereof in which $(R^2)_n$ is 3,4-difluoro and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

Compounds of the formula (I) or salts thereof in which $(R^2)_n$ is 3,5-difluoro and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

Compounds of the formula (I) or salts thereof in which $(R^2)_n$ is (3-Cl-2-F) and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

Compounds of the formula (I) or salts thereof in which $(R^2)_n$ is (3-Cl-4-F) and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

Compounds of the formula (I) or salts thereof in which $(R^2)_n$ is (3-Cl-5-F) and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

Compounds of the formula (I) or salts thereof in which $(R^2)_n$ is (3-Cl-6-F) and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

Compounds of the formula (I) or salts thereof in which $(R^2)_n$ is (4-Cl-2-F) and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

Compounds of the formula (I) or salts thereof in which $(R^2)_n$ is (4-Cl-3-F) and $(R^1)_m$ is 3-chloro, 4-chloro, 3-fluoro, 4-fluoro, 3-cyano, 3,4-difluoro, 3,5-difluoro, 3,4-dichloro, 3,5-dichloro, (3-Cl-4-F), (3-Cl-5-F) or (4-Cl-3-F) or else (3-CN-4-F), (3-Br-4-F).

More preference is given to compounds of the formula (I) or salts thereof in which m=1.

More preference is given to compounds of the formula (I) or salts thereof in which m=1 and $R^2$ is halogen, such as fluorine or chlorine.

More preference is given to compounds of the formula (I) or salts thereof in which m=2 or 3, in particular 2.

More preference is given to compounds of the formula (I) or salts thereof in which m=2 and each $R^2$ is selected from the group consisting of halogen, preferably fluorine or chlorine, in particular fluorine.

In general, from among the compounds having the above-mentioned meanings for individual groups or combinations of groups $(R^1)_m$ and/or $(R^2)_n$, preference is given to those in which the remaining groups or combinations of groups in the compounds are defined according to the meanings mentioned as preferred.

Preference is also given to compounds (I) in which
L represents a radical of the formula

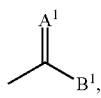

$A^1$ represents oxygen, sulphur or =N—$R^4$, preferably oxygen, $B^1$ represents a radical of the formulae (B1) to (B14) mentioned, $R^4$ has the meaning mentioned above, preferably represents hydrogen, hydroxy, $(C_1-C_4)$-alkoxy, $(C_1-C_4)$-alkyl, $(C_1-C_4)$-haloalkyl, phenyl which is unsubstituted or substituted by one or more radicals from the group consisting of halogen, $(C_1-C_4)$-alkyl, $(C_1-C_4)$-haloalkyl, $(C_1-C_4)$-alkoxy, $(C_1-C_4)$-haloalkoxy, or benzyl which is unsubstituted in the phenyl moiety or substituted by one or more radicals from the group consisting of halogen, $(C_1-C_4)$-alkyl, $(C_1-C_4)$-haloalkyl, $(C_1-C_4)$-alkoxy, $(C_1-C_4)$-haloalkoxy, or —NR*R**, where R*, R** independently of one another each represent H, $(C_1-C_4)$-alkyl, $(C_2-C_4)$-alkenyl, $(C_2-C_4)$-alkynyl, $(C_1-C_4)$-alkoxy-$(C_1-C_4)$-alkyl, $(C_1-C_4)$-alkanoyl, [$(C_1-C_4)$-haloalkyl]carbonyl, [$(C_1-C_4)$-alkoxy]carbonyl, [$(C_1-C_4)$-haloalkoxy]carbonyl, $(C_3-C_6)$-cycloalkyl, $(C_3-C_6)$-cycloalkyl-$(C_1-C_4)$-alkyl, phenyl, phenyl-$(C_1-C_4)$alkyl, where each of the 4 last-mentioned radicals is unsubstituted in the cycle or substituted by one or more radicals from the group consisting of halogen, $(C_1-C_4)$-alkyl, $(C_1-C_4)$-haloalkyl, $(C_1-C_4)$-alkoxy or $(C_1-C_4)$-haloalkoxy or, in the case of cycloalkyl, also oxo, or R* and R** together with the nitrogen atom represent a 3- to 6-membered and preferably saturated heterocycle which, in addition to the nitrogen atom, may contain one or two further ring heteroatoms from the group consisting of N, O and S and which may be unsubstituted or substituted by one or more radicals from the group consisting of $(C_1-C_4)$-alkyl, $(C_1-C_4)$-haloalkyl and oxo, in particular $R^4$ represents hydrogen, $(C_1-C_4)$-alkyl, phenyl, benzyl or —NR*R**, where R*, R** independently of one another each represent H or $(C_1-C_4)$-alkyl, $(R^1)_m$, $(R^2)_n$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ have the meanings or preferred meanings mentioned above, $W^1$ and $W^6$ independently of one another each represent the divalent group oxygen, sulphur or a group of the formula NH, N—[$(C_1-C_4)$-alkyl], C=O, S=O, $SO_2$ or $CR^{35}R^{36}$, $W^2$, $W^3$, $W^4$, $W^5$ and $W^7$ independently of one another each represent the divalent group of the formula O, S, NH, N—[$(C_1-C_4)$-alkyl], C=O, S=O or $SO_2$, $Q^1$, $Q^2$, $Q^3$, $Q^4$, $Q^5$, $Q^6$, $Q^7$, $Q^8$ and $Q^9$ independently of one another each represent hydroxy, thio, halogen or a group of the formula $OR^{37}$, $SR^{38}$, SM or OM, M represents an equivalent of a cation, $R^{35}$ and $R^{36}$ independently of one another are each as defined for $R^3$ or preferably independently of one another represent H, $(C_1-C_4)$-alkyl or $(C_1-C_4)$-haloalkyl, preferably H or $(C_1-C_2)$-alkyl, in particular H, methyl or ethyl, $R^{37}$, $R^{38}$, $R^{66}$, $R^{67}$, $R^{68}$, $R^{69}$, $R^{70}$, $R^{71}$, $Het^{12}$ and M have the meanings mentioned above, preferably $R^{37}$ and $R^{38}$ independently of one another each represent $(C_1-C_6)$-alkyl, $(C_1-C_6)$-haloalkyl, $(C_1-C_4)$-alkoxy-$(C_1-C_4)$-alkyl, $(C_3-C_6)$-cycloalkyl which is unsubstituted or substituted by one or more radicals from the group consisting of halogen, $(C_1-C_4)$-alkyl and $(C_1-C_4)$-alkoxy, phenyl which is unsubstituted or substituted by one or more radicals from the group consisting of halogen, cyano, hydroxy, nitro, $(C_1-C_4)$-alkyl, $(C_1-C_4)$-haloalkyl and $(C_1-C_4)$-alkoxy, or a group of the formula —C(O)$R^{67}$, —C(O)O$R^{68}$, —C(O)N$R^{69}R^{70}$, —C(O)$Het^{12}$ or —$SO_2R^{71}$, in particular $R^{37}$ and $R^{38}$ independently of one another each represent $(C_1-C_6)$-alkyl, $(C_1-C_4)$-haloalkyl, $(C_3-C_6)$-cycloalkyl, $(C_3-C_6)$-halocycloalkyl, phenyl which is unsubstituted or substituted by one or more radicals from the group consisting of halogen and $(C_1-C_4)$-alkyl, or a group of the formula —C(O)$R^{67}$, —C(O)O$R^{68}$, —C(O)N$R^{69}R^{70}$, —C(O)$Het^{12}$ or —$SO_2R^{71}$, $R^{67}$ represents hydrogen, $(C_1-C_6)$-alkyl, $(C_1-C_4)$-haloalkyl, phenyl or benzyl, where each of the 2 last-mentioned radicals independently of the other is unsubstituted or substituted by one or more radicals from the group consisting of halogen, cyano, $(C_1-C_4)$-alkyl and $(C_1-C_4)$-haloalkyl, in particular H or $(C_1-C_4)$-alkyl, $R^{68}$ is $(C_1-C_6)$-alkyl or $(C_1-C_4)$-haloalkyl, in particular $(C_1-C_4)$-alkyl, $R^{69}$ and $R^{70}$ independently of one another each represent hydrogen, $(C_1-C_4)$-alkyl, benzyl, $(C_3-C_6)$-cycloalkyl or phenyl, where each of the 2 last-mentioned radicals independently of the other is unsubstituted or substituted by one or more radicals from the group consisting of halogen, nitro, cyano, $(C_1-C_4)$-alkyl and $(C_1-C_4)$-haloalkyl, in particular independently of one another each represent H or $(C_1-C_3)$-alkyl, $R^{71}$ represents $(C_1-C_4)$-alkyl, $(C_1-C_4)$-haloalkyl, phenyl or benzyl, where each of the 2 last-mentioned radicals independently of the other is unsubstituted or substituted by one or more radicals from the group consisting of halogen, cyano, $(C_1-C_4)$-alkyl, $(C_2-C_4)$-alkenyl and $(C_1-C_4)$-haloalkyl, in particular $(C_1-C_4)$-alkyl, $(C_1-C_4)$-haloalkyl, benzyl or phenyl which is unsubstituted or substituted by one or more radicals from the group consisting of halogen, $(C_1-C_4)$-alkyl and $(C_1-C_4)$-haloalkyl, $Het^{12}$ represents a saturated or partially unsaturated radical of a heterocycle having 3 to 6 ring atoms and at least one nitrogen atom as ring heteroatom at position 1 of the ring and optionally 1, 2 or 3 further ring heteroatoms from the group consisting of N, O and S, where the radical of the heterocycle at the nitrogen atom in position 1 of the ring is attached to the remainder of the molecule of the compound of the formula (I) and where the heterocycle is unsubstituted or substituted by one or more radicals from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo, in particular unsubstituted or substituted by one or more radicals from the group consisting of $(C_1-C_4)$-alkyl and $(C_1-C_4)$-haloalkyl, in particular a morpholino, piperidino or pyrrolidino group, and M represents an equivalent of a cation, preferably a metal ion equivalent, an ammonium ion which is optionally substituted by 1 to 4 identical or different radicals from the group consisting of $(C_1-C_4)$-alkyl, $(C_3-C_6)$-cycloalkyl, phenyl, $(C_3-C_6)$-cycloalkyl-$(C_1-C_4)$-alkyl and phenyl-$(C_1-C_4)$-alkyl, in particular $(C_1-C_4)$-alkyl, or a tertiary sulphonium ion which is preferably substituted by 3 identical or different radicals from the group consisting of $(C_1-C_4)$-alkyl, $(C_3-C_6)$-cycloalkyl, phenyl, $(C_3-C_6)$-cycloalkyl-$(C_1-C_4)$-alkyl and phenyl-$(C_1-C_4)$-alkyl, in particular $(C_1-C_4)$-alkyl.

Preference is also given to compounds (I) in which $B^1$ represents a radical of the formulae (B1) to (B14) mentioned, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ independently of one another each represent H, halogen, cyano, nitro, hydroxy, $(C_1-C_4)$-alkyl, $(C_1-C_4)$-haloalkyl, $(C_3-C_6)$-cycloalkyl, $(C_1-C_4)$-alkoxy or $(C_1-C_4)$-haloalkoxy, in particular H or $(C_1-C_4)$-alkyl, or $R^3$ and $R^5$ in the group of the formula (B1) together represent a divalent bridge as defined above, $R^{21}$ represents H, $(C_1-C_4)$-alkyl, $(C_1-C_4)$-haloalkyl, $(C_3-C_6)$-cycloalkyl, $(C_3-C_6)$-halocycloalkyl or a group $C(O)OR^{54}$, $C(O)NR^{55}R^{56}$, $C(O)Het^7$, $NR^{57}R^{58}$ or $Het^8$, preferably $(C_1-C_4)$-alkyl, $(C_1-C_4)$-haloalkyl, $(C_3-C_6)$-cycloalkyl or a group $C(O)OR^{54}$, $R^{22}$ represents H, $(C_1-C_4)$-alkyl, $(C_1-C_4)$-haloalkyl, $(C_3-C_6)$-cycloalkyl, $(C_3-C_6)$-halocycloalkyl, $(C_1-C_4)$-alkylthio, $(C_1-C_4)$-alkylsulphonyl or a group of the formula $C(O)OR^{59}$, $C(O)NR^{60}R^{61}$, $C(O)Het^9$, $NR^{62}R^{63}$ or $Het^{10}$, preferably $(C_1-C_4)$-alkyl, $(C_1-C_4)$-haloalkyl, $(C_3-C_6)$-cycloalkyl, $(C_1-C_4)$-alkylsulphonyl or a group $C(O)OR^{59}$, $R^{23}$ and $R^{29}$ independently of one another each represent H, $(C_1-C_4)$-alkyl, $(C_1-C_4)$-haloalkyl, $(C_3-C_6)$-cycloalkyl, $(C_3-C_6)$-halocycloalkyl, $(C_1-C_4)$-alkoxy or $(C_1-C_4)$-haloalkoxy, preferably H, $(C_1-C_4)$-alkyl, $(C_1-C_4)$-haloalkyl, $(C_3-C_6)$-cycloalkyl, for example cyclopropyl, $(C_1-C_4)$-alkoxy or $(C_1-C_2)$-haloalkoxy, $R^{24}$ and $R^{39}$ independently of one another each represent H, halogen, cyano, $(C_1-C_4)$-alkyl, $(C_1-C_4)$-haloalkyl, $(C_3-C_6)$-cycloalkyl, $(C_1-C_4)$-alkoxy or $(C_1-C_4)$-haloalkoxy, preferably H, halogen, cyano, $(C_1-C_4)$-alkyl, $(C_1-C_4)$-haloalkyl, $(C_3-C_6)$-cycloalkyl, for example cyclopropyl, $(C_1-C_4)$-alkoxy or $(C_1-C_2)$-haloalkoxy, $R^{25}$, $R^{26}$, $R^{31}$ and $R^{32}$ independently of one another each represent H, $(C_1-C_4)$-alkyl, $(C_1-C_4)$-haloalkyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_3-C_6)$-cycloalkyl, $(C_3-C_6)$-cycloalkyl, $(C_2-C_6)$-alkenyl, $(C_2-C_6)$-alkynyl, $(C_2-C_6)$-alkylthio, $(C_1-C_4)$-alkylsulphonyl, $NR^{64}R^{65}$ or $Het^{11}$, preferably H, $(C_1-C_4)$-alkyl, $(C_1-C_4)$-haloalkyl, $(C_1-C_4)$-alkoxy, $(C_1-C_4)$-haloalkoxy, $(C_1-C_2)$-alkoxy-$(C_1-C_2)$-alkyl, $(C_1-C_2)$-haloalkoxy-$(C_1-C_2)$-alkyl or $(C_3-C_6)$-cycloalkyl, for example cyclopropyl, $R^{27}$ represents H, $(C_1-C_4)$-alkyl, $(C_1-C_4)$-haloalkyl or $(C_3-C_6)$-cycloalkyl, for example cyclopropyl, preferably H or $(C_1-C_3)$-alkyl, $R^{28}$ represents H, $(C_1-C_4)$-alkyl, $(C_1-C_4)$-haloalkyl or a radical of the formula $C(O)OR^{66}$, preferably H or $(C_1-C_3)$-alkyl, $R^{54}$, $R^{59}$ and $R^{66}$ independently of one another each represent H, $(C_1-C_4)$-alkyl, $(C_1-C_4)$-haloalkyl, $(C_3-C_6)$-cycloalkyl, $(C_2-C_4)$-alkenyl, $(C_2-C_4)$-alkynyl or the group M mentioned, preferably H or $(C_1-C_3)$-alkyl, $R^{55}$, $R^{56}$, $R^{57}$, $R^{58}$, $R^{60}$, $R^{61}$, $R^{62}$, $R^{63}$, $R^{64}$ and $R^{65}$ independently of one another each represent H, $(C_1-C_4)$-alkyl which is unsubstituted or substituted by one or more radicals from the group consisting of halogen, nitro, cyano and phenyl which is unsubstituted or substituted by one or more radicals from the group consisting of halogen, nitro, cyano, $(C_1-C_4)$-alkyl and $(C_1-C_4)$-haloalkyl, or $(C_3-C_6)$-cycloalkyl which is unsubstituted or substituted by one or more radicals from the group consisting of halogen and $(C_1-C_4)$-alkyl and $(C_1-C_4)$-haloalkyl, or phenyl which is unsubstituted or substituted by one or more radicals from the group consisting of halogen, nitro, cyano, $(C_1-C_4)$-alkyl and $(C_1-C_4)$-haloalkyl, $Het^7$, $Het^8$, $Het^9$, $Het^{10}$ and $Het^{11}$ independently of one another each represent a saturated or partially unsaturated radical of a heterocycle having 3 to 6 ring atoms and at least one nitrogen atom as ring heteroatom at position 1 of the ring and optionally 1, 2 or 3 further ring heteroatoms from the group consisting of N, O and S, where the radical of the heterocycle at the nitrogen atom in position 1 of the ring is attached to the remainder of the molecule of the compound of the formula (I) and where the heterocycle is unsubstituted or substituted by one or more radicals from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo, in particular unsubstituted or substituted by one or more radicals from the group consisting of $(C_1-C_4)$-alkyl and $(C_1-C_4)$-haloalkyl, in particular a morpholino, piperidino or pyrrolidino group.

Here, preference is given to compounds (I) in which $B^1$ represents a radical (B1)

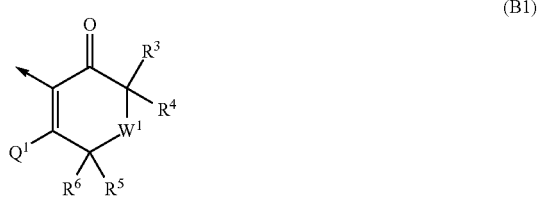

(B1)

in which $W^1$, $Q^1$, $R^3$, $R^4$, $R^5$ and $R^6$ have the meanings or preferred meanings mentioned above, preferably $W^1$ represents the divalent group of the formula O, S, NH, N—[$(C_1-C_4)$-alkyl], C=O, S=O, $SO_2$ or $CR^{35}R^{36}$, in particular the divalent group of the formula O, S, C=O or $CR^{35}R^{36}$, where $R^{35}$ and $R^{36}$ independently of one another each represent hydrogen, $(C_1-C_4)$-alkyl or $(C_1-C_4)$-haloalkyl, in particular $W^1$ represents the divalent group C(O), $CH_2$, $CH(CH_3)$ or $C(CH_3)_2$, $Q^1$ represents hydroxy, thio, halogen or a group of the formula $OR^{37}$, $SR^{38}$, SM or OM, in particular hydroxy, $R^3$, $R^4$, $R^5$ and $R^6$ independently of one another each represent H, halogen, cyano, nitro, hydroxy, $(C_1-C_4)$-alkyl, $(C_1-C_4)$-haloalkyl, $(C_1-C_4)$-alkoxy or $(C_1-C_4)$-haloalkoxy, in particular H or $(C_1-C_4)$-alkyl, or $R^3$ and $R^5$ together represent a divalent bridge of the formula —$CH_2CH_2$—, —$CH_2CH_2CH_2$—, —$CH(CH_3)CH_2$—, —$C(CH_3)_2CH_2$—, —$CH_2CH(CH_3)$—, —$CH_2C(CH_3)_2$—, —$C(CH_3)CH(CH_3)$—, —$CH_2CH_2CH_2$—, —CH=CH—, —CH=$CHCH_2$—, —$CH_2CH$=CH—, —$OCH_2$—, —$CH_2O$—, —$OCH_2CH_2$—, —$CH_2OCH_2$—, —$CH_2CH_2O$— or —$OCH_2O$—, in particular of the formula —$CH_2CH_2$— or —CH=CH—, $R^{37}$, $R^{38}$, $R^{67}$, $R^{68}$, $R^{69}$, $R^{70}$, $R^{71}$, $Het^{12}$ and M have the meanings mentioned above, preferably $R^{37}$ and $R^{38}$ independently of one another each represent $(C_1-C_6)$-alkyl, $(C_1-C_6)$-haloalkyl, $(C_1-C_4)$-alkoxy-$(C_1-$ $C_4$)-alkyl, ($C_3$-$C_6$)-cycloalkyl which is unsubstituted or substituted by one or more radicals from the group consisting of halogen, ($C_1$-$C_4$)-alkyl and ($C_1$-$C_4$)-alkoxy, phenyl which is unsubstituted or substituted by one or more radicals from the group consisting of halogen, cyano, hydroxy, nitro, ($C_1$-$C_4$)-alkyl, ($C_1$-$C_4$)-haloalkyl and ($C_1$-$C_4$)-alkoxy, or a group of the formula —C(O)$R^{67}$, —C(O)O$R^{68}$, —C(O)N$R^{69}R^{70}$, —C(O)Het$^{12}$ or —SO$_2R^{71}$, in particular $R^{37}$ and $R^{38}$ independently of one another each represent ($C_1$-$C_6$)-alkyl, ($C_1$-$C_4$)-haloalkyl, ($C_3$-$C_6$)-cycloalkyl, ($C_3$-$C_6$)-halocycloalkyl, phenyl which is unsubstituted or substituted by one or more radicals from the group consisting of halogen and ($C_1$-$C_4$)-alkyl, or a group of the formula —C(O)$R^{67}$, —C(O)O$R^{68}$, —C(O)N$R^{69}R^{70}$, —C(O)Het$^{12}$ or —SO$_2R^{71}$, more preferably, $R^{37}$ and $R^{38}$ independently of one another each represent ($C_1$-$C_4$)-alkyl, phenyl which is unsubstituted or substituted by one or more radicals from the group consisting of halogen and ($C_1$-$C_4$)-alkyl, or a group of the formula —C(O)$R^{67}$, —C(O)O$R^{68}$ or —SO$_2R^{71}$, $R^{67}$ represents hydrogen, ($C_1$-$C_6$)-alkyl, ($C_1$-$C_4$)-haloalkyl, phenyl or benzyl, where each of the 2 last-mentioned radicals independently of the other is unsubstituted or substituted by one or more radicals from the group consisting of halogen, cyano, ($C_1$-$C_4$)-alkyl and ($C_1$-$C_4$)-haloalkyl, in particular H or ($C_1$-$C_4$)-alkyl, for example H, methyl, ethyl, n-propyl, isopropyl, n-butyl, sec-butyl, isobutyl or t-butyl, $R^{68}$ is ($C_1$-$C_6$)-alkyl or ($C_1$-$C_4$)-haloalkyl, in particular ($C_1$-$C_4$)-alkyl, $R^{69}$ and $R^{70}$ independently of one another each represent hydrogen, ($C_1$-$C_4$)-alkyl, benzyl, ($C_3$-$C_6$)-cycloalkyl or phenyl, where each of the 2 last-mentioned radicals independently of the other is unsubstituted or substituted by one or more radicals from the group consisting of halogen, nitro, cyano, ($C_1$-$C_4$)-alkyl and ($C_1$-$C_4$)-haloalkyl or in particular independently of one another each represent H or ($C_1$-$C_3$)-alkyl, $R^{71}$ represents ($C_1$-$C_4$)-alkyl, ($C_1$-$C_4$)-haloalkyl, phenyl or benzyl, where each of the 2 last-mentioned radicals independently of the other is unsubstituted or substituted by one or more radicals from the group consisting of halogen, cyano, ($C_1$-$C_4$)-alkyl, ($C_2$-$C_4$)-alkenyl and ($C_1$-$C_4$)-haloalkyl, in particular ($C_1$-$C_4$)-alkyl, ($C_1$-$C_4$)-haloalkyl, benzyl or phenyl which is unsubstituted or substituted by one or more radicals from the group consisting of halogen, ($C_1$-$C_4$)-alkyl and ($C_1$-$C_4$)-haloalkyl, Het$^{12}$ represents a morpholino, piperidino or pyrrolidino group, and M represents an equivalent of a cation, preferably a metal ion equivalent, an ammonium ion which is optionally substituted by 1 to 4 identical or different radicals from the group consisting of ($C_1$-$C_4$)-alkyl, ($C_3$-$C_6$)-cycloalkyl, phenyl, ($C_3$-$C_6$)-cycloalkyl-($C_1$-$C_4$)-alkyl and phenyl-($C_1$-$C_4$)-alkyl, in particular ($C_1$-$C_4$)-alkyl, or a tertiary sulphonium ion which is preferably substituted by 3 identical or different radicals from the group consisting of ($C_1$-$C_4$)-alkyl, ($C_3$-$C_6$)-cycloalkyl, phenyl, ($C_3$-$C_6$)-cycloalkyl-($C_1$-$C_4$)-alkyl and phenyl-($C_1$-$C_4$)-alkyl, in particular ($C_1$-$C_4$)-alkyl.

Examples of preferred radicals $B^1$ of the formula (B1) are the radicals of the formulae (B1-1) to (B1-11):

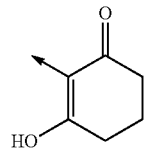
(B1-1)

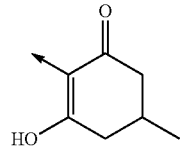
(B1-2)

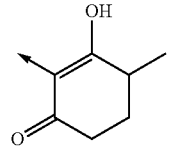
(B1-3)

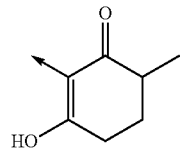
(B1-4)

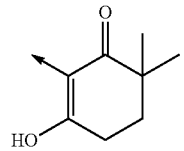
(B1-5)

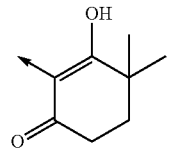
(B1-6)

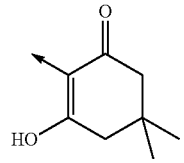
(B1-7)

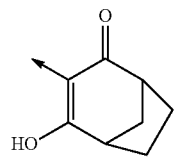
(B1-8)

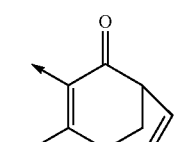
(B1-9)

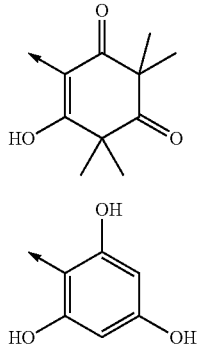

(B1-10)

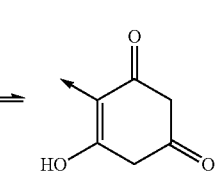

(B1-11)

In the formulae (B1-1) to (B1-11), the substituents "methyl" at the ring system are, in the customary short notation, indicated as a line extending from a ring carbon atom. This notation is also used in subsequent formulae for radicals $B^1$.

The formula (B1-11) also embraces tautomers, where the tautomer drawn on the left-hand side is the thermodynamically more stable tautomer, whereas the tautomer drawn on the right-hand side is the tautomer that formally corresponds exactly to the general formula (B1) if $Q^1$=OH and $W^1$=C(O).

Here, preference is given to compounds (I) in which $B^1$ represents a radical (B4)

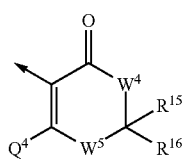

(B4)

in which $W^4$, $W^5$, $Q^4$, $R^{15}$ and $R^{16}$ have the meanings or preferred meanings mentioned above, preferably $W^4$ and $W^5$ each independently of one another represent the divalent group of the formula O, S, NH, N—[($C_1$-$C_4$)-alkyl], C=O, S=O or $SO_2$, in particular the divalent group of the formula O or S, in particular O, $Q^4$ represents hydroxy, thio, halogen or a group of the formula $OR^{37}$, $SR^{38}$, SM or OM, in particular hydroxy, $R^{15}$ and $R^{16}$ independently of one another each represent H, halogen, cyano, nitro, hydroxy, ($C_1$-$C_4$)-alkyl, ($C_1$-$C_4$)-haloalkyl, ($C_1$-$C_4$)-alkoxy or ($C_1$-$C_4$)-haloalkoxy, in particular hydrogen or ($C_1$-$C_4$)-alkyl, $R^{37}$, $R^{38}$ and M have the meanings mentioned above, preferably $R^{37}$ and $R^{38}$ independently of one another each represent ($C_1$-$C_4$)-alkyl, ($C_1$-$C_4$)-haloalkyl, ($C_1$-$C_4$)-alkoxy-($C_1$-$C_4$)-alkyl, ($C_3$-$C_6$)-cycloalkyl which is unsubstituted or substituted by one or more radicals from the group consisting of halogen, ($C_1$-$C_4$)-alkyl and ($C_1$-$C_4$)-alkoxy, phenyl which is unsubstituted or substituted by one or more radicals from the group consisting of halogen, cyano, hydroxy, nitro, ($C_1$-$C_4$)-alkyl, ($C_1$-$C_4$)-haloalkyl and ($C_1$-$C_4$)-alkoxy, or a group of the formula —C(O)$R^{67}$, —C(O)O$R^{68}$, —C(O)N$R^{69}R^{70}$, —C(O)Het$^{12}$ or —$SO_2R^{71}$, in particular $R^{37}$ and $R^{38}$ independently of one another each represent ($C_1$-$C_6$)-alkyl, ($C_1$-$C_4$)-haloalkyl, ($C_3$-$C_6$)-cycloalkyl, ($C_3$-$C_6$)-halocycloalkyl, phenyl which is unsubstituted or substituted by one or more radicals from the group consisting of halogen and ($C_1$-$C_4$)-alkyl, or a group of the formula —C(O)$R^{67}$, —C(O)O$R^{68}$, —C(O)N$R^{69}R^{70}$, —C(O)Het$^{12}$ or —$SO_2R^{71}$, more preferably, $R^{37}$ and $R^{38}$ independently of one another each represent ($C_1$-$C_4$)-alkyl, phenyl which is unsubstituted or substituted by one or more radicals from the group consisting of halogen and ($C_1$-$C_4$)-alkyl, or a group of the formula —C(O)$R^{67}$, —C(O)O$R^{68}$ or —$SO_2R^{71}$, $R^{67}$, $R^{68}$, $R^{69}$, $R^{70}$, $R^{71}$, Het$^{12}$ and M have the meanings mentioned above, preferably $R^{67}$ represents hydrogen, ($C_1$-$C_6$)-alkyl, ($C_1$-$C_4$)-haloalkyl, phenyl or benzyl, where each of the 2 last-mentioned radicals independently of the other is unsubstituted or substituted by one or more radicals from the group consisting of halogen, cyano, ($C_1$-$C_4$)-alkyl and ($C_1$-$C_4$)-haloalkyl, in particular H or ($C_1$-$C_4$)-alkyl, $R^{68}$ is ($C_1$-$C_6$)-alkyl or ($C_1$-$C_4$)-haloalkyl, in particular ($C_1$-$C_4$)-alkyl, $R^{69}$ and $R^{70}$ independently of one another each represent hydrogen, ($C_1$-$C_4$)-alkyl, benzyl, ($C_3$-$C_6$)-cycloalkyl or phenyl, where each of the 2 last-mentioned radicals independently of the other is unsubstituted or substituted by one or more radicals from the group consisting of halogen, nitro, cyano, ($C_1$-$C_4$)-alkyl and ($C_1$-$C_4$)-haloalkyl or in particular independently of one another each represent H or ($C_1$-$C_3$)-alkyl, $R^{71}$ represents ($C_1$-$C_4$)-alkyl, ($C_1$-$C_4$)-haloalkyl, phenyl or benzyl, where each of the 2 last-mentioned radicals independently of the other is unsubstituted or substituted by one or more radicals from the group consisting of halogen, cyano, ($C_1$-$C_4$)-alkyl, ($C_2$-$C_4$)-alkenyl and ($C_1$-$C_4$)-haloalkyl, in particular ($C_1$-$C_4$)-alkyl, ($C_1$-$C_4$)-haloalkyl, benzyl or phenyl which is unsubstituted or substituted by one or more radicals from the group consisting of halogen, ($C_1$-$C_4$)-alkyl and ($C_1$-$C_4$)-haloalkyl, Het$^{12}$ represents a morpholino, piperidino or pyrrolidino group, and M represents an equivalent of a cation, preferably a metal ion equivalent, an ammonium ion which is optionally substituted by 1 to 4 identical or different radicals from the group consisting of ($C_1$-$C_4$)-alkyl, ($C_3$-$C_6$)-cycloalkyl, phenyl, ($C_3$-$C_6$)-cycloalkyl-($C_1$-$C_4$)-alkyl and phenyl-($C_1$-$C_4$)-alkyl, in particular ($C_1$-$C_4$)-alkyl, or a tertiary sulphonium ion which is preferably substituted by 3 identical or different radicals from the group consisting of ($C_1$-$C_4$)-alkyl, ($C_3$-$C_6$)-cycloalkyl, phenyl, ($C_3$-$C_6$)-cycloalkyl-($C_1$-$C_4$)-alkyl and phenyl-($C_1$-$C_4$)-alkyl, in particular ($C_1$-$C_4$)-alkyl.

An example of a preferred radical $B^1$ of the formula (B4) is the radical of the formula (B4-1).

(B4-1)

Preference is also given to compounds (I) in which $B^1$ represents a radical (B5) or (B6)

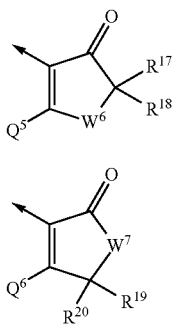
(B5)

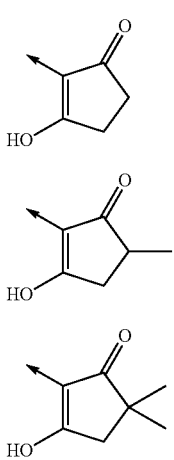
(B6)

in which

W⁶, W⁷, Q⁵, Q⁶, R¹⁷, R¹⁸, R¹⁹ and R²⁰ have the meanings or preferred meanings mentioned above, preferably W⁶ represents the divalent group of the formula O, S, NH, N—[(C₁-C₄)-alkyl], C=O, S=O, SO₂ or a group of the formula CR³⁵R³⁶, in particular the divalent group of the formula O, S, NH, N—[(C₁-C₄)-alkyl] or a group of the formula CR³⁵R³⁶, more preferably O, NH, N—CH₃, N—C₂H₅ or a group of the formula CH₂, CH(CH₃), CH(C₂H₅) or C(CH₃)₂, very particularly O or CH₂, W⁷ represents the divalent group of the formula O, S, NH, N—[(C₁-C₄)-alkyl], C=O, S=O or SO₂, in particular the divalent group of the formula O, S, NH or N—[(C₁-C₄)-alkyl], in particular O, Q⁵ and Q⁶ independently of one another each represent hydroxy, thio, halogen or a group of the formula OR³⁷, SR³⁸, SM or OM, in particular hydroxy, R¹⁷, R¹⁸, R¹⁹ and R²⁰ independently of one another each represent H, halogen, cyano, nitro, hydroxy, (C₁-C₄)-alkyl, (C₁-C₄)-haloalkyl, (C₁-C₄)-alkoxy or (C₁-C₄)-haloalkoxy, in particular H or (C₁-C₄)-alkyl, R³⁵ and R³⁶ independently of one another each represent hydrogen, (C₁-C₄)-alkyl or (C₁-C₄)-haloalkyl, in particular H, methyl or ethyl, R³⁷, R³⁸ and M have the meanings mentioned above, preferably as defined for compounds of the formula (B1) or (B4) above.

Examples of preferred radicals B¹ of the formulae (B5) and (B6) are the radicals of the formulae (B5-1), (B5-2), (B5-3), (B5-4), (B5-5), (B5-6), (B5-7), (B5-8), (B5-9), (B6-1), (B6-2), (B6-3):

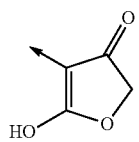
(B5-1)

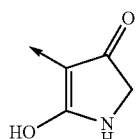
(B5-2)

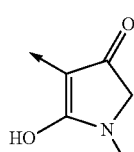
(B5-3)

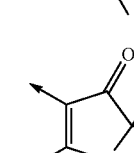
(B5-4)

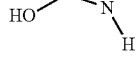
(B5-5)

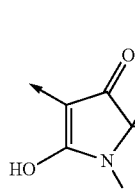
(B5-6)

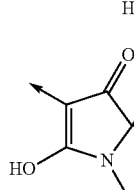
(B5-7)

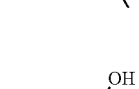
(B5-8)

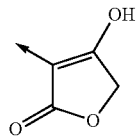
(B5-9)

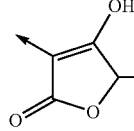
(B6-1)

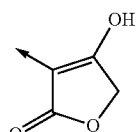
(B6-2)

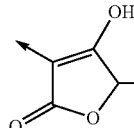
(B6-3)

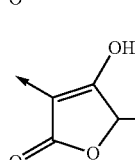

Preference is also given to compounds (I) in which B¹ represents a radical (B7)

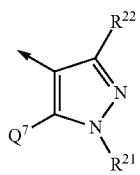
(B7)

in which
Q⁷, R²¹ and R²² have the meanings or preferred meanings mentioned above, preferably
Q⁷ represents hydroxy, thio, halogen or a group of the formula OR³⁷, SR³⁸, SM or OM, in particular hydroxy,
R²¹ represents hydrogen, $(C_1-C_4)$-alkyl, $(C_1-C_4)$-haloalkyl, $(C_3-C_6)$-cycloalkyl, $(C_3-C_6)$-halocycloalkyl or a group C(O)OR⁵⁴, C(O)NR⁵⁵R⁵⁶, C(O)Het⁷, NR⁵⁷R⁵⁸ or Het⁸, in particular H, $(C_1-C_4)$-alkyl, $(C_1-C_4)$-haloalkyl or $(C_3-C_6)$-cycloalkyl, for example cyclopropyl,
R²² represents hydrogen, $(C_1-C_4)$-alkyl, $(C_1-C_4)$-haloalkyl, $(C_3-C_6)$-cycloalkyl, $(C_3-C_6)$-halocycloalkyl, $(C_1-C_4)$-alkylthio, $(C_1-C_4)$-alkylsulphonyl, $(C_1-C_4)$-alkylsulphinyl or a group of the formula C(O)OR⁵⁹, C(O)NR⁶⁰R⁶¹, C(O)Het⁹, NR⁶²R⁶³ or Het¹⁰, in particular H, $(C_1-C_4)$-alkyl, $(C_1-C_4)$-haloalkyl, $(C_3-C_6)$-cycloalkyl, $(C_3-C_6)$-halocycloalkyl, $(C_1-C_4)$-alkylthio, $(C_1-C_4)$-alkylsulphonyl or a group of the formula C(O)OR⁵⁹ and
R⁵⁹ represents hydrogen, $(C_1-C_4)$-alkyl, $(C_1-C_4)$-haloalkyl, $(C_3-C_6)$-cycloalkyl, $(C_3-C_6)$-halocycloalkyl, $(C_2-C_4)$-alkenyl, $(C_2-C_4)$-haloalkenyl, $(C_2-C_4)$-alkynyl or the group M mentioned, preferably hydrogen, $(C_1-C_3)$-alkyl or the group M mentioned.

Examples of preferred radicals B¹ of the formula (B7) are radicals of the formulae (B7-1), (B7-2), (B7-3), (B7-4) and (B7-5):

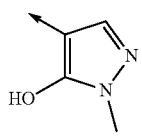
(B7-1)

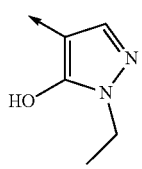
(B7-2)

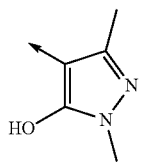
(B7-3)

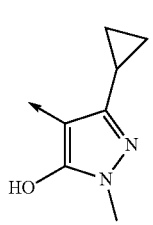
(B7-4)

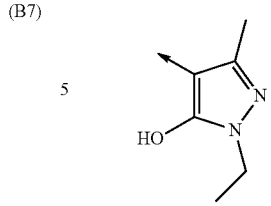
(B7-5)

Preference is also given to compounds (I) in which B¹ represents a radical (B8)

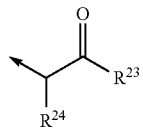
(B8)

in which
R²³ and R²⁴ have the meanings or preferred meanings mentioned above, preferably
R²³ represents hydrogen, $(C_1-C_4)$-alkyl, $(C_1-C_4)$-haloalkyl, $(C_3-C_6)$-cycloalkyl, $(C_3-C_6)$-halocycloalkyl, $(C_1-C_4)$-alkoxy or $(C_1-C_4)$-haloalkoxy, in particular hydrogen, $(C_1-C_4)$-alkyl, $(C_1-C_4)$-haloalkyl, $(C_3-C_6)$-cycloalkyl, $(C_3-C_4)$-halocycloalkyl, $(C_1-C_4)$-alkoxy or $(C_1-C_4)$-haloalkoxy, more preferably methyl, ethyl, n-propyl, isopropyl, n-butyl, isobutyl, s-butyl, t-butyl, methoxy, ethoxy, n-propoxy, isopropoxy, n-butoxy, isobutoxy, s-butoxy or t-butoxy,
R²⁴ represents hydrogen, halogen, cyano, $(C_1-C_4)$-alkyl, $(C_1-C_4)$-haloalkyl, $(C_3-C_6)$-cycloalkyl, for example cyclopropyl, $(C_1-C_4)$-alkoxy or $(C_1-C_4)$-haloalkoxy, in particular hydrogen, $(C_1-C_3)$-alkyl, cyano or cyclopropyl, more preferably cyano.

Examples of preferred radicals B¹ of the formula (B8) are radicals of the formulae (B8-1), (B8-2), (B8-3), (B8-4), (B8-5) and (B8-6):

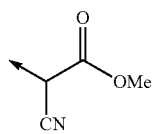
(B8-1)

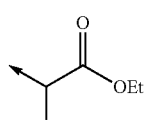
(B8-2)

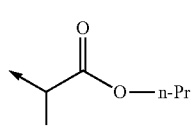
(B8-3)

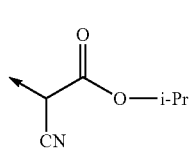
(B8-4)

-continued

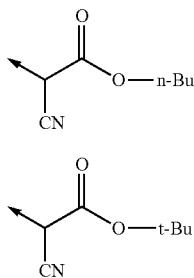
(B8-5)

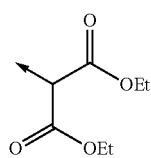
(B8-6)

In the formulae for (B8-1) to (B8-6) and correspondingly in other example formulae, OMe=methoxy, OEt=ethoxy, O-n-Pr=n-propoxy, O-i-Pr=isopropoxy, O-n-Bu=n-butoxy, O-i-Bu=isobutoxy, O-s-Bu=sec-butoxy and O-t-Bu=tert-butoxy.

The compounds of the formula (B8) are tautomers of the compounds of the formulae (B11) and (B12) if $Q^8$=OH or OM and $R^{24}$=$R^{30}$ and $R^{23}$=$R^{29}$. Especially when $R^{24}$ and $R^{30}$ are each CN, in equilibrium a substantial proportion is described by the tautomer of the formula (B11).

Preference is also given to compounds (I) in which $B^1$ represents a radical (B9)

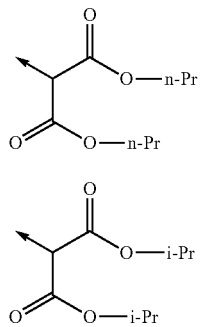
(B9)

in which $R^{25}$ and $R^{26}$ independently of one another each have the meanings or preferred meanings mentioned above, more preferably independently of one another each represent hydrogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_3-C_6)$-cycloalkyl, $(C_3-C_6)$-halocycloalkyl, $(C_3-C_6)$-cycloalkoxy, $(C_2-C_6)$-alkenyl, $(C_2-C_6)$-haloalkenyl, $(C_2-C_6)$-alkynyl, $(C_2-C_6)$-haloalkynyl, $(C_1-C_4)$-alkylthio, $(C_3-C_4)$-alkylsulphonyl, $(C_1-C_4)$-alkylsulphinyl, $NR^{64}R^{65}$ or $Het^{11}$, or more preferably $R^{25}$ represents hydrogen, $(C_1-C_4)$-alkyl, $(C_1-C_4)$-alkoxy, $(C_1-C_4)$-haloalkoxy or $(C_3-C_6)$-cycloalkyl, for example cyclopropyl, in particular $(C_1-C_4)$-alkoxy, and $R^{26}$ represents hydrogen, $(C_1-C_4)$-alkyl, $(C_1-C_4)$-alkoxy, $(C_1-C_4)$-haloalkoxy or $(C_3-C_6)$-cycloalkyl, for example cyclopropyl, in particular $(C_1-C_4)$-alkoxy.

Examples of preferred radicals $B^1$ of the formula (B9) are radicals of the formulae (B9-1), (B9-2), (B9-3), (B9-4), (B9-5), (B9-6), (B9-7), (B9-8) and (B9-9):

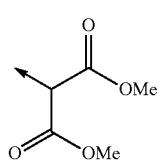
(B9-1)

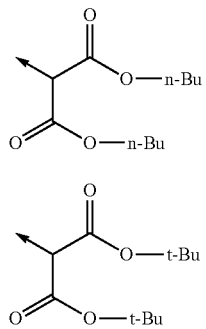
(B9-2)

(B9-3)

(B9-4)

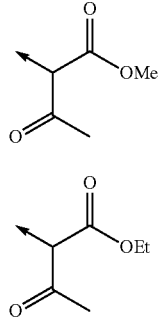
(B9-5)

(B9-6)

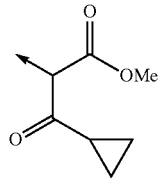
(B9-7)

(B9-8)

(B9-9)

The compounds of the formula (B9) are tautomers of the compounds of the formulae (B13) and (B14) if $Q^9$=OH or OM and $R^{25}$=$R^{31}$ and $R^{26}$=$R^{32}$.

Preference is also given to compounds (I) in which $B^1$ represents a radical (B10)

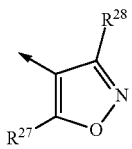
(B10)

in which
R$^{27}$ and R$^{28}$ have the meanings or preferred meanings mentioned above, preferably
R$^{27}$ represents H, (C$_1$-C$_4$)-alkyl, (C$_1$-C$_4$)-haloalkyl or (C$_3$-C$_6$)-cycloalkyl, for example cyclopropyl,
R$^{28}$ represents H, (C$_1$-C$_4$)-alkyl, (C$_1$-C$_4$)-haloalkyl or a radical of the formula C(O)OR$^{66}$, and
R$^{66}$ represents hydrogen, (C$_1$-C$_4$)-alkyl, (C$_1$-C$_4$)-haloalkyl, (C$_3$-C$_6$)-cycloalkyl, (C$_3$-C$_6$)-halocycloalkyl, (C$_2$-C$_4$)-alkenyl, (C$_2$-C$_4$)-haloalkenyl, (C$_2$-C$_4$)-alkynyl or the group M mentioned, preferably hydrogen, (C$_1$-C$_3$)-alkyl or the group M mentioned.

Examples of preferred radicals B$^1$ of the formula (B10) are radicals of the formulae (B10-1), (B10-2), (B10-3) and (B10-4):

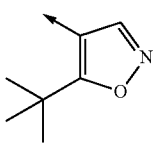
(B10-1)

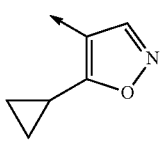
(B10-2)

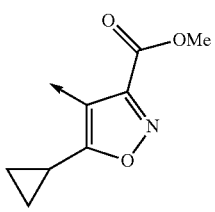
(B10-3)

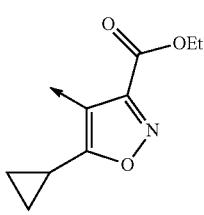
(B10-4)

Preference is also given to compounds (I) in which B$^1$ represents a radical (B11)

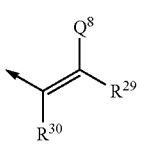
(B11)

in which
Q$^8$, R$^{29}$ and R$^{30}$ have the meanings or preferred meanings mentioned above, preferably
Q$^8$ represents hydroxy, halogen or a group of the formula OR$^{37}$, SR$^{38}$ or OM, in particular hydroxy,
R$^{29}$ represents H, (C$_1$-C$_4$)-alkyl, (C$_1$-C$_4$)-haloalkyl, (C$_3$-C$_6$)-cycloalkyl, for example cyclopropyl, (C$_1$-C$_4$)-alkoxy or (C$_1$-C$_4$)-haloalkoxy,
R$^{30}$ represents H, halogen, cyano, (C$_1$-C$_4$)-alkyl, (C$_1$-C$_4$)-haloalkyl, (C$_3$-C$_6$)-cycloalkyl, for example cyclopropyl, (C$_1$-C$_4$)-alkoxy or (C$_1$-C$_4$)-haloalkoxy.

Examples of preferred radicals B$^1$ of the formula (B11) are radicals of the formulae (B11-1) and (B11-2):

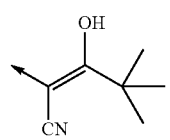
(B11-1)

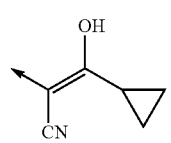
(B11-2)

Preference is also given to compounds (I) in which B$^1$ represents a radical (B13)

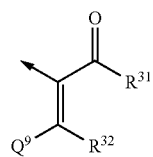
(B13)

in which
Q$^9$, R$^{31}$ and R$^{32}$ have the meanings or preferred meanings mentioned above, preferably
Q$^9$ represents hydroxy, halogen or a group of the formula OR$^{37}$, SR$^{38}$ or OM, in particular hydroxy,
R$^{31}$ and R$^{32}$ independently of one another each represent H, (C$_1$-C$_4$)-alkyl, (C$_1$-C$_4$)-haloalkyl, (C$_1$-C$_4$)-alkoxy, (C$_1$-C$_4$)-haloalkoxy, (C$_1$-C$_4$)-alkoxy-(C$_1$-C$_4$)-alkyl, (C$_1$-C$_4$)-haloalkoxy-(C$_1$-C$_4$)-alkyl, (C$_3$-C$_6$)-cycloalkyl, (C$_3$-C$_6$)-halocycloalkyl, (C$_3$-C$_6$)-cycloalkoxy, (C$_1$-C$_4$)-alkylthio, (C$_1$-C$_4$)-alkylsulphonyl, (C$_1$-C$_4$)-alkylsulphinyl, NR$^{64}$R$^{65}$ or Het$^{11}$, in particular H, (C$_1$-C$_4$)-alkyl, (C$_1$-C$_4$)-haloalkyl, (C$_1$-C$_4$)-alkoxy, (C$_1$-C$_4$)-haloalkoxy, (C$_1$-C$_4$)-alkoxy-(C$_1$-C$_4$)-alkyl, (C$_1$-C$_4$)-haloalkoxy-(C$_1$-C$_4$)-alkyl, (C$_3$-C$_6$)-cycloalkyl, (C$_3$-C$_6$)-halocycloalkyl, (C$_3$-C$_6$)-cycloalkoxy, (C$_1$-C$_4$)-alkylthio.

Examples of preferred radicals B$^1$ of the formula (B13) are radicals of the formulae (B13-1), (B13-2), (B13-3), (B13-4), (B13-5), (B13-6), (B13-7), (B13-8) and (B13-9):

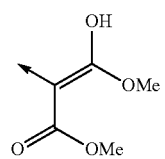
(B13-1)

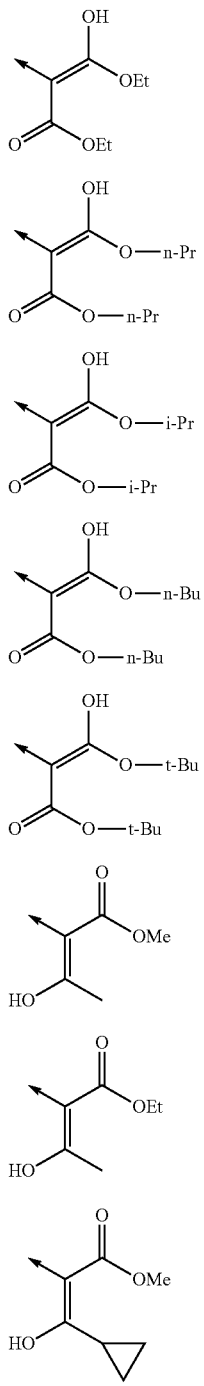

(B13-2)
(B13-3)
(B13-4)
(B13-5)
(B13-6)
(B13-7)
(B13-8)
(B13-9)

Preference is also given to compounds (I) in which
L represents a radical of the formula

$A^2$ represents a radical of the formulae (A1) to (A12) mentioned, $B^2$ represents hydroxy, thio, halogen or a group of the formula $OR^{33}$, OM, $SR^{34}$, SM or —$NR^B R^C$, preferably hydroxy, halogen or a group of the formula $OR^{33}$, OM, $SR^{34}$ or —$NR^B R^C$, $R^B$ and $R^C$ independently of one another have the meaning mentioned above, preferably independently of one another represent hydrogen, hydroxy, ($C_1$-$C_4$)-alkoxy, ($C_1$-$C_4$)-alkyl, ($C_1$-$C_4$)-haloalkyl, phenyl which is unsubstituted or substituted by one or more radicals from the group consisting of halogen, ($C_1$-$C_4$)-alkyl, ($C_1$-$C_4$)-haloalkyl, ($C_1$-$C_4$)-alkoxy, ($C_1$-$C_4$)-haloalkoxy, or benzyl which is unsubstituted in the phenyl moiety or substituted by one or more radicals from the group consisting of halogen, ($C_1$-$C_4$)-alkyl, ($C_1$-$C_4$)-haloalkyl, ($C_1$-$C_4$)-alkoxy, ($C_1$-$C_4$)-haloalkoxy, or —NR*R**, where R*, R** independently of one another each represent H, ($C_1$-$C_4$)-alkyl, ($C_2$-$C_4$)-alkenyl, ($C_2$-$C_4$)-alkynyl, ($C_1$-$C_4$)-alkoxy-($C_1$-$C_4$)-alkyl, ($C_1$-$C_4$)-alkanoyl, [($C_1$-$C_4$)-haloalkyl]carbonyl, [($C_1$-$C_4$)-alkoxy]carbonyl, [($C_1$-$C_4$)-haloalkoxy]carbonyl, ($C_3$-$C_6$)-cycloalkyl, ($C_3$-$C_6$)-cycloalkyl-($C_1$-$C_4$)-alkyl, phenyl, phenyl-($C_1$-$C_4$)alkyl, where each of the 4 last-mentioned radicals is unsubstituted in the cycle or substituted by one or more radicals from the group consisting of halogen, ($C_1$-$C_4$)-alkyl, ($C_1$-$C_4$)-haloalkyl, ($C_1$-$C_4$)-alkoxy or ($C_1$-$C_4$)-haloalkoxy or, in the case of cycloalkyl, also oxo, or R* and R** together with the nitrogen atom represent a 3- to 6-membered and preferably saturated heterocycle which, in addition to the nitrogen atom, may contain one or two further ring heteroatoms from the group consisting of N, O and S and which may be unsubstituted or substituted by one or more radicals from the group consisting of ($C_1$-$C_4$)-alkyl, ($C_1$-$C_4$)-haloalkyl and oxo, or in particular $R^B$ represents hydrogen, hydroxy, ($C_1$-$C_4$)-alkoxy, ($C_1$-$C_4$)-alkyl, phenyl, benzyl or —NR*R**, where R*, R** independently of one another each represent H or ($C_1$-$C_4$)-alkyl, and $R^C$ represents hydrogen, ($C_1$-$C_4$)-alkyl, phenyl or benzyl or the group —$NR^B R^C$ represents a radical of the formula —$NH_2$, —NHOH, —$NHOCH_3$, —$NHCH_3$, —$N(CH_3)_2$, —NH—$NH_2$ or —NH—$N(CH_3)_2$, $(R^1)_m$, $(R^2)_n$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$ and $R^{26}$ have the meanings or preferred meanings mentioned above, $W^1$ and $W^6$ independently of one another each represent the divalent group oxygen, sulphur or a group of the formula NH, N—[($C_1$-$C_4$)-alkyl], C=O, S=O, $SO_2$ or $CR^{35}R^{36}$, $W^2$, $W^3$, $W^4$, $W^5$ and $W^7$ independently of one another each represent the divalent group of the formula O, S, NH, N—[($C_1$-$C_4$)-alkyl], C=O, S=O or $SO_2$, $R^{33}$, $R^{34}$ and M have the meanings or preferred meanings mentioned above, preferably $R^{33}$ and $R^{34}$ independently of one another each represent ($C_1$-$C_4$)-alkyl, ($C_1$-$C_4$)-haloalkyl, ($C_1$-$C_4$)-alkoxy-($C_1$-$C_4$)-alkyl, ($C_3$-$C_6$)-cycloalkyl which is unsubstituted or substituted by one or more radicals from the group consisting of halogen, ($C_1$-$C_4$)-alkyl and ($C_1$-$C_4$)-alkoxy, phenyl which is unsubstituted or substituted by one or more radicals from the group consisting of halogen, cyano, hydroxy, nitro, ($C_1$-$C_4$)-alkyl, ($C_1$-$C_4$)-haloalkyl and ($C_1$-$C_4$)-alkoxy, or a group of the formula —$C(O)R^{67}$, —$O(O)OR^{68}$, —$C(O)NR^{69}R^{70}$, —$C(O)Het^{12}$ or —$SO_2R^{71}$, in particular $R^{33}$ and $R^{34}$ independently of one another each represent $(C_1-C_6)$-alkyl, $(C_1-C_4)$-haloalkyl, $(C_3-C_6)$-cycloalkyl, $(C_3-C_6)$-halocycloalkyl, phenyl which is unsubstituted or substituted by one or more radicals from the group consisting of halogen and $(C_1-C_4)$-alkyl, or a group of the formula —C(O)$R^{67}$, —C(O)O$R^{68}$, —C(O)N$R^{69}R^{70}$, —C(O)Het$^{12}$ or —SO$_2R^{71}$, $R^{35}$ and $R^{36}$ independently of one another are each as defined for $R^3$ or preferably independently of one another represent H, $(C_1-C_4)$-alkyl or $(C_1-C_4)$-haloalkyl, in particular H or $(C_1-C_2)$-alkyl, in particular H, methyl or ethyl, $R^{67}$ represents hydrogen, $(C_1-C_6)$-alkyl, $(C_1-C_4)$-haloalkyl, phenyl or benzyl, where each of the 2 last-mentioned radicals independently of the other is unsubstituted or substituted by one or more radicals from the group consisting of halogen, cyano, $(C_1-C_4)$-alkyl and $(C_1-C_4)$-haloalkyl, in particular H or $(C_1-C_4)$-alkyl, $R^{68}$ is $(C_1-C_6)$-alkyl or $(C_1-C_4)$-haloalkyl, in particular $(C_1-C_4)$-alkyl, $R^{69}$ and $R^{70}$ independently of one another each represent hydrogen, $(C_1-C_4)$-alkyl, benzyl, $(C_3-C_6)$-cycloalkyl or phenyl, where each of the 2 last-mentioned radicals independently of the other is unsubstituted or substituted by one or more radicals from the group consisting of halogen, nitro, cyano, $(C_1-C_4)$-alkyl and $(C_1-C_4)$-haloalkyl or in particular independently of one another each represent H or $(C_1-C_3)$-alkyl, $R^{71}$ represents $(C_1-C_4)$-alkyl, $(C_1-C_4)$-haloalkyl, phenyl or benzyl, where each of the 2 last-mentioned radicals independently of the other is unsubstituted or substituted by one or more radicals from the group consisting of halogen, cyano, $(C_1-C_4)$-alkyl, $(C_2-C_4)$-alkenyl and $(C_1-C_4)$-haloalkyl, in particular $(C_1-C_4)$-alkyl, $(C_1-C_4)$-haloalkyl, benzyl or phenyl which is unsubstituted or substituted by one or more radicals from the group consisting of halogen, $(C_1-C_4)$-alkyl and $(C_1-C_4)$-haloalkyl, Het$^{12}$ represents a saturated or partially unsaturated radical of a heterocycle having 3 to 6 ring atoms and at least one nitrogen atom as ring heteroatom at position 1 of the ring and optionally 1, 2 or 3 further ring heteroatoms from the group consisting of N, O and S, where the radical of the heterocycle at the nitrogen atom in position 1 of the ring is attached to the remainder of the molecule of the compound of the formula (I) and where the heterocycle is unsubstituted or substituted by one or more radicals from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo, in particular unsubstituted or substituted by one or more radicals from the group consisting of $(C_1-C_4)$-alkyl and $(C_1-C_4)$-haloalkyl, in particular a morpholino, piperidino or pyrrolidino group.

Preference is also given to compounds (I) in which $A^2$ represents a radical of the formulae (A1) to (A12) mentioned, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ independently of one another each represent H, halogen, cyano, nitro, hydroxy, $(C_1-C_4)$-alkyl, $(C_1-C_4)$-haloalkyl, $(C_3-C_6)$-cycloalkyl, $(C_1-C_4)$-alkoxy or $(C_1-C_4)$-haloalkoxy, in particular H or $(C_1-C_4)$-alkyl, or $R^3$ and $R^5$ in the group of the formula (A1) together represent a divalent bridge as defined above, $R^{21}$ represents H, $(C_1-C_4)$-alkyl, $(C_1-C_4)$-haloalkyl, $(C_3-C_6)$-cycloalkyl, $(C_3-C_6)$-halocycloalkyl or a group C(O)O$R^{54}$, C(O)N$R^{55}R^{56}$, C(O)Het$^7$, N$R^{57}R^{58}$ or Het$^8$, preferably $(C_1-C_4)$-alkyl, $(C_1-C_4)$-haloalkyl, $(C_3-C_6)$-cycloalkyl or a group C(O)O$R^{54}$, $R^{22}$ represents H, $(C_1-C_4)$-alkyl, $(C_1-C_4)$-haloalkyl, $(C_3-C_6)$-cycloalkyl, $(C_3-C_6)$-halocycloalkyl, $(C_1-C_4)$-alkylthio, $(C_1-C_4)$-alkylsulphonyl or a group of the formula C(O)O$R^{59}$, C(O)N$R^{60}R^{61}$, C(O)Het$^9$, N$R^{62}R^{63}$ or Het$^{10}$, preferably $(C_1-C_4)$-alkyl, $(C_1-C_4)$-haloalkyl, $(C_3-C_6)$-cycloalkyl, $(C_1-C_4)$-alkylsulphonyl or a group C(O)O$R^{59}$, $R^{23}$ represents H, $(C_1-C_4)$-alkyl, $(C_1-C_4)$-haloalkyl, $(C_3-C_6)$-cycloalkyl, $(C_3-C_6)$-halocycloalkyl, $(C_1-C_4)$-alkoxy or $(C_1-C_4)$-haloalkoxy, preferably H, $(C_1-C_4)$-alkyl, $(C_1-C_4)$-haloalkyl, $(C_3-C_6)$-cycloalkyl, for example cyclopropyl, $(C_1-C_4)$-alkoxy or $(C_1-C_2)$-haloalkoxy, $R^{24}$ represents H, halogen, cyano, $(C_1-C_4)$-alkyl, $(C_1-C_4)$-haloalkyl, $(C_3-C_6)$-cycloalkyl, $(C_1-C_4)$-alkoxy or $(C_1-C_4)$-haloalkoxy, preferably H, halogen, cyano, $(C_1-C_4)$-alkyl, $(C_1-C_4)$-haloalkyl, $(C_3-C_6)$-cycloalkyl, for example cyclopropyl, $(C_1-C_4)$-alkoxy or $(C_1-C_2)$-haloalkoxy, $R^{25}$ and $R^{26}$ independently of one another each represent H, $(C_1-C_4)$-alkyl, $(C_1-C_4)$-haloalkyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_3-C_6)$-cycloalkyl, $(C_3-C_6)$-cycloalkoxy, $(C_2-C_6)$-alkenyl, $(C_2-C_6)$-alkynyl, $(C_1-C_4)$-alkylthio, $(C_1-C_4)$-alkylsulphonyl, N$R^{64}R^{65}$ or Het$^{11}$, preferably H, $(C_1-C_4)$-alkyl, $(C_1-C_4)$-haloalkyl, $(C_1-C_4)$-alkoxy, $(C_1-C_4)$-haloalkoxy, $(C_1-C_2)$-alkoxy-$(C_1-C_2)$-alkyl, $(C_1-C_2)$-haloalkoxy-$(C_1-C_2)$-alkyl or $(C_3-C_6)$-cycloalkyl, for example cyclopropyl, $R^{54}$ and $R^{59}$ independently of one another each represent H, $(C_1-C_4)$-alkyl, $(C_1-C_4)$-haloalkyl, $(C_3-C_6)$-cycloalkyl, $(C_2-C_4)$-alkenyl, $(C_2-C_4)$-alkynyl or the group M mentioned, $R^{55}$, $R^{56}$, $R^{57}$, $R^{58}$, $R^{60}$, $R^{61}$, $R^{62}$, $R^{63}$, $R^{64}$ and $R^{65}$ independently of one another each represent H, $(C_1-C_4)$-alkyl which is unsubstituted or substituted by one or more radicals from the group consisting of halogen, nitro, cyano and phenyl which is unsubstituted or substituted by one or more radicals from the group consisting of halogen, nitro, cyano, $(C_1-C_4)$-alkyl and $(C_1-C_4)$-haloalkyl, or $(C_3-C_6)$-cycloalkyl which is unsubstituted or substituted by one or more radicals from the group consisting of halogen and $(C_1-C_4)$-alkyl and $(C_1-C_4)$-haloalkyl, or phenyl which is unsubstituted or substituted by one or more radicals from the group consisting of halogen, nitro, cyano, $(C_1-C_4)$-alkyl and $(C_1-C_4)$-haloalkyl, Het$^7$, Het$^8$, Het$^9$, Het$^{10}$ and Het$^{11}$ independently of one another each represent a saturated or partially unsaturated radical of a heterocycle having 3 to 6 ring atoms and at least one nitrogen atom as ring heteroatom at position 1 of the ring and optionally 1, 2 or 3 further ring heteroatoms from the group consisting of N, O and S, where the radical of the heterocycle at the nitrogen atom in position 1 of the ring is attached to the remainder of the molecule of the compound of the formula (I) and where the heterocycle is unsubstituted or substituted by one or more radicals from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo, in particular unsubstituted or substituted by one or more radicals from the group consisting of $(C_1-C_4)$-alkyl and $(C_1-C_4)$-haloalkyl, in particular a morpholino, piperidino or pyrrolidino group.

Here, preference is given to compounds (I) in which $A^2$ represents one of the radicals (A1) to (A12) and $B^2$ represents hydroxy, thio, halogen or a group of the formula O$R^{33}$, S$R^{34}$, SM or OM, in particular hydroxy, halogen or a group of the formula O$R^{33}$, S$R^{34}$ or OM, more preferably hydroxy, $R^{33}$, $R^{34}$ and M have the meanings or preferred meanings mentioned above, preferably $R^{33}$ and $R^{34}$ independently of one another each represent $(C_1-C_6)$-alkyl, $(C_1-C_6)$-haloalkyl, $(C_1-C_4)$-alkoxy-$(C_1-C_4)$-alkyl, $(C_3-C_6)$-cycloalkyl which is unsubstituted or substituted by one or more radicals from the group consisting of halogen, $(C_1-C_4)$-alkyl and $(C_1-C_4)$-alkoxy, phenyl which is unsubstituted or substituted by one or more radicals from the group consisting of halogen, cyano, hydroxy, nitro, $(C_1-C_4)$-alkyl, $(C_1-C_4)$-haloalkyl and $(C_1-C_4)$-alkoxy, or a group of the formula —C(O)$R^{67}$, —C(O)O$R^{68}$, —C(O)N$R^{69}R^{70}$, —C(O)Het$^{12}$ or —SO$_2R^{71}$, in particular $R^{37}$ and $R^{38}$ independently of one another each represent $(C_1-C_6)$-alkyl, $(C_1-C_4)$-haloalkyl, $(C_3-C_6)$-cycloalkyl, $(C_3-C_6)$-halocycloalkyl, phenyl which is unsubstituted or substituted by one or more radicals from the group consisting of halogen and $(C_1-C_4)$-alkyl, or a group of the formula —C(O)$R^{67}$, —C(O)O$R^{68}$, —C(O)N$R^{69}R^{70}$, —C(O)Het$^{12}$ or —SO$_2R^{71}$, more preferably, $R^{37}$ and $R^{38}$ independently of one another each represent $(C_1-C_4)$-alkyl, phenyl which is unsubstituted or substituted by one or more radicals from the group consisting of halogen and $(C_1-C_4)$-alkyl, or a group of the formula —C(O)$R^{67}$, —C(O)O$R^{68}$ or —SO$_2R^{71}$, $R^{67}$ represents hydrogen, $(C_1-C_6)$-alkyl, $(C_1-C_4)$-haloalkyl, phenyl or benzyl, where each of the 2 last-mentioned radicals independently of the other is unsubstituted or substituted by one or more radicals from the group consisting of halogen, cyano, $(C_1-C_4)$-alkyl and $(C_1-C_4)$-haloalkyl, in particular H or $(C_1-C_4)$-alkyl, for example H, methyl, ethyl, n-propyl, isopropyl, n-butyl, sec-butyl, isobutyl or t-butyl, $R^{68}$ is $(C_1-C_6)$-alkyl or $(C_1-C_4)$-haloalkyl, in particular $(C_1-C_4)$-alkyl, $R^{69}$ and $R^{70}$ independently of one another each represent hydrogen, $(C_1-C_4)$-alkyl, benzyl, $(C_3-C_6)$-cycloalkyl or phenyl, where each of the 2 last-mentioned radicals independently of the other is unsubstituted or substituted by one or more radicals from the group consisting of halogen, nitro, cyano, $(C_1-C_4)$-alkyl and $(C_1-C_4)$-haloalkyl or in particular independently of one another each represent H or $(C_1-C_3)$-alkyl, $R^{71}$ represents $(C_1-C_4)$-alkyl, $(C_1-C_4)$-haloalkyl, phenyl or benzyl, where each of the 2 last-mentioned radicals independently of the other is unsubstituted or substituted by one or more radicals from the group consisting of halogen, cyano, $(C_1-C_4)$-alkyl, $(C_2-C_4)$-alkenyl and $(C_1-C_4)$-haloalkyl, in particular $(C_1-C_4)$-alkyl, $(C_1-C_4)$-haloalkyl, benzyl or phenyl which is unsubstituted or substituted by one or more radicals from the group consisting of halogen, $(C_1-C_4)$-alkyl and $(C_1-C_4)$-haloalkyl, Het$^{12}$ represents a morpholino, piperidino or pyrrolidino group, and M represents an equivalent of a cation, preferably a metal ion equivalent, an ammonium ion which is optionally substituted by 1 to 4 identical or different radicals from the group consisting of $(C_1-C_4)$-alkyl, $(C_3-C_6)$-cycloalkyl, phenyl, $(C_3-C_6)$-cycloalkyl-$(C_1-C_4)$-alkyl and phenyl-$(C_1-C_4)$-alkyl, in particular $(C_1-C_4)$-alkyl, or a tertiary sulphonium ion which is preferably substituted by 3 identical or different radicals from the group consisting of $(C_1-C_4)$-alkyl, $(C_3-C_6)$-cycloalkyl, phenyl, $(C_3-C_6)$-cycloalkyl-$(C_1-C_4)$-alkyl and phenyl-$(C_1-C_4)$-alkyl, in particular $(C_1-C_4)$-alkyl.

Here, preference is given to compounds (I) in which $A^2$ represents a radical (A1)

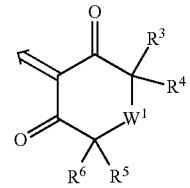

(A1)

in which $W^1$, $R^3$, $R^4$, $R^5$ and $R^6$ have the meanings or preferred meanings mentioned above, preferably $W^1$ represents the divalent group of the formula O, S, NH, N—[$(C_1-C_4)$-alkyl], C=O, S=O, SO$_2$ or C$R^{35}R^{36}$, in particular the divalent group of the formula O, S, C=O or C$R^{35}R^{36}$, where $R^{35}$ and $R^{36}$ independently of one another each represent hydrogen, $(C_1-C_4)$-alkyl or $(C_1-C_4)$-haloalkyl, in particular $W^1$ represents the divalent group C(O), CH$_2$, CH(CH$_3$) or C(CH$_3$)$_2$, $R^3$, $R^4$, $R^5$ and $R^6$ independently of one another each represent H, halogen, cyano, nitro, hydroxy, $(C_1-C_4)$-alkyl, $(C_1-C_4)$-haloalkyl, $(C_1-C_4)$-alkoxy or $(C_1-C_4)$-haloalkoxy, in particular H or $(C_1-C_4)$-alkyl or $R^3$ and $R^5$ together represent a divalent bridge of the formula —CH$_2$CH$_2$—, —CH$_2$CH$_2$CH$_2$—, —CH(CH$_3$)CH$_2$—, —C(CH$_3$)$_2$CH$_2$—, —CH$_2$CH(CH$_3$)—, —CH$_2$C(CH$_3$)$_2$—, —C(CH$_3$)CH(CH$_3$)—, —CH$_2$CH$_2$CH$_2$—, —CH=CH—, —CH=CHCH$_2$—, —CH$_2$CH=CH—, —OCH$_2$—, —CH$_2$O—, —OCH$_2$CH$_2$—, —CH$_2$OCH$_2$—, —CH$_2$CH$_2$O— or —OCH$_2$O—, in particular of the formula —CH$_2$CH$_2$— or —CH=CH—.

Examples of preferred radicals $A^2$ of the formula (A1) are radicals of the formulae (A1-1) to (A1-9):

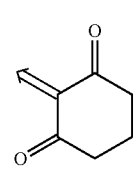

(A1-1)

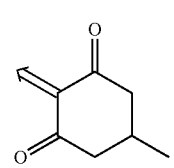

(A1-2)

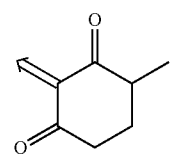

(A1-3)

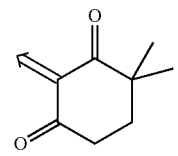

(A1-4)

-continued

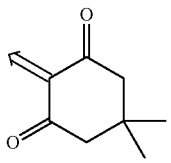 (A1-5)

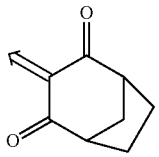 (A1-6)

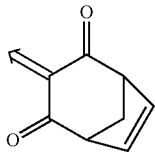 (A1-7)

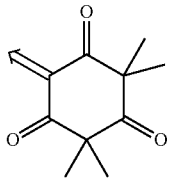 (A1-8)

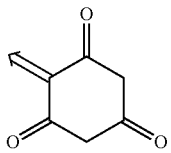 (A1-9)

In the case of the radicals (A1) substituted asymmetrically to the C—C double bond, such as (A1-3) and (A1-4), preference is also given to corresponding double bond isomers embraced by the general formula (A1).

Preference is also given to compounds (I) in which $A^2$ represents a radical (A5)

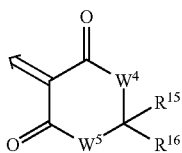 (A5)

in which
W$^4$, W$^5$, R$^{15}$ and R$^{16}$ have the meanings or preferred meanings mentioned above, preferably
W$^4$ and W$^5$ each independently of one another represent the divalent group of the formula O, S, NH, N—[($C_1$-$C_4$)-alkyl], C=O, S=O or SO$_2$, in particular the divalent group of the formula O or S, in particular O and
R$^{15}$ and R$^{16}$ independently of one another each represent H, halogen, cyano, nitro, hydroxy, ($C_1$-$C_4$)-alkyl, ($C_1$-$C_4$)-haloalkyl, ($C_1$-$C_4$)-alkoxy or ($C_1$-$C_4$)-haloalkoxy, in particular hydrogen or ($C_1$-$C_4$)-alkyl.

An example of preferred radicals $A^2$ of the formula (A5) is the radical of the formula (A5-1):

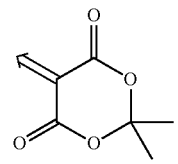 (A5-1)

Preference is also given to compounds (I) in which $A^2$ represents a radical (A6) or (A7)

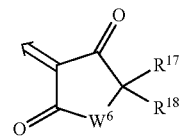 (A6)

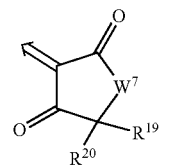 (A7)

in which
W$^6$, W$^7$, R$^{17}$, R$^{18}$, R$^{19}$ and R$^{20}$ have the meanings or preferred meanings mentioned above, preferably
W$^6$ represents the divalent group of the formula O, S, NH, N—[($C_1$-$C_4$)-alkyl], C=O, S=O, SO$_2$ or CR$^{35}$R$^{36}$, in particular the divalent group of the formula O, S, NH, N—[($C_1$-$C_4$)-alkyl] or a group of the formula CR$^{35}$R$^{36}$, more preferably O, NH, N—CH$_3$, N—C$_2$H$_5$ or a group of the formula CH$_2$, CH(CH$_3$), CH(C$_2$H$_5$) or C(CH$_3$)$_2$, very particularly O or CH$_2$,
where R$^{35}$ and R$^{36}$ independently of one another each represent hydrogen, ($C_1$-$C_4$)-alkyl or ($C_1$-$C_4$)-haloalkyl,
in particular W$^6$ represents the divalent group CH$_2$, CH(CH$_3$) or C(CH$_3$)$_2$,
W$^7$ represents the divalent group of the formula O, S, NH, N—[($C_1$-$C_4$)-alkyl], C=O, S=O or SO$_2$, in particular the divalent group of the formula O, S, NH or N—[($C_1$-$C_4$)-alkyl], in particular O and
R$^{17}$, R$^{18}$, R$^{19}$ and R$^{20}$ independently of one another each represent H, halogen, cyano, nitro, hydroxy, ($C_1$-$C_4$)-alkyl, ($C_1$-$C_4$)-haloalkyl, ($C_1$-$C_4$)-alkoxy or ($C_1$-$C_4$)-haloalkoxy, in particular H or ($C_1$-$C_4$)-alkyl.

Examples of preferred radicals $A^2$ of the formula (A6) are radicals of the formulae (A6-1) to (A6-11):

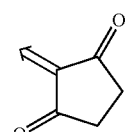 (A6-1)

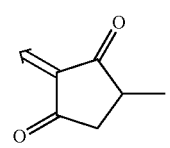 (A6-2)

-continued (A6-3) 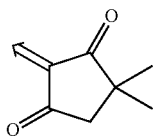

(A6-4) 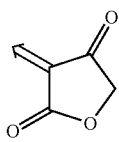

(A6-5) 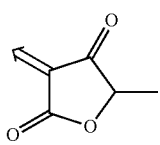

(A6-6) 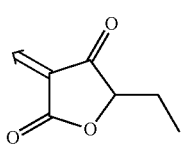

(A6-7) 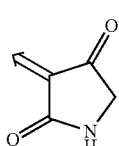

(A6-8) 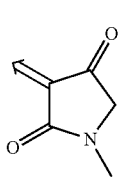

(A6-9) 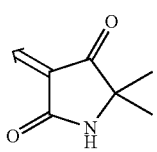

(A6-10) 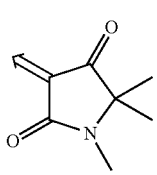

(A6-11) 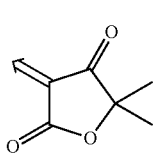

Preferred radicals $A^2$ of the formula (A7) are corresponding radicals of the formulae (A7-4) to (A7-11) (formulae not shown) which represent double bond isomers with respect to the double bond drawn as arrow of the radicals of the formulae (A6-4) to (A6-11).

In the case of the radicals (A6) substituted asymmetrically to the C—C double bond, such as (A6-2) and (A6-3), preference is also given to corresponding double bond isomers embraced by the general formula (A6).

Preference is also given to compounds (I) in which $A^2$ represents a radical (A8) or (A9)

(A8)

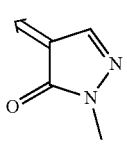

(A9)

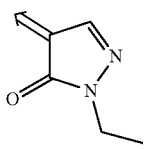

in which $R^{21}$ and $R^{22}$ have the meanings or preferred meanings mentioned above, preferably $R^{21}$ represents hydrogen, $(C_1-C_4)$-alkyl, $(C_1-C_4)$-haloalkyl, $(C_3-C_6)$-cycloalkyl, $(C_3-C_6)$-halocycloalkyl or a group $C(O)OR^{54}$, $C(O)NR^{55}R^{56}$, $C(O)Het^7$, $NR^{57}R^{58}$ or $Het^8$, in particular H, $(C_1-C_4)$-alkyl, $(C_1-C_4)$-haloalkyl or $(C_3-C_6)$-cycloalkyl, for example cyclopropyl, and $R^{22}$ represents hydrogen, $(C_1-C_4)$-alkyl, $(C_1-C_4)$-haloalkyl, $(C_3-C_6)$-cycloalkyl, $(C_3-C_6)$-halocycloalkyl, $(C_1-C_4)$-alkylthio, $(C_1-C_4)$-alkylsulphonyl, $(C_1-C_4)$-alkylsulphinyl or a group of the formula $C(O)OR^{59}$, $C(O)NR^{60}R^{61}$, $C(O)Het^9$, $NR^{62}R^{63}$ or $Het^{10}$, in particular H, $(C_1-C_4)$-alkyl, $(C_1-C_4)$-haloalkyl, $(C_3-C_6)$-cycloalkyl, $(C_3-C_6)$-halocycloalkyl, $(C_1-C_4)$-alkylthio or $(C_1-C_4)$-alkylsulphonyl.

Examples of preferred radicals $A^2$ of the formula (A8) are radicals of the formulae (A8-1) to (A8-5):

(A8-1)

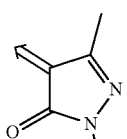

(A8-2)

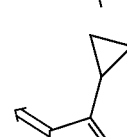

(A8-3)

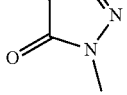

(A8-4)

-continued (A8-5)

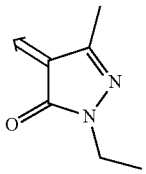

Preferred radicals A² of the formula (A9) are corresponding radicals of the formulae (A9-1) to (A9-5) (formulae not shown) which represent double bond isomers with respect to the double bond drawn as arrow of the radicals of the formulae (A8-1) to (A8-5).

Preference is also given to compounds (I) in which A² represents a radical (A10) or (A11)

(A10)

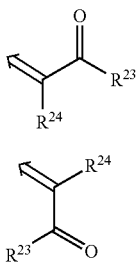

(A11)

in which

R²³ represents H, $(C_1-C_4)$-alkyl, $(C_1-C_4)$-haloalkyl, $(C_3-C_6)$-cycloalkyl, for example cyclopropyl, $(C_1-C_4)$-alkoxy or $(C_1-C_4)$-haloalkoxy, more preferably methyl, ethyl, n-propyl, isopropyl, n-butyl, isobutyl, s-butyl, t-butyl, methoxy, ethoxy, n-propoxy, isopropoxy, n-butoxy, isobutoxy, s-butoxy or t-butoxy, and R²⁴ represents H, halogen, cyano, $(C_1-C_4)$-alkyl, $(C_1-C_4)$-haloalkyl, $(C_3-C_6)$-cycloalkyl, for example cyclopropyl, $(C_1-C_4)$-alkoxy or $(C_1-C_4)$-haloalkoxy, in particular hydrogen, $(C_1-C_3)$-alkyl, cyano or cyclopropyl, more preferably cyano.

Examples of preferred radicals A² of the formula (A10) are the radicals of the formulae (A10-1), (A10-2), (A10-3), (A10-4), (A10-5), (A10-6), (A10-7), (A10-8) and (A10-9):

(A10-1)

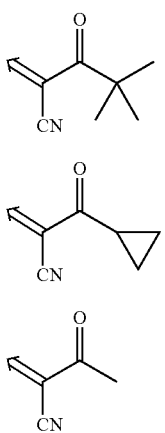

(A10-2)

(A10-3)

(A10-4)

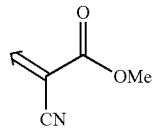

(A10-5)

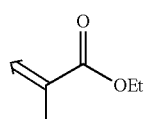

(A10-6)

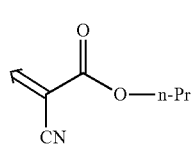

(A10-7)

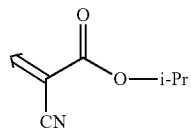

(A10-8)

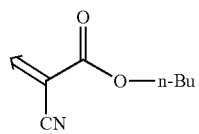

(A10-9)

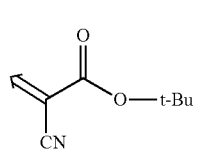

Preferred radicals A² of the formula (A11) are corresponding radicals of the formulae (A11-1) to (A11-9) (formulae not shown) which represent double bond isomers with respect to the double bond drawn as arrow of the radicals of the formulae (A10-1) to (A10-9).

Preference is also given to compounds (I) in which A² represents a radical (A12)

(A12)

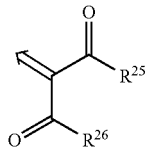

in which

R²⁵ and R²⁶ independently of one another each represent H, $(C_1-C_4)$-alkyl, $(C_1-C_4)$-haloalkyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_3-C_6)$-cycloalkyl, $(C_3-C_6)$-halocycloalkyl, $(C_3-C_6)$-cycloalkoxy, $(C_1-C_4)$-alkylthio, $(C_1-C_4)$-alkylsulphonyl, $(C_1-C_4)$-alkylsulphinyl, $NR^{64}R^{65}$ or $Het^{11}$, in particular H, $(C_1-C_4)$-alkyl, $(C_1-C_4)$-haloalkyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_3-C_6)$-cycloalkyl, $(C_3-C_6)$-halocycloalkyl, $(C_3-C_6)$-cycloalkoxy, $(C_1-C_4)$-alkylthio.

Examples of preferred radicals A² of the formula (A12) are radicals of the formulae (A12-1) to (A12-9):

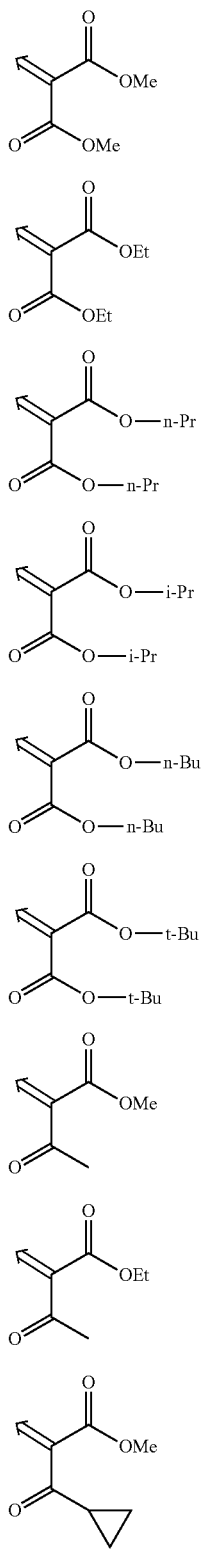

(A12-1)
(A12-2)
(A12-3)
(A12-4)
(A12-5)
(A12-6)
(A12-7)
(A12-8)
(A12-9)

In the case of the radicals (A12) substituted asymmetrically to the C—C double bond, such as (A12-7), (A12-8) and (A12-9), preference also is given to corresponding double bond isomers embraced by the general formula (A12).

The compounds of the formula (I) according to the invention include all stereoisomers which can occur on the basis of the centres of asymmetry or double bonds in the molecule whose configuration is not designated specifically in the formula or which are not specified explicitly, and mixtures thereof, including the racemic compounds and the mixtures enriched partly with particular stereoisomers. The invention also includes all tautomers, such as keto and enol tautomers, and their mixtures and salts, if appropriate functional groups are present.

The present invention also provides processes for preparing the compounds of the general formula (I) and/or their salts. This includes processes which can be carried out analogously to known methods.

(a) By way of example, compounds of the formula (I) and salts thereof, in which L represents a radical of the formula $C(=A^1)\text{-}B^1$, $B^1$ represents a radical of the formulae (B1) to (B9) and (B11) to (B14) and $Q^1$ to $Q^9$ each represent OH, SH, SM or OM and the other radicals are as defined in the respective compound of the formula (I) to be prepared, are obtained according to a process [variant (a)], characterized in that a compound of the formula (II)

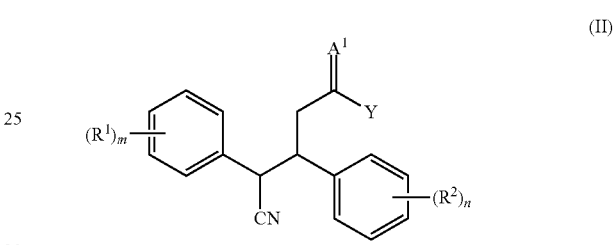

(II)

in which $A^1$, $(R^1)_m$ and $(R^2)_n$ are as defined in formula (I) and Y represents a leaving group, preferably a halogen atom, in particular a chlorine atom, is reacted directly with a compound of the formula H—$B^1$ in which $B^1$ is as defined in the radical L and $Q^1$ to $Q^9$ are each as defined in the compound of the formula (I) to be prepared, to give the compound (I), or to give the O- or S-alkylation product as intermediate, and the O- or S-alkylation intermediate formed is rearranged to give the compound of the formula (I) as C-alkylation product [see the scheme further below where the reactant of the formula (H—B1*) is used as an example for compound H—$B^1$].

According to variant (a), the reactants preferably used are compounds of the formula H—$B^1$, and compounds of the formula (I) are prepared in which $Q^1$ to $Q^9$ in group $B^1$ each represent the radical OH or OM.

The C—C-acylations can be carried out analogously to known processes as base-catalysed reactions of one or more steps.

Analogous one-step processes using bases such as calcium hydroxide are known, for example, from B. S. Jensen, Acta Chem. Scand. 1959, Vol. 13, p. 1668 (see the scheme below for the preparation of the compound (I-A)).

Analogous one-step processes using bases such as sodium hydride have been described, for example, by Mulrooney et al., J. Org. Chem. 75, 2010, 16, and Yadav et al. Chem. Lett. 39, 2010, 280. The reaction can be carried out, for example, in a suitable polar aprotic organic solvent such as dimethylformamide or tetrahydrofuran, at a temperature of from 0 to 120° C.

Analogous one-step processes using organic bases such as triethylamine in the presence of Lewis acids such as magnesium chloride have been described, for example, by Little et al., J. Org. Chem. 65, 2000, 8096. The reaction can be carried out, for example, in a suitable organic aprotic solvent such as dichloromethane, at a temperature of from 0 to 120° C.

Analogous two-step processes where initially a base-catalysed O-acylation and then a rearrangement is carried out are known, for example, from EP-A-0186117, WO 2008/

125213, WO 2011/012248; EP 0625 505 and the literature cited therein; see the scheme below which uses the preparation of the compound (I-A) via the O-alkylation product (I-Zw) as an example, where the compound (I-A) corresponds to the compound (I) in which $B^1$ represents a radical of the formula (B1) and $Q^1$ represents a radical OH.

done or hexamethylphosphoric triamide; esters, such as methyl acetate or ethyl acetate; sulphoxides, such as dimethyl sulphoxide.

When carrying out the rearrangement process, the reaction temperatures can be varied within a relatively wide range. In general, the process is carried out at temperatures between 0°

Scheme

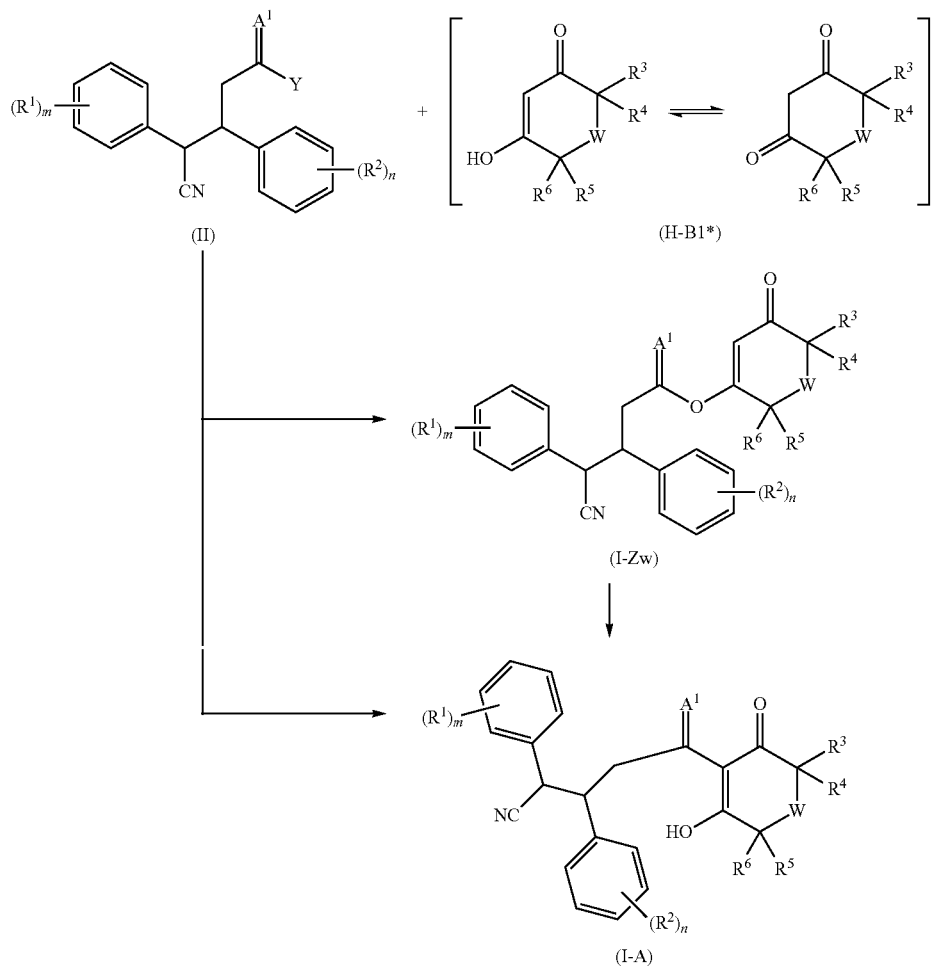

The process involving rearrangement of the compound (I-Zw) or analogous intermediates is optionally carried out using a rearrangement reagent. Used for this purpose are chemicals suitable for rearrangements, for example the reagents trimethylsilyl cyanide, potassium cyanide and acetone cyanohydrin known from analogous reactions.

The rearrangement process for preparing the compounds of the general formula (I) is preferably carried out using one or more diluents. Suitable diluents are especially organic solvents which are inert under the reaction conditions. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methylformanilide, N-methylpyrroli- C. and 150° C., preferably between 10° C. and 120° C. The rearrangement is generally carried out under atmospheric pressure. However, it is also possible to carry out the process under elevated or reduced pressure—in general between 0.1 bar and 10 bar.

In the process mentioned above and in the processes below, in some cases solvents are employed. In this context, "inert solvents" refers in each case to solvents which are inert under the particular reaction conditions, but which do not have to be inert under any reaction conditions.

The process described in each case can be carried out in apparatuses customary in the laboratory, in pilot plants and in plants for preparing commercial amounts and industrial processes, or alternatively also in a microwave oven.

(b) Compounds of the formula (I) and salts thereof in which L represents a radical of the formula $-C(=A^1)-B^1$, $B^1$ represents a radical of the formulae (B1) to (B7) and (B11) to (B14) and $Q^1$ to $Q^9$ in group $B^1$ each represents a group of the formula SH or SM and the other radicals are defined as in the respective compound of the formula (I) to be prepared are obtained, for example, by a process [variant (b)], characterized in that a compound of the formula (I) in which L is a radical of the formula —C(=A$^1$)-B$^1$ where A$^1$ is as defined in formula (I) and B$^1$ is defined analogously to the radical B$^1$ in formula (I), except that Q$^1$ to Q$^9$ in group B$^1$ each represent the group OH or OM, is reacted with a halogenating agent, preferably a carbonyl halide, for example with oxalyl chloride (Cl—CO—CO—Cl), to give the compound (I) in which Q$^1$ to Q$^9$ in group B$^1$ each represent a halogen atom, preferably a chlorine atom, with a sulphurizing agent, preferably a sulphide, for example disodium sulphide, and the desired compound of the formula (I) is optionally removed from the reaction mixture or isolated. Such methods are known in principle to a person skilled in the art and described, for example, in Journal of Heterocyclic Chemistry, 25(3), 901-6; 1988 for the nucleophilic substitution with Na$_2$S.

For instance, the reaction can also be carried out in an aprotic organic solvent such as tetrahedrofuran, if appropriate with heating under reflux; cf. EP 249150.

(c) Compounds of the formula (I) and salts thereof in which L represents a radical of the formula —C(=A$^1$)-B$^1$, B$^1$ represents a radical of the formulae (B1) to (B7) and (B11) to (B14) and Q$^1$ to Q$^9$ in group B$^1$ each represents a group of the formula OR$^{37}$ and the other radicals are defined as in the respective compound of the formula (I) to be prepared are obtained, for example, by a process [variant (c)], characterized in that a compound of the formula (I) in which L is a radical of the formula —C(=A$^1$)-B$^1$ where A$^1$ is as defined in formula (I) and B$^1$ is defined analogously to the radical B$^1$ in formula (I), except that Q$^1$ to Q$^9$ in group B$^1$ each represent the group OH or OM, is reacted with a compound (alkylating, acylating or arylating agent) of the formula Y—R$^{37}$ in which Y represents a leaving group, and the desired compound of the formula (I) is optionally removed from the reaction mixture or isolated. Such methods are known in principle to the person skilled in the art and are described, for example, in DOS 2513750 (=DE 2513750).

Here, the reaction according to variant (c) can be carried out using bases, preferably amine bases such as triethylamine, for example in a suitable organic aprotic solvent such as dichloromethane, preferably at a temperature from 0° C. to 25° C.; cf. WO 2009115788.

(d) Compounds of the formula (I) and salts thereof in which L represents a radical of the formula —C(=A$^1$)-B$^1$, B$^1$ represents a radical of the formulae (B1) to (B7) and (B11) to (B14) and Q$^1$ to Q$^9$ in group B$^1$ each represents a group of the formula SR$^{38}$ and the other radicals are defined as in the respective compound of the formula (I) to be prepared are obtained, for example, by a process [variant (d)], characterized in that a compound of the formula (I) in which L is a radical of the formula —C(=A$^1$)-B$^1$ where A$^1$ is as defined in formula (I) and B$^1$ is defined analogously to the radical B$^1$ in formula (I), except that Q$^1$ to Q$^9$ in group B$^1$ each represent the group SH or SM, is reacted with a compound (alkylating, acylating or arylating agent) of the formula Y'R$^{38}$ in which Y' represents a leaving group, and the desired compound of the formula (I) is optionally removed from the reaction mixture or isolated. Such methods are known in principle to those skilled in the art. Preference is given to reactions in the presence of suitable inorganic or organic bases such as potassium carbonate or potassium tert-butoxide in solvents such as tetrahydrofuran at temperatures of from 0 to 80° C.; cf. WO 2008113089.

(e) Compounds of the formula (I) and salts thereof in which L represents a radical of the formula —C(=A$^1$)-B$^1$, B$^1$ represents a radical of the formulae (B1) to (B7) and (B11) to (B14) and Q$^1$ to Q$^9$ in group B$^1$ each represents a group of the formula SR$^{38}$ and the other radicals are defined as in the respective compound of the formula (I) to be prepared are also obtained, for example, by a process [variant (e)], characterized in that a compound of the formula (I) in which L is a radical of the formula —C(=A$^1$)-B$^1$ where A$^1$ is as defined in formula (I) and B$^1$ is defined analogously to the radical B$^1$ in formula (I), except that Q$^1$ to Q$^9$ in group B$^1$ each represent a halogen atom, preferably chlorine atom, is reacted with a thio compound of the formula H—S—R$^{38}$, and the desired compound of the formula (I) is optionally removed from the reaction mixture or isolated. Such methods are known in principle to a person skilled in the art and described, for example, in WO 2009/018925 (for example page 21 in that document and details for process j) and the literature cited therein.

(f) Compounds of the formula (I) and salts thereof in which L represents a radical of the formula —C(=A$^1$)-B$^1$ and B$^1$ represents a group of the formula (B10) [=compound (I-B10)] are also obtained, for example, by a process [variant (f)], characterized in that a compound of the formula (I) in which L represents a radical of the formula —C(=A$^1$)-B*, A$^1$ is as defined in formula (I) and B* represents a radical of the formula —CH$_2$—CO—R$^{27}$ in which R$^{27}$ is as defined in formula (B10) [=compound (I-B)], Scheme

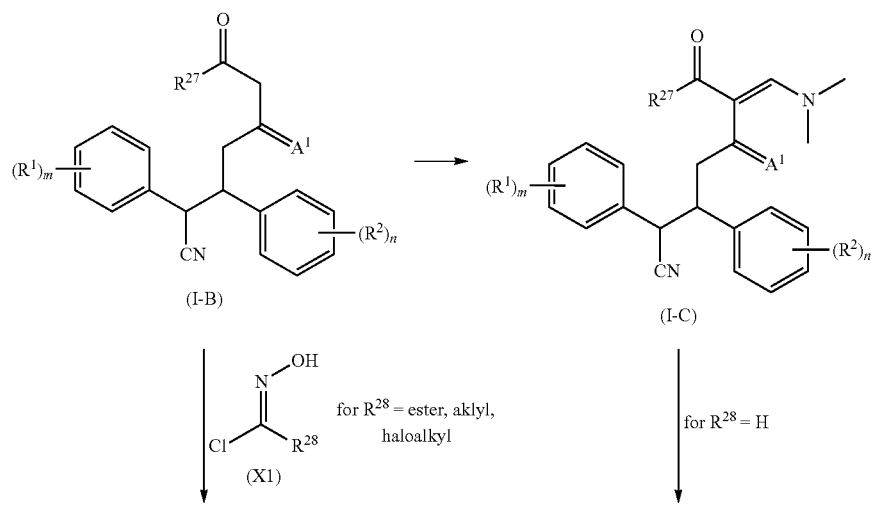

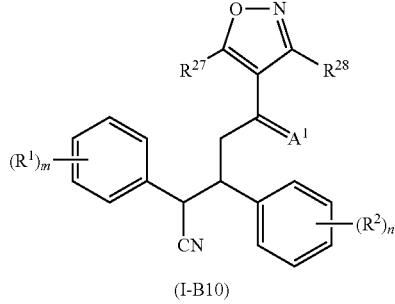

(I-B10)

is reacted with N,N-dimethylformamide dimethyl acetal to give the compound of the formula (I-C) (see scheme) and the compound (I-C) is reacted with ring closure with hydroxylamine or salts thereof to give the compound of the formula (I-B10) in which $R^{28}$=H
or the compound (I-B) is reacted with a compound of the formula (X1)

in which $R^{28}$ is as defined in formula (B10) with ring closure to give the compound of the formula (I-B10) where $R^{28}$ in formula (X1) is defined as in the compound of the formula (I-B10) to be prepared, except $R^{28}$=H.

The reaction with N,N-dimethylformamide dimethyl acetal is known from analogous examples of EP 636622. Ring closure with hydroxylamine or salts thereof can be performed, for example, in a suitable organic polar solvent such as ethanol or acetonitrile, if appropriate with base catalysis, preferably an organic base such as triethylamine, at a temperature in the range from 0° C. to 150° C., preferably in the range from room temperature to the boiling point of the solvent in question; cf. EP 636622.

(g) Compounds of the formula (I) and salts thereof in which L represents a radical of the formula —C(=A$^1$)-B$^1$ and B$^1$ represents a group of the formula (B10) [=compound (I-B10)] are also obtained, for example, according to a process [variant (g)], characterized in that a compound of the formula (II)

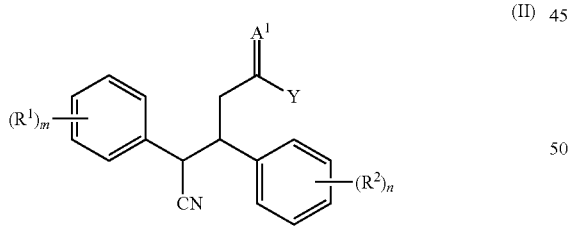

in which A$^1$, (R$^1$)$_m$ and (R$^2$)$_n$ are as defined in formula (I) and Y represents a leaving group, preferably a halogen atom, in particular a chlorine atom,
is reacted with a compound of the formula X-(B10) in which (B10) is defined as in group B$^1$ and X is a leaving group, preferably halogen, in particular iodine, optionally in the presence of a coupling agent, to give the compound of the formula (I) (crosscoupling reaction)
or
with an activated compound of the formula X'—(B10) in which X' represents a metal or a metal derivative group, preferably a Cl—Zn group, and (B10) is as defined in group B$^1$, to give the compound of the formula (I).

Here, the activated compound X'—(B10) can be prepared, for example, initially from the compound of the formula X-(B10) mentioned by reaction with metal or metal salts, for example with Mg and Zn salts (compare the scheme below).

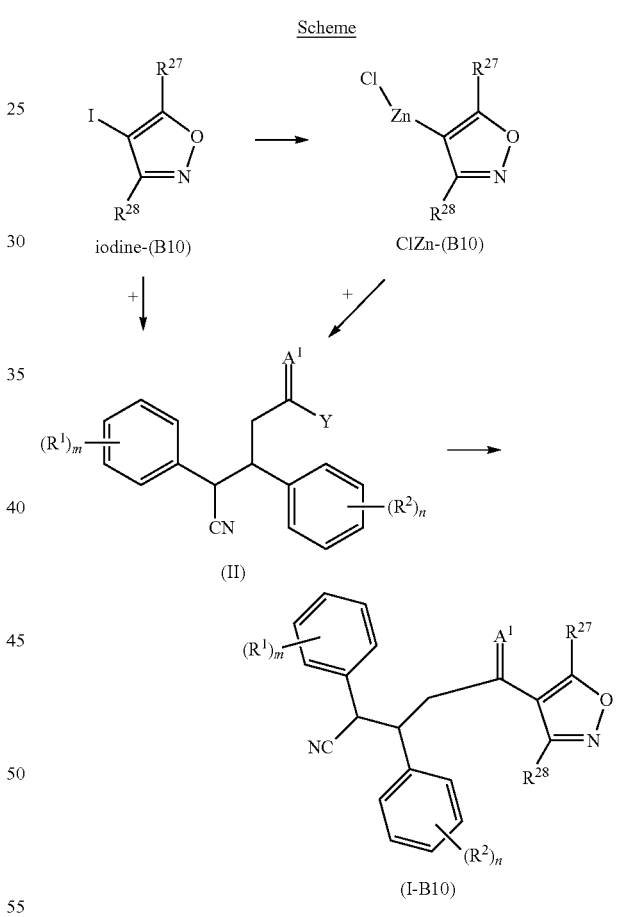

The process of the crosscoupling between (II) and iodine-(B10) or analogous intermediates is optionally carried out using a coupling reagent. Suitable for this purpose are chemicals known to be suitable for coupling, for example the palladium reagents known from analogous reactions, such as tetrakis(triphenylphosphine)palladium(0) (e.g. analogously to Negishi et al., *Tetrahedron Lett.* 24, 1983, 5181).

The process for preparing ClZn—(B10) or analogous compounds can be carried out using suitable metals or metal derivatives. Suitable for ClZn—(B10), for example, is the reaction of iodine-(B10) with magnesium turnings and zinc chloride (see analogously to Knoche) et al. Chem. A Eur. J. 15, 2009, 7192).

The coupling process for preparing the compounds of the general formula (I-B10) is preferably carried out using one or more diluents. Suitable diluents are especially organic solvents which are inert under the reaction conditions. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; amides, such as N,N-dimethylformamide, N-methylpyrrolidone or hexamethylphosphoric triamide.

When carrying out the coupling process, the reaction temperatures can be varied within a relatively wide range. In general, the process is carried out at temperatures between 0° C. and 150° C., preferably between 10° C. and 120° C. The coupling is generally carried out under atmospheric pressure. However, it is also possible to carry out the process under elevated or reduced pressure—in general between 0.1 bar and 10 bar.

(h) Compounds of the formula (I) and salts thereof in which L represents a radical of the formula —C(=A$^2$)-B$^2$ and B$^2$ represents a radical of the formula OR$^{33}$ or SR$^{34}$ are obtained, for example, by a process [variant (h)], characterized in that a compound of the formula (I')

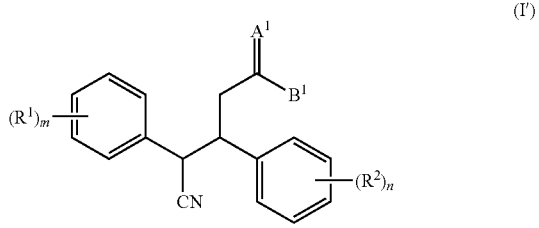

(I')

in which $(R^1)_m$ and $(R^2)_n$ are as defined in formula (I), A$^1$ represents a radical O or S and B$^1$ represents a radical of the formula (B1), (B2), (B3), (B4), (B5), (B6), (B7), (B8), (B9), (B11), (B12), (B13) or (B14) as defined above for compounds (I) in which L represents a radical —C(=A$^1$)-B$^1$, where Q$^1$ to Q$^9$ in the radicals B$^1$ each represent OH or OM, is reacted with a compound of the formula Y'—B$^2$ in which B$^2$ is as defined in the radical L and Y' represents a leaving group, for example chlorine, to give the compound (I) in which B$^2$ represents the radical OR$^{22}$ (if A$^1$=O) or SR$^{34}$ (if A$^1$=S), where the group —C(=A$^2$)- in the compound (I), compared to group —C—B$^1$ in compound (I'), represents the more stable tautomer or preferably a structurally fixed tautomer in which the radical —C(=A$^2$)- corresponds tautomerically to the radical =C(—B$^1$)—.

Here, "structurally fixed tautomer" means that in the radical —C(=A$^2$)-B$^2$ the group B$^2$ represents a radical of the formula OR$^{33}$ or SR$^{34}$ (i.e. not OH, OM, SH or SM).

Depending on the meaning of the radical R$^{33}$ or R$^{34}$, the compound of the formula Y'—B$^2$ is either an alkylating agent, acylating agent or arylating agent. Accordingly, the reaction can be carried out under the conditions for analogous alkylations, acylations or arylations, if appropriate in the presence of suitable catalysts (acids or bases) or special arylation catalysts.

(i) Compounds of the formula (I) and salts thereof in which L represents a radical of the formula —C(=A$^2$)-B$^2$ and B$^2$ represents a radical of the formula —NR$^B$R$^C$ are obtained, for example, by a process [variant (i)], characterized in that a compound of the formula (I')

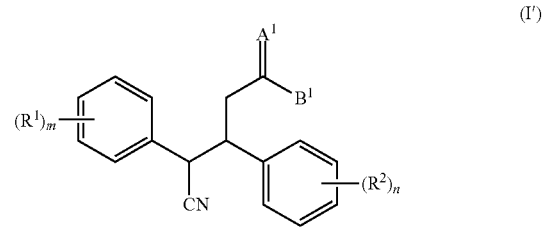

(I')

in which $(R^1)_m$ and $(R^2)_n$ are as defined in formula (I), A$^1$ represents a radical of the formula —NR$^B$ and B$^1$ represents a radical of the formula (B1), (B2), (B3), (B4), (B5), (B6), (B7), (B8), (B9), (B11), (B12), (B13) or (B14) as defined above for compounds (I) in which L represents a radical —C(=A$^1$)-B$^1$, where Q$^1$ to Q$^9$ in the radicals B$^1$ each represent OH or OM, is reacted with a compound of the formula Y'—R$^C$ in which R$^C$ is as defined in the radical —NR$^B$R$^C$ of B$^2$ and Y' represents a leaving group, for example chlorine, to give the compound (I) in which B$^2$ represents the radical —NR$^B$R$^C$, where the group —C(=A$^2$)- in the compound (I), compared to group —C—B$^1$ in compound (I'), represents the more stable tautomer or preferably a structurally fixed tautomer in which the radical —C(=A$^2$)- corresponds tautomerically to the radical =C(—B$^1$)—.

Here, "structurally fixed tautomer" means that in the radical —C(=A$^2$)-B$^2$ the group B$^2$ represents a radical of the formula —NR$^B$R$^C$ (i.e. not OH, OM, SH or SM).

Other compounds of the formula (I) according to the invention can be obtained analogously to known processes from compounds (I) according to the invention by derivatization. For example, hydroxylimino compounds of the formula (I) in which A$^1$ represents a radical of the formula =N—OH can optionally be obtained by reacting compounds (I) in which A$^1$ is an oxygen atom with hydroxylamine.

The compounds of the formula (II) having the reactive group —C(=A$^1$)-Y, which are used to prepare the compounds (I) according to the invention by variant (a), can be prepared from corresponding carboxylic acids or carboxylic esters, i.e. cyanobutyrates (III)

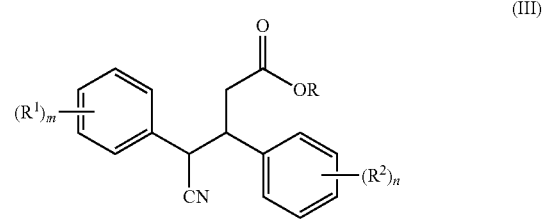

(III)

in which $(R^1)_m$ and $(R^2)_n$ are as defined in formula (I) and R represents hydrogen or a hydrolysable radical by derivatization, for example preparation of the halides if Y represents a halogen atom, analogously to known methods.

The preparation of acid halides having the reactive group —C(=O)-Hal in which Hal is a halogen atom, preferably chlorine atom, from carboxylic acids or carboxylic esters is known in principle to the person skilled in the art; see acid chloride from carboxylic acids using thionyl chloride Houben-Weyl. Vol. VIII (1952), pages 359-680 or using oxalyl chloride according to Heterocycles, 26(5), 1291-302; 1987.

Analogous processes for preparing other reactive groups —C(=A$^1$)-Y are known.

If the reactive group —C(=A$^1$)-Y represents a group of the formula —C(=N—R$^4$)-Hal, it may also be possible to employ corresponding carboxylic acids or carboxylic esters of the formula (III) in which A$^1$ represents an oxygen atom. Here, the compounds having the reactive group C(=O)—OR are initially reduced to the compound having the functional alcohol group (—CH$_2$—OH) and then oxidized to the compound having the functional aldehyde group (—C(=O)H), or they are reduced directly to the compound having the functional aldehyde group (—C(=O)H); for example analogously to István E. Markó et al. Eur. J. Org. Chem. 2009, 1806.

To prepare the compounds having the reactive group —C(=N—R$^4$)-Hal, the compounds having the functional aldehyde group (—C(=O)H) can then be halogenated; for example analogously to R. A. Whitney et al. J. Org. Chem. 1988, 53, 4074; S. Kim et al. Chem. Commun. 2007, 4507; Chemistry—An Asian Journal 2008, 3, 1692; Chem. Commun. 2010, 46, 7822.

Diastereomer mixtures of the cyanobutyrates of the formula (III) mentioned are known in principle; see, for example, EP-A 5341, EP-A 266725, EP-A270 830, JP 04/297454, JP 04/297455, JP 05/058979, WO 2011/003775, WO 2011/003776. Analogously to the synthesis routes described in the publications cited, the compounds can be prepared by standard processes of organic chemistry. For example, compounds of the formula (III) are obtained, characterized in that (aa) compounds of the formula (IV) ("cyanomethylbenzenes"/"phenylacetonitriles")

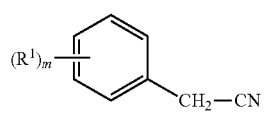

(IV)

are reacted with compounds of the formula (V) (cinnamic acid derivatives) or salts thereof

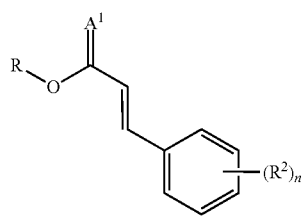

(V)

to give compounds of the formula (III) (diastereomers/racemic)

where A$^1$, R, R$^1$, R$^2$, m and n in the compounds (IV) and (V) are as defined in the respective compound of the formula (III) to be prepared.

The starting materials (IV) and (V) required for preparing the compounds (III) are known from the literature cited or can be prepared analogously to the literature cited.

The reaction according to variant (aa) can be carried out, for example, according to methods and under conditions like those known for Michael additions. The reaction is carried out, for example, at temperatures of from −100° C. to 150° C., preferably from −78° C. to 100° C., in an organic or inorganic solvent, generally in the presence of a base or a catalyst or both [cf. J. Chem. Soc. (1945), p. 438].

Suitable solvents are, for example, organic solvents such as:
- aliphatic hydrocarbons such as pentane, hexane, cyclohexane or petroleum ether;
- aromatic hydrocarbons such as toluene, o-, m- or p-xylene,
- halogenated hydrocarbons such as methylene chloride, chloroform or chlorobenzene,
- ethers, such as diethyl ether, diisopropyl ether, tert-butyl methyl ether, dioxane, anisole and tetrahydrofuran (THF),
- nitriles such as acetonitrile or propionitrile,
- ketones such as acetone, methyl ethyl ketone, diethyl ketone and tert-butyl methyl ketone,
- alcohols such as methanol, ethanol, n-propanol, isopropanol, n-butanol and tert-butanol, and also
- dimethyl sulphoxide, dimethylformamide, dimethylacetamide, sulpholane, mixtures of the organic solvents mentioned.

In individual cases, it is also appropriate to use inorganic solvents such as water or mixtures of organic solvents with water.

Preferred solvents are THF and methanol and mixtures thereof with other organic solvents.

The reaction by preparation variant (aa) is preferably carried out in the presence of a base, for example from the group of the inorganic compounds such as the alkali metal and alkaline earth metal hydroxides, for example lithium hydroxide, sodium hydroxide, potassium hydroxide or calcium hydroxide, the alkali metal and alkaline earth metal oxides, for example lithium oxide, sodium oxide, calcium oxide or magnesium oxide, the alkali metal and alkaline earth metal hydrides, for example lithium hydride, sodium hydride, potassium hydride or calcium hydride, the alkali metal amides, for example lithium amide, sodium amide or potassium amide, the alkali metal and alkaline earth metal carbonates, for example lithium carbonate, potassium carbonate or calcium carbonate, the alkali metal bicarbonates, for example sodium bicarbonate, or the organometallic compounds such as, preferably, the alkali metal alkyls, for example methyllithium, butyllithium or phenyllithium, the alkylmagnesium halides, for example methylmagnesium chloride, or the alkali metal and alkaline earth metal alkoxides, for example sodium methoxide, sodium ethoxide, potassium ethoxide, potassium tert-butoxide or dimethoxymagnesium.

The bases used can also be organic bases, for example from the group of the tertiary aliphatic amines, for example trimethylamine, triethylamine, tributylamine, diisopropylethylamine or N-methylpiperidine, or the aromatic tertiary amines, for example pyridine or substituted pyridines such as collidine, lutidine or 4-dimethylaminopyridine, or the bicyclic amines such as 7-methyl-1,5,7-triazabicyclo[4.4.0]-dec-5-ene or 1,8-diazabicyclo[5.4.0]undec-7ene (DBU). Preferred bases are, for example, potassium tert-butoxide, lithium bis(trimethylsilyl)amide or 7-methyl-1,5,7-triazabicyclo[4.4.0]-dec-5-ene.

The amount of base may generally vary within wide limits. For example, it may be expedient to employ the base in catalytic amounts, in substoichiometric amounts, in equimolar amounts or in excess. A preferably liquid organic base may optionally also be used as solvent.

Suitable catalysts for the Michael addition according to variant (aa) are acidic catalysts, for example from the group of the inorganic acids, for example Broensted acids, such as hydrofluoric acid, hydrochloric acid, hydrobromic acid, sulphuric acid or perchloric acid, or Lewis acids, such as boron trifluoride, aluminium trichloride, iron(III) chloride, tin(IV) chloride, titanium(IV) chloride, scandium(III) triflate or zinc (II) chloride, and also organic acids, for example formic acid, acetic acid, propionic acid, oxalic acid, toluenesulphonic acid, benzenesulphonic acid, camphorsulphonic acid, citric acid or trifluoroacetic acid.

The amount of acidic catalyst may generally vary within wide limits. For example, it may be expedient to employ the acid in catalytic amounts, in substoichiometric amounts, in equimolar amounts or in excess. A preferably liquid acid may optionally also be used as solvent.

For example, compounds of the formula (III) are also obtained by transesterification, characterized in that
(bb) compounds of the formula (III')

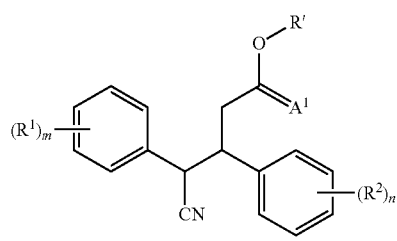

in which R' is a radical from the group of the radicals possible for R, but different from the radical R in the compound (III) to be prepared, are reacted with a compound of the formula R—OH in which R is defined as in formula (III), to give compound (III), where $A^1$, $R^1$, $R^2$, m and n in the compound (III') are as defined in the compound of the formula (III) to be prepared in each case.

The transesterifications (bb) can be carried out, for example, using a suitable alcohol R—OH in the presence of a catalyst, optionally in the presence of an aprotic solvent. Furthermore, in general, those conditions are advantageous where the chemical equilibrium is shifted to the side of the desired product, for example using a large excess of the alcohol R—OH under virtually anhydrous conditions, for example in the presence of a molecular sieve.

The reactions (transesterifications) can generally be carried out at temperatures of from 0° C. to 180° C., preferably from 20° C. to 100° C., in the presence of a Lewis or Broenstedt acid or an enzyme [cf. J. Org. Chem. 2002, 67, 431].

Suitable solvents are, for example, the following organic aprotic solvents:
aliphatic hydrocarbons such as pentane, hexane, cyclohexane or petroleum ether;
aromatic hydrocarbons such as toluene, o-, m- or p-xylene, halogenated hydrocarbons such as methylene chloride (dichloromethane), chloroform or chlorobenzene,
ethers, such as diethyl ether, diisopropyl ether, tert-butyl methyl ether, dioxane, anisole or tetrahydrofuran (THF),
nitriles such as acetonitrile or propionitrile,
ketones such as acetone, methyl ethyl ketone, diethyl ketone and tert-butyl methyl ketone,
dimethyl sulphoxide, dimethylformamide, dimethylacetamide or sulpholane or
mixtures of the organic solvents mentioned.

The preferred solvent is the alcohol R—OH, which is at the same time used as reaction partner for the transesterification, optionally in combination with one of the aprotic organic solvents mentioned.

Alternatively, it is also possible to obtain the desired ester from another ester in two steps by acidic or basic hydrolysis of the other esters to the free acid, i.e. to compounds (III'), in which R is in each case H, and subsequent esterification with an alcohol R—OH.

The esterification from the free acid of the formula (III')/ R═H can be carried out, for example, analogously to customary methods, for example at temperatures of from 0° C. to 120° C., preferably from 20° C. to 50° C., optionally in the presence of a catalyst, in a substantially anhydrous medium or under conditions where the water including the water formed during the esterification is bound or otherwise removed. Suitable catalysts are anhydrous acids and bases, preferably organic acids or bases; see handbooks for chemical processes for esterifying carboxylic acids; see also, for example, J. Am. Chem. Soc. 2007, 129 (43), 13321; J. Org. Chem. 1984, 49 (22), 4287.

Suitable solvents for the esterification are the aprotic organic solvents mentioned above for process variant (bb), including the alcohol R—OH which is at the same time used as a reaction partner for the esterification, optionally in combination with one of the aprotic organic solvents mentioned.

Suitable catalysts for the esterification are the bases or acidic or basic catalysts mentioned for process variant (aa) (Michael addition), in anhydrous form or with a water content which is as low as possible. Preferred catalysts are the bases lithium hydroxide, potassium carbonate or organic amines such as pyridines, substituted pyridines and DBU.

Any hydrolysis carried out before the esterification of other esters of the formula (III'), where R' is in each case not H, can be carried out analogously to customary methods, for example at temperatures of from 0° C. to 120° C., preferably from 20° C. to 50° C., if appropriate in the presence of a catalyst, in a water-containing medium/solvent; see handbooks on chemical processes for hydrolysing carboxylic esters; see also, for example, J. Am. Chem. Soc. 2007, 129 (43), 13321; J. Org. Chem. 1984, 49 (22), 4287.

A suitable solvent for the hydrolysis is water or a water-containing organic solvent, for example the organic solvent mentioned based on process variant (aa) mentioned (Michael addition), preferably water or polar organic solvents containing water, such as THF.

Suitable catalysts for the hydrolysis are the acids, bases or acidic or basic catalysts mentioned for process variant (aa) mentioned (Michael addition), in each case containing water. Preferred catalysts are aqueous acids and bases, in particular bases such as lithium hydroxide, sodium hydroxide, potassium carbonate, pyridines, substituted pyridines and DBU in the presence of organic solvents.

The catalysts for the esterification or the hydrolysis can generally be employed in catalytic amounts. In general, it is also possible to use relatively large amounts including equimolar amounts and a molar excess. Frequently, a use as solvent is also possible.

The reaction mixtures are worked up in a customary manner, for example by mixing with water, separating the phases and, if appropriate, chromatographic purification of the crude products. Some of the intermediates and end products are obtained in the form of colourless or slightly brownish viscous oils which are purified or freed from volatile components under reduced pressure and at moderately elevated temperature.

If the intermediates and end products are obtained as solids, the purification can also be carried out by recrystallization or digestion. If individual compounds (III') or (III) cannot be obtained by the routes described above, they can be prepared by derivatization of other compounds (III') or (III).

To prepare stereochemically enriched compounds of the formula (I), compounds (I) initially obtained as diastereomer mixtures can be separated into the stereoisomers. Alternatively, it may be possible to separate and enrich the desired stereoisomers at the stage of the compounds (III), followed by enantioselective reactions up to the stage of optically active compounds (I).

The compounds of the formulae (I) and (III) or (III') contain two centres of chirality in positions 2 and 3 of the valeronitrile skeleton or positions 3 and 4 of the cyanobutyrate skeleton and may contain one or more further centres of chirality, depending on the substitution pattern.

Owing to the two centres of chirality mentioned, there exist 4 stereoisomers, namely two erythro enantiomers and two threo enantiomers.

To prepare the compounds (I) according to the invention in the form of the preferred stereochemically enriched threo compounds or threo-2 compounds, it is necessary to enrich the threo compounds or the stereoisomer (enantiomer) threo-2 from the mixture of the stereoisomers in an appropriate manner. Accordingly, an expedient process comprises the initial isolation of the threo isomers threo-1 and threo-2 from the diastereomer mixture (I) which still comprises the erythro isomers, and the subsequent optical resolution with isolation or enrichment of the enantiomer threo-2 from the mixture with the enantiomer threo-1.

The isolation of the threo isomers as a racemic mixture can be carried out analogously to the customary separation and purification processes mentioned above (diastereomer separation).

Suitable for the subsequent preparation of compounds of the formula (I) in the form of the stereochemically enriched threo-2 isomers are methods for optical resolution generally known to the person skilled in the art from analogous cases (cf. handbooks of stereochemistry), for example following processes for separating mixtures into diastereomers, for example by physical processes, such as crystallization, chromatographic processes, in particular column chromatography and high-pressure liquid chromatography, distillation, if appropriate under reduced pressure, extraction and other processes, it is possible to separate remaining mixtures of enantiomers, generally by chromatographic separation on chiral solid phases. Suitable for preparative amounts or on an industrial scale are processes such as the crystallization of diastereomeric salts which can be obtained from the diastereomer mixtures using optically active acids and, if appropriate, provided that acidic groups are present, using optically active bases.

Optically active acids which are suitable for optical resolution by crystallization of diastereomeric salts are, for example, camphorsulphonic acid, camphoric acid, bromocamphorsulphonic acid, quinic acid, tartaric acid, dibenzoyltartaric acid and other analogous acids; suitable optically active bases are, for example, quinine, cinchonine, quinidine, brucine, 1-(S)- or 1-(R)-phenylethylamine and other analogous bases.

The crystallizations are then in most cases carried out in aqueous, alcoholic or aqueous-organic solvents, where the diastereomer which is less soluble precipitates first, if appropriate after seeding. One enantiomer of the compound of the formula (I) is then liberated from the precipitated salt, or the other is liberated from the crystals, by acidification or using a base.

Accordingly, the invention also provides the process for preparing the threo-2 isomers of the compounds (I), characterized in that compounds (I) are subjected to an optical resolution and the compound (I) is isolated in a stereochemical purity of from 60 to 100%, preferably from 70 to 100%, more preferably from 80 to 100%, in particular from 90 to 100%, based on the mixture of threo-2 enantiomers present. As an alternative to the optical resolution methods mentioned, enantioselective processes starting with stereochemically pure starting materials are in principle also suitable for preparing the threo-2 enantiomers (I).

The following acids are generally suitable for preparing the acid addition salts of the compounds of the formula (I): hydrohalic acids, such as hydrochloric acid or hydrobromic acid, furthermore phosphoric acid, nitric acid, sulphuric acid, mono- or bifunctional carboxylic acids and hydroxycarboxylic acids, such as acetic acid, maleic acid, succinic acid, fumaric acid, tartaric acid, citric acid, salicylic acid, sorbic acid, or lactic acid, and also sulphonic acids, such as p-toluenesulphonic acid and 1,5-naphthalenedisulphonic acid. The acid addition compounds of the formula (I) can be obtained in a simple manner by the customary methods for forming salts, for example by dissolving a compound of the formula (I) in a suitable organic solvent, such as, for example, methanol, acetone, methylene chloride or benzene, and adding the acid at temperatures of from 0 to 100° C., and they can be isolated in a known manner, for example by filtration, and, if appropriate, purified by washing with an inert organic solvent.

The base addition salts of the compounds of the formula (I) are preferably prepared in inert polar solvents, such as, for example, water, methanol or acetone, at temperatures of from 0 to 100° C. Examples of bases which are suitable for the preparation of the salts according to the invention are alkali metal carbonates, such as potassium carbonate, alkali metal hydroxides and alkaline earth metal hydroxides, for example NaOH or KOH, alkali metal hydrides and alkaline earth metal hydrides, for example NaH, alkali metal alkoxides and alkaline earth metal alkoxides, for example sodium methoxide or potassium tert-butoxide, or ammonia, ethanolamine or quaternary ammonium hydroxide of the formula [NRR'R''R''']$^+$ OH$^-$.

What is meant by the "inert solvents" referred to in the above process variants are in each case solvents which are inert under the particular reaction conditions but need not be inert under all reaction conditions.

Collections of compounds of the formula (I) which can be synthesized by the aforementioned process can also be prepared in a parallel manner, it being possible for this to take place in a manual, partly automated or completely automated manner. In this connection, it is possible to automate the reaction procedure, the work-up or the purification of the products and/or intermediates. Overall, this is understood as meaning a procedure as described, for example, by S. H. DeWitt in "Annual Reports in Combinatorial Chemistry and Molecular Diversity: Automated Synthesis", Volume 1, Verlag Escom, 1997, pages 69 to 77.

For the parallelized reaction procedure and workup it is possible to use a range of commercially available instruments, of the kind offered by, for example, the companies Stem Corporation, Woodrolfe Road, Tollesbury, Essex, CM9 8SE, England, or H+P Labortechnik GmbH, Bruckmannring 28, 85764 Oberschleißheim, Germany. For the parallel purification of compounds (I) or of intermediates produced during the preparation, there are available, inter alia, chromatography apparatuses, for example from ISCO, Inc., 4700 Superior Street, Lincoln, Nebr. 68504, USA. The apparatuses listed allow a modular procedure in which the individual process steps are automated, but between the process steps manual operations have to be carried out. This can be circumvented by using partly or completely integrated automation systems in which the respective automation modules are operated, for example, by robots. Automation systems of this type can be acquired, for example, from Zymark Corporation, Zymark Center, Hopkinton, Mass. 01748, USA.

Besides the methods described here, the preparation of compounds of the formula (I) can take place completely or partially by solid-phase supported methods. For this purpose, individual intermediates or all intermediates in the synthesis or a synthesis adapted for the corresponding procedure are bonded to a synthesis resin. Solid-phase-supported synthesis methods are described extensively in the specialist literature, for example Barry A. Bunin in "The Combinatorial Index", Academic Press, 1998.

The use of solid-phase-supported synthesis methods permits a number of protocols, which are known from the literature and which for their part may be performed manually or in an automated manner, to be carried out. For example, the "teabag method" (Houghten, U.S. Pat. No. 4,631,211; Houghten et al., Proc. Natl. Acad. Sci, 1985, 82, 5131-5135) in which products from IRORI, 11149 North Torrey Pines Road, La Jolla, Calif. 92037, USA, are employed, may be semiautomated. The automation of solid-phase-supported parallel syntheses is performed successfully, for example, by apparatuses from Argonaut Technologies, Inc., 887 Industrial Road, San Carlos, Calif. 94070, USA or MultiSynTech GmbH, Wullener Feld 4, 58454 Witten, Germany.

The preparation according to the processes described herein produces compounds of the formula (I) in the form of substance collections or libraries. Accordingly, the present invention also provides libraries of compounds of the formula (I) which comprise at least two compounds of the formula (I), and precursors thereof.

The compounds of the formula (I) according to the invention (and/or their salts), above and hereinbelow also referred to together as "compounds according to the invention", "compounds (I) according to the invention" or in short as "compounds (I)", have excellent herbicidal efficacy against a broad spectrum of economically important monocotyledonous and dicotyledonous annual harmful plants. The active compounds also have good control over perennial harmful plants which are difficult to control and produce shoots from rhizomes, root stocks or other perennial organs. The present invention therefore also relates to a method for controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seed (for example grains, seeds or vegetative propagules such as tubers or shoot parts with buds), to the soil in or on which the plants grow (for example the soil of cropland or non-cropland) or to the area on which the plants grow (for example the area under cultivation). The compounds according to the invention can be deployed, for example, prior to sowing (if appropriate also by incorporation into the soil), prior to emergence or after emergence. Specific examples may be mentioned of some representatives of the monocotyledonous and dicotyledonous weed flora which can be controlled by the compounds according to the invention, without the enumeration being restricted to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

When the compounds according to the invention are applied to the soil surface before germination, either the weed seedlings are prevented completely from emerging or the weeds grow until they have reached the cotyledon stage, but then stop growing and eventually, after three to four weeks have elapsed, die completely. If the active compounds are applied post-emergence to the green parts of the plants, growth stops after the treatment, and the harmful plants remain at the growth stage of the time of application, or die completely after a certain time, such that competition by the weeds, which is harmful to the crop plants, is thus eliminated very early and in a lasting manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, are damaged only to an insignificant extent, or not at all, depending on the structure of the respective compound according to the invention and its application rate. For these reasons, the present compounds are very suitable for selective control of unwanted plant growth in plant crops such as agriculturally useful plants or ornamentals.

In addition, the compounds according to the invention (depending on their particular structure and the application rate deployed) have outstanding growth-regulating properties in crop plants. They intervene to regulate the plant's metabolism and can thus be used for controlled influence on plant constituents and to facilitate harvesting, for example by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since for example lodging can be reduced, or prevented completely, hereby.

By virtue of their herbicidal and plant growth-regulating properties, the active compounds can also be used for control of harmful plants in crops of genetically modified plants or plants modified by conventional mutagenesis. In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other specific characteristics relate, for example, to the harvested material with regard to quantity, quality, storability, composition and specific constituents. Thus, transgenic plants are known whose starch content is increased, or whose starch quality is altered, or those where the harvested material has a different fatty acid composition.

It is preferred with a view to transgenic crops to use the compounds according to the invention and/or their salts in economically important transgenic crops of useful plants and ornamentals, for example of cereals such as wheat, barley, rye, oats, millet, rice and corn or else crops of sugar beet, cotton, soybean, oilseed rape, potato, tomato, peas and other vegetables.

It is preferred to employ the compounds according to the invention as herbicides in crops of useful plants which are resistant, or have been made resistant by recombinant means, to the phytotoxic effects of the herbicides.

By virtue of their herbicidal and plant-growth-regulatory properties, the active compounds can also be employed for controlling harmful plants in crops of known genetically modified plants or genetically modified plants still to be developed. In general, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other specific characteristics relate, for example, to the harvested material with regard to quantity, quality, storability, composition and specific constituents. Thus, transgenic plants are known whose starch content is increased, or whose starch quality is altered, or those where the harvested material has a different fatty acid composition. Other particular properties may be tolerance or resistance to abiotic stressors, for example heat, low temperatures, drought, salinity and ultraviolet radiation.

It is preferred to use the compounds of the formula (I) according to the invention or salts thereof in economically important transgenic crops of useful plants and ornamental plants, for example of cereals such as wheat, barley, rye, oats, sorghum and millet, rice, cassava and corn or else crops of sugar beet, cotton, soybean, oilseed rape, potato, tomato, peas and other vegetables.

It is preferred to employ the compounds of the formula (I) according to the invention as herbicides in crops of useful plants which are resistant, or have been made resistant by recombinant means, to the phytotoxic effects of the herbicides. Conventional methods of generating novel plants which have modified properties in comparison to plants occurring to date consist, for example, in traditional breeding methods and the generation of mutants. Alternatively, novel plants with altered properties can be generated with the aid of recombinant methods (see, for example, EP-A-0221044, EP-A-0131624). For example, the following have been described in several cases:

recombinant modifications of crop plants for the purpose of modifying the starch synthesized in the plants (for example WO 92/11376, WO 92/14827, WO 91/19806).

transgenic crop plants which are resistant to particular herbicides of the glufosinate type (cf., for example, EP-A-0242236, EP-A-242246) or glyphosate type (WO 92/00377) or the sulphonylureas (EP-A-0257993, U.S. Pat. No. 5,013,659), transgenic crop plants, for example cotton, which is capable of producing *Bacillus thuringiensis* toxins (Bt toxins), which make the plants resistant to certain pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431.

For such recombinant manipulations, nucleic acid molecules which allow mutagenesis or a sequence change by recombination of DNA sequences can be introduced into plasmids. For example, base substitutions can be carried out, part-sequences can be removed, or natural or synthetic sequences may be added with the aid of standard methods. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone", VCH Weinheim 2nd edition 1996.

The production of plant cells with a reduced activity of a gene product can be achieved, for example, by the expression of at least one appropriate antisense RNA, or of a sense RNA for achievement of a cosuppression effect, or the expression of at least one appropriately constructed ribozyme which specifically cleaves transcripts of the abovementioned gene product.

For this purpose, it is firstly possible to use DNA molecules which comprise the entire coding sequence of a gene product including any flanking sequences present, or else DNA molecules which comprise only parts of the coding sequence, in which case these parts must be long enough to bring about an antisense effect in the cells. It is also possible to use DNA sequences which have a high degree of homology to the coding sequences of a gene product, but are not completely identical.

When expressing nucleic acid molecules in plants, the protein synthesized may be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give whole plants. In principle, the transgenic plants may be plants of any desired plant species, i.e. both monocotyledonous and dicotyledonous plants.

Thus, it is possible to obtain transgenic plants whose properties are altered by overexpression, suppression or inhibition of homologous (=natural) genes or gene sequences, or expression of heterologous (=foreign) genes or gene sequences.

It is preferred to employ the compounds (I) according to the invention in transgenic crops which are resistant to growth regulators such as, for example, dicamba, or against herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulphonylureas, glyphosate, glufosinate or benzoylisoxazoles and analogous active compounds.

On employment of the active compounds according to the invention in transgenic crops, not only do the effects toward harmful plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the compounds of the formula (I) according to the invention and/or their salts as herbicides for controlling harmful plants in crops of useful plants or ornamentals, optionally in transgenic crop plants. Preference is given to the use by the pre- or post-emergence method in cereals such as wheat, barley, rye, oats, millet and rice, in particular in wheat by the post-emergence method.

Preference is also given to the use by the pre- or post-emergence method in corn, in particular by the pre-emergence method in corn.

Preference is also given to the use by the pre- or post-emergence method in soybeans, in particular by the post-emergence method in soybeans.

The use according to the invention for the control of harmful plants or for growth regulation of plants also includes the case in which the active compound of the formula (I) or its salt is not formed from a precursor substance ("prodrug") until after application on the plant, in the plant or in the soil.

The invention also provides the method (application method) for controlling harmful plants or for regulating the growth of plants which comprises applying an effective amount of one or more compounds of the formula (I) or salts thereof onto the plants (harmful plants, if appropriate together with the useful plants), plant seeds, the soil in which or on which the plants grow or the area under cultivation.

The compounds (I) according to the invention can be used in the form of wettable powders, emulsifiable concentrates, sprayable solutions, dusting products or granules in the customary formulations. The invention therefore also provides herbicidal and plant growth-regulating compositions which comprise compounds of the formula (I) and/or salts thereof.

The compounds of the formula (I) and/or salts thereof can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for broadcasting and soil application, granules (GR) in the form of microgranules, sprayable granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical technology], volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation auxiliaries, such as inert materials, surfactants, solvents and further additives are likewise known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesell., Stuttgart 1976; Winnacker-Küchler, "Chemische Technologie", volume 7, C. Hanser Verlag Munich, 4th ed. 1986.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulphates, alkanesulphonates, alkylbenzenesulphonates, sodium lignosulphonate, sodium 2,2'-dinaphthylmethane-6,6'-disulphonate, sodium dibutylnaphthalenesulphonate or else sodium oleoylmethyltaurinate. To prepare the wettable powders, the herbicidally active compounds are ground finely, for example in customary apparatus such as hammer mills, blower mills and air-jet mills, and simultaneously or subsequently mixed with the formulation assistants.

Emulsifiable concentrates are produced by dissolving the active compound in an organic solvent, for example butanol, cyclohexanone, dimethylformamide, xylene or else relatively high-boiling aromatics or hydrocarbons or mixtures of the organic solvents, with addition of one or more surfactants of the ionic and/or nonionic type (emulsifiers). The emulsifiers used may, for example, be: alkylarylsulphonic calcium salts, such as calcium dodecylbenzenesulphonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, such as, for example, sorbitan fatty acid esters, or polyoxyethylene sorbitan esters, such as, for example, polyoxyethylene sorbitan fatty acid esters.

Dusting products are obtained by grinding the active compound with finely distributed solid substances, for example talc, natural clays, such as kaolin, bentonite and pyrophyllite, or diatomaceous earth.

Suspension concentrates may be water- or oil-based. They can be produced, for example, by wet grinding by means of commercial bead mills with optional addition of surfactants as already listed above, for example, for the other formulation types. Emulsions, e.g. oil-in-water emulsions (EW), can be prepared, for example, by means of stirrers, colloid mills and/or static mixers using aqueous organic solvents and if appropriate surfactants, as have for example already been listed above in connection with the other types of formulation.

Granules can be produced either by spraying the active compound onto adsorptive granulated inert material or by applying active compound concentrates by means of adhesives, for example polyvinyl alcohol, sodium polyacrylate or mineral oils, to the surface of carrier substances, such as sand, kaolinites or of granulated inert material. Suitable active compounds can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection agents, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations comprise generally from 0.1 to 99% by weight, in particular from 0.1 to 95% by weight, of active compound of the formula (I) and/or salts thereof.

In wettable powders, the active compound concentration is, for example, about 10 to 90% by weight; the remainder to 100% by weight consists of the customary formulation constituents. In the case of emulsifiable concentrates, the active compound concentration can be from about 1 to 90, preferably from 5 to 80, % by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partly on whether the active compound is present in liquid or solid form and on which granulation assistants, fillers, etc., are used. In the water-dispersible granules, the content of active compound is, for example, between 1 and 95% by weight, preferably between 10 and 80% by weight.

In addition, the active compound formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity. Examples of formulation auxiliaries are described, inter alia, in "Chemistry and Technology of Agrochemical Formulations", ed. D. A. Knowles, Kluwer Academic Publishers (1998).

The compounds of the formula (I) or salts thereof can be employed as such or in the form of their preparations (formulations) combined with other pesticidally active compounds, such as, for example, insecticides, acaricides, nematicides, herbicides, fungicides, safeners, fertilizers and/or growth regulators, for example as finished formulation or as tank mixes. The combination formulations can be prepared on the basis of the abovementioned formulations, while taking account of the physical properties and stabilities of the active compounds to be combined.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoen desaturase, photosystem I, photosystem II, protoporphyrinogen oxidase, as are described in, for example, Weed Research 26 (1986) 441-445 or "The Pesticide Manual", 15th edition, The British Crop Protection Council and the Royal Soc. of Chemistry, 2006 and the literature cited therein. Known herbicides or plant growth regulators which can be combined with the compounds according to the invention are, for example, the following active compounds (the compounds are either designated by the common name according to the International Organization for Standardization (ISO) or by the chemical name, or by the code number) and always comprise all use forms such as acids, salts, esters and isomers such as stereoisomers and optical isomers. In this case, one or else, in some cases, more than one use form is mentioned by way of example: acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulphuron, aminocyclopyrachlor, aminocyclopyrachlor-potassium, aminocyclopyrachlor-methyl, aminopyralid, amitrole, ammonium sulphamate, ancymidol, anilofos, asulam, atrazine, azafenidin, azimsulphuron, aziprotryne, beflubutamid, benazolin, benazolin-ethyl, bencarbazone, benfluralin, benfuresate, bensulide, bensulphuron, bensulphuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlortoluron, chlorsulphuron, cinidon, cinidon-ethyl, cinmethylin, cinosulphuron, clethodim, clodinafop, clodinafop-propargyl, clofencet, clofencet-potassium, clomazone, clomeprop, cloprop, clopyralid, cloransulam, cloransulam-methyl, cumyluron, cyanamide, cyanazine, cyclanilide, cycloate, cyclosulphamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dikegulac-sodium, dimefuron, dimepiperate, dimethachlor, dimethametryn, dimethenamid, dimethenamid-P, dimethipin, dimetrasulphuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulphuron, ethametsulphuron-methyl, ethephon, ethidimuron, ethiozin, ethofumesate, ethoxyfen, ethoxyfen-ethyl, ethoxysulphuron, etobenzanid, F-5331, i.e. N-[2-chloro-4-fluoro-5-[4-(3-fluoropropyl)-4,5- dihydro-5-oxo-1H-tetrazol-1-yl]phenyl]ethanesulphonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoprop, fenoxaprop-P, fenoxaprop-ethyl, fenoxaprop-P-ethyl, fenoxasulphone, fentrazamide, fenuron, flamprop, flamprop-M-isopropyl, flamprop-M-methyl, flazasulphuron, florasulam, fluazifop, fluazifop-P, fluazifop-butyl, fluazifop-P-butyl, fluazolate, flucarbazone, flucarbazone-sodium, flucetosulphuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulphuron, flupyrsulphuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulphuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl) O-ethyl isopropylphosphoramidothioate, halosafen, halosulphuron, halosulphuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulphuron, inabenfide, indanofan, indaziflam, indoleacetic acid (IAA), 4-indol-3-ylbutyric acid (IBA), iodosulphuron, iodosulphuron-methyl-sodium, iofensulphuron, iofensulphuron-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulphonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulphuron, mesosulphuron-methyl, mesotrione, methabenzthiazuron, metam, metamifop, metamitron, metazachlor, metazasulphuron, methazole, methiopyrsulphuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulphuron, metsulphuron-methyl, molinate, monalide, monocarbamide, monocarbamide dihydrogensulphate, monolinuron, monosulphuron, monosulphuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulphuron, nipyraclofen, nitralin, nitrofen, nitrophenolate-sodium (isomer mixture), nitrofluorfen, nonanoic acid, norflurazon, orbencarb, orthosulphamuron, oryzalin, oxadiargyl, oxadiazon, oxasulphuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulphuron, primisulphuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulphuron, propyzamide, prosulphalin, prosulphocarb, prosulphuron, prynachlor, pyraclonil, pyraflufen, pyraflufen-ethyl, pyrasulphotole, pyrazolynate (pyrazolate), pyrazosulphuron, pyrazosulphuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulphan, pyrithiobac, pyrithiobac-sodium, pyroxasulphone, pyroxsulam, quinclorac, quinmerac, quinoclamine, quizalofop, quizalofop-ethyl, quizalofop-P, quizalofop-P-ethyl, quizalofop-P-tefuryl, rimsulphuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulphallate (CDEC), sulphentrazone, sulphometuron, sulphometuron-methyl, sulphosate (glyphosate-trimesium), sulphosulphuron, SW-065, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluoron, thiazopyr, thidiazimin, thidiazuron, thiencarbazone, thiencarbazone-methyl, thifensulphuron, thifensulphuron-methyl, thiobencarb, tiocarbazil, topramezone, tralkoxydim, triafamone, triallate, triasulphuron, triaziflam, triazofenamide, tribenuron, tribenuron-methyl, trichloroacetic acid (TCA), triclopyr, tridiphane, trietazine, trifloxysulphuron, trifloxysulphuron-sodium, trifluralin, triflusulphuron, triflusulphuron-methyl, trimeturon, trinexapac, trinexapac-ethyl, tritosulphuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

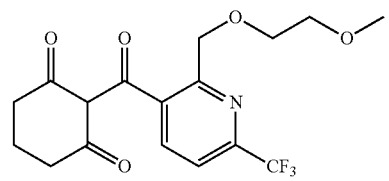

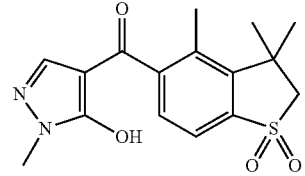

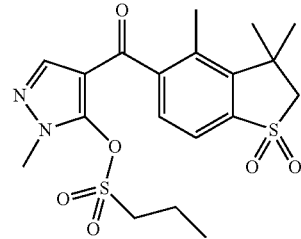

-continued

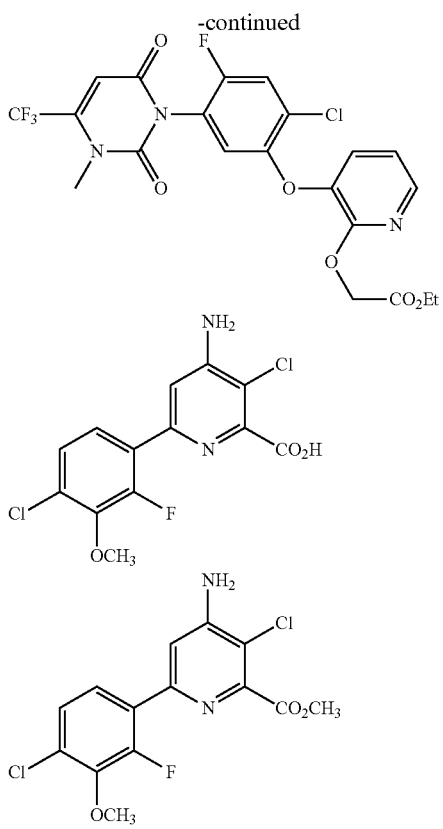

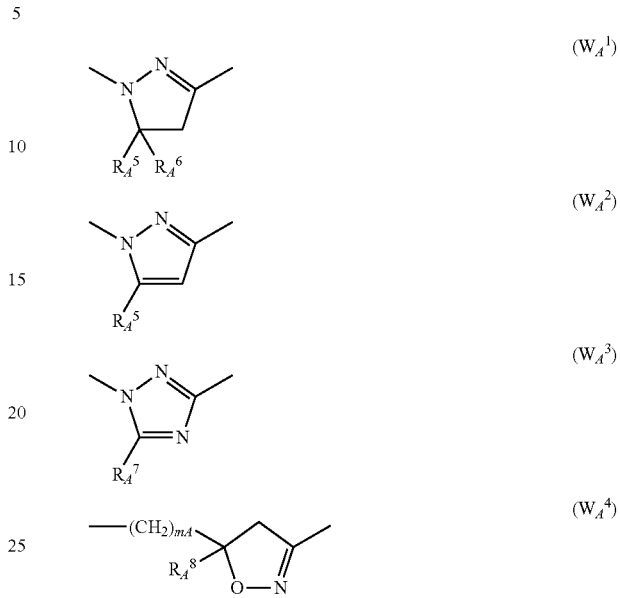

Of particular interest is the selective control of harmful plants in crops of useful plants and ornamentals. Although the compounds (I) according to the invention have already demonstrated very good to adequate selectivity in a large number of crops, in principle, in some crops and in particular also in the case of mixtures with other, less selective herbicides, phytotoxicities on the crop plants may occur. In this connection, combinations of compounds (I) according to the invention are of particular interest which comprise the compounds (I) or their combinations with other herbicides or pesticides and safeners. The safeners, which are used in an antidotically effective amount, reduce the phytotoxic side effects of the herbicides/pesticides employed, for example in economically important crops, such as cereals (wheat, barley, rye, corn, rice, millet), sugar beet, sugar cane, oilseed rape, cotton and soybeans, preferably cereals. The following groups of compounds are suitable, for example, as safeners for the compounds (I) and their combinations with further pesticides:
A) compounds of the formula (S-I)

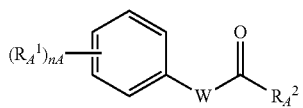 (S-I)

where the symbols and indices have the following meanings:
$n_A$ is a natural number from 0 to 5, preferably from 0 to 3;
$R_A^1$ is halogen, $(C_1-C_4)$-alkyl, $(C_1-C_4)$-alkoxy, nitro or $(C_1-C_4)$-haloalkyl;
$W_A$ is an unsubstituted or substituted divalent heterocyclic radical from the group of the partially unsaturated or aromatic five-membered heterocycles having 1 to 3 ring heteroatoms of the N or O type, where at least one nitrogen atom and at most one oxygen atom is present in the ring, preferably a radical from the group of $(W_A^1)$ to $(W_A^4)$, $m_A$ is 0 or 1;
$R_A^2$ is $OR_A^3$, $SR_A^3$ or $NR_A^3 R_A^4$ or a saturated or unsaturated 3- to 7-membered heterocycle having at least one nitrogen atom and up to 3 heteroatoms, preferably from the group of O and S, which is joined to the carbonyl group in (S-I) via the nitrogen atom and is unsubstituted or substituted by radicals from the group of $(C_1-C_4)$-alkyl, $(C_1-C_4)$-alkoxy or optionally substituted phenyl, preferably a radical of the formula $OR_A^3$, $NHR_A^4$ or $N(CH_3)_2$, especially of the formula $OR_A^3$;
$R_A^3$ is hydrogen or an unsubstituted or substituted aliphatic hydrocarbyl radical preferably having a total of 1 to 18 carbon atoms;
$R_A^4$ is hydrogen, $(C_1-C_6)$-alkyl, $(C_1-C_6)$-alkoxy or substituted or unsubstituted phenyl;
$R_A^5$ is H, $(C_1-C_8)$-alkyl, $(C_1-C_8)$-haloalkyl, $(C_1-C_4)$-alkoxy $(C_1-C_8)$-alkyl, cyano or $COOR_A^9$ in which $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;
$R_A^6$, $R_A^7$, $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl; preferably:
a) compounds of the type of the dichlorophenylpyrazoline-3-carboxylic acid, preferably compounds such as ethyl 1-(2,4-dichlorophenyl)-5-(ethoxycarbonyl)-5-methyl-2-pyrazoline-3-carboxylate (S1-1) ("mefenpyr-diethyl", see Pestic. Man.), and related compounds as described in WO 91/07874;
b) derivatives of dichlorophenylpyrazolecarboxylic acid, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl) pyrazole-3-carboxylate (S1-4), ethyl 1-(2,4-dichlorophenyl)-5-phenylpyrazole-3-carboxylate (S1-5) and related compounds as described in EP-A-333 131 and EP-A-269 806;

c) compounds of the triazolecarboxylic acid type, preferably compounds such as fenchlorazole(-ethyl), i.e. ethyl 1-(2,4-dichlorophenyl)-5-trichloromethyl-(1H)-1,2,4-triazole-3-carboxylate (S1-6), and related compounds as described in EP-A-174 562 and EP-A-346 620;

d) compounds of the type of the 5-benzyl- or 5-phenyl-2-isoxazoline-3-carboxylic acid or the 5,5-diphenyl-2-isoxazoline-3-carboxylic acid, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds, as described in WO 91/08202, or ethyl 5,5-diphenyl-2-isoxazolinecarboxylate (S1-9) ("isoxadifen-ethyl") or n-propyl 5,5-diphenyl-2-isoxazolinecarboxylate (S1-10) or ethyl 5-(4-fluorophenyl)-5-phenyl-2-isoxazoline-3-carboxylate (S1-11), as described in the patent application WO-A-95/07897.

B) Quinoline derivatives of the formula (S-II)

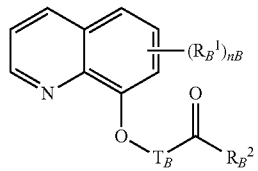

(S-II)

where the symbols and indices have the following meanings:
$R_B^1$ is halogen, $(C_1-C_4)$-alkyl, $(C_1-C_4)$-alkoxy, nitro or $(C_1-C_4)$-haloalkyl;
$n_B$ is a natural number from 0 to 5, preferably from 0 to 3;
$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, preferably from the group consisting of O and S, which is joined to the carbonyl group in (S-II) via the nitrogen atom and is unsubstituted or substituted by radicals from the group of $(C_1-C_4)$-alkyl, $(C_1-C_4)$-alkoxy or optionally substituted phenyl, preferably a radical of the formula $OR_B^3$, $NHR_B^4$ or $N(CH_3)_2$, especially of the formula $OR_B^3$;
$R_B^3$ is hydrogen or an unsubstituted or substituted aliphatic hydrocarbyl radical preferably having a total of 1 to 18 carbon atoms;
$R_B^4$ is hydrogen, $(C_1-C_6)$-alkyl, $(C_1-C_6)$-alkoxy or substituted or unsubstituted phenyl;
$T_B$ is a ($C_1$ or $C_2$)-alkanediyl chain which is unsubstituted or substituted by one or two $(C_1-C_4)$-alkyl radicals or by $[(C_1-C_3)$-alkoxy]carbonyl;
preferably:
a) compounds of the type of the 8-quinolinoxyacetic acid (S2), preferably 1-methylhexyl (5-chloro-8-quinolinoxy)acetate (common name "cloquintocet-mexyl" (S2-1) (see Pestic. Man.), 1,3-dimethyl-but-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxo-prop-1-yl(5-chloro-8-quinolinoxy)acetate (S2-9) and related compounds, as described in EP-A-86 750, EP-A-94 349 and EP-A-191 736 or EP-A-0 492 366, and also their hydrates and salts, as described in WO-A-2002/034048.

b) compounds of the (5-chloro-8-quinolinoxy)malonic acid type, preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

C) Compounds of the formula (S-III)

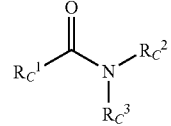

(S-III)

where the symbols and indices have the following meanings:
$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;
$R_C^2$, $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring,
preferably an oxazolidine, thiazolidine, piperidine, morpholine, hexahydropyrimidine or benzoxazine ring;
preferably:
active compounds of the type of the dichloroacetamides which are frequently used as pre-emergence safeners (soil-active safeners), such as, for example, "dichlormid" (see Pestic. Man.)
(=N,N-diallyl-2,2-dichloroacetamide),
"R-29148" (=3-dichloroacetyl-2,2,5-trimethyl-1,3-oxazolidine from Stauffer),
"R-28725" (=3-dichloroacetyl-2,2-dimethyl-1,3-oxazolidine from Stauffer),
"Benoxacor" (see Pestic. Man.) (=4-dichloroacetyl-3,4-dihydro-3-methyl-2H-1,4-benzoxazine),
"PPG-1292" (=N-allyl-N-[(1,3-dioxolan-2-yl)methyl]dichloracetamide from PPG Industries),
"DKA-24" (=N-allyl-N-[(allylaminocarbonyl)methyl]dichloracetamide from Sagro-Chem),
"AD-67" or "MON 4660" (=3-dichloroacetyl-1-oxa-3-aza-spiro[4,5]decane from Nitrokemia or Monsanto),
"TI-35" (=1-dichloroacetylazepane from TRI-Chemical RT)
"diclonon" (dicyclonon) or "BAS145138" or "LAB145138" (=3-dichloroacetyl-2,5,5-trimethyl-1,3-diazabicyclo[4.3.0]nonane from BASF) and
"Furilazol" or "MON 13900" (see Pestic. Man.) (=(RS)-3-dichloroacetyl-5-(2-furyl)-2,2-dimethyloxazolidine)

D) N-Acylsulphonamides of the formula (S-IV) and their salts

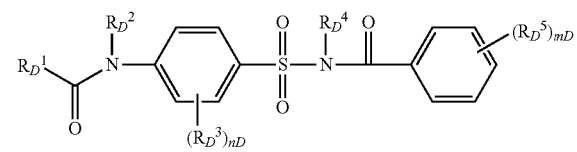

(S-IV)

in which
$R_D^1$ is hydrogen, a hydrocarbon radical, a hydrocarbonoxy radical, a hydrocarbonthio radical or a heterocyclyl radical which is preferably attached via a carbon atom, where each of the 4 lastmentioned radicals is unsubstituted or substituted by one or more identical or different radicals from the group consisting of halogen, cyano, nitro, amino, hydroxyl, carboxyl, formyl, carbonamide, sulphonamide and radicals of the formula —$Z^a$—$R^a$, where each hydrocarbon moiety has preferably 1 to 20 carbon atoms and a carbon-containing radical $R_D^1$ including substituents has preferably 1 to 30 carbon atoms;

$R_D^2$ is hydrogen or $(C_1-C_4)$-alkyl, preferably hydrogen, or $R_D^1$ and $R_D^2$ together with the group of the formula —CO—N— are the radical of a 3- to 8-membered saturated or unsaturated ring;

$R_D^3$ are identical or different and are halogen, cyano, nitro, amino, hydroxyl, carboxyl, formyl, $CONH_2$, $SO_2NH_2$ or a radical of the formula —$Z^b$—$R^b$;

$R_D^4$ is hydrogen or $(C_1-C_4)$-alkyl, preferably H;

$R_D^5$ are identical or different and are halogen, cyano, nitro, amino, hydroxyl, carboxyl, CHO, $CONH_2$, $SO_2NH_2$ or a radical of the formula —$Z^c$—$R^c$;

$R^a$ is a hydrocarbon radical or a heterocyclyl radical, where each of the two last-mentioned radicals is unsubstituted or substituted by one or more identical or different radicals from the group consisting of halogen, cyano, nitro, amino, hydroxyl, mono- and di-[$(C_1-C_4)$-alkyl]amino, or an alkyl radical in which a plurality, preferably 2 or 3, non-adjacent $CH_2$ groups are in each case replaced by an oxygen atom;

$R^b$, $R^c$ are identical or different and are a hydrocarbon radical or a heterocyclyl radical, where each of the two lastmentioned radicals is unsubstituted or substituted by one or more identical or different radicals from the group consisting of halogen, cyano, nitro, amino, hydroxyl, phosphoryl, halo-$(C_1-C_4)$-alkoxy, mono- and di-[$(C_1-C_4)$-alkyl]amino, or an alkyl radical in which a plurality, preferably 2 or 3, non-adjacent $CH_2$ groups are in each case replaced by an oxygen atom;

$Z^a$ is a divalent group of the formula —O—, —S—, —CO—, —CS—, —CO—O—, —CO—S—, —O—CO—, —S—CO—, —SO—, —SO$_2$—, —NR*—, —CO—NR*—, —NR*—CO—, —SO$_2$—NR*— or —NR*—SO$_2$—, where the bond indicated on the right-hand side of the divalent group in question is the bond to the radical $R^a$ and where the R* in the 5 lastmentioned radicals independently of one another are each H, $(C_1-C_4)$-alkyl or halo-$(C_1-C_4)$-alkyl;

$Z^b$, $Z^c$ are independently of one another a direct bond or a divalent group of the formula —O—, —S—, —CO—, —CS—, —CO—O—, —CO—S—, —O—CO—, —S—CO—, —SO—, —SO$_2$—, —NR*—, —SO$_2$—NR*—, —NR*—SO$_2$—, —CO—NR*— or —NR*—CO—, where the bond indicated at the right-hand side of the divalent group in question is the bond to the radical $R^b$ or $R^C$ and where the R* in the 5 lastmentioned radicals independently of one another are each H, $(C_1-C_4)$-alkyl or halo-$(C_1-C_4)$-alkyl;

$n_D$ is an integer from 0 to 4, preferably 0, 1 or 2, particularly preferably 0 or 1, and $m_D$ is an integer from 0 to 5, preferably 0, 1, 2 or 3, in particular 0, 1 or 2;

E) acylsulphamoylbenzamides of the formula (S-V), if appropriate also in salt form,

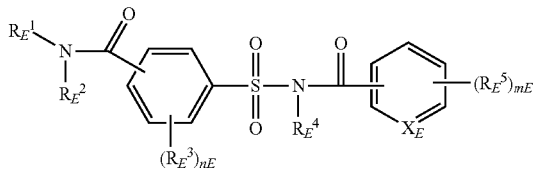

(S-V)

in which $X_E$ is CH or N, $R_E^1$ is hydrogen, heterocyclyl or a hydrocarbon radical, where the two lastmentioned radicals are optionally substituted by one or more identical or different radicals from the group consisting of halogen, cyano, nitro, amino, hydroxyl, carboxyl, CHO, $CONH_2$, $SO_2NH_2$ and $Z^a$—$R^a$;

$R_E^2$ is hydrogen, hydroxy, $(C_1-C_6)$-alkyl, $(C_2-C_6)$-alkenyl, $(C_2-C_6)$-alkynyl, $(C_1-C_6)$-alkoxy, $(C_2-C_6)$-alkenyloxy, where the five last-mentioned radicals are optionally substituted by one or more identical or different radicals from the group consisting of halogen, hydroxy, $(C_1-C_4)$-alkyl, $(C_1-C_4)$-alkoxy and $(C_1-C_4)$-alkylthio, or $R_E^1$ and $R_E^2$ together with the nitrogen atom that carries them are a 3- to 8-membered saturated or unsaturated ring;

$R_E^3$ is halogen, cyano, nitro, amino, hydroxyl, carboxyl, CHO, $CONH_2$, $SO_2NH_2$ or $Z^b$—$R^b$;

$R_E^4$ is hydrogen, $(C_1-C_4)$-alkyl, $(C_2-C_4)$-alkenyl or $(C_2-C_4)$-alkynyl;

$R_E^5$ is halogen, cyano, nitro, amino, hydroxyl, carboxyl, phosphoryl, CHO, $CONH_2$, $SO_2NH_2$ or $Z^c$—$R^C$;

$R^a$ is a $(C_2-C_{20})$-alkyl radical whose carbon chain is interrupted once or more than once by oxygen atoms, is heterocyclyl or a hydrocarbon radical, where the two lastmentioned radicals are optionally substituted by one or more identical or different radicals from the group consisting of halogen, cyano, nitro, amino, hydroxyl, mono- and di-[$(C_1-C_4)$-alkyl]-amino;

$R^b$, $R^c$ are identical or different and are a $(C_2-C_{20})$-alkyl radical whose carbon chain is interrupted once or more than once by oxygen atoms, are heterocyclyl or a hydrocarbon radical, where the two lastmentioned radicals are optionally substituted by one or more identical or different radicals from the group consisting of halogen, cyano, nitro, amino, hydroxyl, phosphoryl, $(C_1-C_4)$-haloalkoxy, mono- and di-[$(C_1-C_4)$-alkyl]amino;

$Z^a$ is a divalent unit from the group consisting of O, S, CO, CS, C(O)O, C(O)S, SO, $SO_2$, $NR^d$, $C(O)NR^d$ and $SO_2NR^d$;

$Z^b$, $Z^c$ are identical or different and are a direct bond or divalent unit from the group consisting of O, S, CO, CS, C(O)O, C(O)S, SO, $SO_2$, $NR^d$, $SO_2NR^d$ and $C(O)NR^d$;

$R^d$ is hydrogen, $(C_1-C_4)$-alkyl or $(C_1-C_4)$-haloalkyl;

$n_E$ is an integer from 0 to 4, and $m_E$ if X is CH, is an integer from 0 to 5, and, if X is N, is an integer from 0 to 4; from among these, preference is given to compounds (also in the form of their salts) of the type of the acylsulphamoylbenzamides, for example of the formula (S-VI) below, which are known, for example, from WO 99/16744,

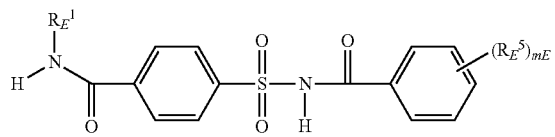

(S-VI)

for example those in which $R_E^1$=cyclopropyl and $R_E^5$=2-OMe ("cyprosulphamide", S3-1), $R_E^1$=cyclopropyl and $R_E^5$=5-Cl-2-OMe (S3-2), $R_E^1$=ethyl and $R_E^5$=2-OMe (S3-3), $R_E^1$=isopropyl and $R_E^5$=5-Cl-2-OMe (S3-4) and $R_E^1$=isopropyl and $R_E^5$=2-OMe (S3-5);

F) compounds of the type of the N-acylsulphamoylphenylureas of the formula (S-VII), which are known, for example, from EP-A-365484

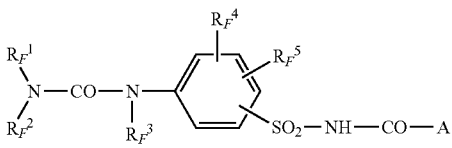

(S-VII)

in which

A is a radical from the group consisting of

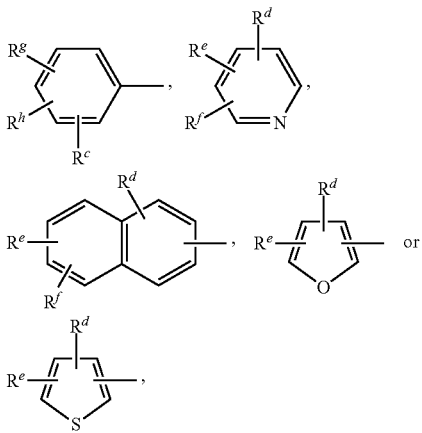

$R_F^1$ and $R_F^2$ independently of one another are hydrogen, $(C_1-C_8)$-alkyl, $(C_3-C_8)$-cycloalkyl, $(C_3-C_6)$-alkenyl, $(C_3-C_6)$-alkynyl,

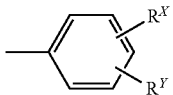

or by $(C_1-C_4)$-alkoxy or

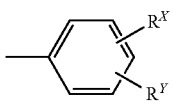

substituted $(C_1-C_4)$-alkoxy, or $R_F^1$ and $R_F^2$ together are a $(C_4-C_6)$-alkylene bridge and a $(C_4-C_6)$-alkylene bridge interrupted by oxygen, sulphur, SO, $SO_2$, NH or $—N(C_1-C_4$-alkyl)-, $R_F^3$ is hydrogen or $(C_1-C_4)$-alkyl, $R_F^4$ and $R_F^5$ independently of one another are hydrogen, halogen, cyano, nitro, trifluoromethyl, $C_1-C_4$-alkyl, $C_1-C_4$-alkoxy, $C_1-C_4$-alkylthio, $C_1-C_4$-alkylsulphinyl, $C_1-C_4$-alkylsulphonyl, $—COOR^j$, $—CONR^kR^m$, $—COR^n$, $—SO_2NR^kR^m$ or $—OSO_2—C_1-C_4$-alkyl, or $R^a$ and $R^b$ together are a $(C_3-C_4)$-alkylene bridge which may be interrupted by halogen or $C_1-C_4$-alkyl, or a $(C_3-C_4)$-alkenylene bridge which may be interrupted by halogen or $(C_1-C_4)$-alkyl, or a $C_4$-alkadienylene bridge which may be substituted by halogen or $(C_1-C_4)$-alkyl, and $R^g$ and $R^h$ independently of one another are hydrogen, halogen, $C_1-C_4$-alkyl, trifluoromethyl, methoxy, methylthio or $—COOR^j$, where $R^c$ is hydrogen, halogen, $(C_1-C_4)$-alkyl or methoxy, $R^d$ is hydrogen, halogen, nitro, $(C_1-C_4)$-alkyl, $(C_1-C_4)$-alkoxy, $(C_1-C_4)$-alkylthio, $(C_1-C_4)$-alkylsulphinyl, $(C_1-C_4)$-alkylsulphonyl, $—COOR^j$ or $—CONR^kR^m$, $R^e$ is hydrogen, halogen, $C_1-C_4$-alkyl, $—COOR^j$, trifluoromethyl or methoxy, or $R^d$ and $R^e$ together are a $(C_3-C_4)$-alkylene bridge, $R^f$ is hydrogen, halogen or $(C_1-C_4)$-alkyl, $R^X$ and $R^Y$ independently of one another are hydrogen, halogen, $(C_1-C_4)$-alkyl, $(C_1-C_4)$-alkoxy, $(C_1-C_4)$-alkylthio, $—COOR^4$, trifluoromethyl, nitro or cyano, $R^j$, $R^k$ and $R^m$ independently of one another are hydrogen or $(C_1-C_4)$-alkyl, $R^k$ and $R^m$ together are a $(C_4-C_6)$-alkylene bridge or a $(C_4-C_6)$-alkylene bridge interrupted by oxygen, NH or $—N(C_1-C_4$-alkyl)-, and $R^n$ is $(C_1-C_4)$-alkyl, phenyl or phenyl substituted by halogen, $(C_1-C_4)$-alkyl, methoxy, nitro or trifluoromethyl, from among these, preference is given to:
1-[4-(N-2-methoxybenzoylsulphamoyl)phenyl]-3-methylurea, 1-[4-(N-2-methoxybenzoylsulphamoyl)phenyl]-3,3-dimethylurea, 1-[4-(N-4,5-dimethylbenzoylsulphamoyl)phenyl]-3-methylurea, 1-[4-(N-naphthoylsulphamoyl)phenyl]-3,3-dimethylurea, including the stereoisomers and the salts customary in agriculture, G) active compounds from the class of the hydroxyaromatics and aromatic-aliphatic carboxylic acid derivatives, for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 1,2-dihydro-2-oxo-6-trifluoromethylpyridine-3-carboxamide, 2-hydroxycinnamic acid, 2,4-dichlorocinnamic acid, as described in WO 2004084631, WO 2005015994, WO 2006007981, WO 2005016001;

H) active compounds from the class of the 1,2-dihydroquinoxalin-2-ones, for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulphonylaminoethyl)-3-(2-thienyl)-1,2-dihydro-quinoxalin-2-one, as described in WO 2005112630, I) active compounds which, in addition to a herbicidal action against harmful plants also have safener action on crop plants such as rice, such as, for example,
"dimepiperate" or "MY-93" (see Pestic. Man.) (=S-1-methyl-1-phenylethyl piperidine-1-thiocarboxylate), which is known as safener for rice against damage caused by the herbicide molinate,
"daimuron" or "SK 23" (see Pestic. Man.) (=1-(1-methyl-1-phenylethyl)-3-p-tolyl-urea), which is known as a safener for rice against damage caused by the herbicide imazosulphuron,
"cumyluron"="JC-940" (=3-(2-chlorophenylmethyl)-1-(1-methyl-1-phenylethyl)urea, see JP-A-60087254), which is known as a safener for rice against damage caused by some herbicides,
"methoxyphenon" or "NK 049" (=3,3'-dimethyl-4-methoxybenzophenone), which is known as a safener for rice against damage caused by some herbicides,
"CSB" (=1-bromo-4-(chloromethylsulphonyl)benzene) (CAS reg. no. 54091-06-4 from Kumiai), which is known as a safener for rice against damage caused by some herbicides, K) compounds of the formula (S-IX), as described in WO-A-1998/38856,

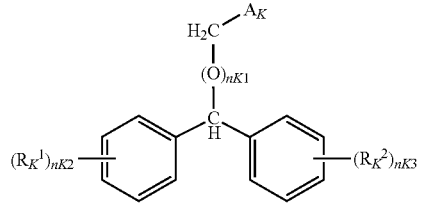

(S-IX)

where the symbols and indices have the following meanings:
$R_K^1$, $R_K^2$ independently of one another are halogen, $(C_1\text{-}C_4)$-alkyl, $(C_1\text{-}C_4)$-alkoxy, $(C_1\text{-}C_4)$-haloalkyl, $(C_1\text{-}C_4)$-alkylamino, di$(C_1\text{-}C_4)$-alkylamino, nitro;
$A_K$ is $COOR_K^3$ or $COOR_K^4$
$R_K^3$, $R_K^4$ independently of one another are hydrogen, $(C_1\text{-}C_4)$-alkyl, $(C_2\text{-}C_6)$-alkenyl, $(C_2\text{-}C_4)$-alkynyl, cyanoalkyl, $(C_1\text{-}C_4)$-haloalkyl, phenyl, nitrophenyl, benzyl, halobenzyl, pyridinylalkyl and alkylammonium,
$n_K^1$ is 0 or 1 and
$n_K^2$, $n_K^3$ independently of one another are 0, 1 or 2;
preferably:
methyl (diphenylmethoxy)acetate (CAS reg no: 41858-19-9), L) compounds of the formula (S-X)
as described in WO A-98/27049

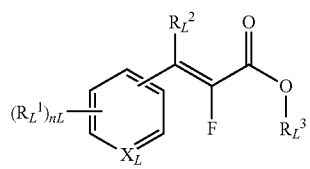

(S-X)

where the symbols and indices have the following meanings:
$X_L$ is CH or N,
$n_L$ if X=N, is an integer from 0 to 4 and
in the case that X=CH, an integer from 0 to 5,
$R_L^1$ is halogen, $(C_1\text{-}C_4)$-alkyl, $(C_1\text{-}C_4)$-haloalkyl, $(C_1\text{-}C_4)$-alkoxy, $(C_1\text{-}C_4)$-haloalkoxy, nitro, $(C_1\text{-}C_4)$-alkylthio, $(C_1\text{-}C_4)$-alkylsulphonyl, $(C_1\text{-}C_4)$-alkoxycarbonyl, optionally substituted phenyl, optionally substituted phenoxy,
$R_L^2$ is hydrogen or $(C_1\text{-}C_4)$-alkyl
$R_L^3$ is hydrogen, $(C_1\text{-}C_8)$-alkyl, $(C_1\text{-}C_4)$-alkenyl, $(C_1\text{-}C_4)$-alkynyl, or aryl, where each of the aforementioned carbon-containing radicals is unsubstituted or substituted by one or more, preferably up to three identical or different radicals from the group consisting of halogen and alkoxy; or salts thereof.

M) active compounds from the class of the 3-(5-tetrazolylcarbonyl)-2-quinolones, for example 1,2-dihydro-4-hydroxy-1-ethyl-3-(5-tetrazolylcarbonyl)-2-quinolone (CAS Reg. No.: 219479-18-2), 1,2-dihydro-4-hydroxy-1-methyl-3-(5-tetrazolylcarbonyl)-2-quinolone (CAS Reg. No.: 95855-00-8), as described in WO-A-1999000020, N) compounds of the formula (S-XI) or (S-XII) as described in WO-A-2007023719 and WO-A-2007023764

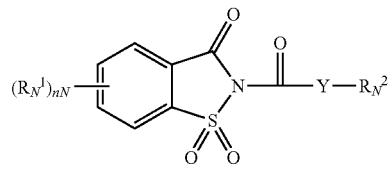

(S-XI)

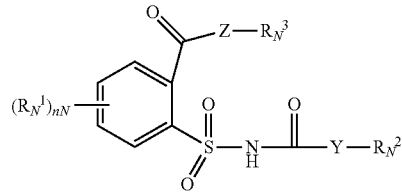

(S-XII)

in which
$R_N^1$ is halogen, $(C_1\text{-}C_4)$-alkyl, methoxy, nitro, cyano, $CF_3$, $OCF_3$,
Y, Z independently of one another are O or S,
$n_N$ is an integer from 0 to 4,
$R_N^2$ is $(C_1\text{-}C_{16})$-alkyl, $(C_2\text{-}C_6)$-alkenyl, $(C_3\text{-}C_6)$-cycloalkyl, aryl; benzyl, halobenzyl,
$R_N^3$ is hydrogen, $(C_1\text{-}C_6)$-alkyl;
O) one or more compounds from the group consisting of:
1,8-naphthalic anhydride, O,O-diethyl S-2-ethylthioethyl phosphorodithioate (disulphoton), 4-chlorophenyl methylcarbamate (mephenate), O,O-diethyl O-phenyl phosphorothioate (dietholate), 4-carboxy-3,4-dihydro-2H-1-benzopyran-4-acetic acid (CL-304415, CAS Reg. No.: 31541-57-8), 2-propenyl 1-oxa-4-azaspiro[4.5]decane-4-carbodithioate (MG-838, CAS Reg. No.: 133993-74-5), methyl [(3-oxo-1H-2-benzothiopyran-4(3H)-ylidene)methoxy]acetate (from WOA98/13361; CAS Reg. No.: 205121-04-6), cyanomethoxyimino (phenyl)acetonitrile (cyometrinil), 1,3-dioxolan-2-yl-methoxyimino(phenyl)acetonitrile (oxabetrinil), 4'-chloro-2,2,2-trifluoroacetophenone O-1,3-dioxolan-2-ylmethyloxime (fluxofenim), 4,6-dichloro-2-phenylpyrimidine (fenclorim), benzyl 2-chloro-4-trifluoromethyl-1,3-thiazole-5-carboxylate (flurazole), 2-dichloromethyl-2-methyl-1,3-dioxolane (MG-191), including the stereoisomers possible in each case and including agriculturally customary salts.

The weight ratios of herbicide (mixture) to safener depend generally on the herbicide application rate and the efficacy of the safener in question and may vary within wide limits, for example in the range from 200:1 to 1:200, preferably 100:1 to 1:100, in particular 20:1 to 1:20. Analogously to the compounds (I) or mixtures thereof, the safeners can be formulated with further herbicides/pesticides and be provided and employed as a finished formulation or tankmix with the herbicides.

For application, the herbicide or herbicide/safener formulations present in commercial form are, if appropriate, diluted in a customary manner, for example in the case of wettable powders, emulsifiable concentrates, dispersions and water-dispersible granules with water. Preparations in the form of dusts, granules for soil application or granules for broadcasting and sprayable solutions are usually not diluted further with other inert substances prior to application.

The required application rate of the compounds of the formula (I) and/or their salts varies according to the external conditions such as, inter alia, temperature, humidity and the type of herbicide used. It can vary within wide limits. For the application of herbicide for controlling harmful plants, it is, for example, in the range of from 0.001 to 10.0 kg/ha or more of active substance, preferably in the range of from 0.005 to 5 kg/ha, in particular in the range of from 0.01 to 1 kg/ha, of active substance. This applies both to the pre-emergence and the post-emergence application.

When used as plant growth regulator, for example as culm stabilizer for crop plants like those mentioned above, preferably cereal plants, such as wheat, barley, rye, triticale, millet, rice or corn, the application rate is, for example, in the range of from 0.001 to 2 kg/ha or more of active substance, preferably in the range of from 0.005 to 1 kg/ha, in particular in the range of from 10 to 500 g/ha of active substance, very particularly from 20 to 250 g/ha of active substance. (please check whether this should be mentioned). This applies both to application by the pre-emergence method and the post-emergence method, the post-emergence treatment generally being preferred.

The application as culm stabilizer may take place at various stages of the growth of the plants. Preferred is, for example, the application after the tillering phase, at the beginning of the longitudinal growth.

As an alternative, application as plant growth regulator is also possible by treating the seed, which includes various techniques for dressing and coating seed. Here, the application rate depends on the particular techniques and can be determined in preliminary tests.

In an exemplary manner, some synthesis examples of compounds of the general formula (I) are described below. In the examples, the amounts (including percentages) refer to the weight, unless especially stated otherwise.

The symbols ">" and "<" mean "greater than" and "smaller than", respectively. The symbol "≥" means "greater than or equal to", the symbol "≤" means "smaller than or equal to".

If, in the context of the description and the examples, the terms "R" and "S" are given for the absolute configuration on a centre of chirality of the stereoisomers of the formula (I), this RS nomenclature follows, unless defined differently, the Cahn-Ingold-Prelog rule.

(A) SYNTHESIS EXAMPLES

Example A1

Preparation of an erythro/threo diastereomer mixture of 5-(2,6-dioxocyclohexyl)-2-(3-fluorophenyl)-3-(4-fluorophenyl)-5-oxopentanenitrile [Table 2 Example Iaa20]

Step 1: Methyl 4-cyano-4-(3-fluorophenyl)-3-(4-fluorophenyl)butanoate

Under protective gas (Ar), 0.767 g (5.0 mmol) of (3-fluorophenyl)acetonitrile and 0.1 ml of sodium methoxide solution (30% in methanol) were added to 0.820 g (4.55 mmol) of methyl 3-(4-fluorophenyl)acrylate in 15.0 ml of toluene, and the mixture was stirred in a closed vessel at 65° C. for 15 h. The solvent was removed under reduced pressure, the residue was taken up in ethyl acetate and the mixture was washed twice with in each case 25 ml of water. The combined organic phases were dried over sodium sulphate and the solvent was removed under reduced pressure. Chromatography of the residue on silica gel (ethyl acetate/heptane=20:80) gave 0.950 g (57% of theory) of the diastereomeric methyl 4-cyano-4-(3-fluorophenyl)-3-(4-fluorophenyl)butanoate (erythro:threo=54:46 according to integration of the methyl singlets in the $^1$H-NMR in CDCl$_3$ at 3.66 and 3.56 ppm).

Step 2: 4-Cyano-3-(4-fluorophenyl)-4-(3-fluorophenyl)butanoic acid

Under protective gas (Ar), 10 ml of 2 molar aqueous sodium hydroxide solution were added to 1.75 g (5.55 mmol) of methyl 4-cyano-4-(3-fluorophenyl)-3-(4-fluorophenyl)butanoate in 50.0 ml of methanol, and the mixture was stirred at 25° C. for 8 h. The methanol was removed under reduced pressure. The residue was acidified with concentrated hydrochloric acid (pH=3) and extracted three times with in each case 15 ml of dichloromethane. The combined organic phases were dried over sodium sulphate and the solvent was removed under reduced pressure. This gave 1.62 g (96.9% of theory) of the title compound in the form of colourless crystals (erythro:threo=49:51, comparison of the multiplets in the $^1$H-NMR in CDCl$_3$ at 2.60 and 2.85 ppm).

Step 3: 3-Oxocyclohex-1-en-1-yl 4-cyano-4-(3-fluorophenyl)-3-(4-fluorophenyl)butanoate 1.79 g (15 mmol) of thionyl chloride were added to 0.452 g (1.5 mmol) of 4-cyano-3-(4-fluorophenyl)-4-(3-fluorophenyl)butanoic acid, and the mixture was stirred at 80° C. for 1.5 h. Excess thionyl chloride was removed under reduced pressure. The reaction mixture concentrated in this manner (which contains acid chloride) was dissolved in 3 ml of dichloromethane and, at 0° C., added dropwise (about 30 min) to a mixture of 0.252 g (2.25 mmol) of 1,3-cyclohexanedione and 0.304 g (3 mmol) of triethylamine in dichloromethane (10 ml). After 3 h of stirring at 25° C., the solvent was removed under reduced pressure, the residue was taken up in ethyl acetate and the mixture was washed twice with in each case 25 ml of water. The combined organic phases were dried over sodium sulphate and the solvent was removed under reduced pressure.

The resulting crude product was reacted further in Step 4.

Step 4: 5-(2,6-Dioxocyclohexyl)-2-(3-fluorophenyl)-3-(4-fluorophenyl)-5-oxopentanenitrile 0.013 g (0.15 mmol) of acetocyanohydrin and 0.273 g (2.0 mmol) of triethylamine were added to 0.593 g (1.50 mmol) of 3-oxocyclohex-1-en-1-yl 4-cyano-4-(3-fluorophenyl)-3-(4-fluorophenyl)butanoate in 5.0 ml of acetonitrile, and the mixture was stirred in a closed vessel at 25° C. overnight. The solvent was removed under reduced pressure, the residue was taken up in ethyl acetate and the mixture was washed twice with in each case 25 ml of water. The combined organic phases were dried over sodium sulphate and the solvent was removed under reduced pressure. Preparative chromatography [(90 ml/min acetonitrile/water (trifluoroacetic acid 0.05%)] on a solid phase [Nucleodur C18, HTec C18, 10 μm, (250×50)-mm column] gave 0.267 g (45% of theory) of an erythro/threo diastereomer mixture of 5-(2,6-dioxocyclohexyl)-2-(3-fluorophenyl)-3-(4-fluorophenyl)-5-oxopentanenitrile (erythro:threo=63:37 according to integration of the doublets in the $^1$H-NMR in CDCl$_3$ at 4.30 ppm and 4.03 ppm);

$^1$H-NMR in CDCl$_3$ erythro: 17.47 (s, 1H), 4.30 (d, 1H), threo: 17.46 (s, 1H), 4.03 (d, 1H)

mass spectrum: molecular peak 394 [M−1]+ retention time in HPLC: 1.58 min

Example A2

Diastereomer mixture of 2-[3-(4-chlorophenyl)-4-cyano-4-(3-fluorophenyl)butanoyl]-3-oxocyclohex-1-en-1-yl 2,2-dim ethylpropanoate [Table 2 Example Iaa32]

0.091 g (0.656 mmol) of triethylamine and, at 0° C., 0.069 g (0.568 mmol) of 2,2-dimethylpropanoyl chloride were added to 0.180 g (0.43 mmol) of 5-(2,6-dioxocyclohexyl)-2-(3-fluorophenyl)-3-(4-chlorophenyl)-5-oxopentanonitrile in 3.0 ml of dichloromethane, and the mixture was stirred in a closed vessel at 25° C. for 3 h. The solvent was removed under reduced pressure, the residue was taken up in ethyl acetate and the mixture was washed twice with in each case 25 ml of water. The combined organic phases were dried over sodium sulphate and the solvent was removed under reduced pressure. Preparative chromatography [(90 ml/min acetonitrile/water (trifluoroacetic acid 0.05%)] on a solid phase [Nucleodur C18, HTec C18, 10 µm, (250×50)-mm column] gave 114 mg (8% of theory) of an erythro/threo diastereomer mixture of 2-[3-(4-chlorophenyl)-4-cyano-4-(3-fluorophenyl)butanoyl]-3-oxocyclohex-1-en-1-yl 2,2-dimethylpropanoate (erythro:threo=70:30 according to integration of the tert-butyl singlets in the $^1$H-NMR in CDCl$_3$ at 1.15 ppm and 1.06 ppm).

Example A3

Diastereomer mixture of methyl 2,6-dicyano-6-(3-fluorophenyl)-5-(4-fluorophenyl)-3-oxohexanoate [Table 26 Example IB8aa1]

Step 1: Methyl 4-cyano-4-(3-fluorophenyl)-3-(4-fluorophenyl)butanoate

Under protective gas (Ar), 0.767 g (5.0 mmol) of (3-fluorophenyl)acetonitrile and 0.1 ml of sodium methoxide solution (30% in methanol) were added to 0.820 g (4.55 mmol) of methyl 3-(4-fluorophenyl)acrylate in 15.0 ml of toluene, and the mixture was stirred in a closed vessel at 65° C. for 15 h. The solvent was removed under reduced pressure, the residue was taken up in ethyl acetate and the mixture was washed twice with in each case 25 ml of water. The combined organic phases were dried over sodium sulphate and the solvent was removed under reduced pressure. Chromatography of the residue on silica gel (ethyl acetate/heptane=20:80) gave 0.950 g (57% of theory) of an erythro/threo diastereomer mixture of methyl 4-cyano-(3-fluorophenyl)-3-(4-fluorophenyl)butanoate (erythro:threo=54:46 according to integration of the methyl singlets in the $^1$H-NMR in CDCl$_3$ at 3.66 and 3.56 ppm).

Step 2: 4-Cyano-3-(4-fluorophenyl)-4-(3-fluorophenyl)butanoic acid

Under protective gas (Ar), 10 ml of 2 molar aqueous sodium hydroxide solution were added to 1.75 g (5.55 mmol) of methyl 4-cyano-3-(4-fluorophenyl)-4-(3-fluorophenyl) butanoate (Example A1) in 50.0 ml of methanol, and the mixture was stirred at 25° C. for 8 h. The methanol was removed under reduced pressure. The residue was acidified with concentrated hydrochloric acid (pH=3) and extracted three times with in each case 15 ml of dichloromethane. The combined organic phases were dried over sodium sulphate and the solvent was removed under reduced pressure. This gave 1.62 g (96.9% of theory) of the title compound in the form of colourless crystals (erythro:threo=49:51 according to comparison of the multiplets in the $^1$H-NMR in CDCl$_3$ at 2.60 and 2.85 ppm).

Step 3: Methyl 2,6-dicyano-6-(3-fluorophenyl)-5-(4-fluorophenyl)-3-oxohexanoate 1.79 g (20 mmol) of thionyl chloride were added to 0.603 g (2.0 mmol) of 4-cyano-3-(4-fluorophenyl)-4-(3-fluorophenyl)butanoic acid, and the mixture was stirred at 80° C. for 1.5 h. Excess thionyl chloride was removed under reduced pressure (residue=acid chloride). 0.297 g (3.00 mmol) of methyl cyanoacetate, 0.012 g (0.1 mmol) of 4-dimethylaminopyridine and the acid chloride dissolved in dichloromethane (5 ml) were added to 0.405 g (4.00 mmol) of triethylamine in 10 ml of dichloromethane, and the mixture was stirred at 25° C. for 2 h. 50 ml of ethyl acetate were then added, and the mixture was extracted twice with 25 ml of water each. The combined organic phases were dried over sodium sulphate and the solvent was removed under reduced pressure. Preparative chromatography [(90 ml/min acetonitrile/water (trifluoroacetic acid 0.05%)] on a solid phase [Nucleodur C18, HTec C18, 10 µm, (250×50)-mm column] gave 0.019 g (8% of theory) of an erythro/threo diastereomer mixture of methyl 2,6-dicyano-6-(3-fluorophenyl)-5-(4-fluorophenyl)-3-oxohexanoate (erythro:threo=52:48 according to integration of the doublets in the $^1$H-NMR in CDCl$_3$ at 4.09 ppm and 3.99 ppm).

Example A4

Diastereomers of methyl 2-acetyl-6-cyano-6-(3-fluorophenyl)-5-(4-fluorophenyl)-3-oxohexanoate [Table 27 Example IBXaa20]

Step 1: Methyl 4-cyano-4-(3-fluorophenyl)-3-(4-fluorophenyl)butanoate

Under protective gas (Ar), 0.767 g (5.0 mmol) of (3-fluorophenyl)acetonitrile and 0.1 ml of sodium methoxide solution (30% in methanol) were added to 0.820 g (4.55 mmol) of methyl 3-(4-fluorophenyl)acrylate in 15.0 ml of toluene, and the mixture was stirred in a closed vessel at 65° C. for 15 h. The solvent was removed under reduced pressure, the residue was taken up in ethyl acetate and the mixture was washed twice with in each case 25 ml of water. The combined organic phases were dried over sodium sulphate and the solvent was removed under reduced pressure. Chromatography of the residue on silica gel (ethyl acetate/heptane=20:80) gave 0.950 g (57% of theory) of an erythro/threo diastereomer mixture of methyl 4-cyano-(3-fluorophenyl)-3-(4-fluorophenyl)butanoate (erythro:threo=54:46 according to integration of the methyl singlets in the $^1$H-NMR in CDCl$_3$ at 3.66 and 3.56 ppm).

Step 2: 4-Cyano-3-(4-fluorophenyl)-4-(3-fluorophenyl)butanoic acid

Under protective gas (Ar), 10 ml of 2 molar aqueous sodium hydroxide solution were added to 1.75 g (5.55 mmol) of methyl 4-cyano-3-(4-fluorophenyl)-4-(3-fluorophenyl) butanoate (Example A1) in 50.0 ml of methanol, and the mixture was stirred at 25° C. for 8 h. The methanol was removed under reduced pressure. The residue was acidified with concentrated hydrochloric acid (pH=3) and extracted three times with in each case 15 ml of dichloromethane. The combined organic phases were dried over sodium sulphate and the solvent was removed under reduced pressure. This gave 1.62 g (96.9% of theory) of the title compound in the form of colourless crystals (erythro:threo=49:51 according to comparison of the multiplets in the ¹H-NMR in CDCl₃ at 2.60 and 2.85 ppm).

Step 3: Methyl 2-acetyl-6-cyano-6-(3-fluorophenyl)-5-(4-fluorophenyl)-3-oxohexanoate 2.379 g (20 mmol) of thionyl chloride were added to 0.603 g (2.0 mmol) of 4-cyano-3-(4-fluorophenyl)-4-(3-fluorophenyl)butanoic acid, and the mixture was stirred at 80° C. for 1.5 h. Excess thionyl chloride was removed under reduced pressure, giving the acid chloride as residue. At 0° C., 0.316 g (4.00 mmol) of pyridine and then the acid chloride dissolved in dichloromethane (5 ml) were added to 0.190 g (2.00 mmol) of magnesium chloride and 0.464 g (4.00 mmol) of methyl 3-oxobutanoate in dichloromethane (5 ml), and the mixture was stirred at 25° C. for 1 h. The residue was taken up in ethyl acetate and washed twice with in each case 25 ml of water. The combined organic phases were dried over sodium sulphate and the solvent was removed under reduced pressure. Preparative chromatography [(90 ml/min acetonitrile/water (trifluoroacetic acid 0.05%)] on a solid phase [Nucleodur C18, HTec C18, 10 μm, (250×50)-mm column] gave 0.422 g (52% of theory) of the erythro/threo diastereomer mixture of methyl 2-acetyl-6-cyano-6-(3-fluorophenyl)-5-(4-fluorophenyl)-3-oxohexanoate (erythro:threo=53:47 according to integration of the singlets in the ¹H-NMR in CDCl₃ at 17.74 ppm and 17.62 ppm).

Example A5

2-(3,4-Difluorophenyl)-3-(3-fluorophenyl)-5-(5-methyl-1,2-oxazol-4-yl)-5-oxopentanonitrile (see Table 35, Compound No. IB10ga6)

Step 1: Methyl 4-cyano-4-(3,4-difluorophenyl)-3-(3-fluorophenyl)butanoate

Under protective gas (Ar), 3.828 g (25.0 mmol) of (3,4-difluorophenyl)acetonitrile and 0.281 mg of potassium tert-butoxide were added to 4.099 g (22.7 mmol) of methyl 3-(3-fluorophenyl)acrylate in 25.0 ml of toluene, and the mixture was stirred in a closed vessel at 65° C. for 5 h. The solvent was removed under reduced pressure, the residue was taken up in ethyl acetate and the mixture was washed twice with in each case 25 ml of water. The combined organic phases were dried over sodium sulphate and the solvent was removed under reduced pressure. Chromatography of the residue on silica gel (ethyl acetate/heptane=20:80) gave 7.3 g (87% of theory) of the diastereomeric methyl 4-cyano-4-(3,4-difluorophenyl)-3-(3-fluorophenyl)butanoate (erythro:threo=65:35 according to integration of the methyl singlets in the ¹H-NMR in CDCl₃ at 3.68 and 3.59 ppm).

Step 2: 4-Cyano-4-(3,4-fluorophenyl)-3-(3-fluorophenyl)butanoic acid

Under protective gas (Ar), 23.5 ml of 2 molar aqueous sodium hydroxide solution were added to 4.7 g (14.1 mmol) of methyl 4-cyano-4-(3,4-difluorophenyl)-3-(3-fluorophenyl)butanoate in 95.0 ml of methanol, and the mixture was stirred at 25° C. overnight. The methanol was removed under reduced pressure. The residue was acidified with concentrated hydrochloric acid (pH=3) and extracted three times with in each case 100 ml of dichloromethane. The combined organic phases were dried over sodium sulphate and the solvent was removed under reduced pressure. This gave 4.50 g (99.9% of theory) of the title compound in the form of colourless crystals (erythro:threo=52:48, comparison of the doublets in the ¹H-NMR in CDCl₃ at 4.34 and 4.04 ppm).

Step 3: 2-(3,4-Difluorophenyl)-3-(3-fluorophenyl)-5-(5-methyl-1,2-oxazol-4-yl)-5-oxopentanonitrile In a dry, argon-filled Schlenk tube with a magnetic stirrer bar and septum, magnesium turnings (291 mg, 11.9 mmol), zinc chloride (717 mg, 5.26 mmol) and lithium chloride (254 mg, 5.98 mmol) were initially charged in THF (5 ml) and activated by addition of DIBAL-H (0.2 ml, 1 M in THF). After 5 min of stirring, 4-iodo-5-methyl-1,2-oxazole (1.0 g, 4.78 mmol) in anhydrous THF (3 ml) was added dropwise at 20° C. Thereafter, the reaction mixture was stirred at 25° C. for another 30 min. The resulting crude solution is then reacted further with the acid chloride below.

6.84 g (57.5 mmol) of thionyl chloride were added to 1.83 g (5.75 mmol) of 4-cyano-4-(3,4-difluorophenyl)-3-(3-fluorophenyl)butanoic acid, and the mixture was stirred at 80° C. for 1.5 h. Excess thionyl chloride was removed under reduced pressure. The reaction mixture concentrated in this manner (contains acid chloride) was dissolved in 3 ml of dichloromethane and, at −10° C., added dropwise (about 30 min) to the crude solution above and then stirred at 25° C. for a further 2 h. The solvent was removed under reduced pressure, the residue was taken up in ethyl acetate and the mixture was washed twice with in each case 25 ml of water. The combined organic phases were dried over sodium sulphate and the solvent was removed under reduced pressure. Chromatography of the residue on silica gel (ethyl acetate/heptane=20:80) gave 810 mg (44% of theory) of the mixture of the diastereomeric 2-(3,4-difluorophenyl)-3-(3-fluorophenyl)-5-(5-methyl-1,2-oxazol-4-yl)-5-oxopentanonitrile (erythro:threo=63:37 according to integration of the methyl singlets in the ¹H-NMR in CDCl₃ at 8.54 and 8.48 ppm).

NMR (erythro): 8.54 (s, 1H), 7.22 (m, 1H), 7.09 (m, 1H), 6.98 (m, 2H), 6.82 (m, 3H), 4.51 (d, 1H), 3.71 (m, 1H), 3.50 (dd, 1H), 3.27 (dd, 1H), 2.75 (s, 3H);

MS: 385 [M+1]+; HPLC (rt): 1.57 min

Example No. IB10ga6

NMR (threo): 8.48 (s, 1H), 7.27 (m, 1H), 7.12 (m, 1H), 6.96 (m, 5H), 4.13 (d, 1H), 3.82 (m, 1H), 3.39 (dd, 1H), 3.23 (dd, 1H), 2.65 (s, 3H);

MS: 385 [M+1]+; HPLC (rt): 1.57 min

The compounds described in the tables below are obtained according to or analogously to the examples described above, if appropriate with additional use of the general methods described further above.

In the tables below:
H=hydrogen (atom)
Me=methyl or CH₃
Et=ethyl
n-Pr=n-propyl
i-Pr=isopropyl
n-Bu=n-butyl
i-Bu=isobutyl
rt=retention time
F, Cl, Br, I=fluorine, chlorine, bromine and iodine, respectively, in accordance with the conventional chemical atom symbol
MeO or OMe=methoxy
CN=cyano
NO₂=nitro
Ph=phenyl The position of a substituent at the phenyl ring, for example in position 2, is stated as a prefix to the symbol or the abbreviation of the radical, for example 2-Cl=2-chloro 2-Me=2-methyl Numerations of the substituent positions for di- or trisubstituted substitution patterns are analogously stated as a prefix, for example 3,5-Me$_2$=3,5-dimethyl (e.g. as substitution at the phenyl ring)

2,3-Cl$_2$=2,3-dichloro (e.g. as substitution at the phenyl ring)

3,4-F$_2$=3,4-difluoro (e.g. as substitution at the phenyl ring)

Other abbreviations are to be understood analogously to the examples stated above.

"$(R^1)_m$="H"=unsubstituted cycle (m=0)

"$(R^2)_n$="H"=unsubstituted cycle (n=0)

In addition, the customary chemical symbols and formulae apply, such as, for example, CH$_2$ for methylene or CF$_3$ for trifluoromethyl or OH for hydroxyl. Correspondingly, composite meanings are defined as composed of the abbreviations mentioned.

TABLE 1

Definitions of structural combinations of groups Q, $(R^1)_m$ and $(R^2)_n$ for the tables of compounds of the general formula (I) according to the invention below

| No. | Q | $(R^1)_m$ | $(R^2)_n$ |
|---|---|---|---|
| 1 | OH | 3-F | 4-Cl |
| 2 | OH | 3-F | 3-F |
| 3 | OH | 3,4-F$_2$ | 4-Cl |
| 4 | OH | 3-F | 4-Br |
| 5 | OH | 3-Cl | 3-F |
| 6 | OH | 3,4-F$_2$ | 3-F |
| 7 | OH | H | 3-Br |
| 8 | OH | 4-F | 3-F |
| 9 | OH | 3-F | 3-Cl |
| 10 | OH | 3,4-F$_2$ | 3-Cl |
| 11 | OH | 3-Br | 3-F |
| 12 | OH | 2,5-F$_2$ | 3-F |
| 13 | OH | 3-F | 2-F |
| 14 | OH | 3,4,5-F$_3$ | 4-Cl |
| 15 | OH | 4-F | 3-Cl |
| 16 | OH | 3,4-F$_2$ | 3-F, 4-Cl |
| 17 | OH | 3,4-F$_2$ | 2-F |
| 18 | OH | 3-F | 2,3-F$_2$ |
| 19 | OH | 4-F | 3,5-F$_2$ |
| 20 | OH | 3-F | 4-F |
| 21 | OH | 3,4-F$_2$ | 3-Cl, 5-F |
| 22 | OH | 3-F | 3-Cl, 5-F |
| 23 | OH | 3-F | 2,5-F$_2$ |
| 24 | OH | 3,4-F$_2$ | 2,3-F$_2$ |
| 25 | OH | 3,4-F$_2$ | 2,5-F$_2$ |
| 26 | OH | 3-Cl | 3-Cl, 5-F |
| 27 | OH | 3-F, 4-Cl | 3-Cl |
| 28 | OH | 3,4-F$_2$ | 3-NO$_2$ |
| 29 | OH | 3,4-F$_2$ | H |
| 30 | OH | 3-Cl, 4-F | 3-F |
| 31 | OH | 3,4-F$_2$ | 4-OMe |
| 32 | O—C(O)—t-Bu | 3-F | 4-Cl |
| 33 | O—C(O)Me | 3-F | 4-Cl |
| 34 | SPh | 3-F | 4-Cl |
| 35 | SMe | 3-F | 4-Cl |
| 36 | OSO$_2$(4-Me—Ph) | 3-F | 4-Cl |
| 37 | Cl | 3-F | 4-Cl |
| 38 | O—CO$_2$Me | 3-F | 4-Cl |
| 39 | O—C(O)—t-Bu | 3-F | 3-F |
| 40 | O—C(O)Me | 3-F | 3-F |
| 41 | SPh | 3-F | 3-F |
| 42 | SMe | 3-F | 3-F |
| 43 | OSO$_2$(4-Me—Ph) | 3-F | 3-F |
| 44 | Cl | 3-F | 3-F |
| 45 | O—CO$_2$Me | 3-F | 3-F |
| 46 | O—C(O)—t-Bu | 3,4-F$_2$ | 3-F |
| 47 | O—C(O)Me | 3,4-F$_2$ | 3-F |
| 48 | O—C(O)Et | 3,4-F$_2$ | 3-F |
| 49 | SMe | 3,4-F$_2$ | 3-F |
| 50 | OSO$_2$(4-Me—Ph) | 3,4-F$_2$ | 3-F |
| 51 | Cl | 3,4-F$_2$ | 3-F |
| 52 | CO$_2$Me | 3,4-F$_2$ | 3-F |
| 53 | O—C(O)—t-Bu | 3,4-F$_2$ | 3-Cl |
| 54 | O—C(O)Me | 3,4-F$_2$ | 3-Cl |
| 55 | SPh | 3,4-F$_2$ | 3-Cl |
| 56 | SMe | 3,4-F$_2$ | 3-Cl |
| 57 | OSO$_2$(4-Me—Ph) | 3,4-F$_2$ | 3-Cl |
| 58 | Cl | 3,4-F$_2$ | 3-Cl |
| 59 | O—CO$_2$Me | 3,4-F$_2$ | 3-Cl |
| 60 | O—C(O)—t-Bu | 3-Br | 3-F |
| 61 | O—C(O)Me | 2,5-F$_2$ | 3-F |
| 62 | SPh | 3-F | 2-F |
| 63 | O—C(O)—t-Bu | 3,4,5-F$_3$ | 4-Cl |
| 64 | O—C(O)Me | 4-F | 3-Cl |
| 65 | SPh | 3,4-F$_2$ | 3-F, 4-Cl |
| 66 | O—C(O)—t-Bu | 3,4-F$_2$ | 2-F |
| 67 | O—C(O)Me | 3-F | 2,3-F$_2$ |
| 68 | SPh | 4-F | 3,5-F$_2$ |
| 69 | O—C(O)—t-Bu | 3-F | 4-F |
| 70 | O—C(O)Me | 3,4-F$_2$ | 3-Cl, 5-F |
| 71 | SPh | 3-F | 3-Cl, 5-F |
| 72 | O—C(O)—t-Bu | 3-F | 2,5-F$_2$ |
| 73 | O—C(O)Me | 3,4-F$_2$ | 2,3-F$_2$ |
| 74 | SPh | 3,4-F$_2$ | 2,5-F$_2$ |
| 75 | O—C(O)—t-Bu | 3-Cl | 3-Cl, 5-F |
| 76 | O—C(O)Me | 3-F, 4-Cl | 3-Cl |
| 77 | SPh | 3,4-F$_2$ | 3-NO$_2$ |
| 78 | O—C(O)—t-Bu | 3,4-F$_2$ | H |
| 79 | O—C(O)Me | 3-Cl, 4-F | 3-F |
| 80 | SPh | 3,4-F$_2$ | 4-OMe |
| 81 | OH | 3-F | H |
| 82 | OH | 3-F | 2,4-F$_2$ |
| 83 | OH | 3-F | 2,6-F$_2$ |
| 84 | OH | 3-F | 3,4-F$_2$ |
| 85 | OH | 3-F | 3,5-F$_2$ |
| 86 | OH | 3-F | 2-Cl |
| 87 | OH | 3-F | 2,3-Cl$_2$ |
| 88 | OH | 3-F | 2,4-Cl$_2$ |
| 89 | O—C(O)—t-Bu | 3-F | 2,5-Cl$_2$ |
| 90 | SPh | 3-F | 2,6-Cl$_2$ |
| 91 | OH | 3-F | 3,4-Cl$_2$ |
| 92 | OH | 3-F | 3,5-Cl$_2$ |
| 93 | O—C(O)—t-Bu | 3,4-F$_2$ | 4-F |
| 94 | OH | 3,4-F$_2$ | 2,4-F$_2$ |
| 95 | OH | 3,4-F$_2$ | 2,6-F$_2$ |
| 96 | OH | 3,4-F$_2$ | 3,4-F$_2$ |
| 97 | OH | 3,4-F$_2$ | 3,5-F$_2$ |
| 98 | SPh | 3,4-F$_2$ | 2-Cl |
| 99 | O—C(O)—t-Bu | 3,4-F$_2$ | 2,3-Cl$_2$ |
| 100 | OH | 3,4-F$_2$ | 2,4-Cl$_2$ |
| 101 | O—C(O)—t-Bu | 3,4-F$_2$ | 2,5-Cl$_2$ |
| 102 | OH | 3,4-F$_2$ | 2,6-Cl$_2$ |
| 103 | SPh | 3,4-F$_2$ | 3,4-Cl$_2$ |
| 104 | OH | 3,4-F$_2$ | 3-Br |
| 105 | OH | 3-Cl | 3-NO$_2$ |
| 106 | OH | 3-Cl | 4-NO$_2$ |
| 107 | OH | 3-Cl | 4-CN |
| 108 | OH | 3-Cl | 2-Br |
| 109 | O—C(O)—t-Bu | 3-Cl | 2,4-F$_2$ |
| 110 | OH | 3-Br | 2,5-F$_2$ |
| 111 | OH | 3-Cl | 2,6-F$_2$ |
| 112 | O—C(O)—t-Bu | 3-Cl | 3,4-F$_2$ |
| 113 | OH | 3-Br | 3,5-F$_2$ |
| 114 | OH | 3-Cl | 2-Cl |
| 115 | OH | 3-Br | 3-Cl |

TABLE 1-continued

Definitions of structural combinations of groups Q, $(R^1)_m$ and $(R^2)_n$ for the tables of compounds of the general formula (I) according to the invention below

| No. | Q | $(R^1)_m$ | $(R^2)_n$ |
|---|---|---|---|
| 116 | SPh | 3-Cl | 4-Cl |
| 117 | OH | 3-Br | 2,3-Cl$_2$ |
| 118 | OH | 3-Br | 2,4-Cl$_2$ |
| 119 | OH | 3-Cl | 2,5-Cl$_2$ |
| 120 | SPh | 3-Cl | 2,6-Cl$_2$ |
| 121 | SPh | 3-Cl | 3,4-Cl$_2$ |
| 122 | OH | 3-Cl | 3,5-Cl$_2$ |
| 123 | O—C(O)Me | 3,4-Cl$_2$ | H |
| 124 | O—C(O)Me | 3,4-Cl$_2$ | 2-F |
| 125 | O—C(O)Me | 3,4-Cl$_2$ | 3-F |
| 126 | O—C(O)Me | 3,4-Cl$_2$ | 4-F |
| 127 | O—C(O)Me | 3,4-Cl$_2$ | 2,3-F$_2$ |
| 128 | O—C(O)Me | 3,4-Cl$_2$ | 2,4-F$_2$ |
| 129 | OH | 3,4-Cl$_2$ | 2,5-F$_2$ |
| 130 | O—C(O)Me | 3,4-Cl$_2$ | 2,6-F$_2$ |
| 131 | O—C(O)—t-Bu | 3,4-Cl$_2$ | 3,4-F$_2$ |
| 132 | O—C(O)Et | 3,4-Cl$_2$ | 3,5-F$_2$ |
| 133 | O—C(O)Et | 3,4-Cl$_2$ | 2-Cl |
| 134 | O—C(O)Et | 3,4-Cl$_2$ | 3-Cl |
| 135 | O—C(O)—t-Bu | 3,4-Cl$_2$ | 4-Cl |
| 136 | SPh | 3,4-Cl$_2$ | 2,3-Cl$_2$ |
| 137 | O—C(O)-t-Bu | 3,4-Cl$_2$ | 2,4-Cl$_2$ |
| 138 | O—C(O)Me | 3,4-Cl$_2$ | 2,5-Cl$_2$ |
| 139 | O—C(O)Et | 3,4-Cl$_2$ | 2,6-Cl$_2$ |
| 140 | O—C(O)Me | 3,4-Cl$_2$ | 3,4-Cl$_2$ |
| 141 | O—C(O)Me | 3,4-Cl$_2$ | 3,5-Cl$_2$ |
| 142 | O—C(O)Et | 3-Cl, 4-F | H |
| 143 | SMe | 3-Cl, 4-F | 2-F |
| 144 | O—C(O)Me | 3-Cl, 4-F | 4-F |
| 145 | O—C(O)Et | 3-Cl, 4-F | 2,3-F$_2$ |
| 146 | O—C(O)—t-Bu | 3-Cl, 4-F | 2,4-F$_2$ |
| 147 | O—C(O)Me | 3-Cl, 4-F | 2,5-F$_2$ |
| 148 | SPh | 3-Cl, 4-F | 2,6-F$_2$ |
| 149 | O—C(O)Et | 3-Cl, 4-F | 3,4-F$_2$ |
| 150 | OSO$_2$(4-Me—Ph) | 3-Cl, 4-F | 3,5-F$_2$ |
| 151 | O—C(O)Me | 3-Cl, 4-F | 2-Cl |
| 152 | OH | 3-Cl, 4-F | 3-Br |
| 153 | O—C(O)Me | 3-Cl, 4-F | 4-Cl |
| 154 | O—C(O)Me | 3-Cl, 4-F | 2,3-Cl$_2$ |
| 155 | O—C(O)Et | 3-Cl, 4-F | 2,4-Cl$_2$ |
| 156 | O—C(O)Me | 3-Cl, 4-F | 2,5-Cl$_2$ |
| 157 | O—C(O)Me | 3-Cl, 4-F | 2,6-Cl$_2$ |
| 158 | O—C(O)Et | 3-Cl, 4-F | 3,4-Cl$_2$ |
| 159 | O—C(O)Me | 3-Cl, 4-F | 3,5-Cl$_2$ |
| 160 | O—C(O)Me | 3-Cl, 4-F | H |
| 161 | O—C(O)Et | 3-F, 4-Cl | 2-F |
| 162 | O—C(O)Me | 3-F, 4-Cl | 3-F |
| 163 | O—C(O)Me | 3-F, 4-Cl | 4-F |
| 164 | OH | 3-F, 4-Cl | 2,3-F$_2$ |
| 165 | O—C(O)Et | 3-F, 4-Cl | 2,4-F$_2$ |
| 166 | SPh | 3-F, 4-Cl | 2,5-F$_2$ |
| 167 | O—C(O)Me | 3-F, 4-Cl | 2,6-F$_2$ |
| 168 | O—C(O)Me | 3-F, 4-Cl | 3,4-F$_2$ |
| 169 | OH | 3-F, 4-Cl | 3,5-F$_2$ |
| 170 | O—C(O)Me | 3-F, 4-Cl | 2-Cl |
| 171 | O—C(O)Et | 3-F, 4-Cl | 4-Cl |
| 172 | SPh | 3-F, 4-Cl | 2,3-Cl$_2$ |
| 173 | SPh | 3-F, 4-Cl | 2,4-Cl$_2$ |
| 174 | SPh | 3-F, 4-Cl | 2,5-Cl$_2$ |
| 175 | SPh | 3-F, 4-Cl | 2,6-Cl$_2$ |
| 176 | SPh | 3-F, 4-Cl | 3,4-Cl$_2$ |
| 177 | SPh | 3-F, 4-Cl | 3,5-Cl$_2$ |
| 178 | O—C(O)—i-Pr | 3-F | 2,6-F$_2$ |
| 179 | O—C(O)Me | 3-F | 2,6-F$_2$ |
| 180 | SEt | 3-F | 2,6-F$_2$ |
| 181 | OH | 3,4-F$_2$ | 3,4-Cl$_2$ |
| 182 | OH | 3,4-F$_2$ | 3,5-Cl$_2$ |
| 183 | OH | 3-Cl | H |
| 184 | OH | 3-Cl | 2-F |
| 185 | OH | 3-Cl | 4-F |
| 186 | OH | 3-Cl | 2,3-F$_2$ |
| 187 | OH | 3-Cl | 2,4-F$_2$ |
| 188 | OH | 3-Cl | 2,5-F$_2$ |
| 189 | O—C(O)—t-Bu | 3-Cl | 2,6-F$_2$ |
| 190 | OH | 3-Cl | 3,4-F$_2$ |
| 191 | OH | 3-Cl | 3,5-F$_2$ |
| 192 | SPh | 3-Cl | 2-Cl |
| 193 | OH | 3-Cl | 3-Cl |
| 194 | OH | 3-Cl | 4-Cl |
| 195 | OH | 3-Cl | 2,3-Cl$_2$ |
| 196 | OH | 3-Cl | 2,4-Cl$_2$ |
| 197 | O—C(O)—t-Bu | 3-Cl | 2,5-Cl$_2$ |
| 198 | OH | 3-Cl | 2,6-Cl$_2$ |
| 199 | O—C(O)—t-Bu | 3-Cl | 3,4-Cl$_2$ |
| 200 | O—C(O)Me | 3-Cl | 3,5-Cl$_2$ |
| 201 | OH | 3,4-Cl$_2$ | H |
| 202 | OH | 3,4-Cl$_2$ | 2-F |
| 203 | OH | 3,4-Cl$_2$ | 3-F |
| 204 | OH | 3,4-Cl$_2$ | 4-F |
| 205 | O—C(O)—t-Bu | 3,4-Cl$_2$ | 2,3-F$_2$ |
| 206 | O—C(O)Me | 3,4-Cl$_2$ | 2,4-F$_2$ |
| 207 | SPh | 3,4-Cl$_2$ | 2,5-F$_2$ |
| 208 | OH | 3,4-Cl$_2$ | 2,6-F$_2$ |
| 209 | OSO$_2$(4-Me—Ph) | 3,4-Cl$_2$ | 3,4-F$_2$ |
| 210 | OH | 3,4-Cl$_2$ | 3,5-F$_2$ |
| 211 | OH | 3,4-Cl$_2$ | 2-Cl |
| 212 | OH | 3,4-Cl$_2$ | 3-Cl |
| 213 | OH | 3,4-Cl$_2$ | 4-Cl |
| 214 | O—C(O)—t-Bu | 3,4-Cl$_2$ | 2,3-Cl$_2$ |
| 215 | OH | 3,4-Cl$_2$ | 2,4-Cl$_2$ |
| 216 | OH | 3,4-Cl$_2$ | 2,5-Cl$_2$ |
| 217 | OH | 3,4-Cl$_2$ | 2,6-Cl$_2$ |
| 218 | OH | 3,4-Cl$_2$ | 3,4-Cl$_2$ |
| 219 | OH | 3,4-Cl$_2$ | 3,5-Cl$_2$ |
| 220 | OH | 3-Cl, 4-F | H |
| 221 | OH | 3-Cl, 4-F | 2-F |
| 222 | OH | 3-Cl, 4-F | 4-F |
| 223 | OH | 3-Cl, 4-F | 2,3-F$_2$ |
| 224 | OH | 3-Cl, 4-F | 2,4-F$_2$ |
| 225 | OH | 3-Cl, 4-F | 2,5-F$_2$ |
| 226 | OH | 3-Cl, 4-F | 2,6-F$_2$ |
| 227 | OH | 3-Cl, 4-F | 3,4-F$_2$ |
| 228 | OH | 3-Cl, 4-F | 3,5-F$_2$ |
| 229 | OH | 3-Cl, 4-F | 2-Cl |
| 230 | OH | 3-Cl, 4-F | 3-Cl |
| 231 | OH | 3-Cl, 4-F | 4-Cl |
| 232 | OH | 3-Cl, 4-F | 2,3-Cl$_2$ |
| 233 | OH | 3-Cl, 4-F | 2,4-Cl$_2$ |
| 234 | OH | 3-Cl, 4-F | 2,5-Cl$_2$ |
| 235 | OH | 3-Cl, 4-F | 2,6-Cl$_2$ |
| 236 | OH | 3-Cl, 4-F | 3,4-Cl$_2$ |
| 237 | OH | 3-Cl, 4-F | 3,5-Cl$_2$ |
| 238 | OH | 3-Cl, 4-F | H |
| 239 | OH | 3-F, 4-Cl | 2-F |
| 240 | OH | 3-F, 4-Cl | 3-F |
| 241 | OH | 3-F, 4-Cl | 4-F |
| 242 | SPh | 3-F, 4-Cl | 2,3-F$_2$ |
| 243 | OH | 3-F, 4-Cl | 2,4-F$_2$ |
| 244 | OH | 3-F, 4-Cl | 2,5-F$_2$ |
| 245 | OH | 3-F, 4-Cl | 2,6-F$_2$ |
| 246 | OH | 3-F, 4-Cl | 3,4-F$_2$ |
| 247 | OH | 3-F, 4-Cl | 3,5-F$_2$ |
| 248 | OH | 3-F, 4-Cl | 2-Cl |
| 249 | OH | 3-F, 4-Cl | 4-Cl |
| 250 | SPh | 3-F, 4-Cl | 2,3-Cl$_2$ |
| 251 | OH | 3-F, 4-Cl | 2,4-Cl$_2$ |
| 252 | OH | 3-F, 4-Cl | 2,5-Cl$_2$ |
| 253 | OH | 3-F, 4-Cl | 2,6-Cl$_2$ |
| 254 | OH | 3-F, 4-Cl | 3,4-Cl$_2$ |
| 255 | OH | 3-F, 4-Cl | 3,5-Cl$_2$ |
| 256 | SPh | 3-F | 2,6-F$_2$ |
| 257 | O—C(O)—t-Bu | 3-F | 2,6-F$_2$ |

TABLE 1-continued

Definitions of structural combinations of groups Q, $(R^1)_m$ and $(R^2)_n$ for the tables of compounds of the general formula (I) according to the invention below

| No. | Q | $(R^1)_m$ | $(R^2)_n$ |
|---|---|---|---|
| 258 | SMe | 3-F | 2,6-$F_2$ |
| 259 | O—C(O)Et | 3,4-$F_2$ | 2,6-$F_2$ |
| 260 | O—C(O)—t-Bu | 3,4-$F_2$ | 2,6-$F_2$ |
| 261 | O—C(O)Me | 3,4-$F_2$ | 2,6-$F_2$ |
| 262 | SPh | 3,4-$F_2$ | 2,6-$F_2$ |
| 263 | SMe | 3,4-$F_2$ | 2,6-$F_2$ |
| 264 | $OSO_2$(4-Me—Ph) | 3,4-$F_2$ | 2,6-$F_2$ |
| 265 | Cl | 3,4-$F_2$ | 2,6-$F_2$ |
| 266 | O—$CO_2$Me | 3,4-$F_2$ | 2,6-$F_2$ |
| 267 | OH | 3-CN | H |
| 268 | OH | 3-CN | 2,5-$F_2$ |
| 269 | OH | 3-CN | 2,6-$F_2$ |
| 270 | OH | 3-CN | 2,3-$F_2$ |
| 271 | OH | 3-CN | 2,4-$F_2$ |
| 272 | OH | 3-CN | 3,4-$F_2$ |
| 273 | OH | 3-CN | 3,5-$F_2$ |
| 274 | OH | 3-CN | 4-Cl |
| 275 | OH | 3-CN | 3-Cl |
| 276 | OH | 3-CN | 2-Cl |
| 277 | OH | 3-CN | 4-F |
| 278 | OH | 3-CN | 3-F |
| 279 | OH | 3-CN | 2-F |
| 280 | OH | 2-CN | 3-F |
| 281 | OH | 2-CN | 4-F |
| 282 | OH | 2-CN | 4-Cl |
| 283 | OH | 3-$NO_2$ | H |
| 284 | OH | 3-$NO_2$ | 2,5-$F_2$ |
| 285 | OH | 3-$NO_2$ | 2,6-$F_2$ |
| 286 | OH | 3-$NO_2$ | 2,3-$F_2$ |
| 287 | OH | 3-$NO_2$ | 2,4-$F_2$ |
| 288 | OH | 3-$NO_2$ | 3,4-$F_2$ |
| 289 | OH | 3-$NO_2$ | 3,5-$F_2$ |
| 290 | OH | 3-$NO_2$ | 4-Cl |
| 291 | OH | 3-$NO_2$ | 3-Cl |
| 292 | OH | 3-$NO_2$ | 2-Cl |
| 293 | OH | 3-$NO_2$ | 4-F |
| 294 | OH | 3-$NO_2$ | 3-F |
| 295 | OH | 3-$NO_2$ | 2-F |
| 296 | OH | H | 2,6-$F_2$ |
| 297 | OH | H | 3,4-$F_2$ |
| 298 | OH | H | 3,5-$F_2$ |
| 299 | OH | H | 2,3-$F_2$ |
| 300 | OH | H | 2,4-$F_2$ |
| 301 | OH | H | 2,5-$F_2$ |
| 302 | OH | H | 2-Cl |
| 303 | OH | H | 3-Cl |
| 304 | OH | H | 4-Cl |
| 305 | OH | H | 2-F |
| 306 | OH | H | 3-F |
| 307 | OH | H | 4-F |
| 308 | OH | H | 2,3-$Cl_2$ |
| 309 | OH | H | 2,4-$Cl_2$ |
| 310 | OH | H | 2,5-$Cl_2$ |
| 311 | OH | H | 2,6-$Cl_2$ |
| 312 | OH | H | 3,4-$Cl_2$ |
| 313 | OH | H | 3,5-$Cl_2$ |
| 314 | O—C(O)Et | 3-CN | 2,5-$F_2$ |
| 315 | O—C(O)—t-Bu | 3-CN | 2,5-$F_2$ |
| 316 | O—C(O)Me | 3-CN | 2,5-$F_2$ |
| 317 | SPh | 3-CN | 2,5-$F_2$ |
| 318 | SMe | 3-CN | 2,5-$F_2$ |
| 319 | $OSO_2$(4-Me—Ph) | 3-CN | 2,5-$F_2$ |
| 320 | Cl | 3-CN | 2,5-$F_2$ |
| 321 | O—$CO_2$Me | 3-CN | 2,5-$F_2$ |
| 322 | O—C(O)Et | 3-CN | 2,6-$F_2$ |
| 323 | O—C(O)—t-Bu | 3-CN | 2,6-$F_2$ |
| 324 | O—C(O)Me | 3-CN | 2,6-$F_2$ |
| 325 | SPh | 3-CN | 2,6-$F_2$ |
| 326 | SMe | 3-CN | 2,6-$F_2$ |
| 327 | $OSO_2$(4-Me—Ph) | 3-CN | 2,6-$F_2$ |
| 328 | Cl | 3-CN | 2,6-$F_2$ |
| 329 | O—$CO_2$Me | 3-CN | 2,6-$F_2$ |
| 330 | O—C(O)Et | 3-CN | 2,3-$F_2$ |
| 331 | O—C(O)—t-Bu | 3-CN | 2,3-$F_2$ |
| 332 | O—C(O)Me | 3-CN | 2,3-$F_2$ |
| 333 | SPh | 3-CN | 2,3-$F_2$ |
| 334 | SMe | 3-CN | 2,3-$F_2$ |
| 335 | $OSO_2$(4-Me—Ph) | 3-CN | 2,3-$F_2$ |
| 336 | Cl | 3-CN | 2,3-$F_2$ |
| 337 | O—$CO_2$Me | 3-CN | 2,3-$F_2$ |
| 338 | O—C(O)Et | 3-CN | 2,4-$F_2$ |
| 339 | O—C(O)—t-Bu | 3-CN | 2,4-$F_2$ |
| 340 | O—C(O)Me | 3-CN | 2,4-$F_2$ |
| 341 | SPh | 3-CN | 2,4-$F_2$ |
| 342 | SMe | 3-CN | 2,4-$F_2$ |
| 343 | $OSO_2$(4-Me—Ph) | 3-CN | 2,4-$F_2$ |
| 344 | Cl | 3-CN | 2,4-$F_2$ |
| 345 | O—$CO_2$Me | 3-CN | 2,4-$F_2$ |
| 346 | O—C(O)Et | 3-CN | 2,4-$F_2$ |
| 347 | O—C(O)—t-Bu | 3-CN | 2,4-$F_2$ |
| 348 | O—C(O)Me | 3-CN | 2,4-$F_2$ |
| 349 | SPh | 3-CN | 2,4-$F_2$ |
| 350 | SMe | 3-CN | 2,4-$F_2$ |
| 351 | $OSO_2$(4-Me—Ph) | 3-CN | 2,4-$F_2$ |
| 352 | Cl | 3-CN | 2,4-$F_2$ |
| 353 | O—$CO_2$Me | 3-CN | 2,4-$F_2$ |
| 354 | O—C(O)Et | 3-CN | 4-Cl |
| 355 | O—C(O)—t-Bu | 3-CN | 4-Cl |
| 356 | O—C(O)Me | 3-CN | 4-Cl |
| 357 | SPh | 3-CN | 4-Cl |
| 358 | SMe | 3-CN | 4-Cl |
| 359 | $OSO_2$(4-Me—Ph) | 3-CN | 4-Cl |
| 360 | Cl | 3-CN | 4-Cl |
| 361 | O—$CO_2$Me | 3-CN | 4-Cl |
| 362 | O—C(O)Et | 3-CN | 3-Cl |
| 363 | O—C(O)—t-Bu | 3-CN | 3-Cl |
| 364 | O—C(O)Me | 3-CN | 3-Cl |
| 365 | SPh | 3-CN | 3-Cl |
| 366 | SMe | 3-CN | 3-Cl |
| 367 | $OSO_2$(4-Me—Ph) | 3-CN | 3-Cl |
| 368 | Cl | 3-CN | 3-Cl |
| 369 | O—$CO_2$Me | 3-CN | 3-Cl |
| 370 | O—C(O)Et | 3-CN | 4-F |
| 371 | O—C(O)—t-Bu | 3-CN | 4-F |
| 372 | O—C(O)Me | 3-CN | 4-F |
| 373 | SPh | 3-CN | 4-F |
| 374 | SMe | 3-CN | 4-F |
| 375 | $OSO_2$(4-Me—Ph) | 3-CN | 4-F |
| 376 | Cl | 3-CN | 4-F |
| 377 | O—$CO_2$Me | 3-CN | 4-F |
| 378 | O—C(O)Et | 3-CN | 3-F |
| 379 | O—C(O)—t-Bu | 3-CN | 3-F |
| 380 | O—C(O)Me | 3-CN | 3-F |
| 381 | SPh | 3-CN | 3-F |
| 382 | SMe | 3-CN | 3-F |
| 383 | $OSO_2$(4-Me—Ph) | 3-CN | 3-F |
| 384 | Cl | 3-CN | 3-F |
| 385 | O—$CO_2$Me | 3-CN | 3-F |
| 386 | O—C(O)Et | 3-$NO_2$ | 2,5-$F_2$ |
| 387 | O—C(O)—t-Bu | 3-$NO_2$ | 2,5-$F_2$ |
| 388 | O—C(O)Me | 3-$NO_2$ | 2,5-$F_2$ |
| 389 | SPh | 3-$NO_2$ | 2,5-$F_2$ |
| 390 | SMe | 3-$NO_2$ | 2,5-$F_2$ |
| 391 | $OSO_2$(4-Me—Ph) | 3-$NO_2$ | 2,5-$F_2$ |
| 392 | Cl | 3-$NO_2$ | 2,5-$F_2$ |
| 393 | O—$CO_2$Me | 3-$NO_2$ | 2,5-$F_2$ |
| 394 | O—C(O)Et | 3-$NO_2$ | 2,6-$F_2$ |
| 395 | O—C(O)—t-Bu | 3-$NO_2$ | 2,6-$F_2$ |
| 396 | O—C(O)Me | 3-$NO_2$ | 2,6-$F_2$ |
| 397 | SPh | 3-$NO_2$ | 2,6-$F_2$ |
| 398 | SMe | 3-$NO_2$ | 2,6-$F_2$ |
| 399 | $OSO_2$(4-Me—Ph) | 3-$NO_2$ | 2,6-$F_2$ |
| 400 | Cl | 3-$NO_2$ | 2,6-$F_2$ |
| 401 | O—$CO_2$Me | 3-$NO_2$ | 2,6-$F_2$ |
| 402 | O—C(O)Et | 3-$NO_2$ | 2,3-$F_2$ |
| 403 | O—C(O)—t-Bu | 3-$NO_2$ | 2,3-$F_2$ |
| 404 | O—C(O)Me | 3-$NO_2$ | 2,3-$F_2$ |
| 405 | SPh | 3-$NO_2$ | 2,3-$F_2$ |

TABLE 1-continued

Definitions of structural combinations of groups Q, $(R^1)_m$ and $(R^2)_n$ for the tables of compounds of the general formula (I) according to the invention below

| No. | Q | $(R^1)_m$ | $(R^2)_n$ |
|---|---|---|---|
| 406 | SMe | 3-$NO_2$ | 2,3-$F_2$ |
| 407 | $OSO_2$(4-Me—Ph) | 3-$NO_2$ | 2,3-$F_2$ |
| 408 | Cl | 3-$NO_2$ | 2,3-$F_2$ |
| 409 | O—$CO_2$Me | 3-$NO_2$ | 2,3-$F_2$ |
| 410 | O—C(O)Et | 3-$NO_2$ | 2,4-$F_2$ |
| 411 | O—C(O)—t-Bu | 3-$NO_2$ | 2,4-$F_2$ |
| 412 | O—C(O)Me | 3-$NO_2$ | 2,4-$F_2$ |
| 413 | SPh | 3-$NO_2$ | 2,4-$F_2$ |
| 414 | SMe | 3-$NO_2$ | 2,4-$F_2$ |
| 415 | $OSO_2$(4-Me—Ph) | 3-$NO_2$ | 2,4-$F_2$ |
| 416 | Cl | 3-$NO_2$ | 2,4-$F_2$ |
| 417 | O—$CO_2$Me | 3-$NO_2$ | 2,4-$F_2$ |
| 418 | O—C(O)Et | 3-$NO_2$ | 2,4-$F_2$ |
| 419 | O—C(O)—t-Bu | 3-$NO_2$ | 2,4-$F_2$ |
| 420 | O—C(O)Me | 3-$NO_2$ | 2,4-$F_2$ |
| 421 | SPh | 3-$NO_2$ | 2,4-$F_2$ |
| 422 | SMe | 3-$NO_2$ | 2,4-$F_2$ |
| 423 | $OSO_2$(4-Me—Ph) | 3-$NO_2$ | 2,4-$F_2$ |
| 424 | Cl | 3-$NO_2$ | 2,4-$F_2$ |
| 425 | O—$CO_2$Me | 3-$NO_2$ | 2,4-$F_2$ |
| 426 | O—C(O)Et | 3-$NO_2$ | 4-Cl |
| 427 | O—C(O)—t-Bu | 3-$NO_2$ | 4-Cl |
| 428 | O—C(O)Me | 3-$NO_2$ | 4-Cl |
| 429 | SPh | 3-$NO_2$ | 4-Cl |
| 430 | SMe | 3-$NO_2$ | 4-Cl |
| 431 | $OSO_2$(4-Me—Ph) | 3-$NO_2$ | 4-Cl |
| 432 | Cl | 3-$NO_2$ | 4-Cl |
| 433 | O—$CO_2$Me | 3-$NO_2$ | 4-Cl |
| 434 | O—C(O)Et | 3-$NO_2$ | 3-Cl |
| 435 | O—C(O)—t-Bu | 3-$NO_2$ | 3-Cl |
| 436 | O—C(O)Me | 3-$NO_2$ | 3-Cl |
| 437 | SPh | 3-$NO_2$ | 3-Cl |
| 438 | SMe | 3-$NO_2$ | 3-Cl |
| 439 | $OSO_2$(4-Me—Ph) | 3-$NO_2$ | 3-Cl |
| 440 | Cl | 3-$NO_2$ | 3-Cl |
| 441 | O—$CO_2$Me | 3-$NO_2$ | 3-Cl |
| 442 | O—C(O)Et | 3-$NO_2$ | 4-F |
| 443 | O—C(O)—t-Bu | 3-$NO_2$ | 4-F |
| 444 | O—C(O)Me | 3-$NO_2$ | 4-F |
| 445 | SPh | 3-$NO_2$ | 4-F |
| 446 | SMe | 3-$NO_2$ | 4-F |
| 447 | $OSO_2$(4-Me—Ph) | 3-$NO_2$ | 4-F |
| 448 | Cl | 3-$NO_2$ | 4-F |
| 449 | O—$CO_2$Me | 3-$NO_2$ | 4-F |
| 450 | O—C(O)Et | 3-$NO_2$ | 3-F |
| 451 | O—C(O)—t-Bu | 3-$NO_2$ | 3-F |
| 452 | O—C(O)Me | 3-$NO_2$ | 3-F |
| 453 | SPh | 3-$NO_2$ | 3-F |
| 454 | SMe | 3-$NO_2$ | 3-F |
| 455 | $OSO_2$(4-Me—Ph) | 3-$NO_2$ | 3-F |
| 456 | Cl | 3-$NO_2$ | 3-F |
| 457 | O—$CO_2$Me | 3-$NO_2$ | 3-F |
| 458 | Me | 3-CN, 4-F | 3-F |
| 459 | Me | 3-CN, 4-F | 3-Cl |
| 460 | Me | 3-CN, 4-F | 3-CN |
| 461 | Me | 3-CN, 4-F | 4-F |
| 462 | Me | 3-CN, 4-F | 4-Cl |
| 463 | Me | 3-CN, 4-F | 2,5-$F_2$ |
| 464 | Me | 3-CN, 4-F | 2,6-$F_2$ |
| 465 | H | 3-CN, 4-F | 3-F |
| 466 | H | 3-CN, 4-F | 3-Cl |
| 467 | H | 3-CN, 4-F | 3-CN |
| 468 | H | 3-CN, 4-F | 4-F |
| 469 | H | 3-CN, 4-F | 4-Cl |
| 470 | H | 3-CN, 4-F | 2,5-$F_2$ |
| 471 | H | 3-CN, 4-F | 2,6-$F_2$ |
| 472 | Me | 3-Br, 4-F | 3-F |
| 473 | Me | 3-Br, 4-F | 3-Cl |
| 474 | Me | 3-Br, 4-F | 3-CN |
| 475 | Me | 3-Br, 4-F | 4-F |
| 476 | Me | 3-Br, 4-F | 4-Cl |
| 477 | Me | 3-Br, 4-F | 2,5-$F_2$ |
| 478 | Me | 3-Br, 4-F | 2,6-$F_2$ |
| 479 | H | 3-Br, 4-F | 3-F |
| 480 | H | 3-Br, 4-F | 3-Cl |
| 481 | H | 3-Br, 4-F | 3-CN |
| 482 | H | 3-Br, 4-F | 4-F |
| 483 | H | 3-Br, 4-F | 4-Cl |
| 484 | H | 3-Br, 4-F | 2,5-$F_2$ |
| 485 | H | 3-Br, 4-F | 2,6-$F_2$ |
| 486 | Me | 3-F, 4-CN | 3-F |
| 487 | Me | 3-F, 4-CN | 3-Cl |
| 488 | Me | 3-F, 4-CN | 3-CN |
| 489 | Me | 3-F, 4-CN | 4-F |
| 490 | Me | 3-F, 4-CN | 4-Cl |
| 491 | Me | 3-F, 4-CN | 2,5-$F_2$ |
| 492 | Me | 3-F, 4-CN | 2,6-$F_2$ |
| 493 | H | 3-F, 4-CN | 3-F |
| 494 | H | 3-F, 4-CN | 3-Cl |
| 495 | H | 3-F, 4-CN | 3-CN |
| 496 | H | 3-F, 4-CN | 4-F |
| 497 | H | 3-F, 4-CN | 4-Cl |
| 498 | H | 3-F, 4-CN | 2,5-$F_2$ |
| 499 | H | 3-F, 4-CN | 2,6-$F_2$ |

Definition of the examples in Tables 2 to 24f below:

For reference purposes, specific numbers (=Example Numbers) have been assigned to the individual compounds in Tables 2 to 24f below, where the Example Number in question is composed of the number of the chemical formula assigned to the respective table and a "row number" (row number) which refers to the same number in the row of the first column of Table 1. The chemical structure of Example No. "(formula number)(row number)" is thus defined unambiguously by the formula above the respective table by formula number and row number of Table 1, for example:

Example No. "Iaa1" of Table 2 is the compound of the formula (Ia) where $A^1$=O [=formula (Iaa)] and Q=OH, $(R^1)_m$=3-F and $(R^2)_n$=4-Cl, defined according to row 1 of Table 1, or a tautomer thereof.

Example No. "Iad204" of Table 2 is the compound of the formula (Ia) where $A^1$=N—OH [=formula (Iad)] and Q=OH, $(R^1)_m$=3,4-$Cl_2$ and $(R^2)_n$=4-F, defined according to row 204 of Table 1, or a tautomer thereof.

This applies correspondingly to the assignment of racemic or optically active threo stereoisomers or erythro stereoisomers. For example, for reference purposes, specific numbers (=Example Numbers) have been assigned to the compounds of Table 2a, where the number "threo-Iaa(row number)" refers to the racemic mixture of the threo enantiomers having the chemical structure of the formulae (threo-1-Iaa) and (threo-2-Iaa), each of which has the structural combination of groups Q, $(R^1)_m$ and $(R^2)_n$ according to the row number of Table 1.

TABLE 2

Compounds of the formulae (Ia), (Iaa), (Iab), (Iac), (Iad), (Iae), (Iaf), (Iag) and (Iah), where Q, $(R^1)_m$ and $(R^2)_n$ are each as defined in Table 1:

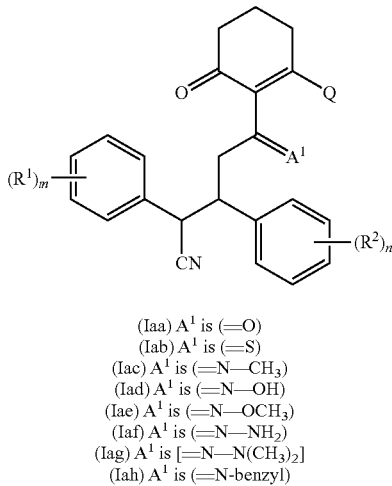

(Iaa) $A^1$ is (=O)
(Iab) $A^1$ is (=S)
(Iac) $A^1$ is (=N—CH$_3$)
(Iad) $A^1$ is (=N—OH)
(Iae) $A^1$ is (=N—OCH$_3$)
(Iaf) $A^1$ is (=N—NH$_2$)
(Iag) $A^1$ is [=N—N(CH$_3$)$_2$]
(Iah) $A^1$ is (=N-benzyl)

Table 2, examples of erythro/threo mixtures (ratios 70:30 to 30:70):

Examples of compounds of the formulae (Iaa) to (Iah) are the compounds of the respective formulae (Iaa) to (Iah), in each case in the form of a racemic erythro/threo mixture (ratio 70:30 to 30:70), where the meaning of Q, $(R^1)_m$ and $(R^2)_n$ is defined according to a row number of Table 1. Individual compounds are numbered "(formula)(row number)", without any brackets, for example Iaa50=compound of the formula (Iaa) where Q=OSO$_2$(4-Me-Ph), $(R^1)_m$=3,4-difluoro and $(R^2)_n$=3-fluoro according to row 50 of Table 1.

Tables 2a to 2f: Compounds of the formulae (threo-Iaa) and (threo-2-Iaa), where Q, $(R^1)_m$ and $(R^2)_n$ are each as defined in Table 1:

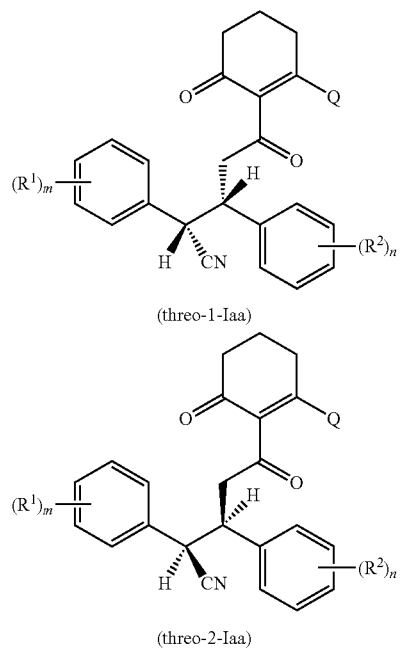

(threo-Iaa) = (threo-1-Iaa) + (threo-2-Iaa) (50:50) = (rac.)

Table 2a (threo racemates), examples:
Compounds of the formula (Iaa) in the form of the racemic mixture of the threo isomers [=formula (threo-Iaa)], where the structural combination of groups Q, $(R^1)_m$ and $(R^2)_n$ is defined according to a row number of Table 1.

The numeration is "threo-Iaa(row number)".

Table 2b (optically active threo-2 compounds), examples:
Optically active threo-2 enantiomers in enriched form [=(2R,3R) form of more than 90% ee] having the chemical structure of the formula (threo-2-Iaa), where the structural combination of groups Q, $(R^1)_m$ and $(R^2)_n$ is defined according to a row number of Table 1.

The numeration is "threo-2-Iaa(row number)".

Table 2c (optically active threo-1 enantiomers), examples:
Optically active threo-1 enantiomers in enriched form [=(2S,3S) form of more than 90% ee] having the chemical structure of the formula (threo-1-Iaa), where the structural combination of groups Q, $(R^1)_m$ and $(R^2)_n$ is defined according to a row number of Table 1.

Here, an individual enantiomer is assigned the number "threo-1-Iaa(row number)". For example, the No. threo-1-Iaa5 refers to the compound of the formula (threo-1-Iaa) where Q=OH, $(R^1)_m$=3-F and $(R^2)_n$=4-Br.

Table 2d (erythro racemates), examples:
Compounds of the formula (Iaa) in the form of the racemic mixture of the erythro isomers [=formula (erythro-Iaa)], where the structural combination of groups Q, $(R^1)_m$ and $(R^2)_n$ is defined according to a row number of Table 1.

The numeration is "erythro-Iaa(row number)".

Table 2e (erythro-1 enantiomers), examples:
Optically active erythro-1 enantiomers in enriched form [=(2R,3S) form of more than 90% ee] having the chemical structure of the formula (Iaa) in the erythro-1 form [=formula (erythro-1-Iaa)], where the structural combination of groups Q, $(R^1)_m$ and $(R^2)_n$ is defined according to a row number of Table 1.

The numeration is "erythro-1-Iaa(row number)".

Table 2f (erythro-2 enantiomers), examples:
Optically active erythro-2 enantiomers in enriched form [=(2S,3R) form of more than 90% ee] having the chemical structure of the formula (Iaa) in the erythro-2 form [=formula (erythro-2-Iaa)], where the structural combination of groups Q, $(R^1)_m$ and $(R^2)_n$ is defined according to a row number of Table 1.

The numeration is "erythro-2-Iaa(row number)".

TABLE 3

Compounds of the formulae (Ib), (Iba), (Ibb), (Ibc), (Ibd), (Ibe), (Ibf), (Ibg) and (Ibh), where Q, $(R^1)_m$ and $(R^2)_n$ are each as defined in Table 1:

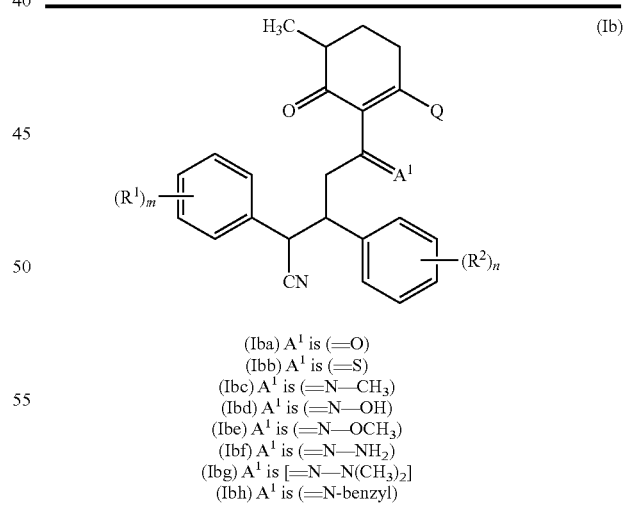

(Iba) $A^1$ is (=O)
(Ibb) $A^1$ is (=S)
(Ibc) $A^1$ is (=N—CH$_3$)
(Ibd) $A^1$ is (=N—OH)
(Ibe) $A^1$ is (=N—OCH$_3$)
(Ibf) $A^1$ is (=N—NH$_2$)
(Ibg) $A^1$ is [=N—N(CH$_3$)$_2$]
(Ibh) $A^1$ is (=N-benzyl)

Table 3, examples of erythro/threo mixtures (ratios 70:30 to 30:70):

Examples are the compounds of the respective formulae (Iaa) to (Iah), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

TABLE 4

Compounds of the formulae (Ic), (Ica), (Icb), (Icc), (Icd), (Ice), (Icf), (Icg) and (Ich), where Q, $(R^1)_m$ and $(R^2)_n$ are each as defined in Table 1:

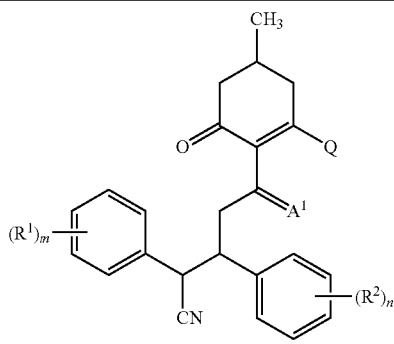

(Ic)

(Ica) $A^1$ is (=O)
(Icb) $A^1$ is (=S)
(Icc) $A^1$ is (=N—CH$_3$)
(Icd) $A^1$ is (=N—OH)
(Ice) $A^1$ is (=N—OCH$_3$)
(Icf) $A^1$ is (=N—NH$_2$)
(Icg) $A^1$ is [=N—N(CH$_3$)$_2$]
(Ich) $A^1$ is (=N-benzyl)

Table 4, examples of erythro/threo mixtures (ratios 70:30 to 30:70):

Examples are the compounds of the respective formulae (Ica) to (Ich), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

TABLE 5

Compounds of the formulae (Id), (Ida), (Idb), (Idc), (Idd), (Ide), (Idf), (Idg) and (Idh), where Q, $(R^1)_m$ and $(R^2)_n$ are each as defined in Table 1:

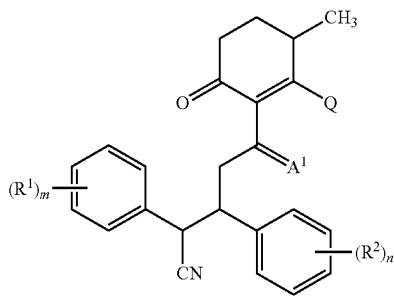

(Id)

(Ida) $A^1$ is (=O)
(Idb) $A^1$ is (=S)
(Idc) $A^1$ is (=N—CH$_3$)
(Idd) $A^1$ is (=N—OH)
(Ide) $A^1$ is (=N—OCH$_3$)
(Idf) $A^1$ is (=N—NH$_2$)
(Idg) $A^1$ is [=N—N(CH$_3$)$_2$]
(Idh) $A^1$ is (=N-benzyl)

Table 5, examples of erythro/threo mixtures (ratios 70:30 to 30:70):

Examples are the compounds of the respective formulae (Ida) to (Idh), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

TABLE 6

Compounds of the formulae (Ie), (Iea), (Ieb), (Iec), (Ied), (Iee), (Ief), (Ieg) and (Ieh), where Q, $(R^1)_m$ and $(R^2)_n$ are each as defined in Table 1:

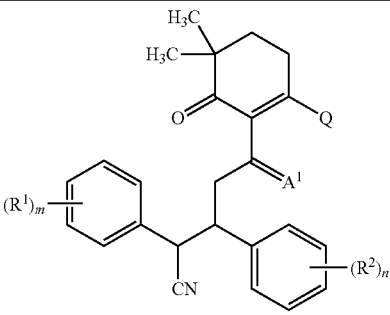

(Ie)

(Iea) $A^1$ is (=O)
(Ieb) $A^1$ is (=S)
(Iec) $A^1$ is (=N—CH$_3$)
(Ied) $A^1$ is (=N—OH)
(Iee) $A^1$ is (=N—OCH$_3$)
(Ief) $A^1$ is (=N —NH$_2$)
(Ieg) $A^1$ is [=N—N(CH$_3$)$_2$]
(Ieh) $A^1$ is (=N-benzyl)

Table 6, examples of erythro/threo mixtures (ratios 70:30 to 30:70):

Examples are the compounds of the respective formulae (Iea) to (Ieh), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

Tables 6a to 6f: Compounds of the formulae (threo-Iea) and (threo-2-Iea), where Q, $(R^1)_m$ and $(R^2)_n$ are each as defined in Table 1:

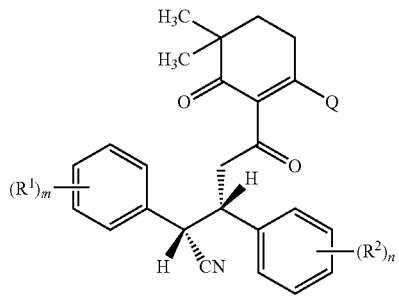

(threo-1-Iea)

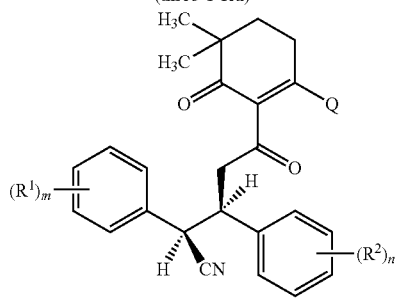

(threo-2-Iea)

(threo-Iea) = (threo-1-Iea) + (threo-2-Iea) (50:50) = (rac.)

Table 6a (racemates), examples:

Compounds of the formula (Iea) in the form of the racemic mixture of the threo isomers [=formula (threo-Iea)], where the structural combination of groups Q, $(R^1)_m$ and $(R^2)_n$ is defined according to a row number of Table 1.

Individual compounds are numbered "threo-Iea(row number)".

Table 6b (optically active threo-2 enantiomers), examples:
Optically active threo-2 enantiomers in enriched form [=(2R,3R) form of more than 90% ee] having the chemical structure of the formula (threo-2-Iea), where the structural combination of groups Q, $(R^1)_m$, and $(R^2)_n$ is defined according to a row number of Table 1. Individual compounds are numbered "threo-2-Iea(row number)".

Table 6c (optically active threo-1 enantiomers), examples:
Optically active threo-1 enantiomers in enriched form [=(2S,3S) form of more than 90% ee] having the chemical structure of the formula (threo-1-Iea), where the structural combination of groups Q, $(R^1)_m$ and $(R^2)_n$ is defined according to a row number of Table 1. Individual compounds are numbered "threo-1-Iea(row number)".

Table 6d (erythro racemates), examples:
Compounds of the formula (Iea) in the form of the racemic mixture of the erythro isomers [=formula (erythro-Iea)], where the structural combination of groups Q, $(R^1)_m$ and $(R^2)_n$ is defined according to a row number of Table 1. Individual compounds are numbered "erythro-Iea(row number)".

Table 6e (erythro-1 enantiomers), examples:
Optically active erythro-1 enantiomers in enriched form [=(2R,3S) form of more than 90% ee] having the chemical structure of the formula (Iea) in the erythro-1 form [=formula (erythro-1-Iea)], where the structural combination of groups Q, $(R^1)_m$ and $(R^2)_n$ is defined according to a row number of Table 1. Individual compounds are numbered "erythro-1-Iea (row number)".

Table 6f (erythro-2 enantiomers), examples:
Optically active erythro-2 enantiomers in enriched form [=(2S,3R) form of more than 90% ee] having the chemical structure of the formula (Iea) in the erythro-2 form [=formula (erythro-2-Iea)], where the structural combination of groups Q, $(R^1)_m$ and $(R^2)_n$ is defined according to a row number of Table 1. Individual compounds are numbered "erythro-2-Iea (row number)".

TABLE 7

Compounds of the formulae (If), (Ifa), (Ifb), (Ifc), (Ifd), (Ife), (Iff), (Ifg) and (Ifh), where Q, $(R^1)_m$ and $(R^2)_n$ are each as defined in Table 1:

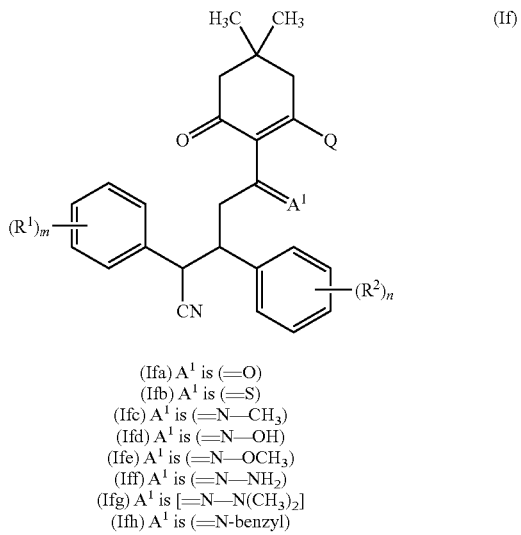

(Ifa) $A^1$ is (=O)
(Ifb) $A^1$ is (=S)
(Ifc) $A^1$ is (=N—CH$_3$)
(Ifd) $A^1$ is (=N—OH)
(Ife) $A^1$ is (=N—OCH$_3$)
(Iff) $A^1$ is (=N—NH$_2$)
(Ifg) $A^1$ is [=N—N(CH$_3$)$_2$]
(Ifh) $A^1$ is (=N-benzyl)

Table 7, examples of erythro/threo mixtures (ratios 70:30 to 30:70):
Examples are the compounds of the respective formulae (Ifa) to (Ifh), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

Tables 7a to 7f: Compounds of the formulae (threo-Ifa) and (threo-2-Ifa), where Q, $(R^1)_m$ and $(R^2)_n$ are each as defined in Table 1:

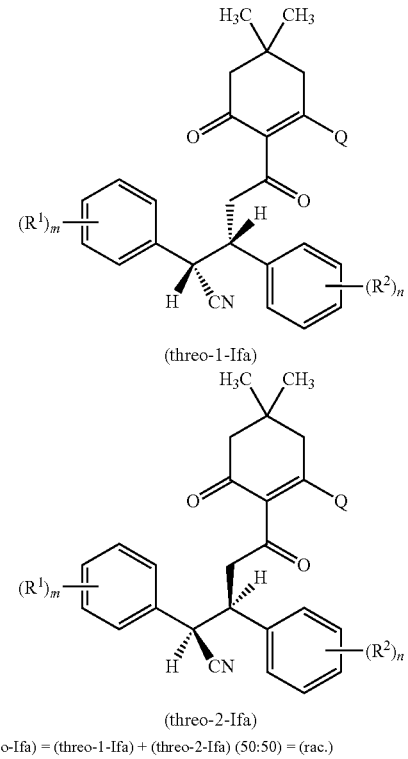

(threo-Ifa) = (threo-1-Ifa) + (threo-2-Ifa) (50:50) = (rac.)

Table 7a (threo racemates), examples:
Compounds of the formula (Ifa) in the form of the racemic mixture of the threo isomers [=formula (threo-Ifa)], where the structural combination of groups Q, $(R^1)_m$ and $(R^2)_n$ is defined according to a row number of Table 1.
Individual compounds are numbered "threo-2-Ifa(row number)".

Table 7b (optically active threo-2 compounds), examples:
Optically active threo-2 enantiomers in enriched form [=(2R,3R) form of more than 90% ee] having the chemical structure of the formula (threo-2-Ifa), where the structural combination of groups Q, $(R^1)_m$ and $(R^2)_n$ is defined according to a row number of Table 1. Individual compounds are numbered "threo-2-Ifa(row number)".

Table 7c (optically active threo-1 enantiomers), examples:
Optically active threo-1 enantiomers in enriched form [=(2S,3S) form of more than 90% ee] having the chemical structure of the formula (threo-1-Ifa), where the structural combination of groups Q, $(R^1)_m$ and $(R^2)_n$ is defined according to a row number of Table 1. Individual compounds are numbered "threo-1-Ifa(row number)".

Table 7d (erythro racemates), examples:
Compounds of the formula (Ifa) in the form of the racemic mixture of the erythro isomers [=formula (erythro-Ifa)], where the structural combination of groups Q, $(R^1)_m$ and $(R^2)_n$ is defined according to a row number of Table 1. Individual compounds are numbered "erythro-Ifa(row number)".

Table 7e (erythro-1 enantiomers), examples:
Optically active erythro-1 enantiomers in enriched form [=(2R,3S) form of more than 90% ee] having the chemical structure of the formula (Ifa) in the erythro-1 form [=formula (erythro-1-Ifa)], where the structural combination of groups Q, $(R^1)_m$ and $(R^2)_n$ is defined according to a row number of Table 1. Individual compounds are numbered "erythro-1-Ifa (row number)".

Table 7f (erythro-2 enantiomers), examples:

Optically active erythro-2 enantiomers in enriched form [=(2S,3R) form of more than 90% ee] having the chemical structure of the formula (Ifa) in the erythro-2 form [=formula (erythro-2-Ifa)], where the structural combination of groups Q, $(R^1)_m$ and $(R^2)_n$ is defined according to a row number of Table 1. Individual compounds are numbered "erythro-2-Ifa (row number)".

TABLE 8

Compounds of the formulae (Ig), (Iga), (Igb), (Igc), (Igd), (Ige), (Igf), (Igg) and (Igh), where Q, $(R^1)_m$ and $(R^2)_n$ are each as defined in Table 1:

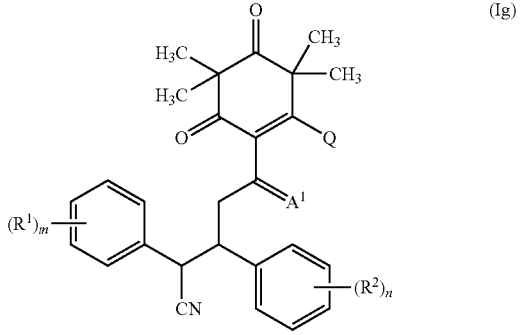

(Ig)

(Iga) $A^1$ is (=O)
(Igb) $A^1$ is (=S)
(Igc) $A^1$ is (=N—CH$_3$)
(Igd) $A^1$ is (=N—OH)
(Ige) $A^1$ is (=N—OCH$_3$)
(Igf) $A^1$ is (=N—NH$_2$)
(Igg) $A^1$ is [=N—N(CH$_3$)$_2$]
(Igh) $A^1$ is (=N-benzyl)

Table 8, examples of erythro/threo mixtures (ratios 70:30 to 30:70):

Examples are the compounds of the respective formulae (Iga) to (Igh), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

TABLE 9

Compounds of the formulae (Ih), (Iha), (Ihb), (Ihc), (Ihd), (Ihe), (Ihf), (Ihg) and (Ihh), where Q, $(R^1)_m$ and $(R^2)_n$ are each as defined in Table 1:

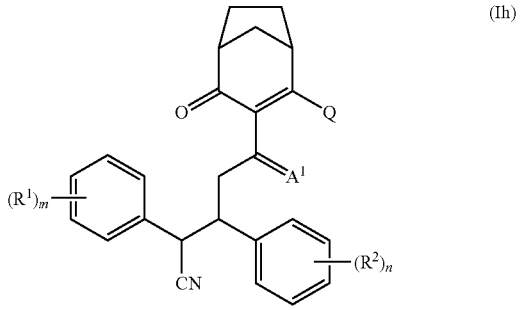

(Ih)

(Iha) $A^1$ is (=O)
(Ihb) $A^1$ is (=S)
(Ihc) $A^1$ is (=N—CH$_3$)
(Ihd) $A^1$ is (=N—OH)
(Ihe) $A^1$ is (=N—OCH$_3$)
(Ihf) $A^1$ is (=N—NH$_2$)
(Ihg) $A^1$ is [=N—N(CH$_3$)$_2$]
(Ihh) $A^1$ is (=N-benzyl)

Table 9, examples of erythro/threo mixtures (ratios of 70:30 to 30:70):

Examples are the compounds of the respective formulae (Iha) to (Ihh), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

Tables 9a to 9f: Compounds of the formulae (threo-Iha) and (threo-2-Iha), where Q, $(R^1)_m$ and $(R^2)_n$ are each as defined in Table 1:

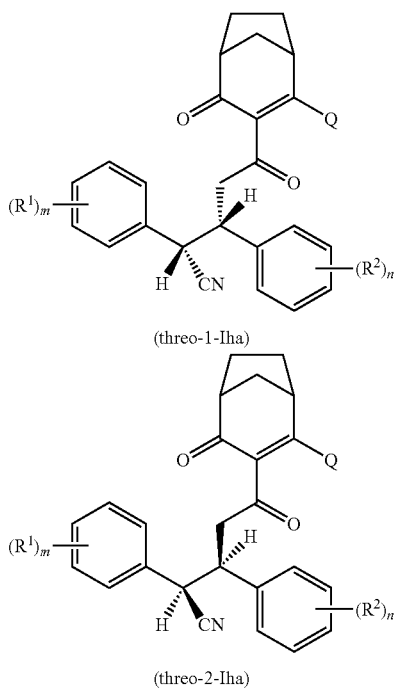

(threo-1-Iha)

(threo-2-Iha)

(threo-Iha) = (threo-1-Iha) + (threo-2-Iha) (50:50) = (rac.)

Table 9a (threo racemates), examples:

Compounds of the formula (Iha) in the form of the racemic mixture of the threo isomers [=formula (threo-Iha)], where the structural combination of groups Q, $(R^1)_m$ and $(R^2)_n$ is defined according to a row number of Table 1. Individual compounds are numbered "threo-2-Iha(row number)".

Table 9b (optically active threo-2 compounds), examples:

Optically active threo-2 enantiomers in enriched form [=(2R,3R) form of more than 90% ee] having the chemical structure of the formula (threo-2-Iha), where the structural combination of groups Q, $(R^1)_m$ and $(R^2)_n$ is defined according to a row number of Table 1. Individual compounds are numbered "threo-2-Iha(row number)".

Table 9c (optically active threo-1 enantiomers), examples:

Optically active threo-1 enantiomers in enriched form [=(2S,3S) form of more than 90% ee] having the chemical structure of the formula (threo-1-Iha), where the structural combination of groups Q, $(R^1)_m$ and $(R^2)_n$ is defined according to a row number of Table 1. Individual compounds are numbered "threo-1-Iha(row number)".

Table 9d (erythro racemates), examples:

Compounds of the formula (Iha) in the form of the racemic mixture of the erythro isomers [=formula (erythro-Ifa)], where the structural combination of groups Q, $(R^1)_m$ and $(R^2)_n$ is defined according to a row number of Table 1. Individual compounds are numbered "erythro-Iha(row number)".

Table 9e (erythro-1 enantiomers), examples:

Optically active erythro-1 enantiomers in enriched form [=(2R,3S) form of more than 90% ee] having the chemical structure of the formula (Iha) in the erythro-1 form [=formula (erythro-1-Iha)], where the structural combination of groups Q, $(R^1)_m$ and $(R^2)_n$ is defined according to a row number of Table 1. Individual compounds are numbered "erythro-1-Iha (row number)".

Table 9f (erythro-2 enantiomers), examples:

Optically active erythro-2 enantiomers in enriched form [=(2S,3R) form of more than 90% ee] having the chemical structure of the formula (Iha) in the erythro-2 form [=formula (erythro-2-Iha)], where the structural combination of groups Q, $(R^1)_m$ and $(R^2)_n$ is defined according to a row number of Table 1. Individual compounds are numbered "erythro-2-Iha (row number)".

TABLE 10

Compounds of the formulae (Ii), (Iia), (Iib), (Iic), (Iid), (Iie), (Iif), (Iig) and (Iih), where Q, $(R^1)_m$ and $(R^2)_n$ are each as defined in Table 1:

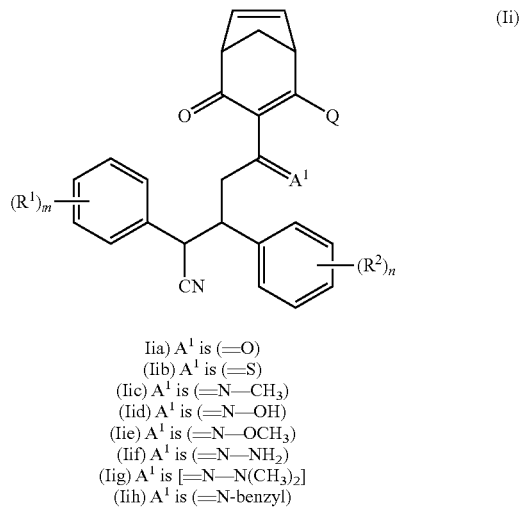

(Iia) $A^1$ is (=O)
(Iib) $A^1$ is (=S)
(Iic) $A^1$ is (=N—CH$_3$)
(Iid) $A^1$ is (=N—OH)
(Iie) $A^1$ is (=N—OCH$_3$)
(Iif) $A^1$ is (=N—NH$_2$)
(Iig) $A^1$ is [=N—N(CH$_3$)$_2$]
(Iih) $A^1$ is (=N-benzyl)

Table 10, examples of erythro/threo mixtures (ratios 70:30 to 30:70):

Examples are the compounds of the respective formulae (Iia) to (Iih), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

TABLE 11

Compounds of the formulae (Ik), (Ika), (Ikb), (Ikc), (Ikd), (Ike), (Ikf), (Ikg) and (Ikh), where Q, $(R^1)_m$ and $(R^2)_n$ are each as defined in Table 1:

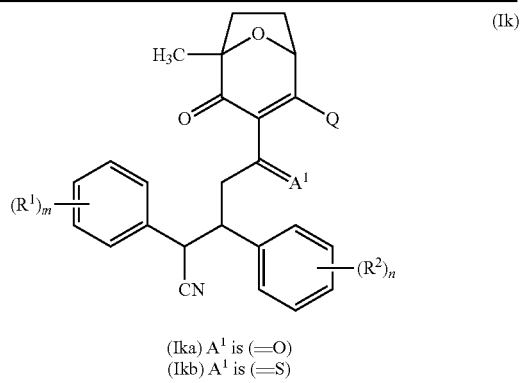

(Ika) $A^1$ is (=O)
(Ikb) $A^1$ is (=S)

TABLE 11-continued

Compounds of the formulae (Ik), (Ika), (Ikb), (Ikc), (Ikd), (Ike), (Ikf), (Ikg) and (Ikh), where Q, $(R^1)_m$ and $(R^2)_n$ are each as defined in Table 1:

(Ikc) $A^1$ is (=N—CH$_3$)
(Ikd) $A^1$ is (=N—OH)
(Ike) $A^1$ is (=N—OCH$_3$)
(Ikf) $A^1$ is (=N—NH$_2$)
(Ikg) $A^1$ is [=N—N(CH$_3$)$_2$]
(Ikh) $A^1$ is (=N-benzyl)

Table 11, examples of erythro/threo mixtures (ratios 70:30 to 30:70):

Examples are the compounds of the respective formulae (Ika) to (Ikh), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

TABLE 12

Compounds of the formulae (IL), (ILa), (ILb), (ILc), (ILd), (ILe), (ILf), (ILg) and (ILh), where Q, $(R^1)_m$ and $(R^2)_n$ are each as defined in Table 1:

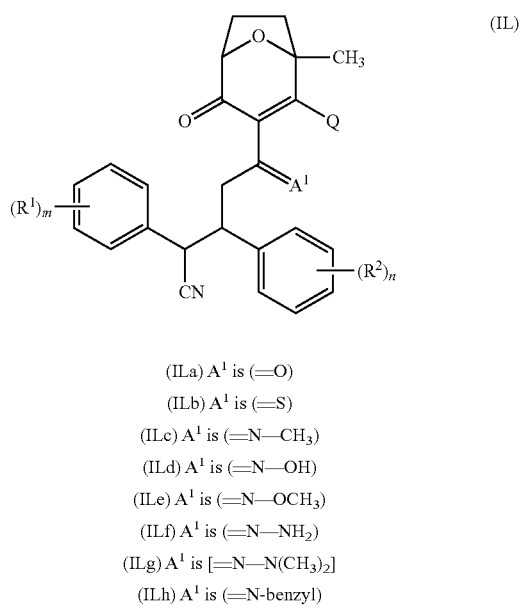

(ILa) $A^1$ is (=O)
(ILb) $A^1$ is (=S)
(ILc) $A^1$ is (=N—CH$_3$)
(ILd) $A^1$ is (=N—OH)
(ILe) $A^1$ is (=N—OCH$_3$)
(ILf) $A^1$ is (=N—NH$_2$)
(ILg) $A^1$ is [=N—N(CH$_3$)$_2$]
(ILh) $A^1$ is (=N-benzyl)

Table 12, examples of erythro/threo mixtures (ratios 70:30 to 30:70):

Examples are the compounds of the respective formulae (ILa) to (ILh), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

TABLE 13

Compounds of the formulae (Im), (Ima), (Imb), (Imc), (Imd), (Ime), (Imf), (Img) and (Imh), where Q, $(R^1)_m$ and $(R^2)_n$ are each as defined in Table 1:

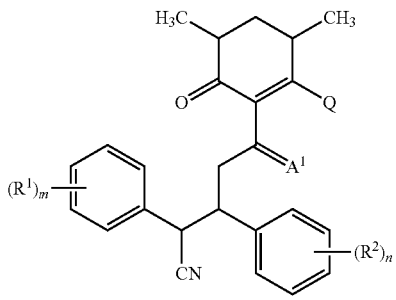
(Im)

(Ima) $A^1$ is (=O)
(Imb) $A^1$ is (=S)
(Imc) $A^1$ is (=N—CH$_3$)
(Imd) $A^1$ is (=N—OH)
(Ime) $A^1$ is (=N—OCH$_3$)
(Imf) $A^1$ is (=N—NH$_2$)
(Img) $A^1$ is [=N—N(CH$_3$)$_2$]
(Imh) $A^1$ is (=N-benzyl)

Table 13, examples of erythro/threo mixtures (ratios 70:30 to 30:70):

Examples are the compounds of the respective formulae (Ima) to (Imh), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

TABLE 14

Compounds of the formulae (In), (Ina), (Inb), (Inc), (Ind), (Ine), (Inf), (Ing) and (Inh), where Q, $(R^1)_m$ and $(R^2)_n$ are each as defined in Table 1:

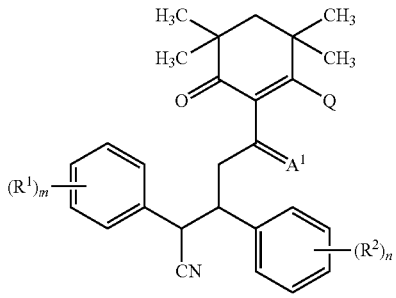
(In)

(Ina) $A^1$ is (=O)
(Inb) $A^1$ is (=S)
(Inc) $A^1$ is (=N—CH$_3$)
(Ind) $A^1$ is (=N—OH)
(Ine) $A^1$ is (=N—OCH$_3$)
(Inf) $A^1$ is (=N—NH$_2$)
(Ing) $A^1$ is [=N—N(CH$_3$)$_2$]
(Inh) $A^1$ is (=N-benzyl)

Table 14, examples of erythro/threo mixtures (ratios 70:30 to 30:70):

Examples are the compounds of the respective formulae (Ina) to (Inh), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

TABLE 15

Compounds of the formulae (Io), (Ioa), (Iob), (Ioc), (Iod), (Ioe), (Iof), (Iog) and (Ioh), where Q, $(R^1)_m$ and $(R^2)_n$ are each as defined in Table 1:

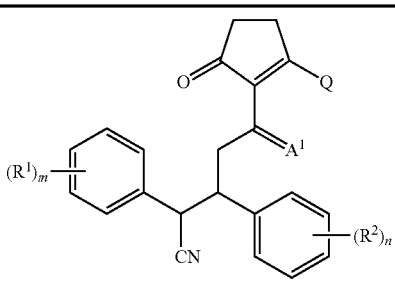
(Io)

(Ioa) $A^1$ is (=O)
(Iob) $A^1$ is (=S)
(Ioc) $A^1$ is (=N—CH$_3$)
(Iod) $A^1$ is (=N—OH)
(Ioe) $A^1$ is (=N—OCH$_3$)
(Iof) $A^1$ is (=N—NH$_2$)
(Iog) $A^1$ is [=N—N(CH$_3$)$_2$]
(Ioh) $A^1$ is (=N-benzyl)

Table 15, examples of erythro/threo mixtures (ratios 70:30 to 30:70):

Examples are the compounds of the respective formulae (Ioa) to (Ioh), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

TABLE 16

Compounds of the formulae (Ip), (Ipa), (Ipb), (Ipc), (Ipd), (Ipe), (Ipf), (Ipg) and (Iph), where Q, $(R^1)_m$ and $(R^2)_n$ are each as defined in Table 1:

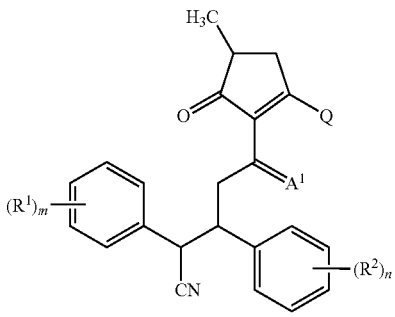
(Ip)

(Ipa) $A^1$ is (=O)
(Ipb) $A^1$ is (=S)
(Ipc) $A^1$ is (=N—CH$_3$)
(Ipd) $A^1$ is (=N—OH)
(Ipe) $A^1$ is (=N—OCH$_3$)
(Ipf) $A^1$ is (=N—NH$_2$)
(Ipg) $A^1$ is [=N—N(CH$_3$)$_2$]
(Iph) $A^1$ is (=N-benzyl)

Table 16, examples of erythro/threo mixtures (ratios 70:30 to 30:70):

Examples are the compounds of the respective formulae (Ipa) to (Iph), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

TABLE 17

Compounds of the formulae (Iq), (Iqa), (Iqb), (Iqc), (Iqd), (Iqe), (Iqf), (Iqg) and (Iqh), where Q, $(R^1)_m$ and $(R^2)_n$ are each as defined in Table 1:

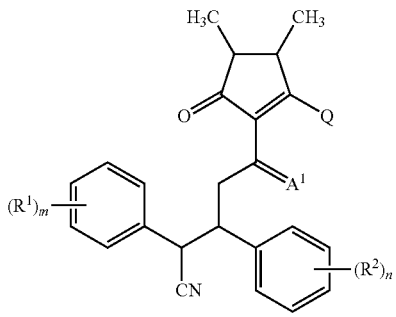

(Iqa) $A^1$ is (=O)
(Iqb) $A^1$ is (=S)
(Iqc) $A^1$ is (=N—CH$_3$)
(Iqd) $A^1$ is (=N—OH)
(Iqe) $A^1$ is (=N—OCH$_3$)
(Iqf) $A^1$ is (=N—NH$_2$)
(Iqg) $A^1$ is [=N—N(CH$_3$)$_2$]
(Iqh) $A^1$ is (=N-benzyl)

Table 17, examples of erythro/threo mixtures (ratios 70:30 to 30:70):

Examples are the compounds of the respective formulae (Iqa) to (Iqh), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

TABLE 18

Compounds of the formulae (Ir), (Ira), (Irb), (Irc), (Ird), (Ire), (Irf), (Irg) and (Irh), where Q, $(R^1)_m$ and $(R^2)_n$ are each as defined in Table 1:

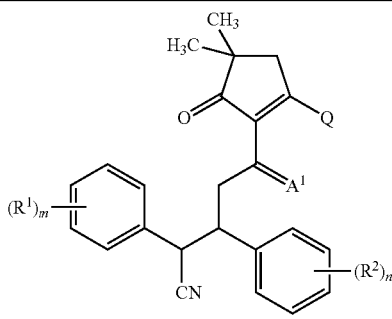

(Ira) $A^1$ is (=O)
(Irb) $A^1$ is (=S)
(Irc) $A^1$ is (=N—CH$_3$)
(Ird) $A^1$ is (=N—OH)
(Ire) $A^1$ is (=N—OCH$_3$)
(Irf) $A^1$ is (=N—NH$_2$)
(Irg) $A^1$ is [=N—N(CH$_3$)$_2$]
(Irh) $A^1$ is (=N-benzyl)

Table 18, examples of erythro/threo mixtures (ratios 70:30 to 30:70):

Examples are the compounds of the respective formulae (Ira) to (Irh), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

TABLE 19

Compounds of the formulae (Is), (Isa), (Isb), (Isc), (Isd), (Ise), (Isf), (Isg) and (Ish), where Q, $(R^1)_m$ and $(R^2)_n$ are each as defined in Table 1:

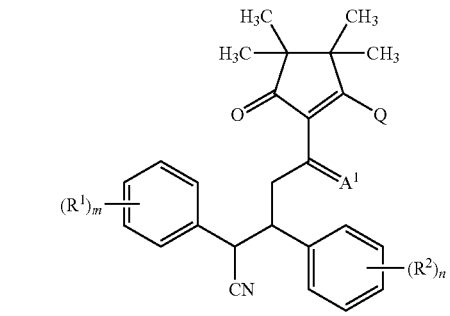

(Isa) $A^1$ is (=O)
(Isb) $A^1$ is (=S)
(Isc) $A^1$ is (=N—CH$_3$)
(Isd) $A^1$ is (=N—OH)
(Ise) $A^1$ is (=N—OCH$_3$)
(Isf) $A^1$ is (=N—NH$_2$)
(Isg) $A^1$ is [=N—N(CH$_3$)$_2$]
(Ish) $A^1$ is (=N-benzyl)

Table 19, examples of erythro/threo mixtures (ratios 70:30 to 30:70):

Examples are the compounds of the respective formulae (Isa) to (Ish), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

TABLE 20

Compounds of the formulae (It), (Ita), (Itb), (Itc), (Itd), (Ite), (Itf), (Itg) and (Ith), where Q, $(R^1)_m$ and $(R^2)_n$ are each as defined in Table 1:

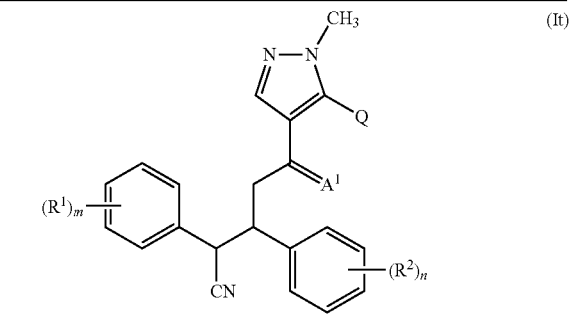

(Ita) $A^1$ is (=O)
(Itb) $A^1$ is (=S)
(Itc) $A^1$ is (=N—CH$_3$)
(Itd) $A^1$ is (=N—OH)
(Ite) $A^1$ is (=N—OCH$_3$)
(Itf) $A^1$ is (=N—NH$_2$)
(Itg) $A^1$ is [=N—N(CH$_3$)$_2$]
(Ith) $A^1$ is (=N-benzyl)

Table 20, examples of erythro/threo mixtures (ratios 70:30 to 30:70):

Examples are the compounds of the respective formulae (Ita) to (Ith), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

Tables 20a to 20f: Compounds of the formulae (threo-Ita) and (threo-2-Ita), where Q, $(R^1)_m$ and $(R^2)_n$ are each as defined in Table 1:

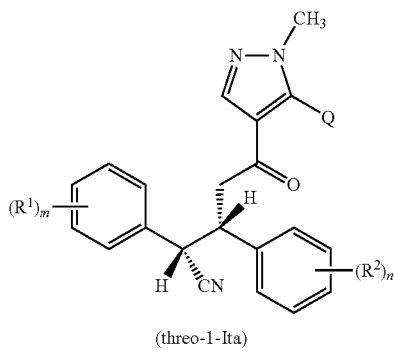

(threo-1-Ita)

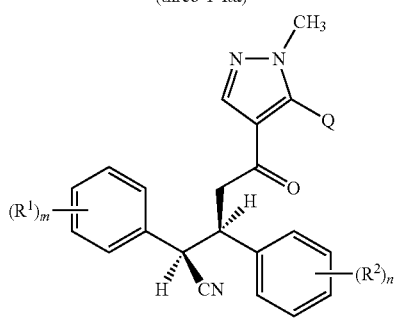

(threo-2-Ita)

(threo-Ita) = (threo-1-Ita) + (threo-2-Ita) (50:50) = (rac.)

Table 20a (threo racemates), examples:

Compounds of the formula (Ita) in the form of the racemic mixture of the threo isomers [=formula (threo-Ita)], where the structural combination of groups Q, $(R^1)_m$ and $(R^2)_n$ is defined according to a row number of Table 1. Individual compounds are numbered "threo-Ita(row number)".

Table 20b (optically active threo-2 compounds), examples:

Optically active threo-2 enantiomers in enriched form [=(2R,3R) form of more than 90% ee] having the chemical structure of the formula (threo-2-Ita), where the structural combination of groups Q, $(R^1)_m$ and $(R^2)_n$ is defined according to a row number of Table 1. Individual compounds are numbered "threo-2-Ita(row number)".

Table 20c (optically active threo-1 enantiomers), examples:

Optically active threo-1 enantiomers in enriched form [=(2S,3S) form of more than 90% ee] having the chemical structure of the formula (threo-1-Ita), where the structural combination of groups Q, $(R^1)_m$ and $(R^2)_n$ is defined according to a row number of Table 1. Individual compounds are numbered "threo-1-Ita(row number)".

Table 20d (erythro racemates), examples:

Compounds of the formula (Ita) in the form of the racemic mixture of the erythro isomers [=formula (erythro-Ita)], where the structural combination of groups Q, $(R^1)_m$ and $(R^2)_n$ is defined according to a row number of Table 1. Individual compounds are numbered "erythro-Ita(row number)".

Table 20e (erythro-1 enantiomers), examples:

Optically active erythro-1 enantiomers in enriched form [=(2R,3S) form of more than 90% ee] having the chemical structure of the formula (Ita) in the erythro-1 form [=formula (erythro-1-Ita)], where the structural combination of groups Q, $(R^1)_m$ and $(R^2)_n$ is defined according to a row number of Table 1. Individual compounds are numbered "erythro-1-Ita (row number)".

Table 20f (erythro-2 enantiomers), examples:

Optically active erythro-2 enantiomers in enriched form [=(2S,3R) form of more than 90% ee] having the chemical structure of the formula (Ita) in the erythro-2 form [=formula (erythro-2-Ita)], where the structural combination of groups Q, $(R^1)_m$ and $(R^2)_n$ is defined according to a row number of Table 1. Individual compounds are numbered "erythro-2-Ita (row number)" (analogously to Tab. 20b).

TABLE 21

Compounds of the formulae (Iu), (Iua), (Iub), (Iuc), (Iud), (Iue), (Iuf), (Iug) and (Iuh), where Q, $(R^1)_m$ and $(R^2)_n$ are each as defined in Table 1:

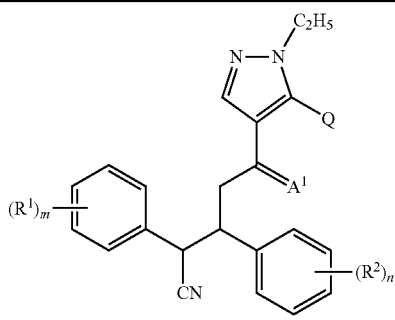

(Iua) $A^1$ is (=O)
(Iub) $A^1$ is (=S)
(Iuc) $A^1$ is (=N—CH$_3$)
(Iud) $A^1$ is (=N—OH)
(Iue) $A^1$ is (=N—OCH$_3$)
(Iuf) $A^1$ is (=N—NH$_2$)
(Iug) $A^1$ is [=N—N(CH$_3$)$_2$]
(Iuh) $A^1$ is (=N-benzyl)

Table 21, examples of erythro/threo mixtures (ratios 70:30 to 30:70):

Examples are the compounds of the respective formulae (Iua) to (Iuh), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

Tables 21a to 21f: Compounds of the formulae (threo-Iua) and (threo-2-Iua), where Q, $(R^1)_m$ and $(R^2)_n$ are each as defined in Table 1:

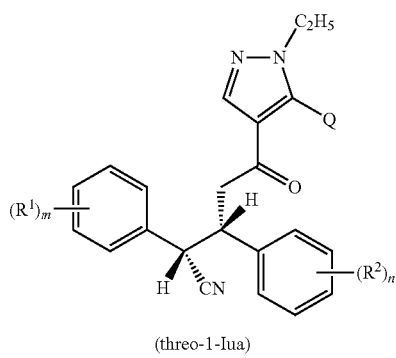

(threo-1-Iua)

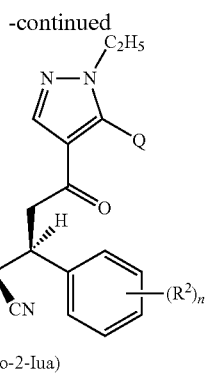

(threo-2-Iua)

(threo-Iua) = (threo-1-Iua) + (threo-2-Iua) (50:50) = (rac.)

Table 21a (threo racemates), examples:

Compounds of the formula (Iua) in the form of the racemic mixture of the threo isomers [=formula (threo-Iua)], where the structural combination of groups Q, $(R^1)_m$ and $(R^2)_n$ is defined according to a row number of Table 1. Individual compounds are numbered "threo-Iua(row number)".

Table 21b (optically active threo-2 compounds), examples:

Optically active threo-2 enantiomers in enriched form [=(2R,3R) form of more than 90% ee] having the chemical structure of the formula (threo-2-Iua), where the structural combination of groups Q, $(R^1)_m$ and $(R^2)_n$ is defined according to a row number of Table 1. Individual compounds are numbered "threo-2-Iua(row number)".

Table 21c (optically active threo-1 enantiomers), examples:

Optically active threo-1 enantiomers in enriched form [=(2S,3S) form of more than 90% ee] having the chemical structure of the formula (threo-1-Iua), where the structural combination of groups Q, $(R^1)_m$ and $(R^2)_n$ is defined according to a row number of Table 1. Individual compounds are numbered "threo-1-Iua(row number)".

Table 21d (erythro racemates), examples:

Compounds of the formula (Iua) in the form of the racemic mixture of the erythro isomers [=formula (erythro-Iua)], where the structural combination of groups Q, $(R^1)_m$ and $(R^2)_n$ is defined according to a row number of Table 1. Individual compounds are numbered "erythro-Iua(row number)".

Table 21e (erythro-1 enantiomers), examples:

Optically active erythro-1 enantiomers in enriched form [=(2R,3S) form of more than 90% ee] having the chemical structure of the formula (Iua) in the erythro-1 form [=formula (erythro-1-Iua)], where the structural combination of groups Q, $(R^1)_m$ and $(R^2)_n$ is defined according to a row number of Table 1. Individual compounds are numbered "erythro-1-Iua (row number)".

Table 21f (erythro-2 enantiomers), examples:

Optically active erythro-2 enantiomers in enriched form [=(2S,3R) form of more than 90% ee] having the chemical structure of the formula (Iua) in the erythro-2 form [=formula (erythro-2-Iua)], where the structural combination of groups Q, $(R^1)_m$ and $(R^2)_n$ is defined according to a row number of Table 1. Individual compounds are numbered "erythro-2-Iua (row number)".

TABLE 22

Compounds of the formulae (Iv), (Iva), (Ivb), (Ivc), (Ivd), (Ive), (Ivf), (Ivg) and (Ivh), where Q, $(R^1)_m$ and $(R^2)_n$ are each as defined in Table 1:

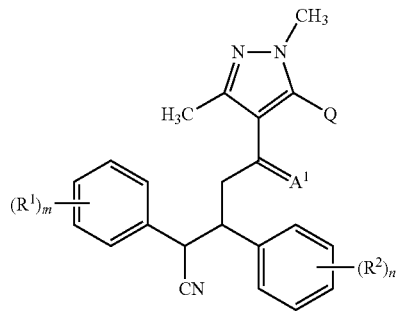

(Iv)

(Iva) $A^1$ is (=O)
(Ivb) $A^1$ is (=S)
(Ivc) $A^1$ is (=N—$CH_3$)
(Ivd) $A^1$ is (=N—OH)
(Ive) $A^1$ is (=N—$OCH_3$)
(Ivf) $A^1$ is (=N—$NH_2$)
(Ivg) $A^1$ is [=N—N($CH_3$)$_2$]
(Ivh) $A^1$ is (=N-benzyl)

Table 22, examples of erythro/threo mixtures (ratios 70:30 to 30:70):

Examples are the compounds of the respective formulae (Iva) to (Ivh), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

Tables 22a to 22f: Compounds of the formulae (threo-Iva) and (threo-2-Iva), where Q, $(R^1)_m$ and $(R^2)_n$ are each as defined in Table 1:

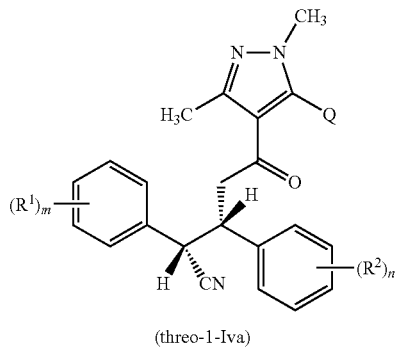

(threo-1-Iva)

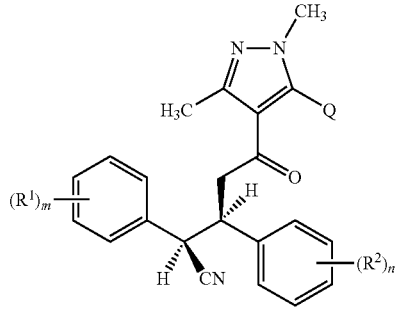

(threo-2-Iva)

(threo-Iva) = (threo-1-Iva) + (threo-2-Iva) (50:50) = (rac.)

Table 22a (threo racemates), examples:

Compounds of the formula (Iva) in the form of the racemic mixture of the threo isomers [=formula (threo-Iva)], where the structural combination of groups Q, $(R^1)_m$ and $(R^2)_n$ is defined according to a row number of Table 1. Individual compounds are numbered "threo-Iva(row number)".

Table 22b (optically active threo-2 compounds), examples:

Optically active threo-2 enantiomers in enriched form [=(2R,3R) form of more than 90% ee] having the chemical structure of the formula (threo-2-Iva), where the structural combination of groups Q, $(R^1)_m$ and $(R^2)_n$ is defined according to a row number of Table 1. Individual compounds are numbered "threo-2-Iva(row number)".

Table 22c (optically active threo-1 enantiomers), examples:

Optically active threo-1 enantiomers in enriched form [=(2S,3S) form of more than 90% ee] having the chemical structure of the formula (threo-1-Iva), where the structural combination of groups Q, $(R^1)_m$ and $(R^2)_n$ is defined according to a row number of Table 1. Individual compounds are numbered "threo-1-Iva(row number)".

Table 22d (erythro racemates), examples:

Compounds of the formula (Iva) in the form of the racemic mixture of the erythro isomers [=formula (erythro-Iva)], where the structural combination of groups Q, $(R^1)_m$ and $(R^2)_n$ is defined according to a row number of Table 1. Individual compounds are numbered "erythro-Iva(row number)".

Table 22e (erythro-1 enantiomers), examples:

Optically active erythro-1 enantiomers in enriched form [=(2R,3S) form of more than 90% ee] having the chemical structure of the formula (Iva) in the erythro-1 form [=formula (erythro-1-Iva)], where the structural combination of groups Q, $(R^1)_m$ and $(R^2)_n$ is defined according to a row number of Table 1. Individual compounds are numbered "erythro-1-Iva (row number)".

Table 22f (erythro-2 enantiomers), examples:

Optically active erythro-2 enantiomers in enriched form [=(2S,3R) form of more than 90% ee] having the chemical structure of the formula (Iva) in the erythro-2 form [=formula (erythro-2-Iva)], where the structural combination of groups Q, $(R^1)_m$ and $(R^2)_n$ is defined according to a row number of Table 1. Individual compounds are numbered "erythro-2-Iva (row number)".

TABLE 23

Compounds of the formulae (Iw), (Iwa), (Iwb), (Iwc), (Iwd), (Iwe), (Iwf), (Iwg) and (Iwh), where Q, $(R^1)_m$ and $(R^2)_n$ are each as defined in Table 1:

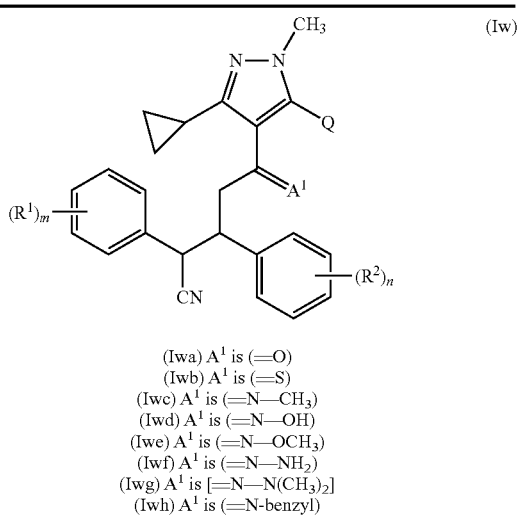

(Iwa) $A^1$ is (=O)
(Iwb) $A^1$ is (=S)
(Iwc) $A^1$ is (=N—CH$_3$)
(Iwd) $A^1$ is (=N—OH)
(Iwe) $A^1$ is (=N—OCH$_3$)
(Iwf) $A^1$ is (=N—NH$_2$)
(Iwg) $A^1$ is [=N—N(CH$_3$)$_2$]
(Iwh) $A^1$ is (=N-benzyl)

Table 23, examples of erythro/threo mixtures (ratios 70:30 to 30:70):

Examples are the compounds of the respective formulae (Iwa) to (Iwh), in each case in the form of a racemic erythro/threo mixture (ratio 70:30 to 30:70), where the meanings of Q, $(R^1)_m$ and $(R^2)_n$ are defined according to a row number of Table 1. Individual compounds are numbered "(formula)(row number)", without any brackets.

Tables 23a to 23f: Compounds of the formulae (threo-Iwa) and (threo-2-Iwa), where Q, $(R^1)_m$ and $(R^2)_n$ are each as defined in Table 1:

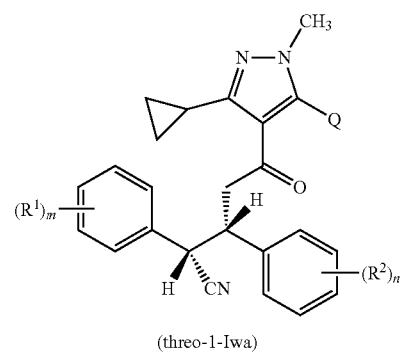

(threo-1-Iwa)

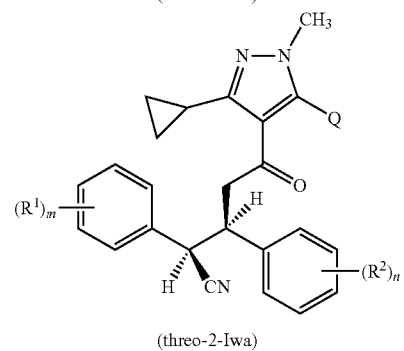

(threo-2-Iwa)

(threo-Iwa) = (threo-1-Iwa) + (threo-2-Iwa) (50:50) = (rac.)

Table 23a (threo racemates), examples:

Compounds of the formula (Iwa) in the form of the racemic mixture of the threo isomers [=formula (threo-Iwa)], where the structural combination of groups Q, $(R^1)_m$ and $(R^2)_n$ is defined according to a row number of Table 1. Individual compounds are numbered "threo-Iwa(row number)".

Table 23b (optically active threo-2 compounds), examples:

Optically active threo-2 enantiomers in enriched form [=(2R,3R) form of more than 90% ee] having the chemical structure of the formula (threo-1-Iwa), where the structural combination of groups Q, $(R^1)_m$ and $(R^2)_n$ is defined according to a row number of Table 1. Individual compounds are numbered "threo-2-Iwa(row number)". Table 23c (optically active threo-1 enantiomers), examples:

Optically active threo-1 enantiomers in enriched form [=(2S,3S) form of more than 90% ee] having the chemical structure of the formula (threo-1-Iwa), where the structural combination of groups Q, $(R^1)_m$ and $(R^2)_n$ is defined according to a row number of Table 1. Individual compounds are numbered "threo-1-Iwa(row number)".

Table 23d (erythro racemates), examples:

Compounds of the formula (Iwa) in the form of the racemic mixture of the erythro isomers [=formula (erythro-Iwa)], where the structural combination of groups Q, $(R^1)_m$ and ($R^2$)$_n$ is defined according to a row number of Table 1. Individual compounds are numbered "erythro-Iwa(row number)".

Table 23e (erythro-1 enantiomers), examples:

Optically active erythro-1 enantiomers in enriched form [=(2R,3S) form of more than 90% ee] having the chemical structure of the formula (Iwa) in the erythro-1 form [=formula (erythro-1-Iwa)], where the structural combination of groups Q, ($R^1$)$_m$ and ($R^2$)$_n$ is defined according to a row number of Table 1. Individual compounds are numbered "erythro-1-Iwa (row number)".

Table 23f (erythro-2 enantiomers), examples:

Optically active erythro-2 enantiomers in enriched form [=(2S,3R) form of more than 90% ee] having the chemical structure of the formula (Iwa) in the erythro-2 form [=formula (erythro-2-Iwa)], where the structural combination of groups Q, ($R^1$)$_m$ and ($R^2$)$_n$ is defined according to a row number of Table 1. Individual compounds are numbered "erythro-2-Iwa (row number)".

TABLE 24

Compounds of the formulae (Ix), (Ixa), (Ixb), (Ixc), (Ixd), (Ixe), (Ixf), (Ixg) and (Ixh), where Q, ($R^1$)$_m$ and ($R^2$)$_n$ are each as defined in Table 1:

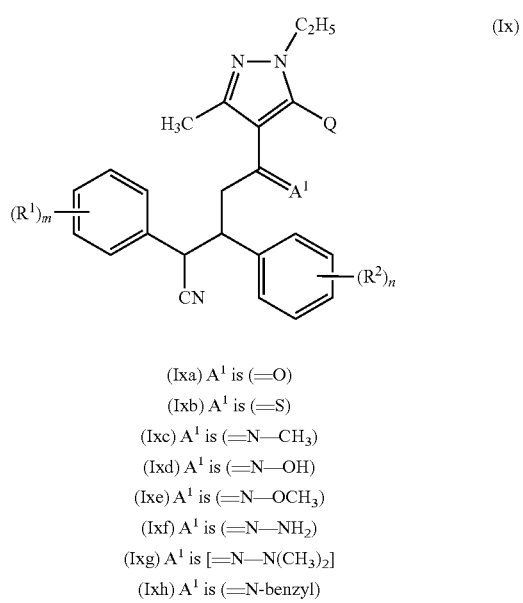

(Ixa) $A^1$ is (=O)
(Ixb) $A^1$ is (=S)
(Ixc) $A^1$ is (=N—CH$_3$)
(Ixd) $A^1$ is (=N—OH)
(Ixe) $A^1$ is (=N—OCH$_3$)
(Ixf) $A^1$ is (=N—NH$_2$)
(Ixg) $A^1$ is [=N—N(CH$_3$)$_2$]
(Ixh) $A^1$ is (=N-benzyl)

Table 24, examples of erythro/threo mixtures (ratios 70:30 to 30:70):

Examples are the compounds of the respective formulae (Ixa) to (Ixh), in each case in the form of a racemic erythro/threo mixture (ratio 70:30 to 30:70), where the meanings of Q, ($R^1$)$_m$ and ($R^2$)$_n$ are defined according to a row number of Table 1. Individual compounds are numbered "(formula)(row number)", without any brackets.

Tables 24a to 24f: Compounds of the formulae (threo-Ixa) and (threo-2-Ixa), where Q, ($R^1$)$_m$ and ($R^2$)$_n$ are each as defined in Table 1:

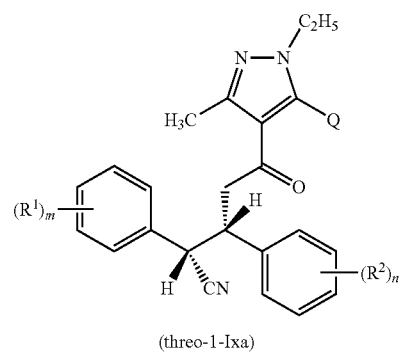

(threo-1-Ixa)

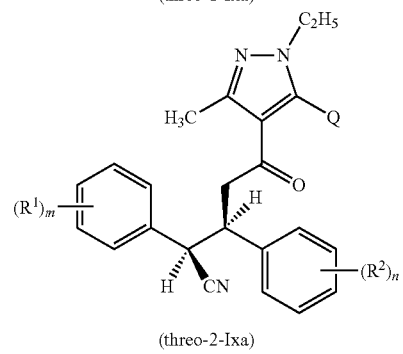

(threo-2-Ixa)

(threo-Ixa) = (threo-1-Ixa) + (threo-2-Ixa) (50:50) = (rac.)

Table 24a (threo racemates), examples:

Compounds of the formula (Ixa) in the form of the racemic mixture of the threo isomers [=formula (threo-Ixa)], where the structural combination of groups Q, ($R^1$)$_m$ and ($R^2$)$_n$ is defined according to a row number of Table 1. Individual compounds are numbered "threo-Ixa(row number)".

Table 24b (optically active threo-2 compounds), examples:

Optically active threo-2 enantiomers in enriched form [=(2R,3R) form of more than 90% ee] having the chemical structure of the formula (threo-2-Ixa), where the structural combination of groups Q, ($R^1$)$_m$ and ($R^2$)$_n$ is defined according to a row number of Table 1. Individual compounds are numbered "threo-2-Ixa(row number)".

Table 24c (optically active threo-1 enantiomers), examples:

Optically active threo-1 enantiomers in enriched form [=(2S,3S) form of more than 90% ee] having the chemical structure of the formula (threo-1-Ixa), where the structural combination of groups Q, ($R^1$)$_m$ and ($R^2$)$_n$ is defined according to a row number of Table 1. Individual compounds are numbered "threo-1-Ixa(row number)".

Table 24d (erythro racemates), examples:

Compounds of the formula (Ixa) in the form of the racemic mixture of the erythro isomers [=formula (erythro-Ixa)], where the structural combination of groups Q, ($R^1$)$_m$ and ($R^2$)$_n$ is defined according to a row number of Table 1. Individual compounds are numbered "erythro-Ixa(row number)".

Table 24e (erythro-1 enantiomers), examples:

Optically active erythro-1 enantiomers in enriched form [=(2R,3S) form of more than 90% ee] having the chemical structure of the formula (Ixa) in the erythro-1 form [=formula (erythro-1-Ixa)], where the structural combination of groups Q, ($R^1$)$_m$ and ($R^2$)$_n$ is defined according to a row number of Table 1. Individual compounds are numbered "erythro-1-Ixa (row number)".

Table 24f (erythro-2 enantiomers), examples:

Optically active erythro-2 enantiomers in enriched form [=(2S,3R) form of more than 90% ee] having the chemical structure of the formula (Ixa) in the erythro-2 form [=formula (erythro-2-Ixa)], where the structural combination of groups Q, $(R^1)_m$ and $(R^2)_n$ is defined according to a row number of Table 1. Individual compounds are numbered "erythro-2-Iwa (row number)".

TABLE 25

Definitions of structural combinations of groups $(R^1)_m$ and $(R^2)_n$ for the tables of compounds of the general formula (I) according to the invention below

| No. | $(R^1)_m$ | $(R^2)_n$ |
|---|---|---|
| 1 | 3-F | 4-Cl |
| 2 | 3-F | 3-F |
| 3 | 3,4-F$_2$ | 4-Cl |
| 4 | 3-F | 4-Br |
| 5 | 3-Cl | 3-F |
| 6 | 3,4-F$_2$ | 3-F |
| 7 | H | 3-F |
| 8 | 4-F | 3-F |
| 9 | 3-F | 3-Cl |
| 10 | 3,4-F$_2$ | 3-Cl |
| 11 | 3-Br | 3-F |
| 12 | 2,5-F$_2$ | 3-F |
| 13 | 3-F | 2-F |
| 14 | 3,4,5-F$_3$ | 4-Cl |
| 15 | 4-F | 3-Cl |
| 16 | 3,4-F$_2$ | 3-F, 4-Cl |
| 17 | 3,4-F$_2$ | 2-F |
| 18 | 3-F | 2,3-F$_2$ |
| 19 | 4-F | 3,5-F$_2$ |
| 20 | 3-F | 4-F |
| 21 | 3,4-F$_2$ | 3-Cl, 5-F |
| 22 | 3-F | 3-Cl, 5-F |
| 23 | 3-F | 2,5-F$_2$ |
| 24 | 3,4-F$_2$ | 2,3-F$_2$ |
| 25 | 3,4-F$_2$ | 2,5-F$_2$ |
| 26 | 3-Cl | 3-Cl, 5-F |
| 27 | 3-F, 4-Cl | 3-Cl |
| 28 | 3,4-F$_2$ | 3-NO$_2$ |
| 29 | 3,4-F$_2$ | H |
| 30 | 3-Cl, 4-F | 3-F |
| 31 | 3,4-F$_2$ | 4-OMe |
| 32 | 3-F | H |
| 33 | 3-F | 2,4-F$_2$ |
| 34 | 3-F | 2,6-F$_2$ |
| 35 | 3-F | 3,4-F$_2$ |
| 36 | 3-F | 3,5-F$_2$ |
| 37 | 3-F | 2-Cl |
| 38 | 3-F | 2,3-Cl$_2$ |
| 39 | 3-F | 2,4-Cl$_2$ |
| 40 | 3-F | 3,4-Cl$_2$ |
| 41 | 3-F | 3,5-Cl$_2$ |
| 42 | 3,4-F$_2$ | 2,4-F$_2$ |
| 43 | 3,4-F$_2$ | 2,6-F$_2$ |
| 44 | 3,4-F$_2$ | 3,4-F$_2$ |
| 45 | 3,4-F$_2$ | 3,5-F$_2$ |
| 46 | 3,4-F$_2$ | 2,4-Cl$_2$ |
| 47 | 3,4-F$_2$ | 2,6-Cl$_2$ |
| 48 | 3,4-F$_2$ | 3,5-Cl$_2$ |
| 49 | 3-Cl | H |
| 50 | 3-Cl | 2-F |
| 51 | 3-Cl | 4-F |
| 52 | 3-Cl | 2,3-F$_2$ |
| 53 | 3-Cl | 2,5-F$_2$ |
| 54 | 3-Cl | 2,6-F$_2$ |
| 55 | 3-Cl | 3,5-F$_2$ |
| 56 | 3-Cl | 2-Cl |
| 57 | 3-Cl | 3-Cl |
| 58 | 3-Cl | 2,3-Cl$_2$ |
| 59 | 3-Cl | 2,4-Cl$_2$ |
| 60 | 3-Cl | 2,5-Cl$_2$ |
| 61 | 3-Cl | 3,5-Cl$_2$ |
| 62 | 3,4-Cl$_2$ | 2,5-F$_2$ |
| 63 | 3-Cl, 4-F | 3-Cl |
| 64 | 3-F, 4-Cl | 2,3-F$_2$ |
| 65 | 3-F, 4-Cl | 3,5-F$_2$ |
| 66 | 3,4-F$_2$ | 3,4-Cl$_2$ |
| 67 | 3,4-F$_2$ | 3,5-Cl$_2$ |
| 68 | 3-Cl | H |
| 69 | 3-Cl | 2,4-F$_2$ |
| 70 | 3-Cl | 3,4-F$_2$ |
| 71 | 3-Cl | 4-Cl |
| 72 | 3-Cl | 2,6-Cl$_2$ |
| 73 | 3,4-Cl$_2$ | H |
| 74 | 3,4-Cl$_2$ | 2-F |
| 75 | 3,4-Cl$_2$ | 3-F |
| 76 | 3,4-Cl$_2$ | 4-F |
| 77 | 3,4-Cl$_2$ | 2,6-F$_2$ |
| 78 | 3,4-Cl$_2$ | 3,5-F$_2$ |
| 79 | 3,4-Cl$_2$ | 2-Cl |
| 80 | 3,4-Cl$_2$ | 3-Cl |
| 81 | 3,4-Cl$_2$ | 4-Cl |
| 82 | 3,4-Cl$_2$ | 2,4-Cl$_2$ |
| 83 | 3,4-Cl$_2$ | 2,5-Cl$_2$ |
| 84 | 3,4-Cl$_2$ | 2,6-Cl$_2$ |
| 85 | 3,4-Cl$_2$ | 3,4-Cl$_2$ |
| 86 | 3,4-Cl$_2$ | 3,5-Cl$_2$ |
| 87 | 3-Cl, 4-F | H |
| 88 | 3-Cl, 4-F | 2-F |
| 89 | 3-Cl, 4-F | 4-F |
| 90 | 3-Cl, 4-F | 2,3-F$_2$ |
| 91 | 3-Cl, 4-F | 2,4-F$_2$ |
| 92 | 3-Cl, 4-F | 2,5-F$_2$ |
| 93 | 3-Cl, 4-F | 2,6-F$_2$ |
| 94 | 3-Cl, 4-F | 3,4-F$_2$ |
| 95 | 3-Cl, 4-F | 3,5-F$_2$ |
| 96 | 3-Cl, 4-F | 2-Cl |
| 97 | 3-Cl, 4-F | 3-Cl |
| 98 | 3-Cl, 4-F | 4-Cl |
| 99 | 3-Cl, 4-F | 2,3-Cl$_2$ |
| 100 | 3-Cl, 4-F | 2,4-Cl$_2$ |
| 101 | 3-Cl, 4-F | 2,5-Cl$_2$ |
| 102 | 3-Cl, 4-F | 2,6-Cl$_2$ |
| 103 | 3-Cl, 4-F | 3,4-Cl$_2$ |
| 104 | 3-Cl, 4-F | 3,5-Cl$_2$ |
| 105 | 3-Cl, 4-F | H |
| 106 | 3-F, 4-Cl | 2-F |
| 107 | 3-F, 4-Cl | 3-F |
| 108 | 3-F, 4-Cl | 4-F |
| 109 | 3-F, 4-Cl | 2,4-F$_2$ |
| 110 | 3-F, 4-Cl | 2,5-F$_2$ |
| 111 | 3-F, 4-Cl | 2,6-F$_2$ |
| 112 | 3-F, 4-Cl | 3,4-F$_2$ |
| 113 | 3-F, 4-Cl | 2-Cl |
| 114 | 3-F, 4-Cl | 4-Cl |
| 115 | 3-F, 4-Cl | 2,4-Cl$_2$ |
| 116 | 3-F, 4-Cl | 2,5-Cl$_2$ |
| 117 | 3-F, 4-Cl | 2,6-Cl$_2$ |
| 118 | 3-F, 4-Cl | 3,4-Cl$_2$ |
| 119 | 3-F, 4-Cl | 3,5-Cl$_2$ |
| 120 | 3-CN | H |
| 121 | 3-CN | 2,5-F$_2$ |
| 122 | 3-CN | 2,6-F$_2$ |
| 123 | 3-CN | 2,3-F$_2$ |
| 124 | 3-CN | 2,4-F$_2$ |
| 125 | 3-CN | 3,4-F$_2$ |
| 126 | 3-CN | 3,5-F$_2$ |
| 127 | 3-CN | 4-Cl |
| 128 | 3-CN | 3-Cl |
| 129 | 3-CN | 2-Cl |
| 130 | 3-CN | 4-F |
| 131 | 3-CN | 3-F |
| 132 | 3-CN | 2-F |
| 133 | 2-CN | 3-F |
| 134 | 2-CN | 4-F |
| 135 | 2-CN | 4-Cl |
| 136 | 3-NO$_2$ | H |
| 137 | 3-NO$_2$ | 2,5-F$_2$ |

TABLE 25-continued

Definitions of structural combinations of groups $(R^1)_m$ and $(R^2)_n$ for the tables of compounds of the general formula (I) according to the invention below

| No. | $(R^1)_m$ | $(R^2)_n$ |
|---|---|---|
| 138 | 3-NO$_2$ | 2,6-F$_2$ |
| 139 | 3-NO$_2$ | 2,3-F$_2$ |
| 140 | 3-NO$_2$ | 2,4-F$_2$ |
| 141 | 3-NO$_2$ | 3,4-F$_2$ |
| 142 | 3-NO$_2$ | 3,5-F$_2$ |
| 143 | 3-NO$_2$ | 4-Cl |
| 144 | 3-NO$_2$ | 3-Cl |
| 145 | 3-NO$_2$ | 2-Cl |
| 146 | 3-NO$_2$ | 4-F |
| 147 | 3-NO$_2$ | 3-F |
| 148 | 3-NO$_2$ | 2-F |
| 149 | H | 2,6-F$_2$ |
| 150 | H | 3,4-F$_2$ |
| 151 | H | 3,5-F$_2$ |
| 152 | H | 2,3-F$_2$ |
| 153 | H | 2,4-F$_2$ |
| 154 | H | 2,5-F$_2$ |
| 155 | H | 2-Cl |
| 156 | H | 3-Cl |
| 157 | H | 4-Cl |
| 158 | H | 2-F |
| 159 | H | 4-F |
| 160 | H | 2,3-Cl$_2$ |
| 161 | H | 2,4-Cl$_2$ |
| 162 | H | 2,5-Cl$_2$ |
| 163 | H | 2,6-Cl$_2$ |
| 164 | H | 3,4-Cl$_2$ |
| 165 | H | 3,5-Cl$_2$ |
| 166 | 3-CN, 4-F | 3-F |
| 167 | 3-CN, 4-F | 3-Cl |
| 168 | 3-CN, 4-F | 3-CN |
| 169 | 3-CN, 4-F | 4-F |
| 170 | 3-CN, 4-F | 4-Cl |
| 171 | 3-CN, 4-F | 2,5-F$_2$ |
| 172 | 3-CN, 4-F | 2,6-F$_2$ |
| 173 | 3-CN, 4-F | 3-F |
| 174 | 3-CN, 4-F | 3-Cl |
| 175 | 3-CN, 4-F | 3-CN |
| 176 | 3-CN, 4-F | 4-F |
| 177 | 3-CN, 4-F | 4-Cl |
| 178 | 3-CN, 4-F | 2,5-F$_2$ |
| 179 | 3-CN, 4-F | 2,6-F$_2$ |
| 180 | 3-Br, 4-F | 3-F |
| 181 | 3-Br, 4-F | 3-Cl |
| 182 | 3-Br, 4-F | 3-CN |
| 183 | 3-Br, 4-F | 4-F |
| 184 | 3-Br, 4-F | 4-Cl |
| 185 | 3-Br, 4-F | 2,5-F$_2$ |
| 186 | 3-Br, 4-F | 2,6-F$_2$ |
| 187 | 3-Br, 4-F | 3-F |
| 188 | 3-Br, 4-F | 3-Cl |
| 189 | 3-Br, 4-F | 3-CN |
| 190 | 3-Br, 4-F | 4-F |
| 191 | 3-Br, 4-F | 4-Cl |
| 192 | 3-Br, 4-F | 2,5-F$_2$ |
| 193 | 3-Br, 4-F | 2,6-F$_2$ |
| 194 | 3-F, 4-CN | 3-F |
| 195 | 3-F, 4-CN | 3-Cl |
| 196 | 3-F, 4-CN | 3-CN |
| 197 | 3-F, 4-CN | 4-F |
| 198 | 3-F, 4-CN | 4-Cl |
| 199 | 3-F, 4-CN | 2,5-F$_2$ |
| 200 | 3-F, 4-CN | 2,6-F$_2$ |
| 201 | 3-F, 4-CN | 3-F |
| 202 | 3-F, 4-CN | 3-Cl |
| 203 | 3-F, 4-CN | 3-CN |
| 204 | 3-F, 4-CN | 4-F |
| 205 | 3-F, 4-CN | 4-Cl |
| 206 | 3-F, 4-CN | 2,5-F$_2$ |
| 207 | 3-F, 4-CN | 2,6-F$_2$ |

For reference purposes, specific numbers (=Example Numbers) have been assigned to the individual compounds in Tables 26 to 35 below, where the Example Number in question is composed of the number of the chemical formula assigned to the respective table and a "row number" (row number) which refers to the same number in the row of the first column of Table 25. The chemical structure of Example No. "(formula number)(row number)" is thus defined unambiguously by the formula above the respective table by formula number and row number of Table 25, for example:

Example No. "IB8aa1" of Table 26 is the compound of the formula (IB8) where R=methyl and $A^1$=O[=formula (IB8aa), see the Table below of the subformulae for formula (IB8)] and $(R^1)_m$=3-F and $(R^2)_n$=4-Cl are defined according to row 1 of Table 25, or a tautomer thereof.

Example No. "IB8af136" of Table 26 is the compound of the formula (IB8) where R=methyl and $A^1$=N—NH$_2$ [=formula (IB8af)] and $(R^1)_m$=3-NO$_2$ and $(R^2)_n$=H (n=0, unsubstituted) are defined according to row 136 of Table 25, or a tautomer thereof.

TABLE 26

Compounds of the formula (IB8), where $(R^1)_m$ and $(R^2)_n$ are each as defined in Table 25:

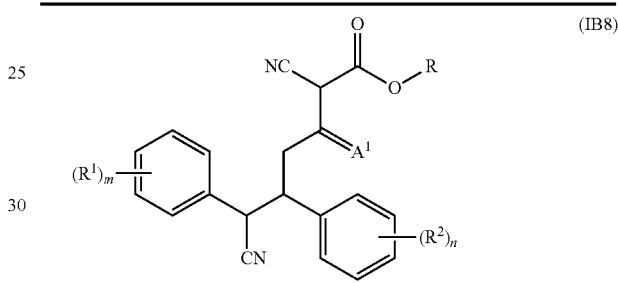
(IB8)

Definition of the subformulae for formula (IB8) with fixed radicals R and $A^1$:

| Subformula for (IB8) | R | $A^1$ |
|---|---|---|
| (IB8a) | CH$_3$ | $A^1$ |
| (IB8aa) | CH$_3$ | O |
| (IB8ab) | CH$_3$ | S |
| (IB8ac) | CH$_3$ | =N—CH$_3$ |
| (IB8ad) | CH$_3$ | =N—OH |
| (IB8ae) | CH$_3$ | =N—OCH$_3$ |
| (IB8af) | CH$_3$ | =N—NH$_2$ |
| (IB8ag) | CH$_3$ | =N—N(CH$_3$)$_2$ |
| (IB8ah) | CH$_3$ | =N—CH$_2$—C$_6$H$_5$ |
| (IB8b) | C$_2$H$_5$ | $A^1$ |
| (IB8ba) | C$_2$H$_5$ | O |
| (IB8bb) | C$_2$H$_5$ | S |
| (IB8bc) | C$_2$H$_5$ | =N—CH$_3$ |
| (IB8bd) | C$_2$H$_5$ | =N—OH |
| (IB8be) | C$_2$H$_5$ | =N—OCH$_3$ |
| (IB8bf) | C$_2$H$_5$ | =N—NH$_2$ |
| (IB8bg) | C$_2$H$_5$ | =N—N(CH$_3$)$_2$ |
| (IB8bh) | C$_2$H$_5$ | =N—CH$_2$—C$_6$H$_5$ |
| (IB8c) | n-C$_3$H$_7$ | $A^1$ |
| (IB8ca) | n-C$_3$H$_7$ | O |
| (IB8cb) | n-C$_3$H$_7$ | S |
| (IB8cc) | n-C$_3$H$_7$ | =N—CH$_3$ |
| (IB8cd) | n-C$_3$H$_7$ | =N—OH |
| (IB8ce) | n-C$_3$H$_7$ | =N—OCH$_3$ |
| (IB8cf) | n-C$_3$H$_7$ | =N—NH$_2$ |
| (IB8cg) | n-C$_3$H$_7$ | =N—N(CH$_3$)$_2$ |
| (IB8ch) | n-C$_3$H$_7$ | =N—CH$_2$—C$_6$H$_5$ |
| (IB8d) | i-C$_3$H$_7$ | $A^1$ |
| (IB8da) | i-C$_3$H$_7$ | O |
| (IB8db) | i-C$_3$H$_7$ | S |
| (IB8dc) | i-C$_3$H$_7$ | =N—CH$_3$ |
| (IB8dd) | i-C$_3$H$_7$ | =N—OH |
| (IB8de) | i-C$_3$H$_7$ | =N—OCH$_3$ |

-continued

| Subformula for (IB8) | R | A¹ |
|---|---|---|
| (IB8df) | i-C₃H₇ | =N—NH₂ |
| (IB8dg) | i-C₃H₇ | =N—N(CH₃)₂ |
| (IB8dh) | i-C₃H₇ | =N—CH₂—C₆H₅ |

Table 26, examples of erythro/threo mixtures (ratios 70:30 to 30:70):

Examples are the compounds of the respective formulae (IB8aa) to (IB8ah), (IB8ba) to (IB8bh), (IB8ca) to (IB8ch) and (IB8da) to (IB8dh), in each case in the form of a racemic erythro/threo mixture (ratio 70:30 to 30:70), where the meanings of $(R^1)_m$ and $(R^2)_n$ are defined according to a row number of Table 25. Individual compounds are numbered "(formula) (row number)", without any brackets.

Tables 26a to 26f: Compounds of the formulae (threo-IB8), (threo-1-IB8) and (threo-2-1B8), where $(R^1)_m$ and $(R^2)_n$ are each as defined in Table 25:

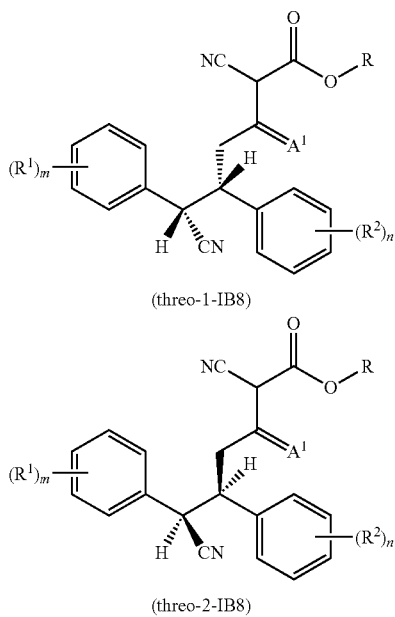

(threo-1-IB8)

(threo-2-IB8)
(threo-IB8) = (threo-1-IB8) + (threo-2-IB8) (50:50) = (rac.)

Definition of the subformulae for formulae threo-(IB8), threo-1-(IB8) and threo-2-(IB8) with fixed radicals R and A¹:

| Subformula | R | A¹ | Stereochemistry |
|---|---|---|---|
| threo-(IB8a) | CH₃ | A¹ | (2S,3S)/(2R,3R), racemic |
| threo-1-(IB8a) | CH₃ | A¹ | (2S,3S), optically active |
| threo-2-(IB8a) | CH₃ | A¹ | (2R,3R), optically active |
| threo-(IB8aa) | CH₃ | O | (2S,3S)/(2R,3R), racemic |
| threo-1-(IB8aa) | CH₃ | O | (2S,3S), optically active |
| threo-2-(IB8aa) | CH₃ | O | (2R,3R), optically active |
| threo-(IB8b) | C₂H₅ | A¹ | (2S,3S)/(2R,3R), racemic |
| threo-1-(IB8b) | C₂H₅ | A¹ | (2S,3S), optically active |
| threo-2-(IB8b) | C₂H₅ | A¹ | (2R,3R), optically active |
| threo-(IB8ba) | C₂H₅ | O | (2S,3S)/(2R,3R), racemic |
| threo-1-(IB8ba) | C₂H₅ | O | (2S,3S), optically active |
| threo-2-(IB8ba) | C₂H₅ | O | (2R,3R), optically active |
| threo-(IB8c) | n-C₃H₇ | A¹ | (2S,3S)/(2R,3R), racemic |
| threo-1-(IB8c) | n-C₃H₇ | A¹ | (2S,3S), optically active |
| threo-2-(IB8c) | n-C₃H₇ | A¹ | (2R,3R), optically active |
| threo-(IB8ca) | n-C₃H₇ | O | (2S,3S)/(2R,3R), racemic |

-continued

| Subformula | R | A¹ | Stereochemistry |
|---|---|---|---|
| threo-1-(IB8ca) | n-C₃H₇ | O | (2S,3S), optically active |
| threo-2-(IB8ca) | n-C₃H₇ | O | (2R,3R), optically active |
| threo-(IB8d) | i-C₃H₇ | A¹ | (2S,3S)/(2R,3R), racemic |
| threo-1-(IB8d) | i-C₃H₇ | A¹ | (2S,3S), optically active |
| threo-2-(IB8d) | i-C₃H₇ | A¹ | (2R,3R), optically active |
| threo-(IB8da) | i-C₃H₇ | O | (2S,3S)/(2R,3R), racemic |
| threo-1-(IB8da) | i-C₃H₇ | O | (2S,3S), optically active |
| threo-2-(IB8da) | i-C₃H₇ | O | (2R,3R), optically active |

Table 26a (threo racemates), examples:

Compounds of the formulae threo-(IB8aa), threo-(IB8ba), threo-(IB8ca) and threo-(IB8da), in each case in the form of the racemic mixture of the threo isomers, where the structural combination of groups $(R^1)_m$ and $(R^2)_n$ is defined according to a row number of Table 25.

Individual compounds are numbered "threo-IB8aa(row number)", "threo-IB8ba(row number)", "threo-IB8ca(row number)" and "threo-IB8da(row number)".

Table 26b (optically active threo-2 compounds), examples:

Compounds of the formulae threo-2-(IB8aa), threo-2-(IB8ba), threo-2-(IB8ca) and threo-2-(IB8da), in each case in stereochemically enriched form [=(2R,3R) form of more than 90% ee], where the structural combination of groups $(R^1)_m$ and $(R^2)_n$ is defined according to a row number of Table 25.

Individual compounds are numbered "threo-2-IB8aa(row number)", "threo-2-IB8ba(row number)", "threo-2-IB8ca(row number)" and "threo-2-IB8da(row number)".

Table 26c (optically active threo-1 enantiomers), examples:

Optically active enantiomeric compounds of the formulae threo-1-(IB8aa), threo-1-(IB8ba), threo-1-(IB8ca) and threo-1-(IB8da), in each case in stereochemically enriched form [=(2S,3S) form of more than 90% ee], where the structural combination of groups $(R^1)_m$ and $(R^2)_n$ is defined according to a row number of Table 25. Individual compounds are numbered "threo-1-IB8aa(row number)", "threo-1-IB8ba (row number)", "threo-1-IB8ca(row number)" and "threo-1-IB8da(row number)".

Table 26d (erythro racemates), examples:

Compounds of the formulae erythro-(IB8aa), erythro-(IB8ba), erythro-(IB8ca) and erythro-(IB8da), in each case in the form of the racemic mixture of the erythro isomers, where the structural combination of groups $(R^1)_m$ and $(R^2)_n$ is defined according to a row number of Table 25. Individual compounds are numbered "erythro-IB8aa(row number)", "erythro-IB8ba(row number)", "erythro-IB8ca(row number)" and "erythro-IB8da(row number)".

Table 26e (erythro-1 enantiomers), examples:

Optically active enantiomeric compounds of the formulae erythro-1-(IB8aa), erythro-1-(IB8ba), erythro-1-(IB8ca) and erythro-1-(IB8da), in each case in stereochemically enriched form [=(2R,3S) form of more than 90% ee], where the structural combination of groups $(R^1)_m$ and $(R^2)_n$ is defined according to a row number of Table 25. Individual compounds are numbered "erythro-1-IB8aa(row number)", "erythro-1-IB8ba(row number)", "erythro-1-IB8ca(row number)" and "erythro-1-IB8da(row number)".

Table 26f (erythro-2 enantiomers), examples:

Optically active enantiomeric compounds of the formulae erythro-2-(IB8aa), erythro-2-(IB8ba), erythro-2-(IB8ca) and erythro-2-(IB8da), in each case in stereochemically enriched form [=(2S,3R) form of more than 90% ee], where the structural combination of groups $(R^1)_m$ and $(R^2)_n$ is defined according to a row number of Table 25. Individual compounds are numbered "erythro-2-IB8aa(row number)", "erythro-2-IB8ba(row number)", "erythro-2-IB8ca(row number)" and "erythro-2-IB8da(row number)".

TABLE 27

Compounds of the formula (IBX), where $(R^1)_m$ and $(R^2)_n$ are each as defined in Table 25:

(IBX)

Definition of the subformulae for formula (IBX) with fixed radicals R and $A^1$:

| Subformula for (IBX) | R | $A^1$ |
|---|---|---|
| (IBXa) | $CH_3$ | $A^1$ |
| (IBXaa) | $CH_3$ | O |
| (IBXab) | $CH_3$ | S |
| (IBXac) | $CH_3$ | =N—$CH_3$ |
| (IBXad) | $CH_3$ | =N—OH |
| (IBXae) | $CH_3$ | =N—$OCH_3$ |
| (IBXaf) | $CH_3$ | =N—$NH_2$ |
| (IBXag) | $CH_3$ | =N—$N(CH_3)_2$ |
| (IBXah) | $CH_3$ | =N—$CH_2$—$C_6H_5$ |
| (IBXb) | $C_2H_5$ | $A^1$ |
| (IBXba) | $C_2H_5$ | O |
| (IBXbb) | $C_2H_5$ | S |
| (IBXbc) | $C_2H_5$ | =N—$CH_3$ |
| (IBXbd) | $C_2H_5$ | =N—OH |
| (IBXbe) | $C_2H_5$ | =N—$OCH_3$ |
| (IBXbf) | $C_2H_5$ | =N—$NH_2$ |
| (IBXbg) | $C_2H_5$ | =N—$N(CH_3)_2$ |
| (IBXbh) | $C_2H_5$ | =N—$CH_2$—$C_6H_5$ |
| (IBXc) | n-$C_3H_7$ | $A^1$ |
| (IBXca) | n-$C_3H_7$ | O |
| (IBXcb) | n-$C_3H_7$ | S |
| (IBXcc) | n-$C_3H_7$ | =N—$CH_3$ |
| (IBXcd) | n-$C_3H_7$ | =N—OH |
| (IBXce) | n-$C_3H_7$ | =N—$OCH_3$ |
| (IBXcf) | n-$C_3H_7$ | =N—$NH_2$ |
| (IBXcg) | n-$C_3H_7$ | =N—$N(CH_3)_2$ |
| (IBXch) | n-$C_3H_7$ | =N—$CH_2$—$C_6H_5$ |
| (IBXd) | i-$C_3H_7$ | $A^1$ |
| (IBXda) | i-$C_3H_7$ | O |
| (IBXdb) | i-$C_3H_7$ | S |
| (IBXdc) | i-$C_3H_7$ | =N—$CH_3$ |
| (IBXdd) | i-$C_3H_7$ | =N—OH |
| (IBXde) | i-$C_3H_7$ | =N—$OCH_3$ |
| (IBXdf) | i-$C_3H_7$ | =N—$NH_2$ |
| (IBXdg) | i-$C_3H_7$ | =N—$N(CH_3)_2$ |
| (IBXdh) | i-$C_3H_7$ | =N—$CH_2$—$C_6H_5$ |

Table 27, examples of erythro/threo mixtures (ratios 70:30 to 30:70):

Examples are the compounds of the respective formulae (IBXaa) to (IBXah), (IBXba) to (IBXbh), (IBXca) to (IBXch) and (IBXda) to (IBXdh), in each case in the form of a racemic erythro/threo mixture (ratio 70:30 to 30:70), where the meanings of $(R^1)_m$ and $(R^2)_n$ are defined according to a row number of Table 25. Individual compounds are numbered "(formula) (row number)", without any brackets.

Tables 27a to 27f: Compounds of the formulae (threo-IBX), (threo-1-IBX) and (threo-2-IBX), where $(R^1)_m$ and $(R^2)_n$ are each as defined in Table 25:

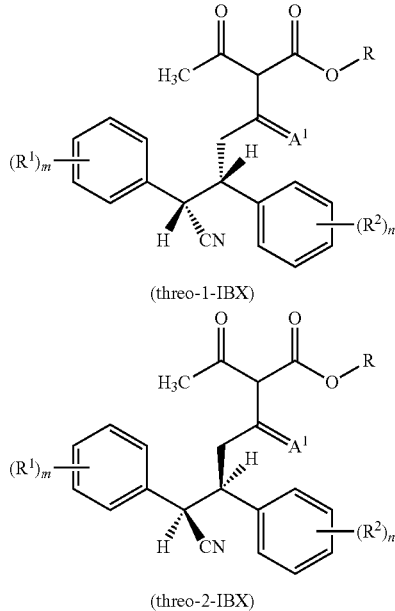

(threo-1-IBX)

(threo-2-IBX)

(threo-IBX) = (threo-1-IBX) + (threo-2-IBX) (50:50) = (rac.)

Definition of the subformulae for formulae threo-(IBX), threo-1-(IBX) and threo-2-(IBX) with fixed radicals R and $A^1$:

| Subformula | R | $A^1$ | Stereochemistry |
|---|---|---|---|
| threo-(IBXa) | $CH_3$ | $A^1$ | (2S,3S)/(2R,3R), racemic |
| threo-1-(IBXa) | $CH_3$ | $A^1$ | (2S,3S), optically active |
| threo-2-(IBXa) | $CH_3$ | $A^1$ | (2R,3R), optically active |
| threo-(IBXaa) | $CH_3$ | O | (2S,3S)/(2R,3R), racemic |
| threo-1-(IBXaa) | $CH_3$ | O | (2S,3S), optically active |
| threo-2-(IBXaa) | $CH_3$ | O | (2R,3R), optically active |
| threo-(IBXb) | $C_2H_5$ | $A^1$ | (2S,3S)/(2R,3R), racemic |
| threo-1-(IBXb) | $C_2H_5$ | $A^1$ | (2S,3S), optically active |
| threo-2-(IBXb) | $C_2H_5$ | $A^1$ | (2R,3R), optically active |
| threo-(IBXba) | $C_2H_5$ | O | (2S,3S)/(2R,3R), racemic |
| threo-1-(IBXba) | $C_2H_5$ | O | (2S,3S), optically active |
| threo-2-(IBXba) | $C_2H_5$ | O | (2R,3R), optically active |
| threo-(IBXc) | n-$C_3H_7$ | $A^1$ | (2S,3S)/(2R,3R), racemic |
| threo-1-(IBXc) | n-$C_3H_7$ | $A^1$ | (2S,3S), optically active |
| threo-2-(IBXc) | n-$C_3H_7$ | $A^1$ | (2R,3R), optically active |
| threo-(IBXca) | n-$C_3H_7$ | O | (2S,3S)/(2R,3R), racemic |
| threo-1-(IBXca) | n-$C_3H_7$ | O | (2S,3S), optically active |
| threo-2-(IBXca) | n-$C_3H_7$ | O | (2R,3R), optically active |
| threo-(IBXd) | i-$C_3H_7$ | $A^1$ | (2S,3S)/(2R,3R), racemic |
| threo-1-(IBXd) | i-$C_3H_7$ | $A^1$ | (2S,3S), optically active |
| threo-2-(IBXd) | i-$C_3H_7$ | $A^1$ | (2R,3R), optically active |
| threo-(IBXda) | i-$C_3H_7$ | O | (2S,3S)/(2R,3R), racemic |
| threo-1-(IBXda) | i-$C_3H_7$ | O | (2S,3S), optically active |
| threo-2-(IBXda) | i-$C_3H_7$ | O | (2R,3R), optically active |

Table 27a (threo racemates), examples:

Compounds of the formulae threo-(IBXaa), threo-(IBXba), threo-(IBXca) and threo-(IBXda), in each case in the form of the racemic mixture of the threo isomers, where the structural combination of groups $(R^1)_m$ and $(R^2)_n$ is defined according to a row number of Table 25.

Individual compounds are numbered "threo-IBXaa(row number)", "threo-IBXba(row number)", "threo-IBXca(row number)" and "threo-IBXda(row number)".

Table 27b (optically active threo-2 compounds), examples:

Compounds of the formulae threo-2-(IBXaa), threo-2-(IBXba), threo-2-(IBXca) and threo-2-(IBXda), in each case in stereochemically enriched form [=(2R,3R) form of more than 90% ee], where the structural combination of groups $(R^1)_m$ and $(R^2)_n$ is defined according to a row number of Table 25.

Individual compounds are numbered "threo-2-IBXaa(row number)", "threo-2-IBXba(row number)", "threo-2-IBXca(row number)" and "threo-2-IBXda(row number)".

Table 27c (optically active threo-1 enantiomers), examples:

Optically active enantiomeric compounds of the formulae threo-1-(IBXaa), threo-1-(IBXba), threo-1-(IBXca) and threo-1-(IBXda), in each case in stereochemically enriched form [=(2S,3S) form of more than 90% ee], where the structural combination of groups $(R^1)_m$ and $(R^2)_n$ is defined according to a row number of Table 25. Individual compounds are numbered "threo-1-IBXaa(row number)", "threo-1-IBXba(row number)", "threo-1-IBXca(row number)" and "threo-1-IBXda(row number)".

Table 27d (erythro racemates), examples:

Compounds of the formulae erythro-(IBXaa), erythro-(IBXba), erythro-(IBXca) and erythro-(IBXda), in each case in the form of the racemic mixture of the threo isomers, where the structural combination of groups $(R^1)_m$ and $(R^2)_n$ is defined according to a row number of Table 25. Individual compounds are numbered "erythro-IBXaa(row number)", "erythro-IBXba(row number)", "erythro-IBXca(row number)" and "erythro-IBXda(row number)".

Table 27e (erythro-1 enantiomers), examples:

Optically active enantiomeric compounds of the formulae erythro-1-(IBXaa), erythro-1-(IBXba), erythro-1-(IBXca) and erythro-1-(IBXda), in each case in stereochemically enriched form [=(2R,3S) form of more than 90% ee], where the structural combination of groups $(R^1)_m$ and $(R^2)_n$ is defined according to a row number of Table 25. Individual compounds are numbered "erythro-1-IBXaa(row number)", "erythro-1-IBXba(row number)", "erythro-1-IBXca(row number)" and "erythro-1-IBXda(row number)".

Table 27f (erythro-2 enantiomers), examples:

Optically active enantiomeric compounds of the formulae erythro-2-(IBXaa), erythro-2-(IBXba), erythro-2-(IBXca) and erythro-2-(IBXda), in each case in stereochemically enriched form [=(2S,3R) form of more than 90% ee], where the structural combination of groups $(R^1)_m$ and $(R^2)_n$ is defined according to a row number of Table 25. Individual compounds are numbered "erythro-2-IBXaa(row number)", "erythro-2-IBXba(row number)", "erythro-2-IBXca(row number)" and "erythro-2-IBXda(row number)".

TABLE 28

Compounds of the formula (IB9), where $(R^1)_m$ and $(R^2)_n$ are each as defined in Table 25:

Definition of the subformulae for formula (IB9) with fixed radicals R and $A^1$:

| Subformula for (IB9) | R | $A^1$ |
|---|---|---|
| (IB9a) | $CH_3$ | $A^1$ |
| (IB9aa) | $CH_3$ | O |
| (IB9ab) | $CH_3$ | S |
| (IB9ac) | $CH_3$ | =N—$CH_3$ |
| (IB9ad) | $CH_3$ | =N—OH |
| (IB9ae) | $CH_3$ | =N—$OCH_3$ |
| (IB9af) | $CH_3$ | =N—$NH_2$ |
| (IB9ag) | $CH_3$ | =N—$N(CH_3)_2$ |
| (IB9ah) | $CH_3$ | =N—$CH_2$—$C_6H_5$ |
| (IB9b) | $C_2H_5$ | $A^1$ |
| (IB9ba) | $C_2H_5$ | O |
| (IB9bb) | $C_2H_5$ | S |
| (IB9bc) | $C_2H_5$ | =N—$CH_3$ |
| (IB9bd) | $C_2H_5$ | =N—OH |
| (IB9be) | $C_2H_5$ | =N—$OCH_3$ |
| (IB9bf) | $C_2H_5$ | =N—$NH_2$ |
| (IB9bg) | $C_2H_5$ | =N—$N(CH_3)_2$ |
| (IB9bh) | $C_2H_5$ | =N—$CH_2$—$C_6H_5$ |
| (IB9c) | n-$C_3H_7$ | $A^1$ |
| (IB9ca) | n-$C_3H_7$ | O |
| (IB9cb) | n-$C_3H_7$ | S |
| (IB9cc) | n-$C_3H_7$ | =N—$CH_3$ |
| (IB9cd) | n-$C_3H_7$ | =N—OH |
| (IB9ce) | n-$C_3H_7$ | =N—$OCH_3$ |
| (IB9cf) | n-$C_3H_7$ | =N—$NH_2$ |
| (IB9cg) | n-$C_3H_7$ | =N—$N(CH_3)_2$ |
| (IB9ch) | n-$C_3H_7$ | =N—$CH_2$—$C_6H_5$ |
| (IB9d) | i-$C_3H_7$ | $A^1$ |
| (IB9da) | i-$C_3H_7$ | O |
| (IB9db) | i-$C_3H_7$ | S |
| (IB9dc) | i-$C_3H_7$ | =N—$CH_3$ |
| (IB9dd) | i-$C_3H_7$ | =N—OH |
| (IB9de) | i-$C_3H_7$ | =N—$OCH_3$ |
| (IB9df) | i-$C_3H_7$ | =N—$NH_2$ |
| (IB9dg) | i-$C_3H_7$ | =N—$N(CH_3)_2$ |
| (IB9dh) | i-$C_3H_7$ | =N—$CH_2$—$C_6H_5$ |

Table 27, examples of erythro/threo mixtures (ratios 70:30 to 30:70):

Examples are the compounds of the respective formulae (IB9aa) to (IB9ah), (IB9ba) to (IB9bh), (IB9ca) to (IB9ch) and (IB9da) to (IB9dh), in each case in the form of a racemic erythro/threo mixture (ratio 70:30 to 30:70), where the meanings of $(R^1)_m$ and $(R^2)_n$ are defined according to a row number of Table 25. Individual compounds are numbered "(formula) (row number)", without any brackets.

Tables 28a to 28f: Compounds of the formulae (threo-IB9), (threo-1-IB9) and (threo-2-IB9), where $(R^1)_m$ and $(R^2)_n$ are each as defined in Table 25:

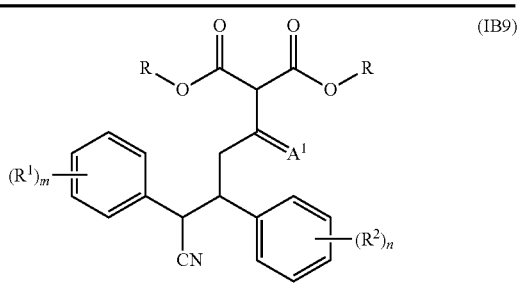

(threo-1-IB9)

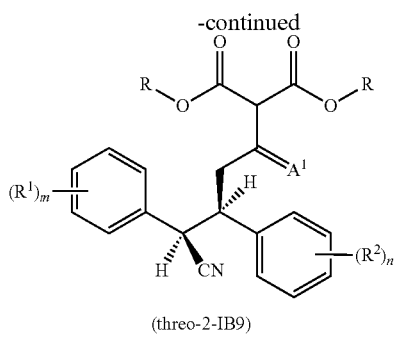

(threo-2-IB9)

(threo-IB9) = (threo-1-IB9) + (threo-2-IB9) (50:50) = (rac.)

Definition of the subformulae for formulae threo-(IB9), threo-1-(IB9) and threo-2-(IB9) with fixed radicals R and $A^1$:

| Subformula | R | $A^1$ | Stereochemistry |
|---|---|---|---|
| threo-(IB9a) | $CH_3$ | $A^1$ | (2S,3S)/(2R,3R), racemic |
| threo-1-(IB9a) | $CH_3$ | $A^1$ | (2S,3S), optically active |
| threo-2-(IB9a) | $CH_3$ | $A^1$ | (2R,3R), optically active |
| threo-(IB9aa) | $CH_3$ | O | (2S,3S)/(2R,3R), racemic |
| threo-1-(IB9aa) | $CH_3$ | O | (2S,3S), optically active |
| threo-2-(IB9aa) | $CH_3$ | O | (2R,3R), optically active |
| threo-(IB9b) | $C_2H_5$ | $A^1$ | (2S,3S)/(2R,3R), racemic |
| threo-1-(IB9b) | $C_2H_5$ | $A^1$ | (2S,3S), optically active |
| threo-2-(IB9b) | $C_2H_5$ | $A^1$ | (2R,3R), optically active |
| threo-(IB9ba) | $C_2H_5$ | O | (2S,3S)/(2R,3R), racemic |
| threo-1-(IB9ba) | $C_2H_5$ | O | (2S,3S), optically active |
| threo-2-(IB9ba) | $C_2H_5$ | O | (2R,3R), optically active |
| threo-(IB9c) | $n-C_3H_7$ | $A^1$ | (2S,3S)/(2R,3R), racemic |
| threo-1-(IB9c) | $n-C_3H_7$ | $A^1$ | (2S,3S), optically active |
| threo-2-(IB9c) | $n-C_3H_7$ | $A^1$ | (2R,3R), optically active |
| threo-(IB9ca) | $n-C_3H_7$ | O | (2S,3S)/(2R,3R), racemic |
| threo-1-(IB9ca) | $n-C_3H_7$ | O | (2S,3S), optically active |
| threo-2-(IB9ca) | $n-C_3H_7$ | O | (2R,3R), optically active |
| threo-(IB9d) | $i-C_3H_7$ | $A^1$ | (2S,3S)/(2R,3R), racemic |
| threo-1-(IB9d) | $i-C_3H_7$ | $A^1$ | (2S,3S), optically active |
| threo-2-(IB9d) | $i-C_3H_7$ | $A^1$ | (2R,3R), optically active |
| threo-(IB9da) | $i-C_3H_7$ | O | (2S,3S)/(2R,3R), racemic |
| threo-1-(IB9da) | $i-C_3H_7$ | O | (2S,3S), optically active |
| threo-2-(IB9da) | $i-C_3H_7$ | O | (2R,3R), optically active |

Table 28a (threo racemates), examples:

Compounds of the formulae threo-(IB9aa), threo-(IB9ba), threo-(IB9ca) and threo-(IB9da), in each case in the form of the racemic mixture of the threo isomers, where the structural combination of groups $(R^1)_m$ and $(R^2)_n$ is defined according to a row number of Table 25. Individual compounds are numbered "threo-IB9aa(row number)", "threo-IB9ba(row number)", "threo-IB9ca(row number)" and "threo-IB9da (row number)".

Table 28b (optically active threo-2 compounds), examples:

Compounds of the formulae threo-2-(IB9aa), threo-2-(IB9ba), threo-2-(IB9ca) and threo-2-(IB9da), in each case in stereochemically enriched form [=(2R,3R) form of more than 90% ee], where the structural combination of groups $(R^1)_m$ and $(R^2)_n$ is defined according to a row number of Table 25. Individual compounds are numbered "threo-2-IB9aa(row number)", "threo-2-IB9ba(row number)", "threo-2-IB9ca (row number)" and "threo-2-IB9da(row number)".

Table 28c (optically active threo-1 enantiomers), examples:

Optically active enantiomeric compounds of the formulae threo-1-(IB9aa), threo-1-(IB9ba), threo-1-(IB9ca) and threo-1-(IB9da), in each case in stereochemically enriched form [=(2S,3S) form of more than 90% ee], where the structural combination of groups $(R^1)_m$ and $(R^2)_n$ is defined according to a row number of Table 25. Individual compounds are numbered "threo-1-IB9aa(row number)", "threo-1-IB9ba (row number)", "threo-1-IB9ca(row number)" and "threo-1-IB9da(row number)".

Table 28d (erythro racemates), examples:

Compounds of the formulae erythro-(IB9aa), erythro-(IB9ba), erythro-(IB9ca) and erythro-(IB9da), in each case in the form of the racemic mixture of the threo isomers, where the structural combination of groups $(R^1)_m$ and $(R^2)_n$ is defined according to a row number of Table 25. Individual compounds are numbered "erythro-IB9aa(row number)", "erythro-IB9ba(row number)", "erythro-IB9ca(row number)" and "erythro-IB9da(row number)".

Table 28e (erythro-1 enantiomers), examples:

Optically active enantiomeric compounds of the formulae of individual compounds erythro-1-(IB9aa), erythro-1-(IB9ba), erythro-1-(IB9ca) and erythro-1-(IB9da), in each case in stereochemically enriched form [=(2R,3S) form of more than 90% ee], where the structural combination of groups $(R^1)_m$ and $(R^2)_n$ is defined according to a row number of Table 25. Individual compounds are numbered "erythro-1-IB9aa(row number)", "erythro-1-IB9ba(row number)", "erythro-1-IB9ca(row number)" and "erythro-1-IB9da(row number)".

Table 28f (erythro-2 enantiomers), examples:

Optically active enantiomeric compounds of the formulae erythro-2-(IB9aa), erythro-2-(IB9ba), erythro-2-(IB9ca) and erythro-2-(IB9da), in each case in stereochemically enriched form [=(2S,3R) form of more than 90% ee], where the structural combination of groups $(R^1)_m$ and $(R^2)_n$ is defined according to a row number of Table 25. Individual compounds are numbered "erythro-2-IB9aa(row number)", "erythro-2-IB9ba(row number)", "erythro-2-IB9ca(row number)" and "erythro-2-IB9da(row number)".

TABLE 29

Compounds of the formulae (IB10a), (IB10aa), (IB10ab), (IB10ac), (IB10ad), (IB10ae), (IB10af), (IB10ag) and (IB10ah), where $(R^1)_m$ and $(R^2)_n$ are each as defined in Table 25:

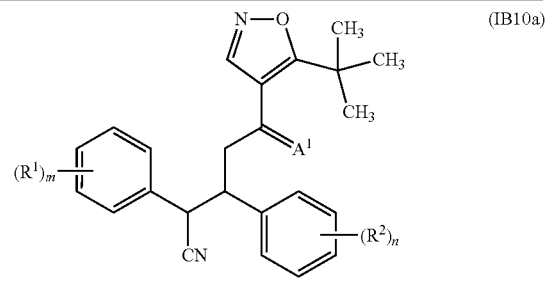

(IB10aa) $A^1$ is (=O)
(IB10ab) $A^1$ is (=S)
(IB10ac) $A^1$ is (=N—$CH_3$)
(IB10ad) $A^1$ is (=N—OH)
(IB10ae) $A^1$ is (=N—$OCH_3$)
(IB10af) $A^1$ is (=N—$NH_2$)
(IB10ag) $A^1$ is [=N—$N(CH_3)_2$]
(IB10ah) $A^1$ is (=N-benzyl)

Table 29, examples of erythro/threo mixtures (ratios 70:30 to 30:70):

Examples are the compounds of the respective formulae (IB10aa) to (IB10ah), in each case in the form of a racemic erythro/threo mixture (ratio 70:30 to 30:70), where the meanings of $(R^1)_m$ and $(R^2)_n$ are defined according to a row number of Table 25. Individual compounds are numbered "(formula) (row number)", without any brackets.

Tables 29a to 29f: Compounds of the formulae (threo-IB10aa) and (threo-2-IB10aa), where $(R^1)_m$ and $(R^2)_n$ are each as defined in Table 25:

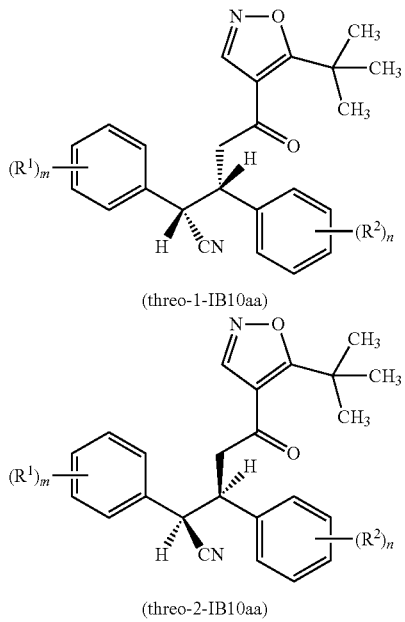

(threo-1-IB10aa)

(threo-2-IB10aa)

(threo-IB10aa) = (threo-1-IB10aa) + (threo-2-IB10aa) (50:50) = (rac.)

Table 29a (threo racemates), examples:

Compounds of the formula (IB10aa) in the form of the racemic mixture of the threo isomers [=formula (threo-IB10aa)], where the structural combination of groups Q, $(R^1)_m$ and $(R^2)_n$ is defined according to a row number of Table 25.

Individual compounds are numbered "threo-IB10aa(row number)".

Table 29b (optically active threo-2 compounds), examples:

Optically active threo-2 enantiomers in enriched form [=(2R,3R) form of more than 90% ee] having the chemical structure of the formula (threo-2-IB10aa), where the structural combination of groups Q, $(R^1)_m$ and $(R^2)_n$ is defined according to a row number of Table 25. Individual compounds are numbered "threo-2-IB10aa(row number)".

Table 29c (optically active threo-1 enantiomers), examples:

Optically active threo-1 enantiomers in enriched form [=(2S,3S) form of more than 90% ee] having the chemical structure of the formula (threo-1-IB10aa), where the structural combination of groups Q, $(R^1)_m$ and $(R^2)_n$ is defined according to a row number of Table 25. Individual compounds are numbered "threo-1-IB10aa(row number)".

Table 29d (erythro racemates), examples:

Compounds of the formula (IB10aa) in the form of the racemic mixture of the erythro isomers [=formula (erythro-IB10aa)], where the structural combination of groups Q, $(R^1)_m$ and $(R^2)_n$ is defined according to a row number of Table 25. Individual compounds are numbered "erythro-IB10aa (row number)".

Table 29e (erythro-1 enantiomers), examples:

Optically active erythro-1 enantiomers in enriched form [=(2R,3S) form of more than 90% ee] having the chemical structure of the formula (IB10aa) in the erythro-1 form [=formula (erythro-1-IB10aa)], where the structural combination of groups Q, $(R^1)_m$ and $(R^2)_n$ is defined according to a row number of Table 25. Individual compounds are numbered "erythro-1-IB10aa(row number)".

Table 29f (erythro-2 enantiomers), examples:

Optically active erythro-2 enantiomers in enriched form [=(2S,3R) form of more than 90% ee] having the chemical structure of the formula (IB10aa) in the erythro-2 form [=formula (erythro-2-IB10aa)], where the structural combination of groups Q, $(R^1)_m$ and $(R^2)_n$ is defined according to a row number of Table 25.

The numeration is "erythro-2-IB10aa(row number)".

TABLE 30

Compounds of the formulae (IB10b), (IB10ba), (IB10bb), (IB10bc), (IB10bd), (IB10be), (IB10bf), (IB10bg) and (IB10bh), where $(R^1)_m$ and $(R^2)_n$ are each as defined in Table 25

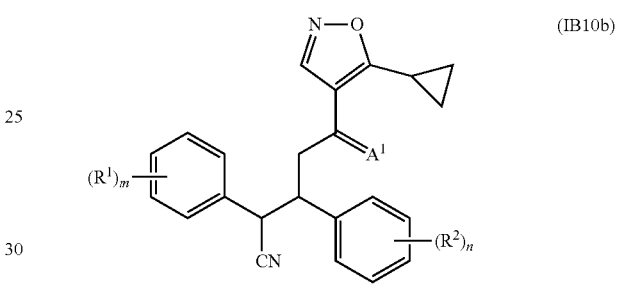

(IB10ba) $A^1$ is (=O)
(IB10bb) $A^1$ is (=S)
(IB10bc) $A^1$ is (=N—CH$_3$)
(IB10bd) $A^1$ is (=N—OH)
(IB10be) $A^1$ is (=N—OCH$_3$)
(IB10bf) $A^1$ is (=N—NH$_2$)
(IB10bg) $A^1$ is [=N—N(CH$_3$)$_2$]
(IB10bh) $A^1$ is (=N-benzyl)

Table 30, examples of erythro/threo mixtures (ratios 70:30 to 30:70):

Examples are the compounds of the respective formulae (IB10ba) to (IB10bh), in each case in the form of a racemic erythro/threo mixture (ratio 70:30 to 30:70), where the meanings of $(R^1)_m$ and $(R^2)_n$ are defined according to a row number of Table 25. Individual compounds are numbered "(formula) (row number)", without any brackets.

Tables 30a to 30f: Compounds of the formulae (threo-IB10ba) and (threo-2-IB10ba), where $(R^1)_m$ and $(R^2)_n$ are each as defined in Table 25:

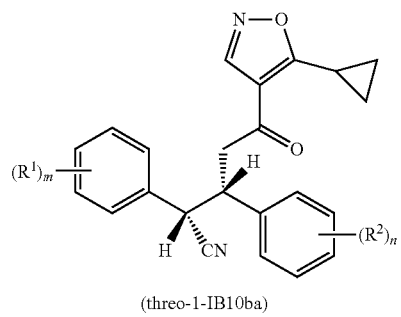

(threo-1-IB10ba)

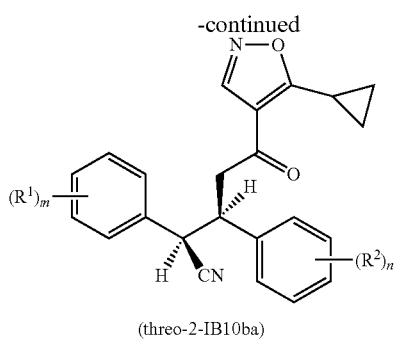

(threo-2-IB10ba)
(threo-IB10ba) = (threo-1-IB10ba) + (threo-2-IB10ba) (50:50) = (rac.)

Table 30a (threo racemates), examples:

Compounds of the formula (IB10ba) in the form of the racemic mixture of the threo isomers [=formula (threo-IB10ba)], where the structural combination of groups Q, $(R^1)_m$ and $(R^2)_n$ is defined according to a row number of Table 25. Individual compounds are numbered "threo-IB10ba(row number)".

Table 30b (optically active threo-2 compounds), examples:

Optically active threo-2 enantiomers in enriched form [=(2R,3R) form of more than 90% ee] having the chemical structure of the formula (threo-2-IB10ba), where the structural combination of groups Q, $(R^1)_m$ and $(R^2)_n$ is defined according to a row number of Table 25. Individual compounds are numbered "threo-2-IB10ba(row number)".

Table 30c (optically active threo-1 enantiomers), examples:

Optically active threo-1 enantiomers in enriched form [=(2S,3S) form of more than 90% ee] having the chemical structure of the formula (threo-1-IB10ba), where the structural combination of groups Q, $(R^1)_m$ and $(R^2)_n$ is defined according to a row number of Table 25. Individual compounds are numbered "threo-1-IB10ba(row number)".

Table 30d (erythro racemates), examples:

Compounds of the formula (IB10ba) in the form of the racemic mixture of the erythro isomers [=formula (erythro-IB10ba)], where the structural combination of groups Q, $(R^1)_m$ and $(R^2)_n$ is defined according to a row number of Table 25. Individual compounds are numbered "erythro-IB10ba (row number)".

Table 30e (erythro-1 enantiomers), examples:

Optically active erythro-1 enantiomers in enriched form [=(2R,3S) form of more than 90% ee] having the chemical structure of the formula (IB10ba) in the erythro-1 form [=formula (erythro-1-IB10ba)], where the structural combination of groups Q, $(R^1)_m$ and $(R^2)_n$ is defined according to a row number of Table 25. Individual compounds are numbered "erythro-1-IB10ba(row number)".

Table 30f (erythro-2 enantiomers), examples:

Optically active erythro-2 enantiomers in enriched form [=(2S,3R) form of more than 90% ee] having the chemical structure of the formula (IB10ba) in the erythro-2 form [=formula (erythro-2-IB10ba)], where the structural combination of groups Q, $(R^1)_m$ and $(R^2)_n$ is defined according to a row number of Table 25. Individual compounds are numbered "erythro-2-IB10ba(row number)".

TABLE 31

Compounds of the formulae (IB10c), (IB10ca), (IB10cb), (IB10cc), (IB10cd), (IB10ce), (IB10cf), (IB10cg) and (IB10ch), where $(R^1)_m$ and $(R^2)_n$ are each as defined in Table 25:

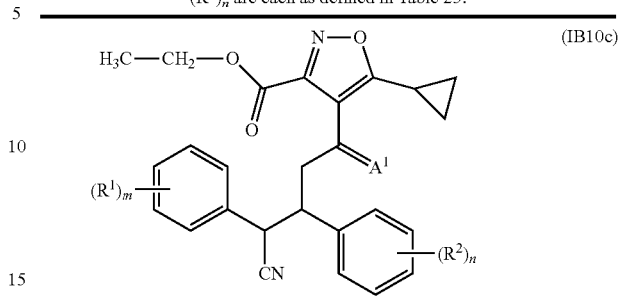

(IB10c)

(IB10ca) $A^1$ is (=O)
(IB10cb) $A^1$ is (=S)
(IB10cc) $A^1$ is (=N—CH$_3$)
(IB10cd) $A^1$ is (=N—OH)
(IB10ce) $A^1$ is (=N—OCH$_3$)
(IB10cf) $A^1$ is (=N—NH$_2$)
(IB10cg) $A^1$ is [=N—N(CH$_3$)$_2$]
(IB10ch) $A^1$ is (=N-benzyl)

Table 31, examples of erythro/threo mixtures (ratios 70:30 to 30:70):

Examples are the compounds of the respective formulae (IB10ca) to (IB10ch), in each case in the form of a racemic erythro/threo mixture (ratio 70:30 to 30:70), where the meanings of $(R^1)_m$ and $(R^2)_n$ are defined according to a row number of Table 25. Individual compounds are numbered "(formula) (row number)", without any brackets.

Tables 31a to 31f: Compounds of the formulae (threo-IB10ca) and (threo-2-IB10ca), where $(R^1)_m$ and $(R^2)_n$ are each as defined in Table 25:

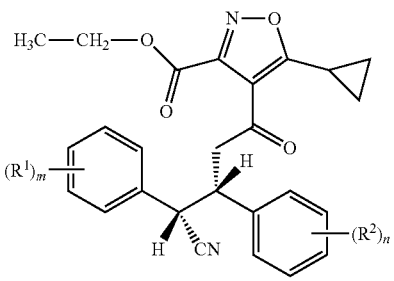

(threo-1-IB10ca)

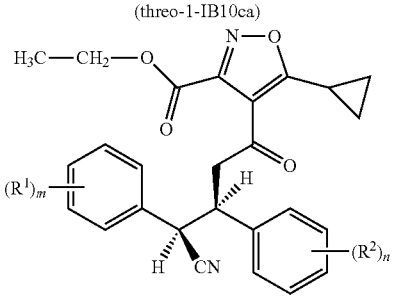

(threo-2-IB10ca)
(threo-IB10ca) = (threo-1-IB10ca) + (threo-2-IB10ca) (50:50) = (rac.)

Table 31a (threo racemates), examples:

Compounds of the formula (IB10ca) in the form of the racemic mixture of the threo isomers [=formula (threo-IB10ca)], where the structural combination of groups Q, $(R^1)_m$ and $(R^2)_n$ is defined according to a row number of Table 25. Individual compounds are numbered "threo-IB10ca(row number)".

Table 31b (optically active threo-2 compounds), examples:

Optically active threo-2 enantiomers in enriched form [=(2R,3R) form of more than 90% ee] having the chemical structure of the formula (threo-2-IB10ca), where the structural combination of groups Q, $(R^1)_m$ and $(R^2)_n$ is defined according to a row number of Table 25. Individual compounds are numbered "threo-2-IB10ca(row number)".

Table 31c (optically active threo-1 enantiomers), examples:

Optically active threo-1 enantiomers in enriched form [=(2S,3S) form of more than 90% ee] having the chemical structure of the formula (threo-1-IB10ca), where the structural combination of groups Q, $(R^1)_m$ and $(R^2)_n$ is defined according to a row number of Table 25. Individual compounds are numbered "threo-1-IB10ca(row number)".

Table 31d (erythro racemates), examples:

Compounds of the formula (IB10ca) in the form of the racemic mixture of the erythro isomers [=formula (erythro-IB10ca)], where the structural combination of groups Q, $(R^1)_m$ and $(R^2)_n$ is defined according to a row number of Table 25. Individual compounds are numbered "erythro-IB10ca (row number)".

Table 31e (erythro-1 enantiomers), examples:

Optically active erythro-1 enantiomers in enriched form [=(2R,3S) form of more than 90% ee] having the chemical structure of the formula (IB10ca) in the erythro-1 form [=formula (erythro-1-IB10ca)], where the structural combination of groups Q, $(R^1)_m$ and $(R^2)_n$ is defined according to a row number of Table 25. Individual compounds are numbered "erythro-1-IB10ca(row number)".

Table 31f (erythro-2 enantiomers), examples:

Optically active erythro-2 enantiomers in enriched form [=(2S,3R) form of more than 90% ee] having the chemical structure of the formula (IB10ca) in the erythro-2 form [=formula (erythro-2-IB10ca)], where the structural combination of groups Q, $(R^1)_m$ and $(R^2)_n$ is defined according to a row number of Table 25. Individual compounds are numbered "erythro-2-IB10ca(row number)".

TABLE 32

Compounds of the formulae (IB10d), (IB10da), (IB10db), (IB10dc), (IB10dd), (IB10de), (IB10df), (IB10dg) and (IB10dh), where $(R^1)_m$ and $(R^2)_n$ are each as defined in Table 25:

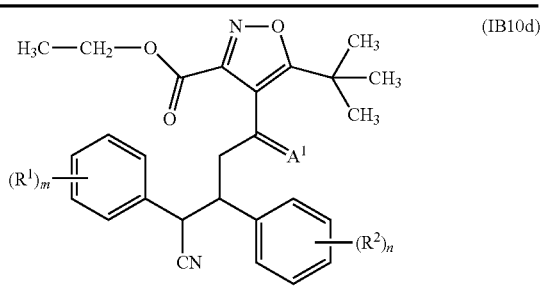

(IB10da) $A^1$ is (=O)
(IB10db) $A^1$ is (=S)
(IB10dc) $A^1$ is (=N—CH$_3$)
(IB10dd) $A^1$ is (=N—OH)
(IB10de) $A^1$ is (=N—OCH$_3$)
(IB10df) $A^1$ is (=N—NH$_2$)
(IB10dg) $A^1$ is [=N—N(CH$_3$)$_2$]
(IB10dh) $A^1$ is (=N-benzyl)

Table 32, examples of erythro/threo mixtures (ratios 70:30 to 30:70):

Examples are the compounds of the respective formulae (IB10da) to (IB10dh), in each case in the form of a racemic erythro/threo mixture (ratio 70:30 to 30:70), where the meanings of $(R^1)_m$ and $(R^2)_n$ are defined according to a row number of Table 25. Individual compounds are numbered "(formula)(row number)", without any brackets.

Tables 32a to 32f: Compounds of the formulae (threo-IB10da) and (threo-2-IB10da), where $(R^1)_m$ and $(R^2)_n$ are each as defined in Table 25:

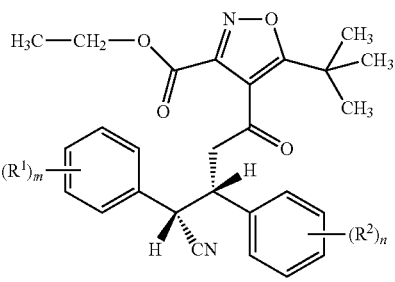

(threo-1-IB10da)

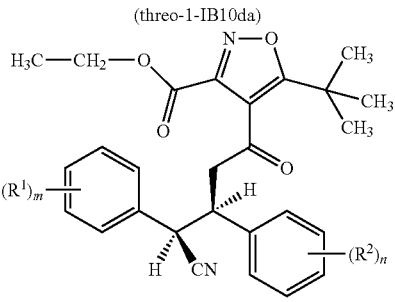

(threo-2-IB10da)
(threo-IB10da) = (threo-1-IB10da) + (threo-2-IB10da) (50:50) = (rac.)

Table 32a (threo racemates), examples:

Compounds of the formula (IB10da) in the form of the racemic mixture of the threo isomers [=formula (threo-IB10da)], where the structural combination of groups Q, $(R^1)_m$ and $(R^2)_n$ is defined according to a row number of Table 25. Individual compounds are numbered "threo-IB10da(row number)".

Table 32b (optically active threo-2 compounds), examples:

Optically active threo-2 enantiomers in enriched form [=(2R,3R) form of more than 90% ee] having the chemical structure of the formula (threo-2-IB10da), where the structural combination of groups Q, $(R^1)_m$ and $(R^2)_n$ is defined according to a row number of Table 25. Individual compounds are numbered "threo-2-IB10da(row number)".

Table 32c (optically active threo-1 enantiomers), examples:

Optically active threo-1 enantiomers in enriched form [=(2S,3S) form of more than 90% ee] having the chemical structure of the formula (threo-1-IB10da), where the structural combination of groups Q, $(R^1)_m$ and $(R^2)_n$ is defined according to a row number of Table 25. Individual compounds are numbered "threo-1-IB10da(row number)".

Table 32d (erythro racemates), examples:

Compounds of the formula (IB10da) in the form of the racemic mixture of the erythro isomers [=formula (erythro-IB10da)], where the structural combination of groups Q, $(R^1)_m$ and $(R^2)_n$ is defined according to a row number of Table 25. Individual compounds are numbered "erythro-IB10da (row number)".

Table 32e (erythro-1 enantiomers), examples:

Optically active erythro-1 enantiomers in enriched form [=(2R,3S) form of more than 90% ee] having the chemical structure of the formula (IB10da) in the erythro-1 form [=formula (erythro-1-IB10da)], where the structural combination of groups Q, $(R^1)_m$ and $(R^2)_n$ is defined according to a row number of Table 25. Individual compounds are numbered "erythro-1-IB10da(row number)".

Table 32f (erythro-2 enantiomers), examples:

Optically active erythro-2 enantiomers in enriched form [=(2S,3R) form of more than 90% ee] having the chemical structure of the formula (IB10da) in the erythro-2 form [=formula (erythro-2-IB10da)], where the structural combination of groups Q, $(R^1)_m$ and $(R^2)_n$ is defined according to a row number of Table 25. Individual compounds are numbered "erythro-2-IB10da(row number)".

TABLE 33

Compounds of the formulae (IB10e), (IB10ea), (IB10eb), (IB10ec), (IB10ed), (IB10ee), (IB10ef), (IB10eg) and (IB10eh), where $(R^1)_m$ and $(R^2)_n$ are each as defined in Table 25:

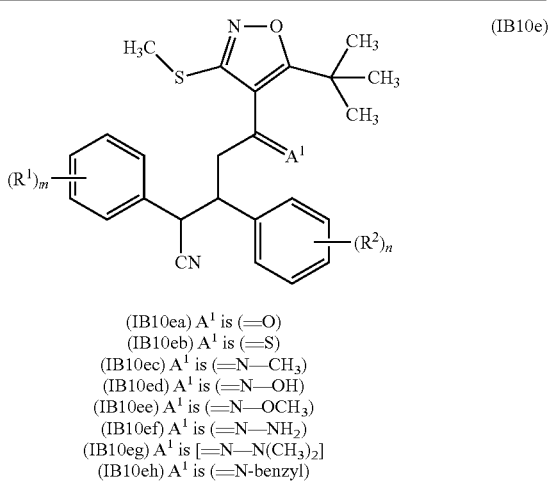

(IB10e)

(IB10ea) $A^1$ is (=O)
(IB10eb) $A^1$ is (=S)
(IB10ec) $A^1$ is (=N—CH$_3$)
(IB10ed) $A^1$ is (=N—OH)
(IB10ee) $A^1$ is (=N—OCH$_3$)
(IB10ef) $A^1$ is (=N—NH$_2$)
(IB10eg) $A^1$ is [=N—N(CH$_3$)$_2$]
(IB10eh) $A^1$ is (=N-benzyl)

Table 33, examples of erythro/threo mixtures (ratios 70:30 to 30:70):

Examples are the compounds of the respective formulae (IB10ea) to (IB10eh), in each case in the form of a racemic erythro/threo mixture (ratio 70:30 to 30:70), where the meanings of $(R^1)_m$ and $(R^2)_n$ are defined according to a row number of Table 25. Individual compounds are numbered "(formula) (row number)", without any brackets.

TABLE 34

Compounds of the formulae (IB10f), (IB10fa), (IB10fb), (IB10fc), (IB10fd), (IB10fe), (IB10ff), (IB10fg) and (IB10fh), where $(R^1)_m$ and $(R^2)_n$ are each as defined in Table 25:

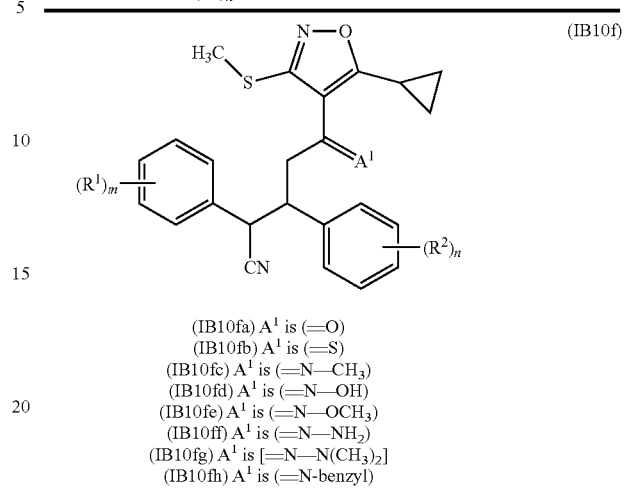

(IB10f)

(IB10fa) $A^1$ is (=O)
(IB10fb) $A^1$ is (=S)
(IB10fc) $A^1$ is (=N—CH$_3$)
(IB10fd) $A^1$ is (=N—OH)
(IB10fe) $A^1$ is (=N—OCH$_3$)
(IB10ff) $A^1$ is (=N—NH$_2$)
(IB10fg) $A^1$ is [=N—N(CH$_3$)$_2$]
(IB10fh) $A^1$ is (=N-benzyl)

Table 34, examples of erythro/threo mixtures (ratios 70:30 to 30:70):

Examples are the compounds of the respective formulae (IB10fa) to (IB10fh), in each case in the form of a racemic erythro/threo mixture (ratio 70:30 to 30:70), where the meanings of $(R^1)_m$ and $(R^2)_n$ are defined according to a row number of Table 25. Individual compounds are numbered "(formula) (row number)", without any brackets.

TABLE 35

Compounds of the formulae (IB10g), (IB10ga), (IB10gb), (IB10gc), (IB10gd), (IB10ge), (IB10gf), (IB10gg) and (IB10gh), where $(R^1)_m$ and $(R^2)_n$ are each as defined in Table 25:

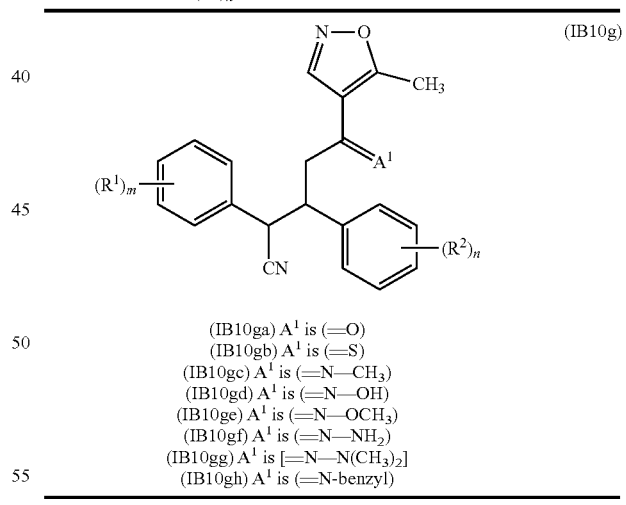

(IB10g)

(IB10ga) $A^1$ is (=O)
(IB10gb) $A^1$ is (=S)
(IB10gc) $A^1$ is (=N—CH$_3$)
(IB10gd) $A^1$ is (=N—OH)
(IB10ge) $A^1$ is (=N—OCH$_3$)
(IB10gf) $A^1$ is (=N—NH$_2$)
(IB10gg) $A^1$ is [=N—N(CH$_3$)$_2$]
(IB10gh) $A^1$ is (=N-benzyl)

Table 35, examples of erythro/threo mixtures (ratios 70:30 to 30:70):

Examples are the compounds of the respective formulae (IB10ga) to (IB10gh), in each case in the form of a racemic erythro/threo mixture (ratio 70:30 to 30:70), where the meanings of $(R^1)_m$ and $(R^2)_n$ are defined according to a row number of Table 25. Individual compounds are numbered "(formula) (row number)", without any brackets.

Tables 35a to 35f: Compounds of the formulae (threo-IB10ga) and (threo-2-IB10ga), where $(R^1)_m$ and $(R^2)_n$ are each as defined in Table 25:

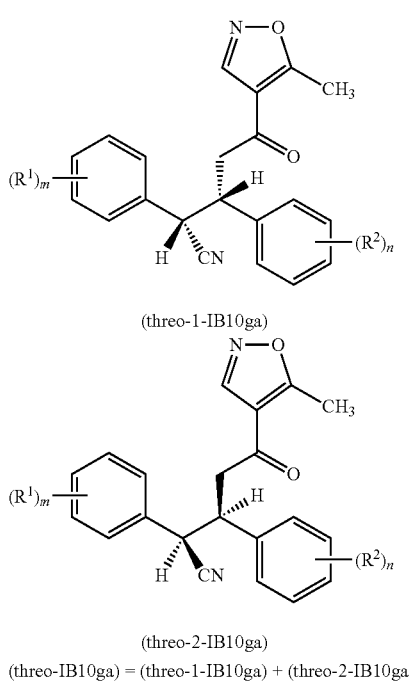

(threo-1-IB10ga)

(threo-2-IB10ga)

(threo-IB10ga) = (threo-1-IB10ga) + (threo-2-IB10ga) (50:50) = (rac.)

Table 35a (threo racemates), examples:

Compounds of the formula (IB10ga) in the form of the racemic mixture of the threo isomers [=formula (threo-IB10ga)], where the structural combination of groups Q, $(R^1)_m$ and $(R^2)_n$ is defined according to a row number of Table 25. Individual compounds are numbered "threo-IB10ga(row number)".

Table 35b (optically active threo-2 compounds), examples:

Optically active threo-2 enantiomers in enriched form [=(2R,3R) form of more than 90% ee] having the chemical structure of the formula (threo-2-IB10ga), where the structural combination of groups Q, $(R^1)_m$ and $(R^2)_n$ is defined according to a row number of Table 25. Individual compounds are numbered "threo-2-IB10ga(row number)".

Table 35c (optically active threo-1 enantiomers), examples:

Optically active threo-1 enantiomers in enriched form [=(2S,3S) form of more than 90% ee] having the chemical structure of the formula (threo-1-IB10ga), where the structural combination of groups Q, $(R^1)_m$ and $(R^2)_n$ is defined according to a row number of Table 25. Individual compounds are numbered "threo-1-IB10ga(row number)".

Table 35d (erythro racemates), examples:

Compounds of the formula (IB10ga) in the form of the racemic mixture of the erythro isomers [=formula (erythro-IB10ga)], where the structural combination of groups Q, $(R^1)_m$ and $(R^2)_n$ is defined according to a row number of Table 25. Individual compounds are numbered "erythro-IB10ga (row number)".

Table 35e (erythro-1 enantiomers), examples:

Optically active erythro-1 enantiomers in enriched form [=(2R,3S) form of more than 90% ee] having the chemical structure of the formula (IB10ga) in the erythro-1 form [=formula (erythro-1-IB10ga)], where the structural combination of groups Q, $(R^1)_m$ and $(R^2)_n$ is defined according to a row number of Table 25. Individual compounds are numbered "erythro-1-IB10ga(row number)".

Table 35f (erythro-2 enantiomers), examples:

Optically active erythro-2 enantiomers in enriched form [=(2S,3R) form of more than 90% ee] having the chemical structure of the formula (IB10ga) in the erythro-2 form [=formula (erythro-2-IB10ga)], where the structural combination of groups Q, $(R^1)_m$ and $(R^2)_n$ is defined according to a row number of Table 25. Individual compounds are numbered "erythro-2-IB10ga(row number)".

TABLE 36

Definitions of structural combinations of groups $B^2$, $(R^1)_m$ and $(R^2)_n$ for the tables of compounds of the general formula (I) according to the invention below

| Ex. | $B^2$ | $(R^1)_m$ | $(R^2)_n$ |
|---|---|---|---|
| 1 | O—C(O)Et | 3-F | 4-Cl |
| 2 | O—C(O)Et | 3-F | 3-F |
| 3 | O—C(O)—i-Pr | 3,4-$F_2$ | 4-Cl |
| 4 | O—C(O)Me | 3-F | 4-Br |
| 5 | NHOH | 3-Cl | 3-F |
| 6 | NHOH | 3,4-$F_2$ | 3-F |
| 7 | NHOH | H | 3-F |
| 8 | NHOMe | 4-F | 3-F |
| 9 | NHOMe | 3-F | 3-Cl |
| 10 | NHOH | 3,4-$F_2$ | 3-Cl |
| 11 | NHNMe$_2$ | 3-Br | 3-F |
| 12 | O—C(O)Me | 2,5-$F_2$ | 3-F |
| 13 | O—C(O)Me | 3-F | 2-F |
| 14 | O—C(O)Me | 3,4,5-$F_3$ | 4-Cl |
| 15 | OSO$_2$Me | 4-F | 3-Cl |
| 16 | OSO$_2$Me | 3,4-$F_2$ | 3-F, 4-Cl |
| 17 | O—C(O)Me | 3,4-$F_2$ | 2-F |
| 18 | O—C(O)Me | 3-F | 2,3-$F_2$ |
| 19 | SMe | 4-F | 3,5-$F_2$ |
| 20 | NHOH | 3-F | 4-F |
| 21 | NHOMe | 3,4-$F_2$ | 3-Cl, 5-F |
| 22 | OCH$_2$OMe | 3-F | 3-Cl, 5-F |
| 23 | OSO$_2$(4-Me—Ph) | 3-F | 2,5-$F_2$ |
| 24 | O—C(O)Me | 3,4-$F_2$ | 2,3-$F_2$ |
| 25 | O—C(O)Me | 3,4-$F_2$ | 2,5-$F_2$ |
| 26 | SMe | 3-Cl | 3-Cl, 5-F |
| 27 | OSO$_2$Me | 3-F, 4-Cl | 3-Cl |
| 28 | O—C(O)Et | 3,4-$F_2$ | 3-NO$_2$ |
| 29 | O—C(O)Me | 3,4-$F_2$ | H |
| 30 | NHOMe | 3-Cl, 4-F | 3-F |
| 31 | NHOH | 3,4-$F_2$ | 4-OMe |
| 32 | O—C(O)—t-Bu | 3-F | 4-Cl |
| 33 | O—C(O)Me | 3-F | 4-Cl |
| 34 | OCH$_2$OMe | 3-F | 4-Cl |
| 35 | SMe | 3-F | 4-Cl |
| 36 | OSO$_2$(4-Me—Ph) | 3-F | 4-Cl |
| 37 | Cl | 3-F | 4-Cl |
| 38 | OCO$_2$Me | 3-F | 4-Cl |
| 39 | NHOMe | 3-F | 4-Cl |
| 40 | NHOH | 3-F | 4-Cl |
| 41 | O—C(O)—t-Bu | 3-F | 3-F |
| 42 | O—C(O)Me | 3-F | 3-F |
| 43 | OCH$_2$Ph | 3-F | 3-F |
| 44 | SMe | 3-F | 3-F |
| 45 | OSO$_2$(4-Me—Ph) | 3-F | 3-F |
| 46 | Cl | 3-F | 3-F |
| 47 | OCO$_2$Me | 3-F | 3-F |
| 48 | O—C(O)—t-Bu | 3,4-$F_2$ | 3-F |
| 49 | O—C(O)Me | 3,4-$F_2$ | 3-F |
| 50 | O—C(O)Et | 3,4-$F_2$ | 3-F |
| 51 | OSO$_2$Me | 3,4-$F_2$ | 3-F |
| 52 | OCH$_2$OMe | 3,4-$F_2$ | 3-F |
| 53 | OSO$_2$(4-Me—Ph) | 3,4-$F_2$ | 3-F |
| 54 | Cl | 3,4-$F_2$ | 3-F |
| 55 | OCO$_2$Me | 3,4-$F_2$ | 3-F |
| 56 | NHOMe | 3,4-$F_2$ | 3-F |
| 57 | O—C(O)—t-Bu | 3,4-$F_2$ | 3-Cl |
| 58 | O—C(O)Me | 3,4-$F_2$ | 3-Cl |
| 59 | O—C(O)Et | 3,4-$F_2$ | 3-Cl |
| 60 | OCH$_2$OMe | 3,4-$F_2$ | 3-Cl |
| 61 | SMe | 3,4-$F_2$ | 3-Cl |
| 62 | OSO$_2$(4-Me—Ph) | 3,4-$F_2$ | 3-Cl |
| 63 | Cl | 3,4-$F_2$ | 3-Cl |

TABLE 36-continued

Definitions of structural combinations of groups $B^2$, $(R^1)_m$ and $(R^2)_n$ for the tables of compounds of the general formula (I) according to the invention below

| Ex. | $B^2$ | $(R^1)_m$ | $(R^2)_n$ |
|---|---|---|---|
| 64 | OCO$_2$Me | 3,4-F$_2$ | 3-Cl |
| 65 | NHOMe | 3,4-F$_2$ | 3-Cl |
| 66 | O—C(O)—t-Bu | 3-Br | 3-F |
| 67 | O—C(O)Me | 2,5-F$_2$ | 3-F |
| 68 | SPh | 3-F | 2-F |
| 69 | O—C(O)—t-Bu | 3,4,5-F$_3$ | 4-Cl |
| 70 | O—C(O)Me | 4-F | 3-Cl |
| 71 | SO$_2$Ph | 3,4-F$_2$ | 3-F, 4-Cl |
| 72 | O—C(O)—t-Bu | 3,4-F$_2$ | 2-F |
| 73 | O—C(O)Me | 3-F | 2,3-F$_2$ |
| 74 | NHNH$_2$ | 4-F | 3,5-F$_2$ |
| 75 | O—C(O)—t-Bu | 3-F | 4-F |
| 76 | O—C(O)Me | 3,4-F$_2$ | 3-Cl, 5-F |
| 77 | NHNHMe | 3-F | 3-Cl, 5-F |
| 78 | O—C(O)—t-Bu | 3-F | 2,5-F$_2$ |
| 79 | O—C(O)Me | 3,4-F$_2$ | 2,3-F$_2$ |
| 80 | SPh | 3,4-F$_2$ | 2,5-F$_2$ |
| 81 | O—C(O)—t-Bu | 3-Cl | 3-Cl, 5-F |
| 82 | O—C(O)Me | 3-F, 4-Cl | 3-Cl |
| 83 | NHOMe | 3,4-F$_2$ | 3-NO$_2$ |
| 84 | O—C(O)—t-Bu | 3,4-F$_2$ | H |
| 85 | O—C(O)Me | 3-Cl, 4-F | 3-F |
| 86 | SPh | 3,4-F$_2$ | 4-OMe |
| 87 | O—C(O)Et | 3-F | H |
| 88 | O—C(O)Et | 3-F | 2,4-F$_2$ |
| 89 | O—C(O)Et | 3-F | 2,6-F$_2$ |
| 90 | O—C(O)Et | 3-F | 3,4-F$_2$ |
| 91 | O—C(O)—i-Pr | 3-F | 3,5-F$_2$ |
| 92 | NHOMe | 3-F | 2-Cl |
| 93 | NHOH | 3-F | 2,3-Cl$_2$ |
| 94 | NHOH | 3-F | 2,4-Cl$_2$ |
| 95 | O—C(O)—t-Bu | 3-F | 2,5-Cl$_2$ |
| 96 | SMe | 3-F | 2,6-Cl$_2$ |
| 97 | NHOMe | 3-F | 3,4-Cl$_2$ |
| 98 | O—C(O)Et | 3-F | 3,5-Cl$_2$ |
| 99 | O—C(O)—t-Bu | 3,4-F$_2$ | 4-F |
| 100 | O—C(O)Me | 3,4-F$_2$ | 2,4-F$_2$ |
| 101 | O—O(O)—i-Pr | 3,4-F$_2$ | 2,6-F$_2$ |
| 102 | NHOMe | 3,4-F$_2$ | 3,4-F$_2$ |
| 103 | NHOH | 3,4-F$_2$ | 3,5-F$_2$ |
| 104 | SPh | 3,4-F$_2$ | 2-Cl |
| 105 | O—C(O)—t-Bu | 3,4-F$_2$ | 2,3-Cl$_2$ |
| 106 | O—O(O)—i-Pr | 3,4-F$_2$ | 2,4-Cl$_2$ |
| 107 | O—C(O)—t-Bu | 3,4-F$_2$ | 2,5-Cl$_2$ |
| 108 | O—C(O)Et | 3,4-F$_2$ | 2,6-Cl$_2$ |
| 109 | NHNH$_2$ | 3,4-F$_2$ | 3,4-Cl$_2$ |
| 110 | NHCH$_2$Ph | 3,4-F$_2$ | 3,5-Cl$_2$ |
| 111 | O—O(O)—i-Pr | 3-Cl | H |
| 112 | O—O(O)—i-Pr | 3-Cl | 2-F |
| 113 | OSO$_2$Me | 3-Cl | 4-F |
| 114 | OSO$_2$Me | 3-Cl | 2,3-F$_2$ |
| 115 | O—C(O)—t-Bu | 3-Cl | 2,4-F$_2$ |
| 116 | NHOMe | 3-Cl | 2,5-F$_2$ |
| 117 | NHCH$_2$Ph | 3-Cl | 2,6-F$_2$ |
| 118 | O—C(O)—t-Bu | 3-Cl | 3,4-F$_2$ |
| 119 | OCH$_2$OMe | 3-Cl | 3,5-F$_2$ |
| 120 | OSO$_2$Me | 3-Cl | 2-Cl |
| 121 | NHOMe | 3-Cl | 3-Cl |
| 122 | SPh | 3-Cl | 4-Cl |
| 123 | O—C(O)—i-Pr | 3-Cl | 2,3-Cl$_2$ |
| 124 | O—C(O)—i-Pr | 3-Cl | 2,4-Cl$_2$ |
| 125 | SMe | 3-Cl | 2,5-Cl$_2$ |
| 126 | OSO$_2$Ph | 3-Cl | 2,6-Cl$_2$ |
| 127 | SPh | 3-Cl | 3,4-Cl$_2$ |
| 128 | OCH$_2$OMe | 3-Cl | 3,5-Cl$_2$ |
| 129 | O—C(O)—i-Pr | 3,4-Cl$_2$ | H |
| 130 | O—C(O)Me | 3,4-Cl$_2$ | 2-F |
| 131 | O—C(O)Me | 3,4-Cl$_2$ | 3-F |
| 132 | O—C(O)Et | 3,4-Cl$_2$ | 4-F |
| 133 | O—C(O)Me | 3,4-Cl$_2$ | 2,3-F$_2$ |
| 134 | O—C(O)Et | 3,4-Cl$_2$ | 2,4-F$_2$ |
| 135 | O—C(O)Et | 3,4-Cl$_2$ | 2,5-F$_2$ |
| 136 | O—C(O)Me | 3,4-Cl$_2$ | 2,6-F$_2$ |
| 137 | NHOMe | 3,4-Cl$_2$ | 3,4-F$_2$ |
| 138 | O—C(O)Et | 3,4-Cl$_2$ | 3,5-F$_2$ |
| 139 | O—O(O)—i-Pr | 3,4-Cl$_2$ | 2-Cl |
| 140 | O—C(O)Et | 3,4-Cl$_2$ | 3-Cl |
| 141 | O—C(O)—t-Bu | 3,4-Cl$_2$ | 4-Cl |
| 142 | SPh | 3,4-Cl$_2$ | 2,3-Cl$_2$ |
| 143 | O—C(O)—t-Bu | 3,4-Cl$_2$ | 2,4-Cl$_2$ |
| 144 | O—C(O)Me | 3,4-Cl$_2$ | 2,5-Cl$_2$ |
| 145 | O—C(O)Et | 3,4-Cl$_2$ | 2,6-Cl$_2$ |
| 146 | O—C(O)Me | 3,4-Cl$_2$ | 3,4-Cl$_2$ |
| 147 | O—C(O)Me | 3,4-Cl$_2$ | 3,5-Cl$_2$ |
| 148 | O—C(O)Et | 3-Cl, 4-F | H |
| 149 | SMe | 3-Cl, 4-F | 2-F |
| 150 | O—C(O)Me | 3-Cl, 4-F | 4-F |
| 151 | O—C(O)Et | 3-Cl, 4-F | 2,3-F$_2$ |
| 152 | O—O(O)—t-Bu | 3-Cl, 4-F | 2,4-F$_2$ |
| 153 | O—C(O)Me | 3-Cl, 4-F | 2,5-F$_2$ |
| 154 | OSO$_2$Me | 3-Cl, 4-F | 2,6-F$_2$ |
| 155 | O—C(O)Et | 3-Cl, 4-F | 3,4-F$_2$ |
| 156 | OSO$_2$(4-Me—Ph) | 3-Cl, 4-F | 3,5-F$_2$ |
| 157 | O—C(O)Me | 3-Cl, 4-F | 2-Cl |
| 158 | OCH$_2$OMe | 3-Cl, 4-F | 3-Cl |
| 159 | O—C(O)Me | 3-Cl, 4-F | 4-Cl |
| 160 | O—C(O)Me | 3-Cl, 4-F | 2,3-Cl$_2$ |
| 161 | O—C(O)Et | 3-Cl, 4-F | 2,4-Cl$_2$ |
| 162 | O—C(O)Me | 3-Cl, 4-F | 2,5-Cl$_2$ |
| 163 | O—O(O)—i-Pr | 3-Cl, 4-F | 2,6-Cl$_2$ |
| 164 | O—C(O)Et | 3-Cl, 4-F | 3,4-Cl$_2$ |
| 165 | O—C(O)Me | 3-Cl, 4-F | 3,5-Cl$_2$ |
| 166 | O—C(O)Me | 3-Cl, 4-F | H |
| 167 | NHOH | 3-F, 4-Cl | 2-F |
| 168 | O—C(O)Me | 3-F, 4-Cl | 3-F |
| 169 | O—C(O)Me | 3-F, 4-Cl | 4-F |
| 170 | NHOMe | 3-F, 4-Cl | 2,3-F$_2$ |
| 171 | O—C(O)Et | 3-F, 4-Cl | 2,4-F$_2$ |
| 172 | SPh | 3-F, 4-Cl | 2,5-F$_2$ |
| 173 | O—C(O)Me | 3-F, 4-Cl | 2,6-F$_2$ |
| 174 | O—C(O)Me | 3-F, 4-Cl | 3,4-F$_2$ |
| 175 | O—C(O)Et | 3-F, 4-Cl | 3,5-F$_2$ |
| 176 | O—C(O)Me | 3-F, 4-Cl | 2-Cl |
| 177 | O—C(O)Et | 3-F, 4-Cl | 4-Cl |
| 178 | SPh | 3-F, 4-Cl | 2,3-Cl$_2$ |
| 179 | NHOMe | 3-F, 4-Cl | 2,4-Cl$_2$ |
| 180 | NHOMe | 3-F, 4-Cl | 2,5-Cl$_2$ |
| 181 | O—C(O)—i-Pr | 3-F, 4-Cl | 2,6-Cl$_2$ |
| 182 | SMe | 3-F, 4-Cl | 3,4-Cl$_2$ |
| 183 | SPh | 3-F, 4-Cl | 3,5-Cl$_2$ |
| 184 | O—C(O)Et | 3-F | 2,5-F$_2$ |
| 185 | O—C(O)Me | 3-F | 2,6-F$_2$ |
| 186 | SPh | 3-F | 2,6-F$_2$ |
| 187 | NHNH$_2$ | 3,4-F$_2$ | 3,4-Cl$_2$ |
| 188 | NHCH$_2$Ph | 3,4-F$_2$ | 3,5-Cl$_2$ |
| 189 | SPh | 3-F | 2,6-F$_2$ |
| 190 | O—C(O)—t-Bu | 3-F | 2,6-F$_2$ |
| 191 | SMe | 3-F | 2,6-F$_2$ |
| 192 | O—C(O)Et | 3,4-F$_2$ | 2,6-F$_2$ |
| 193 | O—C(O)—t-Bu | 3,4-F$_2$ | 2,6-F$_2$ |
| 194 | O—C(O)Me | 3,4-F$_2$ | 2,6-F$_2$ |
| 195 | SPh | 3,4-F$_2$ | 2,6-F$_2$ |
| 196 | SMe | 3,4-F$_2$ | 2,6-F$_2$ |
| 197 | OSO$_2$(4-Me—Ph) | 3,4-F$_2$ | 2,6-F$_2$ |
| 198 | Cl | 3,4-F$_2$ | 2,6-F$_2$ |
| 199 | OCO$_2$Me | 3,4-F$_2$ | 2,6-F$_2$ |
| 200 | OCH$_2$OMe | 3,4-F$_2$ | 2,6-F$_2$ |
| 201 | O—C(O)Et | H | 2,6-F$_2$ |
| 202 | O—C(O)Et | H | 3,4-F$_2$ |
| 203 | O—C(O)Me | H | 3,5-F$_2$ |
| 204 | NHOMe | H | 2-Cl |
| 205 | NHOH | H | 3-Cl |
| 206 | O—C(O)Et | H | 4-Cl |
| 207 | SMe | H | 2,3-Cl$_2$ |
| 208 | SPh | H | 2,4-Cl$_2$ |
| 209 | NHCH$_2$Ph | H | 2,5-Cl$_2$ |
| 210 | O—C(O)Et | H | 2,6-Cl$_2$ |
| 211 | OCH$_2$OMe | H | 3,4-Cl$_2$ |

TABLE 36-continued

Definitions of structural combinations of groups $B^2$, $(R^1)_m$ and $(R^2)_n$ for the tables of compounds of the general formula (I) according to the invention below

| Ex. | $B^2$ | $(R^1)_m$ | $(R^2)_n$ |
|---|---|---|---|
| 212 | OCH$_2$OMe | H | 3,5-Cl$_2$ |
| 213 | O—C(O)Et | 3-CN | 2,5-F$_2$ |
| 214 | O—C(O)—t-Bu | 3-CN | 2,5-F$_2$ |
| 215 | O—C(O)Me | 3-CN | 2,5-F$_2$ |
| 216 | NHOMe | 3-CN | 2,5-F$_2$ |
| 217 | SMe | 3-CN | 2,5-F$_2$ |
| 218 | OSO$_2$(4-Me—Ph) | 3-CN | 2,5-F$_2$ |
| 219 | Cl | 3-CN | 2,5-F$_2$ |
| 220 | OCO$_2$Me | 3-CN | 2,5-F$_2$ |
| 221 | O—C(O)Et | 3-CN | 2,6-F$_2$ |
| 222 | NHOMe | 3-CN | 2,6-F$_2$ |
| 223 | O—C(O)Me | 3-CN | 2,6-F$_2$ |
| 224 | NHOH | 3-CN | 2,6-F$_2$ |
| 225 | SMe | 3-CN | 2,6-F$_2$ |
| 226 | OSO$_2$(4-Me—Ph) | 3-CN | 2,6-F$_2$ |
| 227 | Cl | 3-CN | 2,6-F$_2$ |
| 228 | OCO$_2$Me | 3-CN | 2,6-F$_2$ |
| 229 | O—C(O)Et | 3-CN | 2,3-F$_2$ |
| 230 | O—C(O)—t-Bu | 3-CN | 2,3-F$_2$ |
| 231 | O—C(O)Me | 3-CN | 2,3-F$_2$ |
| 232 | SPh | 3-CN | 2,3-F$_2$ |
| 233 | SMe | 3-CN | 2,3-F$_2$ |
| 234 | NHOH | 3-CN | 2,3-F$_2$ |
| 235 | Cl | 3-CN | 2,3-F$_2$ |
| 236 | OCO$_2$Me | 3-CN | 2,3-F$_2$ |
| 237 | O—C(O)Et | 3-CN | 2,4-F$_2$ |
| 238 | NHNH$_2$ | 3-CN | 2,4-F$_2$ |
| 239 | O—C(O)Me | 3-CN | 2,4-F$_2$ |
| 240 | NHNH2 | 3-CN | 2,4-F$_2$ |
| 241 | SMe | 3-CN | 2,4-F$_2$ |
| 242 | OSO$_2$(4-Me—Ph) | 3-CN | 2,4-F$_2$ |
| 243 | Cl | 3-CN | 2,4-F$_2$ |
| 244 | OCO$_2$Me | 3-CN | 2,4-F$_2$ |
| 245 | O—C(O)Et | 3-CN | 2,4-F$_2$ |
| 246 | O—C(O)—t-Bu | 3-CN | 2,4-F$_2$ |
| 247 | O—C(O)Me | 3-CN | 2,4-F$_2$ |
| 248 | SPh | 3-CN | 2,4-F$_2$ |
| 249 | SMe | 3-CN | 2,4-F$_2$ |
| 250 | OSO$_2$(4-Me—Ph) | 3-CN | 2,4-F$_2$ |
| 251 | Cl | 3-CN | 2,4-F$_2$ |
| 252 | OCO$_2$Me | 3-CN | 2,4-F$_2$ |
| 253 | O—C(O)Et | 3-CN | 4-Cl |
| 254 | NHOMe | 3-CN | 4-Cl |
| 255 | O—C(O)Me | 3-CN | 4-Cl |
| 256 | NHOMe | 3-CN | 4-Cl |
| 257 | SMe | 3-CN | 4-Cl |
| 258 | OSO$_2$(4-Me—Ph) | 3-CN | 4-Cl |
| 259 | Cl | 3-CN | 4-Cl |
| 260 | OCO$_2$Me | 3-CN | 4-Cl |
| 261 | O—C(O)Et | 3-CN | 3-Cl |
| 262 | NHOMe | 3-CN | 3-Cl |
| 263 | O—C(O)Me | 3-CN | 3-Cl |
| 264 | NHOH | 3-CN | 3-Cl |
| 265 | SMe | 3-CN | 3-Cl |
| 266 | OSO$_2$(4-Me—Ph) | 3-CN | 3-Cl |
| 267 | Cl | 3-CN | 3-Cl |
| 268 | OCO$_2$Me | 3-CN | 3-Cl |
| 269 | O—C(O)Et | 3-CN | 4-F |
| 270 | NHOMe | 3-CN | 4-F |
| 271 | O—C(O)Me | 3-CN | 4-F |
| 272 | NHOMe | 3-CN | 4-F |
| 273 | SMe | 3-CN | 4-F |
| 274 | OSO$_2$(4-Me—Ph) | 3-CN | 4-F |
| 275 | Cl | 3-CN | 4-F |
| 276 | OCO$_2$Me | 3-CN | 4-F |
| 277 | O—C(O)Et | 3-CN | 3-F |
| 278 | NHOMe | 3-CN | 3-F |
| 279 | O—C(O)Me | 3-CN | 3-F |
| 280 | NHOH | 3-CN | 3-F |
| 281 | SMe | 3-CN | 3-F |
| 282 | OSO$_2$(4-Me—Ph) | 3-CN | 3-F |
| 283 | Cl | 3-CN | 3-F |
| 284 | OCO$_2$Me | 3-CN | 3-F |
| 285 | O—C(O)Et | 3-NO$_2$ | 2,5-F$_2$ |
| 286 | NHCH$_2$Ph | 3-NO$_2$ | 2,5-F$_2$ |
| 287 | O—C(O)Me | 3-NO$_2$ | 2,5-F$_2$ |
| 288 | NHOMe | 3-NO$_2$ | 2,5-F$_2$ |
| 289 | SMe | 3-NO$_2$ | 2,5-F$_2$ |
| 290 | OSO$_2$(4-Me—Ph) | 3-NO$_2$ | 2,5-F$_2$ |
| 291 | Cl | 3-NO$_2$ | 2,5-F$_2$ |
| 292 | OCO$_2$Me | 3-NO$_2$ | 2,5-F$_2$ |
| 293 | O—C(O)Et | 3-NO$_2$ | 2,6-F$_2$ |
| 294 | O—C(O)—t-Bu | 3-NO$_2$ | 2,6-F$_2$ |
| 295 | O—C(O)Me | 3-NO$_2$ | 2,6-F$_2$ |
| 296 | NHOMe | 3-NO$_2$ | 2,6-F$_2$ |
| 297 | SMe | 3-NO$_2$ | 2,6-F$_2$ |
| 298 | NHOH | 3-NO$_2$ | 2,6-F$_2$ |
| 299 | Cl | 3-NO$_2$ | 2,6-F$_2$ |
| 300 | OCO$_2$Me | 3-NO$_2$ | 2,6-F$_2$ |
| 301 | O—C(O)Et | 3-NO$_2$ | 2,3-F$_2$ |
| 302 | O—C(O)—t-Bu | 3-NO$_2$ | 2,3-F$_2$ |
| 303 | O—C(O)Me | 3-NO$_2$ | 2,3-F$_2$ |
| 304 | SPh | 3-NO$_2$ | 2,3-F$_2$ |
| 305 | SMe | 3-NO$_2$ | 2,3-F$_2$ |
| 306 | OSO$_2$(4-Me—Ph) | 3-NO$_2$ | 2,3-F$_2$ |
| 307 | Cl | 3-NO$_2$ | 2,3-F$_2$ |
| 308 | OCO$_2$Me | 3-NO$_2$ | 2,3-F$_2$ |
| 309 | O—C(O)Et | 3-NO$_2$ | 2,4-F$_2$ |
| 310 | O—C(O)—t-Bu | 3-NO$_2$ | 2,4-F$_2$ |
| 311 | O—C(O)Me | 3-NO$_2$ | 2,4-F$_2$ |
| 312 | NHOMe | 3-NO$_2$ | 2,4-F$_2$ |
| 313 | SMe | 3-NO$_2$ | 2,4-F$_2$ |
| 314 | OSO$_2$(4-Me—Ph) | 3-NO$_2$ | 2,4-F$_2$ |
| 315 | Cl | 3-NO$_2$ | 2,4-F$_2$ |
| 316 | OCO$_2$Me | 3-NO$_2$ | 2,4-F$_2$ |
| 317 | O—C(O)Et | 3-NO$_2$ | 2,4-F$_2$ |
| 318 | O—C(O)—t-Bu | 3-NO$_2$ | 2,4-F$_2$ |
| 319 | O—C(O)Me | 3-NO$_2$ | 2,4-F$_2$ |
| 320 | SPh | 3-NO$_2$ | 2,4-F$_2$ |
| 321 | SMe | 3-NO$_2$ | 2,4-F$_2$ |
| 322 | OSO$_2$(4-Me—Ph) | 3-NO$_2$ | 2,4-F$_2$ |
| 323 | Cl | 3-NO$_2$ | 2,4-F$_2$ |
| 324 | OCO$_2$Me | 3-NO$_2$ | 2,4-F$_2$ |
| 325 | O—C(O)Et | 3-NO$_2$ | 4-Cl |
| 326 | NHOMe | 3-NO$_2$ | 4-Cl |
| 327 | O—C(O)Me | 3-NO$_2$ | 4-Cl |
| 328 | SPh | 3-NO$_2$ | 4-Cl |
| 329 | SMe | 3-NO$_2$ | 4-Cl |
| 330 | NHOH | 3-NO$_2$ | 4-Cl |
| 331 | Cl | 3-NO$_2$ | 4-Cl |
| 332 | OCO$_2$Me | 3-NO$_2$ | 4-Cl |
| 333 | O—C(O)Et | 3-NO$_2$ | 3-Cl |
| 334 | O—C(O)—t-Bu | 3-NO$_2$ | 3-Cl |
| 335 | O—C(O)Me | 3-NO$_2$ | 3-Cl |
| 336 | SPh | 3-NO$_2$ | 3-Cl |
| 337 | SMe | 3-NO$_2$ | 3-Cl |
| 338 | NHOMe | 3-NO$_2$ | 3-Cl |
| 339 | Cl | 3-NO$_2$ | 3-Cl |
| 340 | OCO$_2$Me | 3-NO$_2$ | 3-Cl |
| 341 | O—C(O)Et | 3-NO$_2$ | 4-F |
| 342 | O—C(O)—t-Bu | 3-NO$_2$ | 4-F |
| 343 | O—C(O)Me | 3-NO$_2$ | 4-F |
| 344 | SPh | 3-NO$_2$ | 4-F |
| 345 | SMe | 3-NO$_2$ | 4-F |
| 346 | NHOMe | 3-NO$_2$ | 4-F |
| 347 | Cl | 3-NO$_2$ | 4-F |
| 348 | OCO$_2$Me | 3-NO$_2$ | 4-F |
| 349 | O—C(O)Et | 3-NO$_2$ | 3-F |
| 350 | NHOMe | 3-NO$_2$ | 3-F |
| 351 | O—C(O)Me | 3-NO$_2$ | 3-F |
| 352 | SPh | 3-NO$_2$ | 3-F |
| 353 | SMe | 3-NO$_2$ | 3-F |
| 354 | NHOH | 3-NO$_2$ | 3-F |
| 355 | Cl | 3-NO$_2$ | 3-F |
| 356 | OCO$_2$Me | 3-NO$_2$ | 3-F |
| 357 | O—C(O)Et | 3-CN, 4-F | 2,6-F$_2$ |
| 358 | NHOMe | 3-CN, 4-F | 2,6-F$_2$ |
| 359 | O—C(O)Me | 3-CN, 4-F | 2,6-F$_2$ |

TABLE 36-continued

Definitions of structural combinations of groups $B^2$, $(R^1)_m$ and $(R^2)_n$ for the tables of compounds of the general formula (I) according to the invention below

| Ex. | $B^2$ | $(R^1)_m$ | $(R^2)_n$ |
|---|---|---|---|
| 360 | SPh | 3-CN, 4-F | 2,6-$F_2$ |
| 361 | SMe | 3-CN, 4-F | 2,6-$F_2$ |
| 362 | NHOH | 3-CN, 4-F | 2,6-$F_2$ |
| 363 | Cl | 3-CN, 4-F | 2,6-$F_2$ |
| 364 | $OCO_2Me$ | 3-CN, 4-F | 2,6-$F_2$ |
| 365 | O—C(O)Me | 3-CN, 4-F | 3-Cl |
| 366 | O—C(O)Me | 3-CN, 4-F | 3-CN |
| 367 | O—C(O)Me | 3-CN, 4-F | 4-F |
| 368 | O—C(O)Me | 3-CN, 4-F | 4-Cl |
| 369 | O—C(O)Me | 3-CN, 4-F | 2,5-$F_2$ |
| 370 | O—C(O)Me | 3-CN, 4-F | 2,6-$F_2$ |
| 371 | O—C(O)Et | 3-Br, 4-F | 2,6-$F_2$ |
| 372 | NHOMe | 3-Br, 4-F | 2,6-$F_2$ |
| 373 | O—C(O)Me | 3-Br, 4-F | 2,6-$F_2$ |
| 374 | SPh | 3-Br, 4-F | 2,6-$F_2$ |
| 375 | SMe | 3-Br, 4-F | 2,6-$F_2$ |
| 376 | NHOH | 3-Br, 4-F | 2,6-$F_2$ |
| 377 | Cl | 3-Br, 4-F | 2,6-$F_2$ |
| 378 | $OCO_2Me$ | 3-Br, 4-F | 2,6-$F_2$ |
| 379 | O—C(O)Me | 3-Br, 4-F | 3-Cl |
| 380 | O—C(O)Me | 3-Br, 4-F | 3-CN |
| 381 | O—C(O)Me | 3-Br, 4-F | 4-F |
| 382 | O—C(O)Me | 3-Br, 4-F | 4-Cl |
| 383 | O—C(O)Me | 3-Br, 4-F | 2,5-$F_2$ |
| 384 | O—C(O)Me | 3-Br, 4-F | 2,6-$F_2$ |
| 385 | O—C(O)Et | 3-F, 4-CN | 3-F |
| 386 | NHOMe | 3-F, 4-CN | 3-Cl |
| 387 | O—C(O)Me | 3-F, 4-CN | 3-CN |
| 388 | SPh | 3-F, 4-CN | 4-F |
| 389 | SMe | 3-F, 4-CN | 4-Cl |
| 390 | NHOH | 3-F, 4-CN | 2,5-$F_2$ |
| 391 | Cl | 3-F, 4-CN | 2,6-$F_2$ |
| 392 | $OCO_2Me$ | 3-F, 4-CN | 3-F |
| 393 | O—C(O)Me | 3-F, 4-CN | 3-Cl |
| 394 | O—C(O)Me | 3-F, 4-CN | 3-CN |
| 395 | O—C(O)Me | 3-F, 4-CN | 4-F |
| 396 | O—C(O)Me | 3-F, 4-CN | 4-Cl |
| 397 | O—C(O)Me | 3-F, 4-CN | 2,5-$F_2$ |
| 398 | O—C(O)Me | 3-F, 4-CN | 2,6-$F_2$ |

For reference purposes, specific numbers (=Example Numbers) have been assigned to the individual compounds in Tables 37 to 42f below, where the Example Number in question is composed of the number of the chemical formula assigned to the respective table and a "row number" (row number) which refers to the same number in the row of the first column of Table 36. The chemical structure of Example No. "(formula number)(row number)" is thus defined unambiguously by the formula above the respective table by formula number and row number of Table 36, for example:

Example No. "IA5a1" of Table 37 is the compound of the formula (IA5a) where $B^2$=—O—C(O)-Et, $(R^1)_m$=3-F and $(R^2)_n$=4-Cl, defined according to row 1 of Table 36, or a tautomer thereof.

Example No. "IA12ab344" of Table 38 is the compound of the formula (IA12a) where R=ethyl [=subformula (IA12ab)], where $B^2$=phenylthio, $(R^1)_m$=3-$NO_2$ and $(R^2)_n$=4-F, defined according to row 344 of Table 36, or a tautomer thereof.

TABLE 37

Compounds of the formula (IA5a) where $B^2$, $(R^1)_m$ and $(R^2)_n$ are as defined in Table 36:

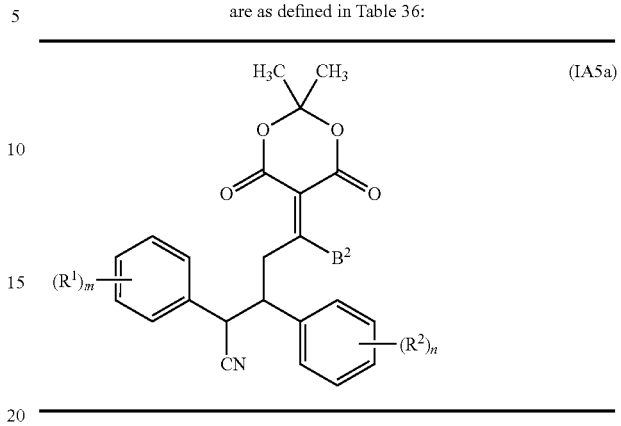

Table 37, examples:

Examples are the compounds of the formula (IA5a), in each case in the form of a racemic erythro/threo mixture (ratio 70:30 to 30:70), where the meanings of $B^2$, $(R^1)_m$ and $(R^2)_n$ are defined according to a row number of Table 36. Individual compounds are numbered "(formula)(row number)", without any brackets.

TABLE 38

Compounds of the formulae (IA12a), (IA12aa), (IA12ab), (IA12ac) and (IA12ad) where $B^2$, $(R^1)_m$ and $(R^2)_n$ are as defined in Table 36:

(IA12aa) R is methyl
(IA12ab) R is ethyl
(IA12ac) R is n-propyl
(IA12ad) R is i-propyl Table 38, examples of erythro/threo mixtures (ratios 70:30 to 30:70):

Examples are the compounds of the formulae (IA12aa) to (IA12ad), in each case in the form of a racemic erythro/threo mixture (ratio 70:30 to 30:70), where the meanings of $B^2$, $(R^1)_m$ and $(R^2)_n$ are defined according to a row number of Table 36. Individual compounds are numbered "(formula)(row number)", without any brackets.

Tables 38a to 38f: Compounds of the formulae (threo-IA12aa), (threo-IA12ab), (threo-IA12ac), (threo-IA12ad), (threo-2-IA12aa), (threo-2-IA12ab), (threo-2-IA12ac) and (threo-2-IA12ad), where $B^2$, $(R^1)_m$ and $(R^2)_n$ are each as defined in Table 36:

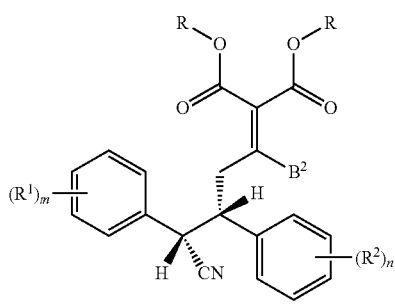

(threo-1-IA12aa) R = OCH₃
(threo-1-IA12ab) R = OC₂H₅
(threo-1-IA12ac) R = n-C₃H₇
(threo-1-IA12ad) R = i-C₃H₇

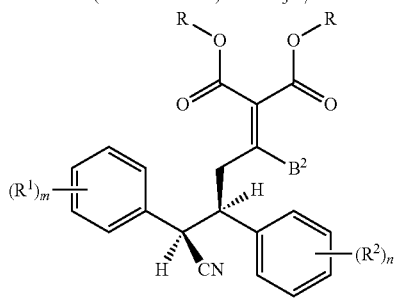

(threo-2-IA12aa) R = OCH₃
(threo-2-IA12ab) R = OC₂H₅
(threo-2-IA12ac) R = n-C₃H₇
(threo-2-IA12ad) R = i-C₃H₇

(threo-IA12aa) = (threo-1-IA12aa) + (threo-2-IA12aa) (50:50) = (rac.)
(threo-IA12ab) = (threo-1-IA12ab) + (threo-2-IA12ab) (50:50) = (rac.)
(threo-IA12ac) = (threo-1-IA12ac) + (threo-2-IA12ac) (50:50) = (rac.)
(threo-IA12ad) = (threo-1-IA12ad) + (threo-2-IA12ad) (50:50) = (rac.)

Table 38a (threo racemates), examples:

Compounds of the formulae threo-(IA12aa), threo-(IA12ab), threo-(IA12ac) and threo-(IA12ad), in each case in the form of the racemic mixture of the threo isomers, where the structural combination of groups $B^2$, $(R^1)_m$ and $(R^2)_n$ is defined according to a row number of Table 36. Individual compounds are numbered "threo-IA12aa(row number)", "threo-IA12ab(row number)", "threo-IA12ac(row number)" and "threo-IA12ad(row number)".

Table 38b, examples (optically active threo-2 enantiomers):

Optically active threo-2 enantiomers in enriched form [=(2R,3R) form of more than 90% ee] having the chemical structure of the formula threo-2-(IA12aa), threo-2-(IA12ab), threo-2-(IA12ac) or threo-2-(IA12ad), where the structural combination of groups $B^2$, $(R^1)_m$ and $(R^2)_n$ is defined according to a row number of Table 36. Individual compounds are numbered "threo-2-IA12aa(row number)", "threo-2-IA12ab (row number)", "threo-2-IA12ac(row number)" and "threo-2-IA12ad(row number)".

Table 38c, examples (optically active threo-1 enantiomers):

Optically active threo-1 enantiomers in enriched form [=(2S,3S) form of more than 90% ee] having the chemical structure of the formula threo-1-(IA12aa), threo-1-(IA12ab), threo-1-(IA12ac) or threo-1-(IA12ad), where the structural combination of groups $B^2$, $(R^1)_m$ and $(R^2)_n$ is defined according to a row number of Table 36. Individual compounds are numbered "threo-1-IA12aa(row number)", "threo-1-IA12ab (row number)", "threo-1-IA12ac(row number)" and "threo-1-IA12ad(row number)".

Table 38d (erythro racemates), examples:

Compounds of the formulae erythro-(IA12aa), erythro-(IA12ab), erythro-(IA12ac) and erythro-(IA12ad), in each case in the form of the racemic mixture of the erythro isomers, where the structural combination of groups $B^2$, $(R^1)_m$ and $(R^2)_n$ is defined according to a row number of Table 36. Individual compounds are numbered "erythro-IA12aa(row number)", "erythro-IA12ab(row number)", "erythro-IA12ac (row number)" and "erythro-IA12ad(row number)".

Table 38e (erythro-1 enantiomers), examples:

Optically active erythro-2-enantiomers in enriched form [=(2R,3S) form of more than 90% ee] having the chemical structure of the formula erythro-1-(IA12aa), erythro-1-(IA12ab), erythro-1-(IA12ac) or erythro-1-(IA12ad), where the structural combination of groups $B^2$, $(R^1)_m$ and $(R^2)_n$ is defined according to a row number of Table 36. Individual compounds are numbered "erythro-1-IA12aa(row number)", "erythro-1-IA12ab(row number)", "erythro-1-IA12ac(row number)" and "erythro-1-IA12ad(row number)".

Table 38f (erythro-2 enantiomers), examples:

Optically active erythro-2 enantiomers in enriched form [=(2S,3R) form of more than 90% ee] having the chemical structure of the formula erythro-2-(IA12aa), erythro-2-(IA12ab), erythro-2-(IA12ac) or erythro-2-(IA12ad), where the structural combination of groups $B^2$, $(R^1)_m$ and $(R^2)_n$ is defined according to a row number of Table 36. Individual compounds are numbered "erythro-2-IA12aa(row number)", "erythro-2-IA12ab(row number)", "erythro-2-IA12ac(row number)" and "erythro-2-IA12ad(row number)".

TABLE 39

Compounds of the formulae (IA10a), (IA10aa), (IA10ab), (IA10ac) and (IA10ad) where $B^2$, $(R^1)_m$ and $(R^2)_n$ are as defined in Table 36:

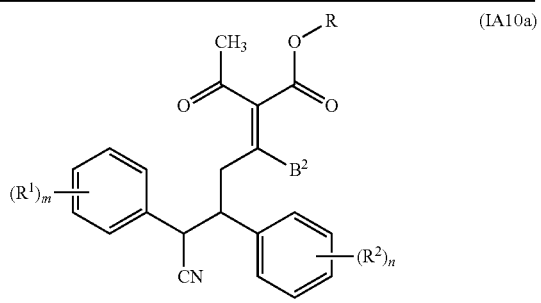

(IA10aa) R is methyl
(IA10ab) R is ethyl
(IA10ac) R is n-propyl
(IA10ad) R is i-propyl Table 39, examples of erythro/threo mixtures (ratios 70:30 to 30:70):

Examples are the compounds of the formulae (IA10aa) to (IA10ad), in each case in the form of a racemic erythro/threo mixture (ratio 70:30 to 30:70), where the meanings of $B^2$, $(R^1)_m$ and $(R^2)_n$ are defined according to a row number of Table 36. Individual compounds are numbered "(formula) (row number)", without any brackets.

Tables 39a to 39f: Compounds of the formulae (threo-IA10aa), (threo-IA10ab), (threo-IA10ac), (threo-IA10ad), (threo-2-IA10aa), (threo-2-IA10ab), (threo-2-IA10ac) and (threo-2-IA10ad), where $B^2$, $(R^1)_m$ and $(R^2)_n$ are each as defined in Table 36:

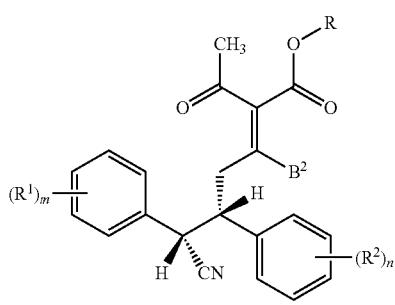

(threo-1-IA10aa) R = OCH$_3$
(threo-1-IA10ab) R = OC$_2$H$_5$
(threo-1-IA10ac) R = n-C$_3$H$_7$
(threo-1-IA10ad) R = i-C$_3$H$_7$

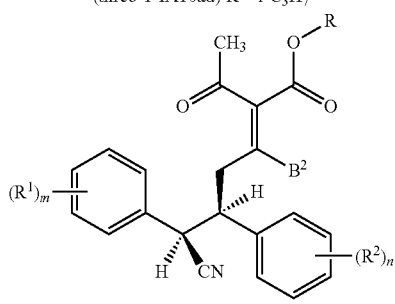

(threo-2-IA10aa) R = OCH$_3$
(threo-2-IA10ab) R = OC$_2$H$_5$
(threo-2-IA10ac) R = n-C$_3$H$_7$
(threo-2-IA10ad) R = i-C$_3$H$_7$ (threo-IA10aa) = (threo-1-IA10aa) + (threo-2-IA10aa) (50:50) = (rac.)
(threo-IA10ab) = (threo-1-IA10ab) + (threo-2-IA10ab) (50:50) = (rac.)
(threo-IA10ac) = (threo-1-IA10ac) + (threo-2-IA10ac) (50:50) = (rac.)
(threo-IA10ad) = (threo-1-IA10ad) + (threo-2-IA10ad) (50:50) = (rac.)

Table 39a (threo racemates), examples:

Compounds of the formulae threo-(IA10aa), threo-(IA10ab), threo-(IA10ac) and threo-(IA10ad), in each case in the form of the racemic mixture of the threo isomers, where the structural combination of groups $B^2$, $(R^1)_m$ and $(R^2)_n$ is defined according to a row number of Table 36.

Individual compounds are numbered "threo-IA10aa(row number)", "threo-IA10ab(row number)", "threo-IA10ac(row number)" and "threo-IA10ad(row number)".

Table 39b (optically active threo-2 enantiomers), examples:

Optically active threo-2 enantiomers in enriched form [=(2R,3R) form of more than 90% ee] having the chemical structure of the formula threo-2-(IA10aa), threo-2-(IA10ab), threo-2-(IA10ac) or threo-2-(IA10ad), where the structural combination of groups $B^2$, $(R^1)_m$ and $(R^2)_n$ is defined according to a row number of Table 36. Individual compounds are numbered "threo-2-IA10aa(row number)", "threo-2-IA10ab (row number)", "threo-2-IA10ac(row number)" and "threo-2-IA10ad(row number)".

Table 39c, examples (optically active threo-1 enantiomers):

Optically active threo-1 enantiomers in enriched form [=(2S,3S) form of more than 90% ee] having the chemical structure of the formula threo-1-(IA10aa), threo-1-(IA10ab), threo-1-(IA10ac) or threo-1-(IA10ad), where the structural combination of groups $B^2$, $(R^1)_m$ and $(R^2)_n$ is defined according to a row number of Table 36. Individual compounds are numbered "threo-1-IA10aa(row number)", "threo-1-IA10ab (row number)", "threo-1-IA10ac(row number)" and "threo-1-IA10ad(row number)".

Table 39d (erythro racemates), examples:

Compounds of the formulae erythro-(IA10aa), erythro-(IA10ab), erythro-(IA10ac) and erythro-(IA10ad), in each case in the form of the racemic mixture of the erythro isomers, where the structural combination of groups $B^2$, $(R^1)_m$ and $(R^2)_n$ is defined according to a row number of Table 36. Individual compounds are numbered "erythro-IA10aa(row number)", "erythro-IA10ab(row number)", "erythro-IA10ac (row number)" and "erythro-IA10ad(row number)".

Table 39e (erythro-1 enantiomers), examples:

Optically active erythro-2 enantiomers in enriched form [=(2R,3S) form of more than 90% ee] having the chemical structure of the formula erythro-1-(IA10aa), erythro-1-(IA10ab), erythro-1-(IA10ac) or erythro-1-(IA10ad), where the structural combination of groups $B^2$, $(R^1)_m$ and $(R^2)_n$ is defined according to a row number of Table 36. Individual compounds are numbered "erythro-1-IA10aa(row number)", "erythro-1-IA10ab(row number)", "erythro-1-IA10ac(row number)" and "erythro-1-IA10ad(row number)".

Table 39f (erythro-2 enantiomers), examples:

Optically active erythro-2 enantiomers in enriched form [=(2S,3R) form of more than 90% ee] having the chemical structure of the formula erythro-2-(IA10aa), erythro-2-(IA10ab), erythro-2-(IA10ac) or erythro-2-(IA10ad), where the structural combination of groups $B^2$, $(R^1)_m$ and $(R^2)_n$ is defined according to a row number of Table 36. Individual compounds are numbered "erythro-2-IA10aa(row number)", "erythro-2-IA10ab(row number)", "erythro-2-IA10ac(row number)" and "erythro-2-IA10ad(row number)".

TABLE 40

Compounds of the formulae (IA10b), (IA10ba), (IA10bb), (IA10bc) and (IA10bd) where $B^2$, $(R^1)_m$ and $(R^2)_n$ are as defined in Table 36:

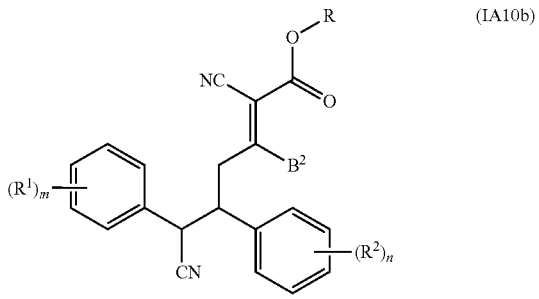

(IA10ba) R is methyl
(IA10bb) R is ethyl
(IA10bc) R is n-propyl
(IA10bd) R is i-propyl Table 40, examples of erythro/threo mixtures (ratios 70:30 to 30:70):

Examples are the compounds of the formulae (IA10ba) to (IA10bd), in each case in the form of a racemic erythro/threo mixture (ratio 70:30 to 30:70), where the meanings of $B^2$, $(R^1)_m$ and $(R^2)_n$ are defined according to a row number of Table 36. Individual compounds are numbered "(formula) (row number)", without any brackets.

Tables 40a to 40f: Compounds of the formulae (threo-IA10ba), (threo-IA10bb), (threo-IA10bc), (threo-IA10bd), (threo-2-IA10ba), (threo-2-IA10bb), (threo-2-IA10bc) and (threo-2-IA10bd), where $B^2$, $(R^1)_m$ and $(R^2)_n$ are each as defined in Table 36:

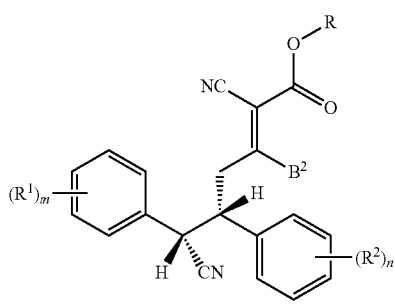

(threo-1-IA10ba) R = OCH₃
(threo-1-IA10bb) R = OC₂H₅
(threo-1-IA10bc) R = n-C₃H₇
(threo-1-IA10bd) R = i-C₃H₇

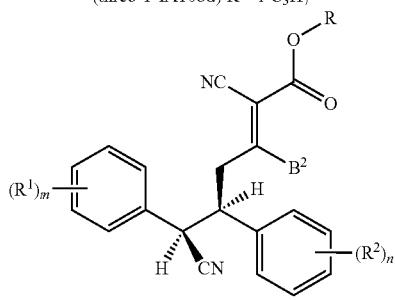

(threo-2-IA10ba) R = OCH₃
(threo-2-IA10bb) R = OC₂H₅
(threo-2-IA10bc) R = n-C₃H₇
(threo-2-IA10bd) R = i-C₃H₇

(threo-IA10ba) = (threo-1-IA10ba) + (threo-2-IA10ba) (50:50) = (rac.)
(threo-IA10bb) = (threo-1-IA10bb) + (threo-2-IA10bb) (50:50) = (rac.)
(threo-IA10bc) = (threo-1-IA10bc) + (threo-2-IA10bc) (50:50) = (rac.)
(threo-IA10bd) = (threo-1-IA10bd) + (threo-2-IA10bd) (50:50) = (rac.)

Table 40a (threo racemates), examples:

Compounds of the formulae threo-(IA10ba), threo-(IA10bb), threo-(IA10bc) and threo-(IA10bd), in each case in the form of the racemic mixture of the threo isomers, where the structural combination of groups $B^2$, $(R^1)_m$ and $(R^2)_n$ is defined according to a row number of Table 36. Individual compounds are numbered "threo-IA10ba(row number)", "threo-IA10bb(row number)", "threo-IA10bc(row number)" and "threo-IA10bd(row number)".

Table 40b (optically active threo-2 enantiomers), examples:

Optically active threo-2 enantiomers in enriched form [=(2R,3R) form of more than 90% ee] having the chemical structure of the formula threo-2-(IA10ba), threo-2-(IA10bb), threo-2-(IA10bc) or threo-2-(IA10bd), where the structural combination of groups $B^2$, $(R^1)_m$ and $(R^2)_n$ is defined according to a row number of Table 36. Individual compounds are numbered "threo-2-IA10ba(row number)", "threo-2-IA10bb (row number)", "threo-2-IA10bc(row number)" and "threo-2-IA10bd(row number)".

Table 40c, examples (optically active threo-1 enantiomers):

Optically active threo-1 enantiomers in enriched form [=(2S,3S) form of more than 90% ee] having the chemical structure of the formula threo-1-(IA10ba), threo-1-(IA10bb), threo-1-(IA10bc) or threo-1-(IA10bd), where the structural combination of groups $B^2$, $(R^1)_m$ and $(R^2)_n$ is defined according to a row number of Table 36. Individual compounds are numbered "threo-1-IA10ba(row number)", "threo-1-IA10bb (row number)", "threo-1-IA10bc(row number)" and "threo-1-IA10bd(row number)".

Table 40d (erythro racemates), examples:

Compounds of the formulae erythro-(IA10ba), erythro-(IA10bb), erythro-(IA10bc) and erythro-(IA10bd), in each case in the form of the racemic mixture of the erythro isomers, where the structural combination of groups $B^2$, $(R^1)_m$ and $(R^2)_n$ is defined according to a row number of Table 36. Individual compounds are numbered "erythro-IA10ba(row number)", "erythro-IA10bb(row number)", "erythro-IA10bc (row number)" and "erythro-IA10bd(row number)".

Table 40e (erythro-1 enantiomers), examples:

Optically active erythro-2 enantiomers in enriched form [=(2R,3S) form of more than 90% ee] having the chemical structure of the formula erythro-1-(IA10ba), erythro-1-(IA10bb), erythro-1-(IA10bc) or erythro-1-(IA10bd), where the structural combination of groups $B^2$, $(R^1)_m$ and $(R^2)_n$ is defined according to a row number of Table 36. Individual compounds are numbered "erythro-1-IA10ba(row number)", "erythro-1-IA10bb(row number)", "erythro-1-IA10bc(row number)" and "erythro-1-IA10bd(row number)".

Table 40f (erythro-2 enantiomers), examples:

Optically active erythro-2 enantiomers in enriched form [=(2S,3R) form of more than 90% ee] having the chemical structure of the formula erythro-2-(IA10ba), erythro-2-(IA10bb), erythro-2-(IA10bc) or erythro-2-(IA10bd), where the structural combination of groups $B^2$, $(R^1)_m$ and $(R^2)_n$ is defined according to a row number of Table 36. Individual compounds are numbered "erythro-2-IA10ba(row number)", "erythro-2-IA10bb(row number)", "erythro-2-IA10bc(row number)" and "erythro-2-IA10bd(row number)".

TABLE 41

Compounds of the formulae (IA11a), (IA11aa), (IA11ab), (IA11ac) and (IA11ad) where $B^2$, $(R^1)_m$ and $(R^2)_n$ are as defined in Table 36:

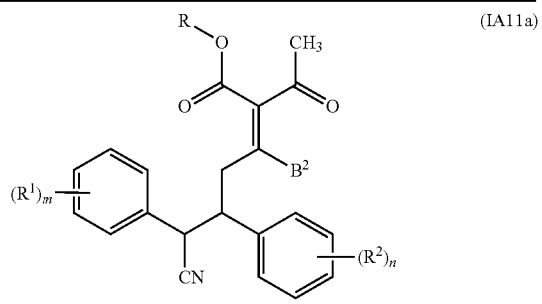

(IA11aa) R is methyl
(IA11ab) R is ethyl
(IA11ac) R is n-propyl
(IA11ad) R is i-propyl Table 41, examples of erythro/threo mixtures (ratios 70:30 to 30:70):

Examples are the compounds of the formulae (IA11aa) to (IA11ad), in each case in the form of a racemic erythro/threo mixture (ratio 70:30 to 30:70), where the meanings of $B^2$, $(R^1)_m$ and $(R^2)_n$ are defined according to a row number of Table 36. Individual compounds are numbered "(formula) (row number)", without any brackets.

Tables 41a to 41f: Compounds of the formulae (threo-IA11aa), (threo-IA11ab), (threo-IA11ac), (threo-IA11ad), (threo-2-IA11aa), (threo-2-IA11ab), (threo-2-IA11ac) and (threo-2-IA11ad), where $B^2$, $(R^1)_m$ and $(R^2)_n$ are each as defined in Table 36:

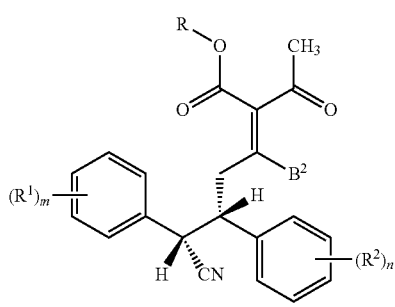

(threo-1-IA11aa) R = OCH$_3$
(threo-1-IA11ab) R = OC$_2$H$_5$
(threo-1-IA11ac) R = n-C$_3$H$_7$
(threo-1-IA11ad) R = i-C$_3$H$_7$

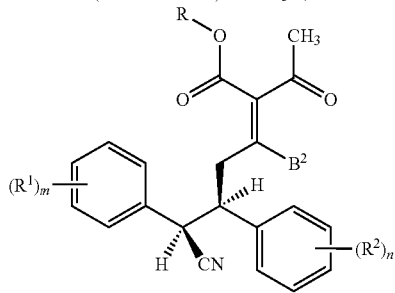

(threo-2-IA11aa) R = OCH$_3$
(threo-2-IA11ab) R = OC$_2$H$_5$
(threo-2-IA11ac) R = n-C$_3$H$_7$
(threo-2-IA11ad) R = i-C$_3$H$_7$ (threo-IA11aa) = (threo-1-IA11aa) + (threo-2-IA11aa) (50:50) = (rac.)
(threo-IA11ab) = (threo-1-IA11ab) + (threo-2-IA11ab) (50:50) = (rac.)
(threo-IA11ac) = (threo-1-IA11ac) + (threo-2-IA11ac) (50:50) = (rac.)
(threo-IA11ad) = (threo-1-IA11ad) + (threo-2-IA11ad) (50:50) = (rac.)

Table 41a (threo racemates), examples:

Compounds of the formulae threo-(IA11aa), threo-(IA11ab), threo-(IA11ac) and threo-(IA11ad), in each case in the form of the racemic mixture of the threo isomers, where the structural combination of groups B$^2$, (R$^1$)$_m$ and (R$^2$)$_n$ is defined according to a row number of Table 36. Individual compounds are numbered "threo-IA11aa(row number)", "threo-IA11ab(row number)", "threo-IA11ac(row number)" and "threo-IA11ad(row number)".

Table 41b (optically active threo-2 enantiomers), examples:

Optically active threo-2 enantiomers in enriched form [=(2R,3R) form of more than 90% ee] having the chemical structure of the formula threo-2-(IA11aa), threo-2-(IA11ab), threo-2-(IA11ac) or threo-2-(IA11ad), where the structural combination of groups B$^2$, (R$^1$)$_m$ and (R$^2$)$_n$ is defined according to a row number of Table 36. Individual compounds are numbered "threo-2-IA11aa(row number)", "threo-2-IA11ab (row number)", "threo-2-IA11ac(row number)" and "threo-2-IA11ad(row number)".

Table 41c, examples (optically active threo-1 enantiomers):

Optically active threo-1 enantiomers in enriched form [=(2S,3S) form of more than 90% ee] having the chemical structure of the formula threo-1-(IA11aa), threo-1-(IA11ab), threo-1-(IA11ac) or threo-1-(IA11ad), where the structural combination of groups B$^2$, (R$^1$)$_m$ and (R$^2$)$_n$ is defined according to a row number of Table 36. Individual compounds are numbered "threo-1-IA11aa(row number)", "threo-1-IA11ab (row number)", "threo-1-IA11ac(row number)" and "threo-1-IA11ad(row number)".

Table 41d (erythro racemates), examples:

Compounds of the formulae erythro-(IA11aa), erythro-(IA11ab), erythro-(IA11ac) and erythro-(IA11ad), in each case in the form of the racemic mixture of the erythro isomers, where the structural combination of groups B$^2$, (R$^1$)$_m$ and (R$^2$)$_n$ is defined according to a row number of Table 36. Individual compounds are numbered "erythro-IA11aa(row number)", "erythro-IA11ab(row number)", "erythro-IA11ac (row number)" and "erythro-IA11ad(row number)".

Table 41e (erythro-1 enantiomers), examples:

Optically active erythro-2 enantiomers in enriched form [=(2R,3S) form of more than 90% ee] having the chemical structure of the formula erythro-1-(IA11aa), erythro-1-(IA11ab), erythro-1-(IA11ac) or erythro-1-(IA11ad), where the structural combination of groups B$^2$, (R$^1$)$_m$ and (R$^2$)$_n$ is defined according to a row number of Table 36. Individual compounds are numbered "erythro-1-IA11aa(row number)", "erythro-1-IA11ab(row number)", "erythro-1-IA11ac(row number)" and "erythro-1-IA11ad(row number)".

Table 41f (erythro-2 enantiomers), examples:

Optically active erythro-2 enantiomers in enriched form [=(2S,3R) form of more than 90% ee] having the chemical structure of the formula erythro-2-(IA11aa), erythro-2-(IA11ab), erythro-2-(IA11ac) or erythro-2-(IA11ad), where the structural combination of groups B$^2$, (R$^1$)$_m$ and (R$^2$)$_n$ is defined according to a row number of Table 36. Individual compounds are numbered "erythro-2-IA11aa(row number)", "erythro-2-IA11ab(row number)", "erythro-2-IA11ac(row number)" and "erythro-2-IA11ad(row number)".

TABLE 42

Compounds of the formulae (IA11b), (IA11ba), (IA11bb), (IA11bc) and (IA11bd) where B$^2$, (R$^1$)$_m$ and (R$^2$)$_n$ are as defined in Table 35:

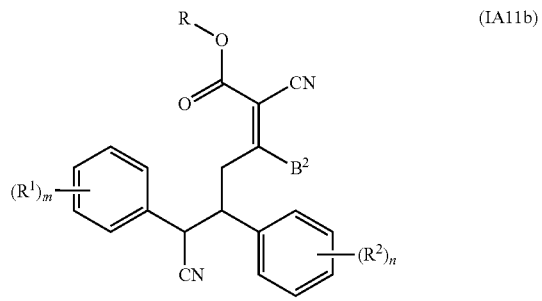

(IA11ba) R is methyl
(IA11bb) R is ethyl
(IA11bc) R is n-propyl
(IA11bd) R is i-propyl Table 42, examples of erythro/threo mixtures (ratios 70:30 to 30:70):

Examples are the compounds of the formulae (IA11ba) to (IA11bd), in each case in the form of a racemic erythro/threo mixture (ratio 70:30 to 30:70), where the meanings of B$^2$, (R$^1$)$_m$ and (R$^2$)$_n$ are defined according to a row number of Table 36. Individual compounds are numbered "(formula) (row number)", without any brackets.

Tables 42a to 42f: Compounds of the formulae (threo-IA11ba), (threo-IA11bb), (threo-IA11bc), (threo-IA11bd), (threo-2-IA11ba), (threo-2-IA11bb), (threo-2-IA11bc) and (threo-2-IA11bd), where B$^2$, (R$^1$)$_m$ and (R$^2$)$_n$ are each as defined in Table 36:

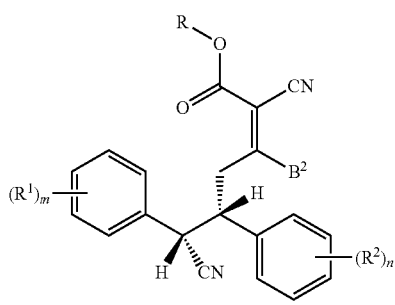

(threo-1-IA11ba) R = OCH$_3$
(threo-1-IA11bb) R = OC$_2$H$_5$
(threo-1-IA11bc) R = n-C$_3$H$_7$
(threo-1-IA11bd) R = i-C$_3$H$_7$

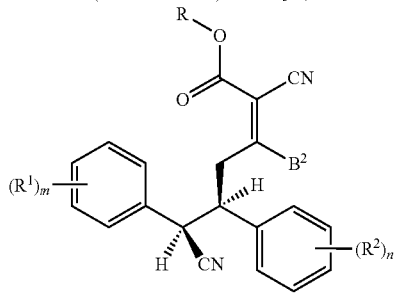

(threo-2-IA11ba) R = OCH$_3$
(threo-2-IA11bb) R = OC$_2$H$_5$
(threo-2-IA11bc) R = n-C$_3$H$_7$
(threo-2-IA11bd) R = i-C$_3$H$_7$ (threo-IA11ba) = (threo-1-IA11ba) + (threo-2-IA11ba) (50:50) = (rac.)
(threo-IA11bb) = (threo-1-IA11bb) + (threo-2-IA11bb) (50:50) = (rac.)
(threo-IA11bc) = (threo-1-IA11bc) + (threo-2-IA11bc) (50:50) = (rac.)
(threo-IA11bd) = (threo-1-IA11bd) + (threo-2-IA11bd) (50:50) = (rac.)

For reference purposes, specific numbers (=Example Numbers) have been assigned to the compounds of Table 42a, where the number "threo-IA11ba(row number)", "threo-IA11bb(row number)", "threo-IA11bc(row number)" and "threo-IA11bd(row number)" refers to the racemic mixture of the threo enantiomers having the chemical structure of the formulae (threo-1-IA11ba) and (threo-2-IA11ba), (threo-1-IA11bb) and (threo-2-IA11bb), (threo-1-IA11bc) and (threo-2-IA11bc) and (threo-1-IA11bd) and (threo-2-IA11bd), respectively, each having the structural combination of groups $B^2$, $(R^1)_m$ and $(R^2)_n$ according to the row number of Table 36. Correspondingly, in Table 42b the number "threo-2-IA11ba(row number)", "threo-2-IA11bb(row number)", "threo-2-IA11bc(row number)" or "threo-2-IA11bd(row number)" refers to the optically active threo-2 enantiomer in enriched form [=(2R,3R) form of more than 90% ee] having the chemical structure of the formula (threo-2-IA11ba(row number)", "(threo-2-IA11bb(row number)", "(threo-2-IA11bc(row number)" and "(threo-2-IA11bd(row number)", respectively, each having the structural combination of groups $B^2$, $(R^1)_m$ and $(R^2)_n$ according to the row number of Table 36.

Table 42a (threo racemates), examples:
Compounds of the formulae threo-(IA11ba), threo-(IA11bb), threo-(IA11bc) and threo-(IA11bd), in each case in the form of the racemic mixture of the threo isomers, where the structural combination of groups $B^2$, $(R^1)_m$ and $(R^2)_n$ is defined according to a row number of Table 36. Individual compounds are numbered "threo-IA11ba(row number)", "threo-IA11bb(row number)", "threo-IA11bc(row number)" and "threo-IA11bd(row number)".

Table 42b (optically active threo-2 enantiomers), examples:
Optically active threo-2 enantiomers in enriched form [=(2R,3R) form of more than 90% ee] having the chemical structure of the formula threo-2-(IA11ba), threo-2-(IA11bb), threo-2-(IA11bc) or threo-2-(IA11bd), where the structural combination of groups $B^2$, $(R^1)_m$ and $(R^2)_n$ is defined according to a row number of Table 36. Individual compounds are numbered "threo-2-IA11ba(row number)", "threo-2-IA11bb (row number)", "threo-2-IA11bc(row number)" and "threo-2-IA11bd(row number)".

Table 42c, examples (optically active threo-1 enantiomers):
Optically active threo-1 enantiomers in enriched form [=(2S,3S) form of more than 90% ee] having the chemical structure of the formula threo-1-(IA11ba), threo-1-(IA11bb), threo-1-(IA11bc) or threo-1-(IA11bd), where the structural combination of groups $B^2$, $(R^1)_m$ and $(R^2)_n$ is defined according to a row number of Table 36. Individual compounds are numbered "threo-1-IA11ba(row number)", "threo-1-IA11bb (row number)", "threo-1-IA11bc(row number)" and "threo-1-IA11bd(row number)".

Table 42d (erythro racemates), examples:
Compounds of the formulae erythro-(IA11ba), erythro-(IA11bb), erythro-(IA11bc) and erythro-(IA11bd), in each case in the form of the racemic mixture of the erythro isomers, where the structural combination of groups $B^2$, $(R^1)_m$ and $(R^2)_n$ is defined according to a row number of Table 36. Individual compounds are numbered "erythro-IA11ba(row number)", "erythro-IA11bb(row number)", "erythro-IA11bc (row number)" and "erythro-IA11bd(row number)".

Table 42e (erythro-1 enantiomers), examples:
Optically active erythro-2 enantiomers in enriched form [=(2R,3S) form of more than 90% ee] having the chemical structure of the formula erythro-1-(IA11ba), erythro-1-(IA11bb), erythro-1-(IA11bc) or erythro-1-(IA11bd), where the structural combination of groups $B^2$, $(R^1)_m$ and $(R^2)_n$ is defined according to a row number of Table 36. Individual compounds are numbered "erythro-1-IA11ba(row number)", "erythro-1-IA11bb(row number)", "erythro-1-IA11bc(row number)" and "erythro-1-IA11bd(row number)".

Table 42f (erythro-2 enantiomers), examples:
Optically active erythro-2 enantiomers in enriched form [=(2S,3R) form of more than 90% ee] having the chemical structure of the formula erythro-2-(IA11ba), erythro-2-(IA11bb), erythro-2-(IA11bc) or erythro-2-(IA11bd), where the structural combination of groups $B^2$, $(R^1)_m$ and $(R^2)_n$ is defined according to a row number of Table 36. Individual compounds are numbered "erythro-2-IA11ba(row number)", "erythro-2-IA11bb(row number)", "erythro-2-IA11bc(row number)" and "erythro-2-IA11bd(row number)".

Selected physical data for examples of Tables 1 to 42f:
Test methods:
1) $^1$H-NMR data (400 MHz, CDCl$_3$); characteristic chemical shifts [in ppm] are indicated for the example in question,
2) MS=mass spectrum, measured using a quadrupole instrument; electrospray ionization (+−), mass range 100-1000; molecular peak M or [M+H]+ or [M−1]+ or [M−2]+ or [M+1]+ indicated for the example in question,
3) HPLC=High Performance Liquid Chromatography, column: Zorbax Eclipse, 50×3.0, C18 1.8 ym, mobile phase: water+0.06% formic acid/acrylonitrile+0.06% formic acid, gradient: 90:10, after 2 min 5:95; detector: DAD (210-400 nm); retention time (rt) indicated for the example in question.
4) HPLC chiral=HPLC on a chiral column, column: Chiralpak IC, 250×4.6 mm, 5 μm DAIC 83325, detector wavelength: 210 nm; column temperature, flow rate and mobile phase indicated for the example in question, Data for Examples:

Example No. Iaa1 (erythro/threo isomer mixture 62:38):
NMR (threo): 17.41 (s, 1H), 4.02 (d, 1H); NMR (erythro): 17.44 (s, 1H), 4.29 (d, 1H);
MS: 412 [M+H]+; HPLC (rt): 1.67 min Example No. IB9aa6 (erythro/threo isomer mixture 54:46):
NMR (threo): 13.54 (s, 1H); NMR (erythro): 13.64 (s, 1H); MS: 432 [M−1]+; HPLC (rt): 1.53 min Example No. IB9aa1 (erythro/threo isomer mixture 53:47):
NMR (threo): 13.50 (s, 1H); NMR (erythro): 13.61 (s, 1H); MS: 430 [M−1]+; HPLC (rt): 1.59 min Example No. IB9aa10 (erythro/threo isomer mixture 60:40):
NMR (threo): 13.54 (s, 1H); NMR (erythro): 13.63 (s, 1H); MS: 448 [M−2]+; HPLC (rt): 1.85 min Example No. IB9aa20 (erythro/threo isomer mixture 63:37):
NMR (threo): 17.46 (s, 1H), 4.03 (d, 1H); NMR (erythro): 17.47 (s, 1H), 4.30 (d, 1H);
MS: 394 [M−1]+; HPLC (rt): 1.58 min Example No. IB8aa10 (erythro/threo isomer mixture 57:43):
NMR (threo): 13.56 (broad s, 1H), 3.99 (d, 1H), 3.83 (s, 3H); NMR (erythro): 13.56 (broad s, 1H), 4.09 (d, 1H), 3.85 (s, 3H); MS: 417 [M+1]+; HPLC (rt): 1.53 min Example No. IB8aa1 (erythro/threo isomer mixture 52:48):
NMR (threo): 13.52 (broad s, 1H), 4.00 (d, 1H), 3.82 (s, 3H); NMR (erythro): 13.58 (broad s, 1H), 4.09 (d, 1H), 3.84 (s, 3H); MS: 383 [M+1]+; HPLC (rt): 1.44 min Example No. IB8aa43 (erythro/threo isomer mixture 59:41):
NMR (erythro): 13.46 (broad s, 1H), 3.81 (s, 3H); NMR (threo): 13.55 (broad s, 1H), 3.84 (s, 3H); MS: 419 [M+1]+; HPLC (rt): 1.46 min Example No. IB9aa20 (erythro/threo isomer mixture 59:41):
NMR (threo): 13.51 (s, 1H); NMR (erythro): 13.62 (s, 1H); MS: 414 [M−1]+; HPLC (rt): 1.51 min Example No. IBXaa20 (erythro/threo isomer mixture 53:47):
NMR (threo): 17.62 (s, 1H), 4.04 (d, 1H), 3.82 (s, 3H), 2.30 (s, 3H);
NMR (erythro): 17.74 (s, 1H), 4.30 (d, 1H), 3.83 (s, 3H), 2.36 (s, 3H);
MS: 398 [M−1]+; HPLC (rt): 1.65 min Example No. IB8aa6 (erythro/threo isomer mixture 57:43):
NMR (threo): 17.62 (s, 1H), 4.04 (d, 1H), 3.82 (s, 3H), 2.30 (s, 3H); NMR (erythro): 13.62 (broad s, 1H), 4.10 (d, 1H), 3.85 (s, 3H); MS: 399 [M−1]+; HPLC (rt): 1.45 min Example No. IB9aa25 (erythro/threo isomer mixture 63:37):
NMR (threo): 13.38 (s, 1H); NMR (erythro): 13.41 (s, 1H); MS: 430 [M−1]+; HPLC (rt): 1.58 min Example No. IA12a57 (erythro/threo isomer mixture 63:37):
NMR (threo): 3.99 (d, 1H), 3.76 (s, 3H), 3.67 (s, 3H), 1.11 (s, 9H);
NMR (erythro): 4.30 (d, 1H), 3.84 (s, 3H), 3.73 (s, 3H), 1.17 (s, 9H);

Example No. Iaa95 (erythro/threo isomer mixture 57:43):
NMR (threo): 17.27 (s, 1H); NMR (erythro): 17.35 (s, 1H); MS: 430 [M−1]+; HPLC (rt): 1.59 min Example No. IB9aa23 (erythro/threo isomer mixture 58:42):
NMR (threo): 13.43 (s, 1H); NMR (erythro): 13.53 (s, 1H); MS: 432 [M−1]+; HPLC (rt): 1.50 min Example No. Iaa23 (erythro/threo isomer mixture 52:48):
NMR (threo): 17.26 (s, 1H); NMR (erythro): 17.31 (s, 1H); MS: 414 [M+1]+; HPLC (rt): 1.58 min Example No. Iaa10 (erythro/threo isomer mixture 61:39):
NMR (threo): 17.36 (s, 1H), 4.01 (d, 1H); NMR (erythro): 17.38 (s, 1H), 4.28 (d, 1H);
MS: 430 [M+1]+; HPLC (rt): 1.68 min Example No. IB9ba6 (erythro/threo isomer mixture 57:43):
NMR (threo): 13.53 (s, 1H); NMR (erythro): 13.63 (s, 1H); MS: 460 [M−1]+; HPLC (rt): 1.67 min Example No. IBXaa6 (erythro/threo isomer mixture 57:43):
NMR (threo): 17.59 (s, 1H), 4.02 (d, 1H), 3.83 (s, 3H), 2.31 (s, 3H); NMR (erythro): 17.67 (s, 1H), 4.30 (d, 1H), 3.83 (s, 3H), 2.36 (s, 3H); MS: 416 [M−1]+; HPLC (rt): 1.67 min Example No. Iaa32 (erythro/threo isomer mixture 70:30):
NMR (threo): 4.08 (d, 1H), 1.06 (s, 9H); NMR (erythro): 4.35 (d, 1H), 1.15 (s, 9H)

Example No. IA12aa23 (erythro/threo isomer mixture 50:50):
NMR (threo): 4.05 (d, 1H), 2.47 (s, 3H); NMR (erythro): 4.17 (d, 1H), 2.50 (s, 3H);
MS: 588 [M+1]+; HPLC (rt): 1.71 min Example No. IA12ab53 (erythro/threo isomer mixture 50:50):
NMR (threo): 2.47 (s, 3H); NMR (erythro): 2.49 (s, 3H); MS: 616 [M+1]+; HPLC (rt): 1.85 min Example No. Ioa95 (erythro/threo isomer mixture 50:50):
NMR (threo): 13.8 (broad s, 1H), 3.80 (d, 1H); NMR (erythro): 13.8 (broad s, 1H), 4.18 (d, 1H); MS: 416 [M+1]+; HPLC (rt): 1.39 min Example No. Iaa53 (erythro/threo isomer mixture 60:34):
NMR (threo): 4.07 (d, 1H), 1.08 (s, 9H); NMR (erythro): 4.35 (d, 1H), 1.16 (s, 9H)

Example No. IA12aa193 (erythro/threo isomer mixture 57:43):
NMR (threo): 3.74 (s, 3H), 3.67 (s, 3H), 1.15 (s, 9H);
NMR (erythro): 3.78 (s, 3H), 3.68 (s, 3H), 1.19 (s, 9H);

Example No. IA12aa1 (erythro/threo isomer mixture 67:33):
NMR (threo): 4.01 (d, 1H), 3.73 (s, 3H), 3.66 (s, 3H), 1.11 (s, 9H);
NMR (erythro): 4.31 (d, 1H), 3.83 (s, 3H), 3.73 (s, 3H), 1.17 (s, 9H)

Example No. IA12aa78 (erythro/threo isomer mixture 66:34):
NMR (threo): 4.11 (d, 1H), 3.79 (s, 3H), 3.66 (s, 3H), 1.14 (s, 9H);
NMR (erythro): 4.30 (d, 1H), 3.81 (s, 3H), 3.71 (s, 3H), 1.19 (s, 9H)

Example No. IA12aa48 (erythro/threo isomer mixture 66:34):
NMR (threo): 3.99 (d, 1H), 3.74 (s, 3H), 3.67 (s, 3H), 1.11 (s, 9H);
NMR (erythro): 4.31 (d, 1H), 3.84 (s, 3H), 3.73 (s, 3H), 1.17 (s, 9H)

Example No. Ioa6 (erythro/threo isomer mixture 59:41):
NMR (threo): 14.0 (broad s, 1H), 4.03 (d, 1H); NMR (erythro): 14.0 (broad s, 1H), 4.30 (d, 1H); MS: 400 [M+1]+; HPLC (rt): 1.40 min Example No. threo-IA12aa57 (threo racemate)
NMR (threo): 3.99 (d, 1H), 3.76 (s, 3H), 3.67 (s, 3H), 3.39 (m, 3H), 1.11 (s, 9H)
HPLC chiral: flow rate: 1 ml/min; column temperature: 30° C.; mobile phase: A=n-heptane (80), B=isopropanol (20), retention time: threo 1: 10.751 min, threo 2: 10.801 min Example No. erythro-2-IA12aa57 (optically active erythro-2 enantiomer)
NMR (erythro): 4.30 (d, 1H), 3.84 (s, 3H), 3.73 (s, 3H), 3.35 (m, 1H), 3.21 (m, 1H), 3.07 (m, 1H), 1.17 (s, 9H); HPLC chiral: flow rate: 1 ml/min; column temperature: 30° C.; mobile phase: A=n-heptane (80), B=isopropanol (20), retention time: 7.481 min Example No. erythro-1-IA12aa57 (optically active erythro-1 enantiomer)
NMR (erythro): 4.30 (d, 1H), 3.84 (s, 3H), 3.73 (s, 3H), 3.35 (m, 1H), 3.21 (m, 1H), 3.07 (m, 1H), 1.17 (s, 9H); HPLC chiral: flow rate: 1 ml/min; column temperature: 30° C.; mobile phase: A=n-heptane (80), B=isopropanol (20), retention time: 6.036 min Example No. IBXaa10 (erythro/threo isomer mixture 58:42):
NMR (threo): 17.59 (s, 1H), 4.02 (d, 1H), 3.83 (s, 3H), 2.29 (s, 3H);
NMR (erythro): 17.67 (s, 1H), 4.29 (d, 1H), 3.84 (s, 3H), 2.36 (s, 3H);
MS: 432 [M+1]+; HPLC (rt): 1.74 min Example No. IBXaa43 (erythro/threo isomer mixture 73:27):
NMR (threo): 17.54 (s, 1H), 4.18 (d, 1H), 3.79 (s, 3H), 2.32 (s, 3H);
NMR (erythro): 17.59 (s, 1H), 4.30 (d, 1H), 3.88 (s, 3H), 2.35 (s, 3H);
MS: 434 [M+1]+; HPLC (rt): 1.66 min Example No. Iaa83 (erythro/threo isomer mixture 61:39):
NMR (threo): 17.26 (s, 1H); NMR (erythro): 17.37 (s, 1H); MS: 414 [M+1]+; HPLC (rt): 1.57 min Example No. Iea6 (erythro/threo isomer mixture 58:42):
NMR (threo): 17.89 (m, 1H), 17.29 (s, 1H); NMR (erythro): 17.92 (m, 1H), 17.31 (s, 1H); MS: 442 [M+1]+; HPLC (rt): 1.79 min Example No. Ica6 (erythro/threo isomer mixture 64:36):
NMR (threo): 17.35 (broad s, 1H), 4.01 (d, 1H); NMR (erythro): 17.36 (broad s, 1H), 4.29 (d, 1H); MS: 428 [M+1]+; HPLC (rt): 1.70 min Example No. threo-IA12aa48 (threo racemate)
NMR (threo): 3.99 (d, 1H), 3.75 (s, 3H), 3.67 (s, 3H), 3.39 (m, 3H), 1.11 (s, 9H)
HPLC chiral: flow rate: 0.6 ml/min; column temperature: 25° C.; mobile phase: A=n-heptane (90), B=isopropanol (10), rt: threo-1: 34.839 min, threo-2: 36.287 min Example No. erythro-IA12aa48 (erythro racemate)
NMR (erythro): 4.31 (d, 1H), 3.84 (s, 3H), 3.73 (s, 3H), 3.39 (m, 1H), 3.23 (m, 1H), 3.08 (m, 1H), 1.17 (s, 9H); HPLC chiral: flow rate: 0.6 ml/min; column temperature: 25° C.; mobile phase: A=n-heptane (90), B=isopropanol (10), rt: erythro 1: 14.380 min, erythro 2: 17.766 min Example No. Ifa6 (erythro/threo isomer mixture 64:36):
NMR (threo): 17.41 (s, 1H), 4.00 (d, 1H), 1.06 (s, 3H), 1.03 (s, 3H); NMR (erythro): 17.42 (s, 1H), 4.29 (d, 1H), 1.08 (s, 3H), 1.05 (s, 3H); MS: 442 [M+1]+; HPLC (rt): 1.75 min Example No. threo-Iaa46 (threo racemate)
NMR (threo): 4.35 (d, 1H), 1.16 (s, 9H); HPLC chiral: flow rate: 1 ml/min; column temperature: 25° C.; mobile phase: A=n-heptane (80), B=isopropanol (20), rt: threo 1: 13.092 min, threo 2: 13.876 min Example No. erythro-Iaa46 (erythro racemate)
NMR (threo): 4.08 (d, 1H), 1.09 (s, 9H); HPLC chiral: flow rate: 1 ml/min; column temperature: 25° C.; mobile phase: A=n-heptane (80), B=isopropanol (20), rt: erythro 1: 10.151 min, erythro 2: 10.355

Example No. Iva6 (erythro/threo isomer mixture 62:38):
NMR (threo): 4.17 (d, 1H), 3.55 (s, 3H), 2.40 (s, 3H); NMR (erythro): 4.52 (d, 1H), 3.59 (s, 3H), 2.44 (s, 3H); MS: 414 [M+1]+; HPLC (rt): 1.24 min Example No. Ita6 (erythro/threo isomer mixture 66:34):
NMR (threo): 7.60 (s, 1H), 4.15 (d, 1H), 3.62 (s, 3H); NMR (erythro): 7.66 (s, 1H), 4.45 (d, 1H), 3.66 (s, 3H); MS: 400 [M+1]+; HPLC (rt): 1.31 min Example No. IA12aa50 (erythro/threo isomer mixture 57:43):
NMR (threo): 2.15 (q, 2H), 1.03 (t, 3H); NMR (erythro): 2.36 (q, 2H), 1.13 (t, 3H);

Example No. IB9aa49 (erythro/threo isomer mixture 59:41):
NMR (threo): 1.91 (s, 3H); NMR (erythro): 2.12 (s, 3H);

Example No. Iea95 (erythro/threo isomer mixture 58:42):
NMR (threo): 17.20 (m, 1H); NMR (erythro): 17.83 (m, 1H); MS: 460 [M+1]+; HPLC (rt): 1.78 min Example No. threo-Iva48 (threo racemate)
NMR (threo): 4.17 (d, 1H), 3.85 (m, 1H), 3.59 (s, 3H), 2.78 (q, 2H), 2.36 (s, 3H), 1.33 (t, 3H)

Example No. erythro-Iva48 (erythro racemate)
NMR (threo): 6.72-7.20 (m, 7H), 4.50 (d, 1H), 3.71 (m, 1H), 3.62 (s, 3H), 3.41 (m, 1H), 3.11 (m, 1H), 2.79 (q, 2H), 2.47 (s, 3H), 1.33 (t, 3H)

Example No. Ifa95 (erythro/threo isomer mixture 61:39):
NMR (threo): 17.30 (s, 1H), 2.47 (s, 3H), 2.30 (s, 3H); NMR (erythro): 17.39 (s, 1H), 2.51 (s, 3H), 2.37 (s, 3H); MS: 460 [M+1]+; HPLC (rt): 1.74 min Example No. Ita95 (erythro/threo isomer mixture 73:27):
NMR (threo): 7.80 (s, 1H), 4.17 (d, 1H), 3.67 (s, 3H), 2.72 (q, 2H), 1.30 (t, 3H);
NMR (erythro): 7.90 (s, 1H), 4.45 (d, 1H), 3.71 (s, 3H), 2.80 (q, 2H), 1.35 (t, 3H);

Example No. Iva6 (erythro/threo isomer mixture 51:49):
NMR (threo): 4.18 (d, 1H), 2.35 (s, 3H); NMR (erythro): 4.38 (d, 1H), 2.45 (s, 3H);
MS: 432 [M+1]+; HPLC (rt): 1.67 min Example No. Ica95 (erythro/threo isomer mixture 58:42):
NMR (threo): 17.23 (m, 1H); NMR (erythro): 17.31 (m, 1H); MS: 446 [M+1]+; HPLC (rt): 1.22 min Example No. Iga95 (erythro/threo isomer mixture 57:43):
NMR (threo): 17.62 (s, 1H); NMR (erythro): 17.69 (s, 1H); MS: 502 [M+1]+; HPLC (rt): 1.68 min Example No. Iva259 (erythro/threo isomer mixture 52:48):
NMR (threo): 4.29-4.37 (m, 1H), 4.13 (d, 1H), 3.59 (s, 3H), 2.80 (q, 2H), 2.37 (s, 3H), 1.35 (t, 3H); NMR (erythro): 4.37 (d, 1H), 3.60 (s, 3H), 2.80 (q, 2H), 2.42 (s, 3H), 1.35 (t, 3H);

Example No. Iaa6 (erythro/threo isomer mixture 61:39):
NMR (threo): 17.38 (s, 1H), 4.01 (d, 1H); NMR (erythro): 17.39 (s, 1H), 4.30 (d, 1H);
MS: 413 [M+1]+; HPLC (rt): 1.52 min Example No. IB9aa43 (erythro/threo isomer mixture 62:38):
NMR (threo): 13.37 (s, 1H); NMR (erythro): 13.41 (s, 1H); MS: 450 [M+1]+; HPLC (rt): 1.51 min Example No. threo-2-IB8aa43 (threo racemate)
NMR (threo): 13.55 (s, 1H), 7.17 (m, 1H), 7.02 (m, 2H), 6.92 (m, 1H), 6.77 (t, 2H), 4.23 (d, 1H), 4.19 (m, 1H), 3.84 (s, 3H), 3.47 (m, 2H); MS: 419 [M+1]+; HPLC (rt): 1.51 min; optical rotation: $[\alpha]_D^{20}$=−52.295 in CHCl$_3$. (concentration=2.157 g/ml).

Example No. Ioa83 (erythro/threo isomer mixture 53:47):
NMR (threo): 13.8 (broad s, 1H), 6.72 (t, 1H); NMR (erythro): 13.8 (broad s, 1H), 6.89 (t, 1H); MS: 400 [M+1]+; HPLC (rt): 1.39 min Example No. Ioa29 (erythro/threo isomer mixture 60:40):
NMR (threo): 13.8 (broad s, 1H), 4.27 (d, 1H); NMR (erythro): 13.8 (broad s, 1H), 4.01 (d, 1H); MS: 382 [M+1]+; HPLC (rt): 1.43 min Example No. Ioa24 (erythro/threo isomer mixture 60:40):
NMR (threo): 13.8 (broad s, 1H), 4.36 (d, 1H); NMR (erythro): 13.8 (broad s, 1H), 4.71 (d, 1H); MS: 418 [M+1]+; HPLC (rt): 1.44 min Example No. Ioa3 (erythro/threo isomer mixture 60:40):
NMR (threo): 13.8 (broad s, 1H), 4.26 (d, 1H); NMR (erythro): 13.8 (broad s, 1H), 3.99 (d, 1H); MS: 416 [M+1]+; HPLC (rt): 1.54 min Example No. Ioa17 (erythro/threo isomer mixture 58:42):
NMR (threo): 13.8 (broad s, 1H), 4.22 (d, 1H); NMR (erythro): 13.8 (broad s, 1H), 4.00 (d, 1H); MS: 400 [M+1]+; HPLC (rt): 1.54 min Example No. Ioa2 (erythro/threo isomer mixture 58:42):
NMR (threo): 13.8 (broad s, 1H), 4.27 (d, 1H); NMR (erythro): 13.8 (broad s, 1H), 4.04 (d, 1H); MS: 382 [M+1]+; HPLC (rt): 1.40 min Example No. Ioa9 (erythro/threo isomer mixture 63:37):
NMR (threo): 13.8 (broad s, 1H), 4.25 (d, 1H); NMR (erythro): 13.8 (broad s, 1H), 4.03 (d, 1H); MS: 398 [M+1]+; HPLC (rt): 1.49 min Example No. Ioa20 (erythro/threo isomer mixture 63:37):
NMR (threo): 13.8 (broad s, 1H), 4.26 (d, 1H); NMR (erythro): 13.8 (broad s, 1H), 4.02 (d, 1H); MS: 382 [M+1]+; HPLC (rt): 1.40 min Example No. Ioa1 (erythro/threo isomer mixture 63:37):
NMR (threo): 13.8 (broad s, 1H), 4.26 (d, 1H); NMR (erythro): 13.8 (broad s, 1H), 4.03 (d, 1H); MS: 398 [M+1]+; HPLC (rt): 1.50 min Example No. Ica83 (erythro/threo isomer mixture 63:37):
NMR (threo): 6.70 (t, 2H); NMR (erythro): 6.88 (t, 2H); MS: 428 [M+1]+; HPLC (rt): 1.68 min Example No. Ifa83 (erythro/threo isomer mixture 64:36):
NMR (threo): 6.70 (t, 2H); NMR (erythro): 6.88 (t, 2H); MS: 442 [M+1]+; HPLC (rt): 1.74 min Example No. Iea83 (erythro/threo isomer mixture 67:33):
NMR (threo): 6.70 (t, 2H); NMR (erythro): 6.88 (t, 2H); MS: 442 [M+1]+; HPLC (rt): 1.79 min Example No. Ica29 (erythro/threo isomer mixture 63:37):
NMR (threo): 4.01 (m, 1H); NMR (erythro): 4.30 (m, 1H); MS: 410 [M+1]+; HPLC (rt): 1.73 min Example No. Ifa29 (erythro/threo isomer mixture 62:38):
NMR (threo): 4.01 (d, 1H); NMR (erythro): 4.30 (m, 1H); MS: 424 [M+1]+; HPLC (rt): 1.79 min Example No. Iea29 (erythro/threo isomer mixture 61:39):
NMR (threo): 4.01 (d, 1H); NMR (erythro): 4.31 (dd, 1H); MS: 424 [M+1]+; HPLC (rt): 1.83 min Example No. Iaa29 (erythro/threo isomer mixture 62:38):
NMR (threo): 4.01 (d, 1H); NMR (erythro): 4.31 (m, 1H); MS: 396 [M+1]+; HPLC (rt): 1.63 min Example No. Ica3 (erythro/threo isomer mixture 62:38):
NMR (threo): 3.98 (dd, 1H); NMR (erythro): 4.29 (d, 1H); MS: 444 [M+1]+; HPLC (rt): 1.82 min Example No. Ifa3 (erythro/threo isomer mixture 62:38):
NMR (threo): 3.99 (dd, 1H); NMR (erythro): 4.29 (d, 1H); MS: 458 [M+1]+; HPLC (rt): 1.88 min Example No. Iea3 (erythro/threo isomer mixture 64:36):
NMR (threo): 4.00 (dd, 1H); NMR (erythro): 4.31 (dd, 1H);
MS: 458 [M+1]+; HPLC (rt): 1.91 min Example No. Iaa3 (erythro/threo isomer mixture 64:36):
NMR (threo): 4.00 (d, 1H); NMR (erythro): 4.29 (d, 1H); MS: 430 [M+1]+; HPLC (rt): 1.73 min Example No. Ica25 (erythro/threo isomer mixture 63:37):
NMR (threo): 4.08 (m, 1H); NMR (erythro): 4.34 (d, 1H); MS: 446 [M+1]+; HPLC (rt): 1.73 min Example No. Ifa25 (erythro/threo isomer mixture 64:36):
NMR (threo): 4.08 (m, 1H), 2.35 (s, 2H); NMR (erythro): 4.34 (d, 1H), 2.51 (s, 2H);
MS: 460 [M+1]+; HPLC (rt): 1.78 min Example No. Iea25 (erythro/threo isomer mixture 59:41):
NMR (threo): 4.08 (m, 1H), 2.51 (m, 2H); NMR (erythro): 4.34 (d, 1H), 2.68 (m, 2H);
MS: 460 [M+1]+; HPLC (rt): 1.82 min Example No. Ica17 (erythro/threo isomer mixture 54:46):
NMR (threo): 4.09 (m, 1H), 2.55 (m, 2H); NMR (erythro): 4.36 (d, 1H), 2.65 (m, 2H);
MS: 428 [M+1]+; HPLC (rt): 1.72 min Example No. Ifa17 (erythro/threo isomer mixture 57:43):
NMR (threo): 2.48 (s, 2H); NMR (erythro): 4.36 (d, 1H), 2.52 (s, 2H);
MS: 442 [M+1]+; HPLC (rt): 1.78 min Example No. Iea17 (erythro/threo isomer mixture 56:44):
NMR (threo): 2.51 (s, 2H); NMR (erythro): 2.66 (s, 2H);
MS: 443 [M+2]+; HPLC (rt): 1.82 min Example No. Iaa17 (erythro/threo isomer mixture 51:49):
NMR (threo): 2.48 (m, 2H); NMR (erythro): 4.36 (d, 1H), 2.63 (m, 2H);
MS: 414 [M+1]+; HPLC (rt): 1.63 min Example No. Ica23 (erythro/threo isomer mixture 54:46):
NMR (threo): 4.12 (d, 1H), 2.53 (m, 2H); NMR (erythro): 4.32 (d, 1H), 2.67 (m, 2H);
MS: 428 [M+1]+; HPLC (rt): 1.70 min Example No. Ifa23 (erythro/threo isomer mixture 56:44):
NMR (threo): 4.13 (d, 1H), 2.49 (s, 2H); NMR (erythro): 4.33 (d, 1H), 2.51 (s, 2H);
MS: 442 [M+1]+; HPLC (rt): 1.76 min Example No. Iea23 (erythro/threo isomer mixture 60:40):
NMR (threo): 2.51 (m, 2H); NMR (erythro): 2.68 (m, 2H);
MS: 442 [M+1]+; HPLC (rt): 1.79 min Example No. Ica2 (erythro/threo isomer mixture 65:35):
NMR (threo): 4.03 (dd, 1H); NMR (erythro): 4.30 (d, 1H); MS: 410 [M+1]+; HPLC (rt): 1.70 min Example No. Iea2 (erythro/threo isomer mixture 60:40):
NMR (threo): 4.02 (d, 1H), 2.48 (s, 2H); NMR (erythro): 4.31 (d, 1H), 2.52 (s, 2H);
MS: 424 [M+1]+; HPLC (rt): 1.76 min Example No. Iea9 (erythro/threo isomer mixture 62:38):
NMR (threo): 4.03 (dd, 1H), 2.51 (m, 2H); NMR (erythro): 4.31 (dd, 1H), 2.67 (m, 2H);
MS: 440 [M+1]+; HPLC (rt): 1.87 min Example No. Ifa9 (erythro/threo isomer mixture 62:38):
NMR (threo): 4.03 (d, 1H), 2.49 (s, 2H); NMR (erythro): 4.29 (d, 1H), 2.52 (s, 2H);
MS: 440 [M+1]+; HPLC (rt): 1.83 min Example No. Iaa9 (erythro/threo isomer mixture 60:40):
NMR (threo): 4.03 (d, 1H), 2.48 (m, 2H); NMR (erythro): 4.29 (d, 1H), 2.64 (m, 2H);
MS: 412 [M+1]+; HPLC (rt): 1.68 min Example No. Ica20 (erythro/threo isomer mixture 64:36):
NMR (threo): 4.02 (dd, 1H), 2.54 (m, 2H); NMR (erythro): 4.29 (d, 1H), 2.66 (m, 2H);
MS: 410 [M+1]+; HPLC (rt): 1.71 min Example No. Ifa20 (erythro/threo isomer mixture 64:36):
NMR (threo): 4.02 (d, 1H), 2.48 (s, 2H); NMR (erythro): 4.30 (d, 1H), 2.52 (s, 2H);
MS: 424 [M+1]+; HPLC (rt): 1.76 min Example No. Iea20 (erythro/threo isomer mixture 59:41):
NMR (threo): 4.02 (dd, 1H), 2.51 (m, 2H); NMR (erythro): 4.32 (dd, 1H), 2.68 (m, 2H);
MS: 424 [M+1]+; HPLC (rt): 1.81 min Example No. Ica1 (erythro/threo isomer mixture 63:37):
NMR (threo): 4.02 (dd, 1H); NMR (erythro): 4.29 (d, 1H);
MS: 426 [M+1]+; HPLC (rt): 1.79 min Example No. Ifa (erythro/threo isomer mixture 62:38):
NMR (threo): 4.01 (d, 1H), 2.48 (s, 2H); NMR (erythro): 4.29 (d, 1H), 2.52 (s, 2H);
MS: 440 [M+1]+; HPLC (rt): 1.85 min Example No. Iea1 (erythro/threo isomer mixture 68:32):
NMR (threo): 4.02 (dd, 1H), 2.50 (m, 2H); NMR (erythro): 4.32 (dd, 1H), 2.67 (m, 2H);
MS: 440 [M+1]+; HPLC (rt): 1.89 min Example No. Iga95 (erythro/threo isomer mixture 68:32):
NMR (threo): 4.02 (dd, 1H), 2.50 (m, 2H); NMR (erythro): 4.32 (dd, 1H), 2.67 (m, 2H);
MS: 502 [M+1]+; HPLC (rt): 1.83 min Example No. Iva83 (erythro/threo isomer mixture 51:49):
NMR (threo): 4.21 (d, 1H), 3.53 (s, 3H), 2.31 (s, 3H); NMR (erythro): 3.53 (s, 3H), 2.45 (s, 3H); MS: 414 [M+1]+; HPLC (rt): 1.20 min Example No. Iva24 (erythro/threo isomer mixture 64:36):
NMR (threo): 3.58 (s, 3H), 2.45 (s, 3H); NMR (erythro): 4.55 (d, 1H), 3.54 (s, 3H), 2.31 (s, 3H); MS: 432 [M+1]+; HPLC (rt): 1.27 min Example No. Iva3 (erythro/threo isomer mixture 72:28):
NMR (threo): 4.17 (d, 1H), 3.54 (s, 3H), 2.39 (s, 3H); NMR (erythro): 4.51 (d, 1H), 3.59 (s, 3H), 2.44 (s, 3H); MS: 430 [M+1]+; HPLC (rt): 1.36 min Example No. Iva17 (erythro/threo isomer mixture 72:28):
NMR (threo): 4.24 (d, 1H), 3.51 (s, 3H), 2.42 (s, 3H); NMR (erythro): 4.55 (d, 1H), 3.55 (s, 3H), 2.41 (s, 3H); MS: 414 [M+1]+; HPLC (rt): 1.25 min Example No. Iva2 (erythro/threo isomer mixture 71:29):
NMR (threo): 4.19 (d, 1H), 3.54 (s, 3H), 2.40 (s, 3H); NMR (erythro): 4.51 (d, 1H), 3.59 (s, 3H), 2.44 (s, 3H); MS: 397 [M+2]+; HPLC (rt): 1.22 min Example No. Iva9 (erythro/threo isomer mixture 71:29):
NMR (threo): 4.19 (d, 1H), 3.54 (s, 3H), 2.40 (s, 3H); NMR (erythro): 4.51 (d, 1H), 3.58 (s, 3H), 2.44 (s, 3H); MS: 412 [M+1]+; HPLC (rt): 1.26 min Example No. Iva20 (erythro/threo isomer mixture 71:29):
NMR (threo): 4.19 (d, 1H), 3.54 (s, 3H), 2.39 (s, 3H); NMR (erythro): 4.50 (d, 1H), 3.59 (s, 3H), 2.44 (s, 3H); MS: 397 [M+2]+; HPLC (rt): 1.22 min Example No. Iva1 (erythro/threo isomer mixture 71:29):
NMR (threo): 4.18 (d, 1H), 3.53 (s, 3H), 2.38 (s, 3H); NMR (erythro): 4.51 (d, 1H), 3.58 (s, 3H), 2.43 (s, 3H); MS: 412 [M+1]+; HPLC (rt): 1.32 min Example No. IB10ga6 (erythro/threo isomer mixture 62:38):
NMR (threo): 8.48 (s, 1H), 7.27 (m, 1H), 7.12 (m, 1H), 6.96 (m, 5H), 4.13 (d, 1H), 3.82 (m, 1H), 3.39 (dd, 1H), 3.23 (dd, 1H), 2.65 (s, 3H); MS: 385 [M+1]+; HPLC (rt): 1.57 min; NMR (erythro): 8.54 (s, 1H), 7.22 (m, 1H), 7.09 (m, 1H), 6.98 (m, 2H), 6.82 (m, 3H), 4.51 (d, 1H), 3.71 (m, 1H), 3.50 (dd, 1H), 3.27 (dd, 1H), 2.75 (s, 3H); MS: 385 [M+1]+; HPLC (rt): 1.57 min Example No. erythro-2-1B10ga6 (optically active erythro-2 isomer)
NMR (erythro): 8.54 (s, 1H), 7.22 (m, 1H), 7.09 (m, 1H), 6.98 (m, 2H), 6.82 (m, 3H), 4.51 (d, 1H), 3.71 (m, 1H), 3.50 (dd, 1H), 3.27 (dd, 1H), 2.75 (s, 3H); MS: 385 [M+1]+; HPLC (rt): 1.57 min Example No. erythro-1-1B10ga6 (optically active erythro-1 isomer)
NMR (erythro): 8.54 (s, 1H), 7.22 (m, 1H), 7.09 (m, 1H), 6.98 (m, 2H), 6.82 (m, 3H), 4.51 (d, 1H), 3.71 (m, 1H), 3.50 (dd, 1H), 3.27 (dd, 1H), 2.75 (s, 3H); MS: 385 [M+1]+; HPLC (rt): 1.57 min Example No. threo-2-1B10ga6 (optically active threo-2 isomer):
NMR (threo): 8.48 (s, 1H), 7.27 (m, 1H), 7.12 (m, 1H), 6.96 (m, 5H), 4.13 (d, 1H), 3.82 (m, 1H), 3.39 (dd, 1H), 3.23 (dd, 1H), 2.65 (s, 3H); MS: 385 [M+1]+; HPLC (rt): 1.57 min Example No. IA12aa194 (erythro/threo isomer mixture 80:20):
NMR (threo): 4.24 (d, 1H), 2.04 (s, 3H); NMR (erythro): 4.16 (d, 1H), 2.02 (s, 3H);
MS: 452 [M−42]+; HPLC (rt): 1.57 min Example No. erythro-IA12aa49:
NMR (erythro): 4.33 (d, 1H), 3.87 (s, 3H), 3.76 (s, 3H), 2.12 (s, 3H);
MS: 434 [M−42]+; HPLC (rt): 1.57 min Example No. threo-1-IA12aa49:
NMR (threo1): 3.95 (d, 1H), 3.75 (s, 3H), 3.96 (s, 3H), 1.91 (s, 3H);
MS: 434 [M−42]+; HPLC (rt): 1.57 min Example No. threo-2-IB12aa49:
NMR (threo2): 3.95 (d, 1H), 3.75 (s, 3H), 3.96 (s, 3H), 1.91 (s, 3H);
MS: 434 [M−42]+; HPLC (rt): 1.57 min (B) FORMULATION EXAMPLES a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium lignosulphonate and 1 part by weight of sodium oleoylmethyltaurate as wetting agent and dispersant, and grinding the mixture in a pinned-disk mill.

c) A readily water-dispersible dispersion concentrate is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of oxyethylated nonylphenol as emulsifier.

e) Water-dispersible granules are obtained by mixing
75 parts by weight of a compound of the formula (I),
10 parts by weight of calcium lignosulphonate,
5 parts by weight of sodium laurylsulphate,
3 parts by weight of polyvinyl alcohol and
7 parts by weight of kaolin, grinding the mixture in a pinned-disk mill, and granulating the powder in a fluidized bed by spray application of water as a granulating liquid.

f) Water-dispersible granules are also obtained by homogenizing and precomminuting
   25 parts by weight of a compound of the formula (I),
   5 parts by weight of sodium 2,2'-dinaphthylmethane-6,6'-disulphonate,
   2 parts by weight of sodium oleoylmethyltaurinate,
   1 part by weight of polyvinyl alcohol,
   17 parts by weight of calcium carbonate and
   50 parts by weight of water,
   on a colloid mill, subsequently grinding the mixture in a bead mill and atomizing and drying the resulting suspension in a spray tower by means of a single-substance nozzle.

The invention claimed is:

1. A compound of formula (I) and/or a salt thereof

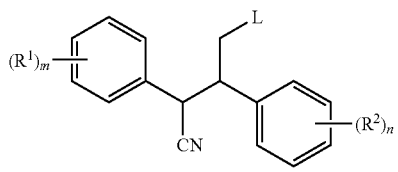
(I)

in which
L represents a radical of formula

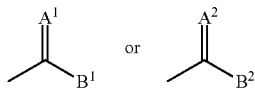

$A^1$ represents oxygen, sulphur or $=N-R^4$,
$B^1$ represents a radical of formulae (B1) to (B14),

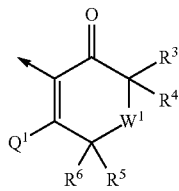
(B1)

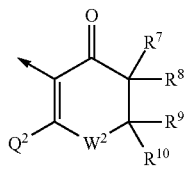
(B2)

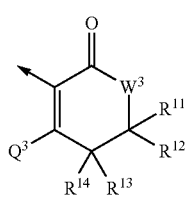
(B3)

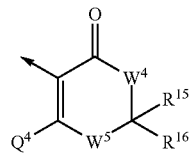
(B4)

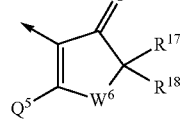
(B5)

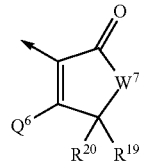
(B6)

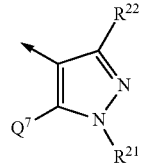
(B7)

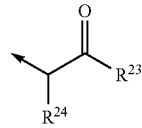
(B8)

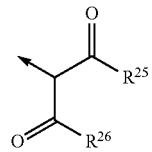
(B9)

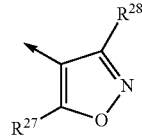
(B10)

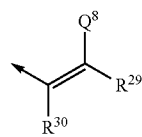
(B11)

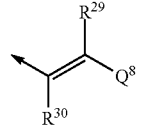
(B12)

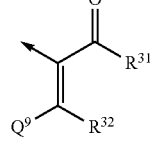
(B13)

-continued

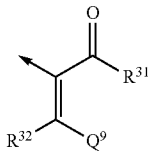
(B14)

A² represents a radical of formulae (A1) to (A12),

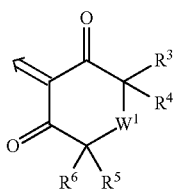
(A1)

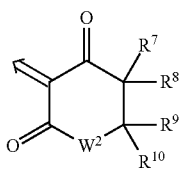
(A2)

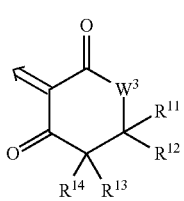
(A3)

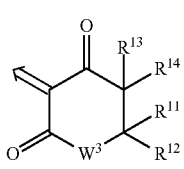
(A4)

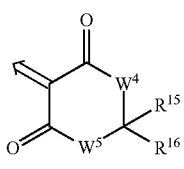
(A5)

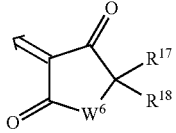
(A6)

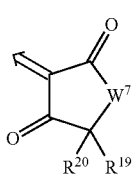
(A7)

-continued

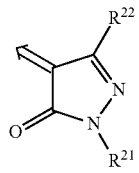
(A8)

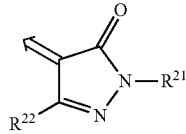
(A9)

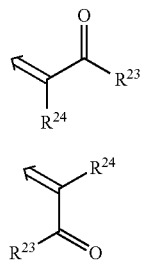
(A10)

(A11)

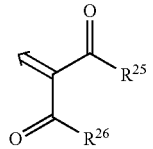
(A12)

B² represents hydroxy, thio, halogen or a group of the formula $OR^{33}$, OM, $SR^{34}$, SM or $-NR^BR^C$, $W^1$ and $W^6$ independently of one another each represent a divalent group oxygen, sulphur or a group of the formula NH, N—[($C_1$-$C_4$)-alkyl], C=O (carbonyl), S=O (sulphinyl), $SO_2$ (sulphonyl) or $CR^{35}R^{36}$, $W^2$, $W^3$, $W^4$, $W^5$ and $W^7$ independently of one another each represent the divalent group oxygen, sulphur or a group of the formula NH, N—[($C_1$-$C_4$)-alkyl], C=O (carbonyl), S=O (sulphinyl) or $SO_2$ (sulphonyl), $Q^1$, $Q^2$, $Q^3$, $Q^4$, $Q^5$, $Q^6$, $Q^7$, $Q^8$ and $Q^9$ independently of one another each represent hydroxy, thio, halogen or a group of the formula $OR^{37}$, $SR^{38}$, SM or OM, M represents an equivalent of a cation, $R^A$, $R^B$ and $R^C$ independently of one another each represent hydrogen, hydroxy, ($C_1$-$C_4$)-alkoxy, ($C_1$-$C_4$)-alkyl, ($C_1$-$C_4$)-haloalkyl, phenyl or benzyl, where each of the two last-mentioned radicals is optionally mono- or polysubstituted by identical or different substituents, or —NR*R**, where R* and R** independently of one another each represent H, ($C_1$-$C_8$)-alkyl, ($C_2$-$C_8$)-alkenyl, ($C_2$-$C_8$)-alkynyl, ($C_1$-$C_4$)-alkoxy-($C_1$-$C_4$)-alkyl, ($C_1$-$C_6$)-alkanoyl, [($C_1$-$C_4$)-haloalkyl]carbonyl, [($C_1$-$C_4$)-alkoxy]carbonyl, [($C_1$-$C_4$)-haloalkoxy]carbonyl, ($C_3$-$C_6$)-cycloalkyl, ($C_3$-$C_6$)-cycloalkyl-($C_1$-$C_4$)-alkyl, phenyl, or phenyl-($C_1$-$C_4$)-alkyl, where each of the 4 last-mentioned radicals is unsubstituted in the cycle or substituted by at least one radical from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy or, in the case of cycloalkyl, also oxo, or R* and R** together with the nitrogen atom represent a 3- to 8-membered heterocycle which, in addition to the nitrogen atom, may contain one or two further ring heteroatoms from the group consisting of N, O and S and which may be unsubstituted or substituted by at least one radical from the group consisting of $(C_1-C_4)$-alkyl, $(C_1-C_4)$-haloalkyl and oxo, $(R^1)_m$ represents m substituents $R^1$, where $R^1$, if m=1, or each of the substituents $R^1$, if m is greater than 1, independently of the others represents halogen, cyano, nitro, hydroxy, $(C_1-C_8)$-alkyl, $(C_2-C_6)$-alkenyl, $(C_2-C_6)$-alkynyl, $(C_1-C_8)$-alkoxy, $(C_1-C_8)$-alkylthio, $(C_1-C_8)$-alkylsulphinyl, $(C_1-C_8)$-alkylsulphonyl, $(C_1-C_6)$-haloalkyl, $(C_1-C_6)$-haloalkoxy, $(C_1-C_6)$-haloalkylthio, $(C_1-C_6)$-haloalkylsulphinyl, $(C_1-C_6)$-haloalkylsulphonyl, $(C_2-C_6)$-haloalkenyl, $(C_2-C_6)$-haloalkynyl, $(C_1-C_6)$-alkoxy-$(C_1-C_4)$-alkyl, $(C_1-C_6)$-haloalkoxy-$(C_1-C_4)$-alkyl, $(C_3-C_6)$-cycloalkyl which is optionally substituted by at least one radical from the group consisting of halogen and $(C_1-C_4)$-alkyl, $(C_3-C_6)$-cycloalkoxy which is optionally substituted by at least one radical from the group consisting of halogen and $(C_1-C_4)$-alkyl, or a radical of formula $C(O)OR^{39}$, $C(O)NR^{40}R^{41}$, $C(O)$-$Het^1$, $NR^{42}R^{43}$ or $Het^2$ or where in each case two groups $R^1$ located ortho at the ring together are a group of the formula —$Z^1$-$A^*$-$Z^2$ in which $A^*$ represents an alkylene group having from 1 to 4 carbon atoms which is optionally substituted by at least one radical from the group consisting of halogen, $(C_1-C_4)$-alkyl, $(C_1-C_4)$-haloalkyl, $(C_1-C_4)$-alkoxy and $(C_1-C_4)$-haloalkoxy, $Z^1$ represents a direct bond, O or S and $Z^2$ represents a direct bond, O or S, where the group —$Z^1$-$A^*$-$Z^2$ together with the carbon atoms, attached to the group, of the phenyl ring form a fused-on 5- or 6-membered ring, and $(R^2)_n$ represents n substituents $R^2$, where $R^2$, if n=1, or each of the substituents $R^2$, if n is greater than 1, independently of one another represents halogen, cyano, nitro, hydroxy, $(C_1-C_8)$-alkyl, $(C_2-C_6)$-alkenyl, $(C_2-C_6)$-alkynyl, $(C_1-C_8)$-alkoxy, $(C_1-C_8)$-alkylthio, $(C_1-C_8)$-alkylsulphinyl, $(C_1-C_8)$-alkylsulphonyl, $(C_1-C_6)$-haloalkyl, $(C_1-C_6)$-haloalkoxy, $(C_1-C_6)$-haloalkylthio, $(C_1-C_6)$-haloalkylsulphinyl, $(C_1-C_6)$-haloalkylsulphonyl, $(C_2-C_6)$-haloalkenyl, $(C_2-C_6)$-haloalkynyl, $(C_1-C_6)$-alkoxy-$(C_1-C_4)$-alkyl, $(C_1-C_6)$-haloalkoxy-$(C_1-C_4)$-alkyl, $(C_3-C_6)$-cycloalkyl which is optionally substituted by at least one radical from the group consisting of halogen and $(C_1-C_4)$-alkyl, $(C_3-C_6)$-cycloalkoxy which is optionally substituted by at least one radical from the group consisting of halogen and $(C_1-C_4)$-alkyl, or a radical of formula $C(O)OR^{44}$, $C(O)NR^{45}R^{46}$, $C(O)$-$Het^3$, $NR^{47}R^{48}$ or $Het^4$ or where in each case two groups $R^2$ located ortho at the ring together are a group of formula —$Z^3$-$A^{}$-$Z^4$ in which $A^{}$ represents an alkylene group having from 1 to 4 carbon atoms which is optionally substituted by at least one radical from the group consisting of halogen, $(C_1-C_4)$-alkyl, $(C_1-C_4)$-haloalkyl, $(C_1-C_4)$-alkoxy and $(C_1-C_4)$-haloalkoxy, $Z^3$ represents a direct bond, O or S and $Z^4$ represents a direct bond, O or S, where the group —$Z^3$-$A^{**}$-$Z^4$ together with the carbon atoms, attached to the group, of the phenyl ring form a fused-on 5- or 6-membered ring, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ independently of one another each represent hydrogen, halogen, cyano, nitro, hydroxy, $(C_1-C_4)$-alkyl, $(C_1-C_4)$-haloalkyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_3-C_6)$-cycloalkyl, $(C_3-C_6)$-halocycloalkyl, $(C_3-C_6)$-cycloalkoxy, $(C_2-C_6)$-alkenyl, $(C_2-C_6)$-haloalkenyl, $(C_2-C_6)$-alkynyl, $(C_2-C_6)$-haloalkynyl, $(C_1-C_4)$-alkylthio, $(C_1-C_4)$-alkylsulphonyl, $(C_1-C_4)$-alkylsulphinyl, phenyl which is optionally substituted, or a group $C(O)OR^{49}$, $C(O)NR^{50}R^{51}$, $C(O)Het^5$, $NR^{52}R^{53}$ or $Het^6$ or $R^3$ and $R^5$ in the group of formula (B1) or (A1) together represent a divalent bridge of a straight-chain alkylene or alkenylene group having 2 or 3 carbon atoms, where a $CH_2$ group in the chain may also be replaced by an oxygen atom and where a $CH_2$ group or CH group in the chain is optionally substituted by at least one radical from the group consisting of $(C_1-C_4)$-alkyl, $(C_1-C_4)$-haloalkyl, $(C_1-C_4)$-alkoxy and $(C_1-C_4)$-haloalkoxy, $R^{21}$ represents hydrogen, $(C_1-C_4)$-alkyl, $(C_1-C_4)$-haloalkyl, $(C_3-C_6)$-cycloalkyl, $(C_3-C_6)$-halocycloalkyl or a group $C(O)OR^{54}$, $C(O)NR^{55}R^{56}$, $C(O)Het^7$, $NR^{57}R^{58}$ or $Het^8$, $R^{22}$ represents hydrogen, $(C_1-C_4)$-alkyl, $(C_1-C_4)$-haloalkyl, $(C_3-C_6)$-cycloalkyl, $(C_3-C_6)$-halocycloalkyl, $(C_1-C_4)$-alkylthio, $(C_1-C_4)$-alkylsulphonyl, $(C_1-C_4)$-alkylsulphinyl or a group of formula $C(O)OR^{59}$, $C(O)NR^{60}R^{61}$, $C(O)Het^9$ $NR^{62}R^{63}$ or $Het^{10}$, $R^{23}$ and $R^{29}$ independently of one another each represent hydrogen, $(C_1-C_4)$-alkyl, $(C_1-C_4)$-haloalkyl, $(C_3-C_6)$-cycloalkyl, $(C_3-C_6)$-halocycloalkyl, $(C_1-C_4)$-alkoxy or $(C_1-C_4)$-haloalkoxy, $R^{24}$ and $R^{30}$ independently of one another each represent hydrogen, halogen, cyano, $(C_1-C_4)$-alkyl, $(C_1-C_4)$-haloalkyl, $(C_3-C_6)$-cycloalkyl, $(C_3-C_6)$-halocycloalkyl, $(C_1-C_4)$-alkoxy or $(C_1-C_4)$-haloalkoxy, $R^{25}$, $R^{26}$, $R^{31}$ and $R^{32}$ independently of one another each represent hydrogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_3-C_6)$-cycloalkyl, $(C_3-C_6)$-halocycloalkyl, $(C_3-C_6)$-cycloalkoxy, $(C_2-C_6)$-alkenyl, $(C_2-C_6)$-haloalkenyl, $(C_2-C_6)$-alkynyl, $(C_2-C_6)$-haloalkynyl, $(C_1-C_4)$-alkylthio, $(C_1-C_4)$-alkylsulphonyl, $(C_1-C_4)$-alkylsulphinyl, $NR^{64}R^{65}$ or $Het^{11}$, $R^{27}$ represents hydrogen, $(C_1-C_6)$-alkyl, $(C_1-C_4)$-haloalkyl, $(C_3-C_6)$-cycloalkyl or $(C_3-C_6)$-halocycloalkyl, $R^{28}$ represents hydrogen, $(C_1-C_6)$-alkyl, $(C_1-C_4)$-haloalkyl or a radical of the formula $C(O)OR^{66}$, $R^{33}$, $R^{34}$, $R^{37}$ and $R^{38}$ independently of one another each represent $(C_1-C_8)$-alkyl, $(C_3-C_6)$-cycloalkyl, phenyl, where each of the three last-mentioned radicals in each case independently of the others is unsubstituted or substituted by at least one radical from the group consisting of halogen, cyano, nitro, hydroxy, $(C_1-C_4)$-alkoxy, $(C_1-C_4)$-alkylthio and, in the case of a cycloalkyl or phenyl radical as parent radical, also $(C_1-C_4)$-alkyl and $(C_1-C_4)$-haloalkyl, or a group of formula —$C(O)R^{67}$, —$C(O)OR^{68}$, —$C(O)NR^{69}R^{70}$, —$C(O)Het^{12}$ or —$SO_2R^{71}$, $R^{35}$ and $R^{36}$ independently of one another are each defined as $R^3$, $R^{39}$, $R^{44}$, $R^{49}$, $R^{54}$, $R^{59}$ and $R^{66}$ independently of one another each represent hydrogen, $(C_1-C_4)$-alkyl, $(C_1-$ $C_4$)-haloalkyl, ($C_3$-$C_6$)-cycloalkyl, ($C_3$-$C_6$)-halocycloalkyl, ($C_2$-$C_4$)-alkenyl, ($C_2$-$C_4$)-haloalkenyl, ($C_2$-$C_4$)-alkynyl or M, $R^{40}$, $R^{41}$, $R^{42}$, $R^{43}$, $R^{45}$, $R^{46}$, $R^{47}$, $R^{48}$, $R^{50}$, $R^{51}$, $R^{52}$, $R^{53}$, $R^{55}$, $R^{56}$, $R^{57}$, $R^{58}$, $R^{60}$, $R^{61}$, $R^{62}$, $R^{63}$, $R^{64}$, $R^{65}$, $R^{69}$ and $R^{70}$ independently of one another each represent hydrogen, ($C_1$-$C_6$)-alkyl, ($C_2$-$C_6$)-alkenyl or ($C_2$-$C_6$)-alkynyl, where each of the 3 last-mentioned radicals in each case independently of the others is unsubstituted or substituted by at least one radical from the group consisting of halogen, nitro, cyano and phenyl, which is optionally substituted, or ($C_3$-$C_6$)-cycloalkyl or phenyl, where each of the 2 last-mentioned radicals in each case independently of the other is unsubstituted or substituted by at least one radical from the group consisting of halogen, nitro, cyano, ($C_1$-$C_4$)-alkyl, ($C_1$-$C_4$)-haloalkyl, phenyl and benzyl, where each of the 2 last-mentioned radicals is optionally substituted, $R^{67}$ represents hydrogen, ($C_1$-$C_8$)-alkyl or ($C_1$-$C_8$)-haloalkyl, where each of the 2 last-mentioned radicals independently of the other is optionally interrupted in the alkyl moiety by oxygen or sulphur, or phenyl or benzyl, where each of the 2 last-mentioned radicals independently of the other is unsubstituted or substituted by at least one radical from the group consisting of halogen, cyano, ($C_1$-$C_4$)-alkyl, ($C_2$-$C_4$)-alkenyl, ($C_2$-$C_4$)-alkynyl, ($C_3$-$C_6$)-cycloalkyl, ($C_1$-$C_4$)-haloalkyl and ($C_3$-$C_6$)-halocycloalkyl, $R^{68}$ represents ($C_1$-$C_8$)-alkyl, ($C_1$-$C_8$)-haloalkyl, ($C_3$-$C_6$)-cycloalkyl, ($C_3$-$C_6$)-halocycloalkyl, ($C_2$-$C_8$)-alkenyl, ($C_2$-$C_8$)-haloalkenyl or ($C_2$-$C_4$)-alkynyl, $R^{71}$ represents ($C_1$-$C_6$)-alkyl, ($C_1$-$C_6$)-haloalkyl or phenyl or benzyl, where each of the 2 last-mentioned radicals independently of the other is unsubstituted or substituted by at least one radical from the group consisting of halogen, cyano, ($C_1$-$C_4$)-alkyl, ($C_2$-$C_4$)-alkenyl, ($C_2$-$C_4$)-alkynyl, ($C_3$-$C_6$)-cycloalkyl, ($C_1$-$C_4$)-haloalkyl and ($C_3$-$C_6$)-halocycloalkyl, Het$^1$, Het$^2$, Het$^3$, Het$^4$, Het$^5$, Het$^6$, Het$^7$, Het$^8$, Het$^9$, Het$^{10}$, Het$^{11}$ and Het$^{12}$ independently of one another are each a saturated or partially unsaturated radical of a heterocycle having from 3 to 9 ring atoms and at least one nitrogen atom as ring heteroatom at position 1 of the ring and optionally 1, 2 or 3 further ring heteroatoms from the group consisting of N, O and S, where the radical of the heterocycle is attached at the nitrogen atom in position 1 of the ring to the remainder of the molecule of the compound of formula (I) and where the heterocycle is unsubstituted or substituted by at least one radical from the group consisting of halogen, ($C_1$-$C_4$)-alkyl, ($C_1$-$C_4$)-haloalkyl, ($C_1$-$C_4$)-alkoxy, ($C_1$-$C_4$)-haloalkoxy, ($C_1$-$C_4$)-alkylthio and oxo, and m, n independently of one another each represent 0, 1, 2, 3, 4 or 5.

2. A compound and/or a salt thereof according to claim 1, wherein $(R^1)_m$ represents m substituents $R^1$, where $R^1$, if m=1, or each of the substituents $R^1$, if m is greater than 1, independently of the others represents halogen, cyano, nitro, hydroxy, ($C_1$-$C_6$)-alkyl, ($C_2$-$C_4$)-alkenyl, ($C_2$-$C_4$)-alkynyl, ($C_1$-$C_6$)-alkoxy, ($C_1$-$C_6$)-alkylthio, ($C_1$-$C_6$)-alkylsulphinyl, ($C_1$-$C_6$)-alkylsulphonyl, ($C_1$-$C_4$)-haloalkyl, ($C_1$-$C_4$)-haloalkoxy, ($C_1$-$C_4$)-haloalkylthio, ($C_1$-$C_4$)-haloalkylsulphinyl, ($C_1$-$C_4$)-haloalkylsulphonyl, ($C_2$-$C_4$)-haloalkenyl, ($C_2$-$C_4$)-haloalkynyl, ($C_1$-$C_4$)-alkoxy-($C_1$-$C_4$)-alkyl, ($C_1$-$C_4$)-haloalkoxy-($C_1$-$C_4$)-alkyl, ($C_3$-$C_6$)-cycloalkyl which is optionally substituted by at least one radical from the group consisting of halogen and ($C_1$-$C_4$)-alkyl, ($C_3$-$C_6$)-cycloalkoxy which is optionally substituted by at least one radical from the group consisting of halogen and ($C_1$-$C_4$)-alkyl, or a radical of formula C(O)OR$^{39}$, C(O)NR$^{40}$R$^{41}$, C(O)-Het$^1$, NR$^{42}$R$^{43}$ or Het$^2$ or where in each case two groups $R^1$ located ortho at the ring together are a group of the formula —$Z^1$-A*-$Z^2$ in which A* represents an alkylene group having from 1 to 4 carbon atoms which is optionally substituted by at least one radical from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^1$ represents a direct bond, O or S and $Z^2$ represents a direct bond, O or S, where the group —$Z^1$-A*-$Z^2$ together with the carbon atoms, attached to the group, of the phenyl ring form a fused-on 5- or 6-membered ring, and $R^{39}$ represents hydrogen, ($C_1$-$C_4$)-alkyl, ($C_1$-$C_4$)-haloalkyl, ($C_3$-$C_6$)-cycloalkyl, ($C_3$-$C_6$)-halocycloalkyl, ($C_2$-$C_4$)-alkenyl, ($C_2$-$C_4$)-haloalkenyl, ($C_2$-$C_4$)-alkynyl or the equivalent of a cation, $R^{40}$, $R^{41}$, $R^{42}$, $R^{43}$ independently of one another each represent hydrogen or ($C_1$-$C_4$)-alkyl which is unsubstituted or substituted by at least one radical from the group consisting of halogen, nitro, cyano and phenyl, or ($C_3$-$C_6$)-cycloalkyl or phenyl, where each of the 2 last-mentioned radicals in each case independently of the other is unsubstituted or substituted by at least one radical from the group consisting of halogen, ($C_1$-$C_4$)-alkyl, ($C_1$-$C_4$)-haloalkyl, phenyl and benzyl, Het$^1$ and Het$^2$ independently of one another each represent a saturated or partially unsaturated radical of a heterocycle having from 3 to 6 ring atoms and at least one nitrogen atom as ring heteroatoms at position 1 of the ring and optionally 1, 2 or 3 further ring heteroatoms from the group consisting of N, O and S, where the radical of the heterocycle is attached at the nitrogen atom in position 1 of the ring to the remainder of the molecule of the compound of formula (I) and where the heterocycle is unsubstituted or substituted by at least one radical from the group consisting of halogen, ($C_1$-$C_4$)-alkyl, ($C_1$-$C_4$)-haloalkyl and oxo, and m represents 0, 1, 2, 3, 4 or 5.

3. A compound and/or a salt thereof according to claim 1, wherein $(R^2)_n$ represents n substituents $R^2$, where $R^2$, if n=1, or each of the substituents $R^2$, if n is greater than 1, independently of one another represents halogen, cyano, nitro, hydroxy, ($C_1$-$C_6$)-alkyl, ($C_2$-$C_4$)-alkenyl, ($C_2$-$C_4$)-alkynyl, ($C_1$-$C_6$)-alkoxy, ($C_1$-$C_6$)-alkylthio, ($C_1$-$C_6$)-alkylsulphinyl, ($C_1$-$C_6$)-alkylsulphonyl, ($C_1$-$C_4$)-haloalkyl, ($C_1$-$C_4$)-haloalkoxy, ($C_1$-$C_4$)-haloalkylthio, ($C_1$-$C_4$)-haloalkylsulphinyl, ($C_1$-$C_4$)-haloalkylsulphonyl, ($C_2$-$C_4$)-haloalkenyl, ($C_2$-$C_4$)-haloalkynyl, ($C_1$-$C_4$)-alkoxy-($C_1$-$C_4$)-alkyl, ($C_1$-$C_4$)-haloalkoxy-($C_1$-$C_4$)-alkyl, ($C_3$-$C_6$)-cycloalkyl which is optionally substituted by at least one radical from the group consisting of halogen and ($C_1$-$C_4$)-alkyl, ($C_3$-$C_6$)-cycloalkoxy which is optionally substituted by at least one radical from the group consisting of halogen and ($C_1$-$C_4$)-alkyl, or a radical of formula C(O)OR$^{44}$, C(O)NR$^{45}$R$^{46}$, C(O)-Het$^3$, NR$^{47}$R$^{48}$ or Het$^4$ or where in each case two groups $R^2$ located ortho at the ring together are a group of the formula $-Z^3-A^{}-Z^4$ in which A represents an alkylene group having from 1 to 4 carbon atoms which is optionally substituted by at least one radical from the group consisting of halogen, $(C_1-C_4)$-alkyl, $(C_1-C_4)$-haloalkyl, $(C_1-C_4)$-alkoxy and $(C_1-C_4)$-haloalkoxy, $Z^3$ represents a direct bond, O or S and $Z^4$ represents a direct bond, O or S, where the group $-Z^3-A^{**}-Z^4$ together with the carbon atoms, attached to the group, of the phenyl ring form a fused-on 5- or 6-membered ring, $R^{44}$ represents hydrogen, $(C_1-C_4)$-alkyl, $(C_1-C_4)$-haloalkyl, $(C_3-C_6)$-cycloalkyl, $(C_3-C_6)$-halocycloalkyl, $(C_2-C_4)$-alkenyl, $(C_2-C_4)$-haloalkenyl, $(C_2-C_4)$-alkynyl or the equivalent of a cation, $R^{45}$, $R^{46}$, $R^{47}$ and $R^{48}$ independently of one another each represent hydrogen or $(C_1-C_4)$-alkyl which is unsubstituted or substituted by at least one radical from the group consisting of halogen, nitro, cyano and phenyl, or $(C_3-C_6)$-cycloalkyl or phenyl, where each of the 2 last-mentioned radicals in each case independently of the other is unsubstituted or substituted by at least one radical from the group consisting of halogen, $(C_1-C_4)$-alkyl, $(C_1-C_4)$-haloalkyl, phenyl and benzyl, $Het^3$ and $Het^4$ independently of one another each represent a saturated or partially unsaturated radical of a heterocycle having from 3 to 6 ring atoms and at least one nitrogen atom as ring heteroatoms at position 1 of the ring and optionally 1, 2 or 3 further ring heteroatoms from the group consisting of N, O and S, where the radical of the heterocycle is attached at the nitrogen atom in position 1 of the ring to the remainder of the molecule of the compound of formula (I) and where the heterocycle is unsubstituted or substituted by at least one radical from the group consisting of halogen, $(C_1-C_4)$-alkyl, $(C_1-C_4)$-haloalkyl and oxo, and n represents 0, 1, 2, 3, 4 or 5.

4. A compound and/or a salt thereof according to claim 1, wherein $(R^1)_m$ represents m substituents $R^1$, where $R^1$, if m=1, or each of the substituents $R^1$, if m is greater than 1, independently of the others represents halogen, cyano, nitro, hydroxy, $(C_1-C_4)$-alkyl, $(C_1-C_4)$-alkoxy, $(C_1-C_4)$-alkylthio, $(C_1-C_4)$-alkylsulphinyl, $(C_1-C_4)$-alkylsulphonyl, $(C_1-C_4)$-haloalkyl, $(C_1-C_4)$-haloalkoxy, $(C_1-C_4)$-haloalkylthio, $(C_1-C_4)$-haloalkylsulphinyl, $(C_1-C_4)$-haloalkylsulphonyl, $(C_1-C_4)$-alkoxy-$(C_1-C_4)$-alkyl, $(C_3-C_6)$-cycloalkyl, or a radical of formula $C(O)OR^{39}$, $C(O)NR^{40}R^{41}$, $C(O)$-$Het^1$, $NR^{42}R^{43}$ or $Het^2$, or where in each case two groups $R^1$ located ortho at the ring together are a group of the formula $-Z^1-A^*-Z^2$ in which A* represents an alkylene group having from 1 to 4 carbon atoms which is optionally substituted by at least one radical from the group consisting of halogen, $(C_1-C_4)$-alkyl, $(C_1-C_4)$-haloalkyl, $(C_1-C_4)$-alkoxy and $(C_1-C_4)$-haloalkoxy, $Z^1$ represents a direct bond, O or S and $Z^2$ represents a direct bond, O or S, where the group $-Z^1-A^*-Z^2$ together with the carbon atoms, attached to the group, of the phenyl ring form a fused-on 5- or 6-membered ring, and $R^{39}$ represents hydrogen, $(C_1-C_4)$-alkyl or the equivalent of a cation, $R^{40}$, $R^{41}$, $R^{42}$ and $R^{43}$ independently of one another each represent hydrogen, $(C_1-C_4)$-alkyl, $(C_1-C_4)$-haloalkyl, benzyl, $(C_3-C_6)$-cycloalkyl or phenyl, $Het^1$ and $Het^2$ independently of one another each represent a morpholino, piperidino or pyrrolidino group, m represents 0, 1, 2, 3, 4 or 5, $(R^2)_n$ represents n substituents $R^2$, where $R^2$, if n=1, or each of the substituents $R^2$, if n is greater than 1, independently of one another represent halogen, cyano, nitro, hydroxy, $(C_1-C_4)$-alkyl, $(C_1-C_4)$-alkoxy, $(C_1-C_4)$-alkylthio, $(C_1-C_4)$-alkylsulphinyl, $(C_1-C_4)$-alkylsulphonyl, $(C_1-C_4)$-haloalkyl, $(C_1-C_4)$-haloalkoxy, $(C_1-C_4)$-haloalkylthio, $(C_1-C_4)$-haloalkylsulphinyl, $(C_1-C_4)$-haloalkylsulphonyl, $(C_1-C_4)$-alkoxy-$(C_1-C_4)$-alkyl, $(C_3-C_6)$-cycloalkyl, or a radical of the formula $C(O)OR^{44}$, $C(O)NR^{45}R^{46}$, $C(O)$-$Het^3$, $NR^{47}R^{48}$ or $Het^4$, or where in each case two groups $R^2$ located ortho at the ring together are a group of the formula $-Z^3-A^{}-Z^4$ in which A represents an alkylene group having from 1 to 4 carbon atoms which is optionally substituted by at least one radical from the group consisting of halogen, $(C_1-C_4)$-alkyl, $(C_1-C_4)$-haloalkyl, $(C_1-C_4)$-alkoxy and $(C_1-C_4)$-haloalkoxy, $Z^3$ represents a direct bond, O or S and $Z^4$ represents a direct bond, O or S, where the group $-Z^3-A^{**}-Z^4$ together with the carbon atoms, attached to the group, of the phenyl ring form a fused-on 5- or 6-membered ring, $R^{44}$ represents hydrogen, $(C_1-C_4)$-alkyl or the equivalent of a cation, $R^{45}$, $R^{46}$, $R^{47}$ and $R^{48}$ independently of one another each represent hydrogen, $(C_1-C_4)$-alkyl, $(C_1-C_4)$-haloalkyl, benzyl, $(C_3-C_6)$-cycloalkyl or phenyl, $Het^3$ and $Het^4$ independently of one another each represent a morpholino, piperidino or pyrrolidino group and n represents 0, 1, 2, 3, 4 or 5.

5. A compound and/or a salt thereof according to claim 1, wherein

L represents a radical of formula

6. A compound and/or a salt thereof according to claim 5, wherein $A^1$ represents oxygen, sulphur or $=N-R^4$, $B^1$ represents a radical of formulae (B1) to (B14), $R^4$ represents hydrogen, hydroxy, $(C_1-C_4)$-alkoxy, $(C_1-C_4)$-alkyl, $(C_1-C_4)$-haloalkyl, phenyl which is unsubstituted or substituted by at least one radical from the group consisting of halogen, $(C_1-C_4)$-alkyl, $(C_1-C_4)$-haloalkyl, $(C_1-C_4)$-alkoxy, $(C_1-C_4)$-haloalkoxy, or benzyl which is unsubstituted in the phenyl moiety or substituted by at least one radical from the group consisting of halogen, $(C_1-C_4)$-alkyl, $(C_1-C_4)$-haloalkyl, $(C_1-C_4)$-alkoxy, and $(C_1-C_4)$-haloalkoxy, or $-NR^*R^{**}$, where $R^*$, and $R^{**}$ independently of one another each represent H, $(C_1-C_4)$-alkyl, $(C_2-C_4)$-alkenyl, $(C_2-C_4)$-alkynyl, $(C_1-C_4)$-alkoxy-$(C_1-C_4)$-alkyl, $(C_1-C_4)$-alkanoyl, $[(C_1-C_4)$-haloalkyl]carbonyl, $[(C_1-C_4)$-alkoxy]carbonyl, $[(C_1-C_4)$- haloalkoxy]carbonyl, $(C_3-C_6)$-cycloalkyl, $(C_3-C_6)$-cycloalkyl-$(C_1-C_4)$-alkyl, phenyl, phenyl-$(C_1-C_4)$alkyl, where each of the 4 last-mentioned radicals is unsubstituted in the cycle or substituted by at least one radical from the group consisting of halogen, $(C_1-C_4)$-alkyl, $(C_1-C_4)$-haloalkyl, $(C_1-C_4)$-alkoxy or $(C_1-C_4)$-haloalkoxy or, in the case of cycloalkyl, also oxo, or R* and R** together with the nitrogen atom represent a 3- to 6-membered heterocycle which, in addition to the nitrogen atom, may contain one or two further ring heteroatoms from the group consisting of N, O and S and which may be unsubstituted or substituted by at least one radical from the group consisting of $(C_1-C_4)$-alkyl, $(C_1-C_4)$-haloalkyl and oxo, $W^1$ and $W^6$ independently of one another each represent a divalent group oxygen, sulphur or a group of the formula NH, N—$[(C_1-C_4)$-alkyl$]$, C=O, S=O, $SO_2$ or $CR^{35}R^{36}$, $W^2$, $W^3$, $W^4$, $W^5$ and $W^7$ independently of one another each represent the divalent group of the formula O, S, NH, N—$[(C_1-C_4)$-alkyl$]$, C=O, S=O or $SO_2$, $Q^1$, $Q^2$, $Q^3$, $Q^4$, $Q^5$, $Q^6$, $Q^7$, $Q^8$ and $Q^9$ independently of one another each represent hydroxy, thio, halogen or a group of the formula $OR^{37}$, $SR^{38}$, SM or OM, M represents the equivalent of a cation, $R^{35}$ and $R^{36}$ independently of one another are each as defined for $R^3$.

7. A compound and/or a salt thereof according to claim 5, wherein $R^{37}$ and $R^{38}$ independently of one another each represent $(C_1-C_6)$-alkyl, $(C_1-C_6)$-haloalkyl, $(C_1-C_4)$-alkoxy-$(C_1-C_4)$-alkyl, $(C_3-C_6)$-cycloalkyl which is unsubstituted or substituted by at least one radical from the group consisting of halogen, $(C_1-C_4)$-alkyl and $(C_1-C_4)$-alkoxy, phenyl which is unsubstituted or substituted by at least one radical from the group consisting of halogen, cyano, hydroxy, nitro, $(C_1-C_4)$-alkyl, $(C_1-C_4)$-haloalkyl and $(C_1-C_4)$-alkoxy, or a group of formula —C(O)$R^{67}$, —C(O)O$R^{68}$, —C(O)N$R^{69}R^{70}$, —C(O)Het$^{12}$ or —$SO_2R^{71}$, $R^{67}$ represents hydrogen, $(C_1-C_6)$-alkyl, $(C_1-C_4)$-haloalkyl, phenyl or benzyl, where each of the 2 last-mentioned radicals independently of the other is unsubstituted or substituted by at least one radical from the group consisting of halogen, cyano, $(C_1-C_4)$-alkyl and $(C_1-C_4)$-haloalkyl, $R^{68}$ represents $(C_1-C_6)$-alkyl or $(C_1-C_4)$-haloalkyl, $R^{69}$ and $R^{70}$ independently of one another each represent hydrogen, $(C_1-C_4)$-alkyl, benzyl, $(C_3-C_6)$-cycloalkyl or phenyl, where each of the 2 last-mentioned radicals independently of the other is unsubstituted or substituted by at least one radical from the group consisting of halogen, nitro, cyano, $(C_1-C_4)$-alkyl and $(C_1-C_4)$-haloalkyl, $R^{71}$ represents $(C_1-C_4)$-alkyl, $(C_1-C_4)$-haloalkyl, phenyl or benzyl, where each of the 2 last-mentioned radicals independently of the other is unsubstituted or substituted by at least one radical from the group consisting of halogen, cyano, $(C_1-C_4)$-alkyl, $(C_2-C_4)$-alkenyl and $(C_2-C_4)$-haloalkyl, Het$^{12}$ represents a saturated or partially unsaturated radical of a heterocycle having from 3 to 6 ring atoms and at least one nitrogen atom as ring heteroatom at position 1 of the ring and optionally 1, 2 or 3 further ring heteroatoms from the group consisting of N, O and S, where the radical of the heterocycle at the nitrogen atom in position 1 of the ring is attached to the remainder of the molecule of the compound of formula (I) and where the heterocycle is unsubstituted or substituted by at least one radical from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo, and M represents a metal ion equivalent, an ammonium ion which is optionally substituted by from 1 to 4 identical or different radicals from the group consisting of $(C_1-C_4)$-alkyl, $(C_3-C_6)$-cycloalkyl, phenyl, $(C_3-C_6)$-cycloalkyl-$(C_1-C_4)$-alkyl and phenyl-$(C_1-C_4)$-alkyl, or a tertiary sulphonium ion which is substituted by 3 identical or different radicals from the group consisting of $(C_1-C_4)$-alkyl, $(C_3-C_6)$-cycloalkyl, phenyl, $(C_3-C_6)$-cycloalkyl-$(C_1-C_4)$-alkyl and phenyl-$(C_1-C_4)$-alkyl.

8. A compound and/or a salt thereof according to claim 1, wherein

L represents a radical of formula

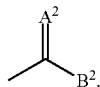

9. A compound and/or a salt thereof according to claim 8, wherein $A^2$ represents a radical of formulae (A1) to (A12), $B^2$ represents hydroxy, thio, halogen or a group of the formula $OR^{33}$, OM, $SR^{34}$, SM or —$NR^BR^C$, $R^B$ and $R^C$ independently of one another represent hydrogen, hydroxy, $(C_1-C_4)$-alkoxy, $(C_1-C_4)$-alkyl, $(C_1-C_4)$-haloalkyl, phenyl which is unsubstituted or substituted by at least one radical from the group consisting of halogen, $(C_1-C_4)$-alkyl, $(C_1-C_4)$-haloalkyl, $(C_1-C_4)$-alkoxy, $(C_1-C_4)$-haloalkoxy, or benzyl which is unsubstituted in the phenyl moiety or substituted by at least one radical from the group consisting of halogen, $(C_1-C_4)$-alkyl, $(C_1-C_4)$-haloalkyl, $(C_1-C_4)$-alkoxy, $(C_1-C_4)$-haloalkoxy, or —NR*R**, where R*, R** independently of one another each represent H, $(C_1-C_4)$-alkyl, $(C_2-C_4)$-alkenyl, $(C_2-C_4)$-alkynyl, $(C_1-C_4)$-alkoxy-$(C_1-C_4)$-alkyl, $(C_1-C_4)$-alkanoyl, [$(C_1-C_4)$-haloalkyl]carbonyl, [$(C_1-C_4)$-alkoxy]carbonyl, [$(C_1-C_4)$-haloalkoxy]carbonyl, $(C_3-C_6)$-cycloalkyl, $(C_3-C_6)$-cycloalkyl-$(C_1-C_4)$-alkyl, phenyl, phenyl-$(C_1-C_4)$alkyl, where each of the 4 last-mentioned radicals is unsubstituted in the cycle or substituted by at least one radical from the group consisting of halogen, $(C_1-C_4)$-alkyl, $(C_1-C_4)$-haloalkyl, $(C_1-C_4)$-alkoxy or $(C_1-C_4)$-haloalkoxy or, in the case of cycloalkyl, also oxo, or R* and R** together with the nitrogen atom represent a 3- to 6-membered and optionally saturated heterocycle which, in addition to the nitrogen atom, may contain one or two further ring heteroatoms from the group consisting of N, O and S and which may be unsubstituted or substituted by at least one radical from the group consisting of $(C_1-C_4)$-alkyl, $(C_1-C_4)$-haloalkyl and oxo, $W^1$ and $W^6$ independently of one another each represent the divalent group oxygen, sulphur or a group of the formula NH, N—$[(C_1-C_4)$-alkyl$]$, C=O, S=O, $SO_2$ or $CR^{35}R^{36}$, $W^2$, $W^3$, $W^4$, $W^5$ and $W^7$ independently of one another each represent the divalent group of the formula O, S, NH, N—$[(C_1-C_4)$-alkyl$]$, C=O, S=O or $SO_2$, $R^{33}$ and $R^{34}$ independently of one another each represent $(C_1-C_4)$-alkyl, $(C_1-C_4)$-haloalkyl, $(C_1-C_4)$-alkoxy-$(C_1-C_4)$-alkyl, $(C_3-C_6)$-cycloalkyl which is unsubstituted or substituted by at least one radical from the group consisting of halogen, $(C_1-C_4)$-alkyl and $(C_1-C_4)$-alkoxy, phenyl which is unsubstituted or substituted by at least one radical from the group consisting of halogen, cyano, hydroxy, nitro, $(C_1-C_4)$-alkyl, $(C_1-C_4)$-haloalkyl and $(C_1-C_4)$-alkoxy, or a group of the formula —C(O)$R^{67}$, —C(O)O$R^{68}$, —C(O)N$R^{69}R^{70}$, —C(O)Het$^{12}$ or —SO$_2R^{71}$, $R^{35}$ and $R^{36}$ independently of one another are each defined as $R^3$, $R^{67}$ represents hydrogen, $(C_1-C_6)$-alkyl, $(C_1-C_4)$-haloalkyl, phenyl or benzyl, where each of the 2 last-mentioned radicals independently of the other is unsubstituted or substituted by at least one radical from the group consisting of halogen, cyano, $(C_1-C_4)$-alkyl and $(C_1-C_4)$-haloalkyl, optionally H or $R^{68}$ is $(C_1-C_6)$-alkyl or $(C_1-C_4)$-haloalkyl, in particular $(C_1-C_4)$-alkyl, $R^{69}$ and $R^{70}$ independently of one another each represent hydrogen, $(C_1-C_4)$-alkyl, benzyl, $(C_3-C_6)$-cycloalkyl or phenyl, where each of the 2 last-mentioned radicals independently of the other is unsubstituted or substituted by at least one radicals from the group consisting of halogen, nitro, cyano, $(C_1-C_4)$-alkyl and $(C_1-C_4)$-haloalkyl, $R^{71}$ represents $(C_1-C_4)$-alkyl, $(C_1-C_4)$-haloalkyl, phenyl or benzyl, where each of the 2 last-mentioned radicals independently of the other is unsubstituted or substituted by at least one radical from the group consisting of halogen, cyano, $(C_1-C_4)$-alkyl, $(C_2-C_4)$-alkenyl and $(C_1-C_4)$-haloalkyl, benzyl or phenyl which is unsubstituted or substituted by at least one radical from the group consisting of halogen, $(C_1-C_4)$-alkyl and $(C_1-C_4)$-haloalkyl, Het$^{12}$ represents a saturated or partially unsaturated radical of a heterocycle having from 3 to 6 ring atoms and at least one nitrogen atom as ring heteroatom at position 1 of the ring and optionally 1, 2 or 3 further ring heteroatoms from the group consisting of N, O and S, where the radical of the heterocycle at the nitrogen atom in position 1 of the ring is attached to the remainder of the molecule of the compound of formula (I) and where the heterocycle is unsubstituted or substituted by at least one radical from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo.

10. A compound and/or a salt thereof according to claim 1, wherein said compound is present as an enriched threo racemate.

11. A compound and/or a salt thereof according to claim 1, wherein said compound is present as an enriched threo-2 enantiomer having stereochemical configuration [2R,3R].

12. A process for preparing a compound of formula (I) as defined in claim 1, and/or a salt thereof, wherein at least one of (a) to (i) is conducted:

(a) to prepare a compound of formula (I) and/or a salt thereof in which L represents a radical of formula C(=$A^1$)-$B^1$, $B^1$ represents a radical of formulae (B1) to (B9) and (B11) to (B14) and $Q^1$ to $Q^9$ each represent OH, SH, SM or OM and the other radicals are as defined in the respective compound of the formula (I) to be prepared, a compound of the formula (II)

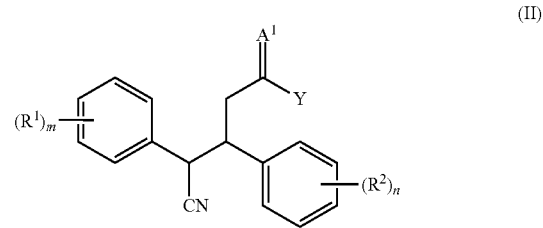

in which $A^1$, $(R^1)_m$ and $(R^2)_n$ are as defined in formula (I) and Y represents a leaving group, is reacted directly with a compound of formula H—$B^1$ in which $B^1$ is as defined in the radical L and $Q^1$ to $Q^9$ are each as defined in the compound of formula (I) to be prepared, to give compound (I), or to give the O- or S-alkylation product as intermediate, and the O- or S-alkylation intermediate formed is rearranged to give compound of formula (I) as C-alkylation product, or (b) to prepare a compound of formula (I) and/or a salt thereof in which L represents a radical of the formula —C(=$A^1$)-$B^1$, $B^1$ represents a radical of formulae (B1) to (B7) and (B11) to (B14) and $Q^1$ to $Q^9$ in group $B^1$ each represent a group of the formula SH or SM and the other radicals are as defined in the respective compound of formula (I) to be prepared, a compound of formula (I) in which L represents a radical of the formula —C(=$A^1$)-$B^1$ where $A^1$ is as defined in formula (I) and $B^1$ is defined analogously to the radical $B^1$ in formula (I), with the difference that $Q^1$ to $Q^9$ in group $B^1$ each represent the group OH or OM, is reacted with a halogenating agent to give compound (I) in which $Q^1$ to $Q^9$ in group $B^1$ each represent a halogen atom and reacted with a sulphurizing agent, and the desired compound of formula (I) is optionally separated from a reaction mixture and/or isolated or (c) to prepare a compound of formula (I) and/or a salt thereof in which L represents a radical of the formula —C(=$A^1$)-$B^1$, $B^1$ represents a radical of the formulae (B1) to (B7) and (B11) to (B 14) and $Q^1$ to $Q^9$ in group $B^1$ each represent a group of the formula O$R^{37}$ and the other radicals are as defined in the respective compound of formula (I) to be prepared, a compound of formula (I) in which L represents a radical of formula —C(=$A^1$)-$B^1$ where $A^1$ is as defined in formula (I) and $B^1$ is defined analogously to the radical $B^1$ in formula (I), with the difference that $Q^1$ to $Q^9$ in group $B^1$ each represent the group OH or OM, is reacted with a compound of the formula Y'—$R^{37}$ in which Y' represents a leaving group and $R^{37}$ is as defined in formula (I), and the desired compound of formula (I) is optionally separated from a reaction mixture and/or isolated or (d) to prepare a compound of formula (I) and/or a salt thereof in which L represents a radical of formula —C(=$A^1$)-$B^1$, $B^1$ represents a radical of the formulae (B1) to (B7) and (B11) to (B14) and $Q^1$ to $Q^9$ in group $B^1$ each represent a group of formula S$R^{38}$ and the other radicals are as defined in the respective compound of formula (I) to be prepared, a compound of formula (I) in which L represents a radical of the formula —C(=$A^1$)-$B^1$ where $A^1$ is as defined in formula (I) and $B^1$ is defined analogously to the radical $B^1$ in formula (I), with the difference that $Q^1$ to $Q^9$ in group $B^1$ each represent the group SH or SM, is reacted with a compound of the formula Y'—R$^{38}$ in which Y' represents a leaving group and R$^{38}$ is as defined in formula (I), and the desired compound of formula (I) is optionally separated from a reaction mixture and/or isolated or (e) to prepare a compound of formula (I) and/or a salt thereof in which L represents a radical of formula —C(=A$^1$)-B$^1$, B$^1$ represents a radical of formulae (B1) to (B7) and (B11) to (B14) and Q$^1$ to Q$^9$ in group B$^1$ each represent a group of formula SR$^{38}$ and the other radicals are as defined in the respective compound of formula (I) to be prepared, a compound of formula (I) in which L represents a radical of the formula —C(=A$^1$)-B$^1$ where A$^1$ is as defined in formula (I) and B$^1$ is defined analogously to the radical B$^1$ in formula (I), with the difference that Q$^1$ to Q$^9$ in group B$^1$ each represent a halogen atom, is reacted with a thio compound of the formula H—S—R$^{38}$, and the desired compound of formula (I) is optionally separated from a reaction mixture and/or isolated or (f) to prepare a compound of formula (I) and/or a salt thereof in which L represents a radical of formula —C(=A$^1$)-B$^1$ and B$^1$ represents a group of formula (B10) [=compound (I-B10)], a compound of formula (I) in which L represents a radical of formula —C(=A$^1$)-B*, A$^1$ is as defined in formula (I) and B* is a radical of the formula —CH$_2$—CO—R$^{27}$ in which R$^{27}$ is as defined in formula (B10) [=compound (I-B)]

is reacted with N,N-dimethylformamide dimethyl acetal to give a compound of formula (I-C) and a compound (I-C) is reacted with ring closure with hydroxylamine or a salt thereof to give a compound of formula (I-B10) in which R$^{28}$=H or the compound (I-B) is reacted with a compound of the formula (X1)

HO—N=C(Cl)—R$^{28}$ (X1)

in which R$^{28}$ is as defined in formula (B10) with ring closure to give a compound of formula (I-B10) where R$^{28}$ in formula (X1) is defined as in a compound of formula (I-B10) to be prepared, except that R$^{28}$=H, or (g) to prepare a compound of formula (I) and/or a salt thereof in which L represents a radical of formula —C(=A$^1$)-B$^1$ and B$^1$ represents a group of formula (B10) [=compound (I-B10)], a compound of formula (II)

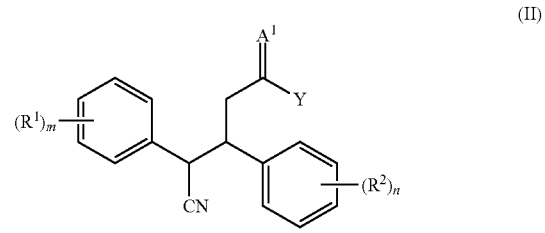

(II)

in which A$^1$, (R$^1$)$_m$ and (R$^2$)$_n$ are as defined in formula (I) and Y represents a leaving group, is reacted with a compound of the formula X-(B10) in which (B10) is defined as in group B$^1$ and X is a leaving Scheme

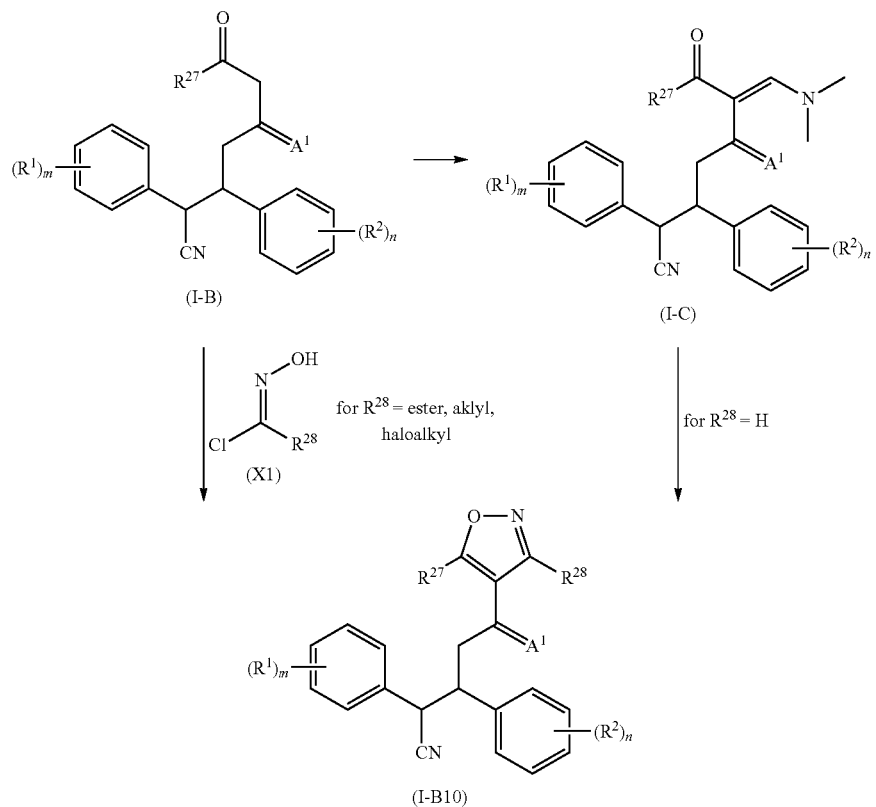

group, optionally in the presence of a coupling agent, to give the compound of formula (I)
or
is reacted with an activated compound of formula X'—(B10) in which X' represents a metal or a metal derivative group, to give a compound of formula (I), (h) to prepare a compound of formula (I) and/or a salt thereof in which L represents a radical of formula —C(=A$^2$)-B$^2$ and B$^2$ represents a radical of formula OR$^{33}$ or SR$^{34}$, a compound of formula (I')

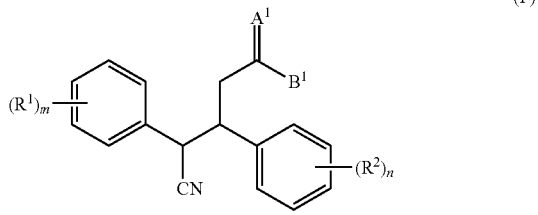

(I')

in which (R$^1$)$_m$ and (R$^2$)$_n$ are as defined in formula (I), A$^1$ represents a radical O or S and B$^1$ represents a radical of formula (B1), (B2), (B3), (B4), (B5), (B6), (B7), (B8), (B9), (B11), (B12), (B13) or (B14) as defined above for compounds (I) in which L represents a radical —C(=A$^1$)-B$^1$, where Q$^1$ to Q$^9$ in the radicals B$^1$ each represent OH or OM, is reacted with a compound of the formula Y'—B$^2$ in which B$^2$ is as defined in the radical L and Y represents a leaving group, to give compound (I) in which B$^2$ represents the radical OR$^{33}$ if A$^1$=O or SR$^{34}$ if A$^1$=S, where the group —C(=A$^2$)- in compound (I), compared to group —C—B$^1$ in compound (I'), represents a more stable tautomer or a structurally fixed tautomer in which the radical —C(=A$^2$)- corresponds tautomerically to the radical =C(—B$^1$)—, or (i) to prepare a compound of formula (I) and/or a salt thereof in which L represents a radical of formula —C(=A$^2$)-B$^2$ and B$^2$ represents a radical of formula —NR$^B$R$^C$, a compound of formula (I')

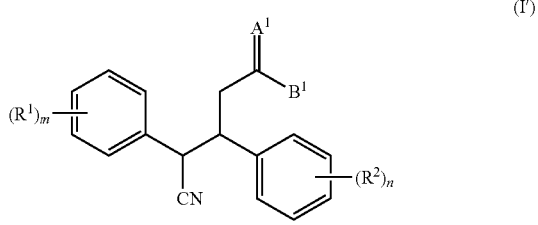

(I')

in which (R$^1$)$_m$ and (R$^2$)$_n$ are as defined in formula (I), A$^1$ represents a radical of formula —NR$^B$ and B$^1$ represents a radical of formula (B1), (B2), (B3), (B4), (B5), (B6), (B7), (B8), (B9), (B11), (B12), (B13) or (B14) as defined above for compounds (I) in which L represents a radical —C(=A$^1$)-B$^1$, where Q$^1$ to Q$^9$ in the radicals B$^1$ each represent OH or OM, is reacted with a compound of formula Y'—R$^C$ in which R$^C$ is as defined in the radical —NR$^B$R$^C$ of B$^2$ and Y represents a leaving group, to give compound (I) in which B$^2$ represents the radical —NR$^B$R$^C$, where the group —C(=A$^2$)- in compound (I), compared to group —C—B$^1$ in compound (I'), represents a more stable tautomer or a structurally fixed tautomer in which the radical —C(=A$^2$)- corresponds tautomerically to the radical =C(—B$^1$)—.

13. A herbicidal and/or plant growth-regulating composition, wherein said composition comprises at least one compound of formula (I) and/or a salt thereof as defined in claim 1 and at least one formulation auxiliary customary in crop protection.

14. A method for controlling a harmful plant and/or for regulating growth of a plant, comprising applying an effective amount of at least one compound of formula (I) and/or a salt thereof as defined in claim 1 onto a plant, a plant seed, soil in which and/or on which a plant grows and/or an area under cultivation.

15. The method according to claim 14, wherein a compound of formula (I) and/or a salt thereof is employed for selective control of a harmful plant and/or for regulating growth in a crop of a useful plant and/or an ornamental plant.

16. The method according to claim 15, wherein the crop plant is a transgenic crop plant.

17. The compound of formula (I) and/or a salt thereof according to claim 1 capable of being used as a herbicide and/or a plant growth regulator.

18. The compound of formula (I) and/or a salt thereof capable of being used according to claim 17, wherein said compound is capable of being applied as a selective herbicide for controlling a harmful plant and/or as a plant growth regulator in a crop of a useful and/or ornamental plant.

* * * * *